US012747223B2

(12) United States Patent
Brånalt et al.

(10) Patent No.: US 12,747,223 B2
(45) Date of Patent: Sep. 29, 2026

(54) N-(2-(3-CYANO-2-AZABICYCLO[3.1.0] HEXAN-2-YL)-2-OXOETHYL)QUINOLINE-4-CARBOXAMIDES

(71) Applicant: AstraZeneca AB, Södertälje (SE)

(72) Inventors: Jonas Brånalt, Gothenburg (SE); Maria Johansson, Gothenburg (SE); Anneli Nordqvist, Gothenburg (SE); Gavin O'Mahony, Gothenburg (SE); Marianne Swanson, Gothenburg (SE)

(73) Assignee: AstraZeneca AB, Södertälje (SE)

(*) Notice: Subject to any disclaimer, the term of this patent is extended or adjusted under 35 U.S.C. 154(b) by 531 days.

(21) Appl. No.: 18/337,476

(22) Filed: Jun. 20, 2023

(65) Prior Publication Data

US 2023/0406840 A1 Dec. 21, 2023

Related U.S. Application Data

(60) Provisional application No. 63/366,700, filed on Jun. 21, 2022.

(51) Int. Cl.
*C07D 401/12* (2006.01)

(52) U.S. Cl.
CPC .................................. *C07D 401/12* (2013.01)

(58) Field of Classification Search
CPC .................................................... C07D 401/12
See application file for complete search history.

(56) References Cited

U.S. PATENT DOCUMENTS

| | | | |
|---|---|---|---|
| 6,680,282 | B2 | 1/2004 | Sawai et al. |
| 7,060,722 | B2 | 6/2006 | Hayashi et al. |
| 7,067,668 | B2 | 6/2006 | Sawai et al. |
| 7,074,794 | B2 | 7/2006 | Hayashi et al. |
| 7,335,677 | B2 | 2/2008 | Evans et al. |
| 7,345,180 | B2 | 3/2008 | Takeda et al. |
| 7,829,501 | B2 | 11/2010 | Yoneda et al. |
| 8,039,420 | B2 | 10/2011 | Yoneda et al. |
| 8,067,436 | B2 | 11/2011 | Buynh et al. |
| 8,183,280 | B2 | 5/2012 | Trim et al. |
| 9,346,814 | B2 | 5/2016 | Oliver et al. |
| 10,266,526 | B2 | 4/2019 | Foley et al. |
| 2020/0157114 | A1 | 5/2020 | Shimada et al. |

FOREIGN PATENT DOCUMENTS

| | | | |
|---|---|---|---|
| AU | 2015315174 | B2 | 9/2015 |
| CN | 108690043 | A | 10/2018 |
| EP | 1776011 | B1 | 8/2005 |
| EP | 1760076 | A1 | 3/2007 |
| EP | 3666770 | A1 | 6/2020 |
| JP | 2003026698 | A | 1/2003 |
| WO | 1998055460 | A1 | 12/1998 |
| WO | 2001002385 | A1 | 1/2001 |
| WO | 0134594 | A1 | 5/2001 |
| WO | 2001058871 | A1 | 8/2001 |
| WO | 2001081304 | A1 | 11/2001 |
| WO | 2001081337 | A1 | 11/2001 |
| WO | 2002014271 | A1 | 2/2002 |
| WO | 2003035057 | A1 | 5/2003 |
| WO | 2004067509 | A1 | 8/2004 |
| WO | 2004071454 | A2 | 8/2004 |
| WO | 2005087742 | A1 | 9/2005 |
| WO | 2006016708 | A1 | 2/2006 |
| WO | 2007017423 | A2 | 2/2007 |
| WO | 2007085895 | A2 | 8/2007 |
| WO | 2008064218 | A2 | 5/2008 |
| WO | 2013033396 | A2 | 3/2013 |
| WO | 2013050454 | A1 | 4/2013 |
| WO | 2013107820 | A1 | 7/2013 |
| WO | 2014016849 | A2 | 1/2014 |

(Continued)

OTHER PUBLICATIONS

Simkova et al. Molecular recognition of fibroblast activation protein for diagnostic and therapeutic applications, Biochimica et Biophysica Acta (BBA)—Proteins and Proteomics vol. 1868, Issue 7, Jul. 2020, 140409.*

Int'l Search Report and Written Opinion for PCT/IB2021/061839 mailed Mar. 9, 2022.

Int'l Search Report and Written Opinion for PCT/EP2023/066560 mailed Aug. 30, 2023.

Int'l Search Report and Written Opinion for PCT/EP2023/066561 mailed Aug. 30, 2023.

Dong, et al., Synthesis and biological activities of fluorescent acridine-containing HIV-1 nucleocapsid proteins for investigation of nucleic acid-NCp7 interactions, J. Peptide Res., 1997, v. 50, pp. 269-278.

(Continued)

*Primary Examiner* — Brian E Mcdowell
(74) *Attorney, Agent, or Firm* — Arnold Porter Kaye Scholer LLP

(57) ABSTRACT

Compounds having the structure of Formula (I):

(I)

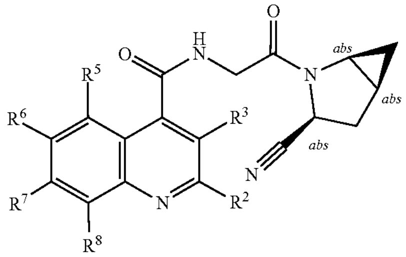

and pharmaceutically acceptable salts thereof, wherein $R^2$, $R^3$, $R^5$, $R^6$, $R^7$, and $R^8$ are as defined in the specification; pharmaceutical compositions comprising such compounds and salts; use of such compounds and salts to treat or prevent Prolyl endopeptidase fibroblast activation protein (FAP)-mediated conditions; kits comprising such compounds and salts; and methods for manufacturing such compounds and salts.

26 Claims, No Drawings

(56) References Cited

FOREIGN PATENT DOCUMENTS

| | | | |
|---|---|---|---|
| WO | 2015144093 | A1 | 10/2015 |
| WO | 2015164374 | A1 | 10/2015 |
| WO | 2016040505 | A1 | 3/2016 |
| WO | 2017189569 | A1 | 11/2017 |
| WO | 2018053267 | A1 | 3/2018 |
| WO | 2018111989 | A1 | 6/2018 |
| WO | 2018161033 | A1 | 9/2018 |
| WO | 2018195439 | A2 | 10/2018 |
| WO | 2018237349 | A1 | 12/2018 |
| WO | 2019031990 | A1 | 2/2019 |
| WO | 2019084271 | A1 | 5/2019 |
| WO | 2019118932 | A1 | 6/2019 |
| WO | 2019125849 | A1 | 6/2019 |
| WO | 2019154886 | A1 | 8/2019 |
| WO | 2020025517 | A1 | 2/2020 |
| WO | 2020032105 | A1 | 2/2020 |
| WO | 2020045334 | A1 | 3/2020 |
| WO | 2020132661 | A2 | 6/2020 |
| WO | 2021060453 | A1 | 4/2021 |
| WO | 2021090245 | A1 | 5/2021 |
| WO | 2022130270 | A1 | 6/2022 |

OTHER PUBLICATIONS

Dwyer, et al., Discovery of pyrazolo[1,5-a]pyrimidine-based Pim inhibitors: A template-based approach, Bioorganic & Medicinal Chem. Ltrs., 2013, v. 23, pp. 6178-6182.

Jansen, et al., J. Med. Chem., Extended Structure-Activity Relationship and Pharmacokinetic Investigation of (4-Quinolinoyl)glycyl-2-cyanopyrrolidine Inhibitors of Fibroblast Activation Protein (FAP), J. Med. Chem., 2014, v.57, pp. 3053-3074.

Kushwaha, et al., Design, Synthesis, Biological Screening, and Molecular Docking Studies of Piperazine-Derived Constrained Inhibitors of DPP-IV for the Treatment of Type 2 Diabetes, Chem. Biol. Drug Des., 2015, v. 85, pp. 439-446.

* cited by examiner

N-(2-(3-CYANO-2-AZABICYCLO[3.1.0]HEXAN-2-YL)-2-OXOETHYL)QUINOLINE-4-CARBOXAMIDES

CROSS-REFERENCE TO RELATED PATENT APPLICATION

This specification claims the benefit of priority to U.S. Provisional Patent Application No. 63/366,700 (filed 21 Jun. 2022). The entire text of the above-referenced patent application is incorporated by reference into this specification.

FIELD

The present disclosure relates generally to N-(2-(3-cyano-2-azabicyclo-[3.1.0]hexan-2-yl)-2-oxoethyl)quinoline-4-carboxamides and pharmaceutically acceptable salts thereof. The specification further relates to pharmaceutical compositions comprising such compounds and salts; use of such compounds and salts to treat or prevent Prolyl endopeptidase fibroblast activation protein (FAP)-mediated conditions; kits comprising such compounds and salts; and methods for manufacturing such compounds and salts.

BACKGROUND

FAP, a type II transmembrane serine protease, is expressed by fibroblast like cells involved in tissue remodeling and healing. In the context of non-alcoholic steatohepatitis (NASH), FAP is upregulated on the cell surface of activated hepatic stellate cells involved in the fibrosis formation (*Hepatology* 1999, 29, 1768), a major aspect of NASH that predicts disease outcome (*Gastroenterology* 2020, 158, 1611). FAP also can be present as a shedded plasma protease. Increased levels of circulating FAP are associated with NASH disease severity (*Diabetes Res Clin Pract* 2015, 108, 466).

FAP has a consensus cleavage motif after Gly-Pro and exhibits both endopeptidase and exopeptidase activity. Known enzymatic activities include cleavage of collagens (*Hepatology* 1999, 29, 1768), α2-antiplasmin (α2AP) (*Blood* 2004, 103, 3783), and fibroblast growth factor 21 (FGF21) (*Biochem J* 2016, 473, 605). FAP activity at the cell surface of activated fibroblasts (including cleavage of collagens) generates a pro-fibrotic environment. FAP cleavage of α2AP gives a more efficient cross-linking of α2AP to fibrin and results in reduced fibrin clearance. FAP cleavage of FGF21 inactivates FGF21 metabolic effects (*Biochem J* 2016, 473, 605). All these activities are associated with a worsening of NASH disease and inhibiting FAP has the potential to treat NASH and other conditions by affecting multiple mechanisms.

Inhibition of FAP activity is a presently unexploited therapeutic approach for treating NASH and other diseases associated with such activity. No approved pharmacological agents that inhibit FAP activity generally, or that inhibit FAP activity specifically, are currently available. Accordingly, there is a need for FAP inhibitors, particularly FAP inhibitors that have pharmacologically appropriate selectivity and bioavailability and therefore are suitable for administration to a subject in need of such treatment. The present disclosure addresses this large unmet need by providing such compounds together with corresponding pharmaceutical compositions and methods for the treatment or prevention of NASH and related conditions.

SUMMARY

In one aspect, the present disclosure provides compounds having the structure of Formula (I):

(I)

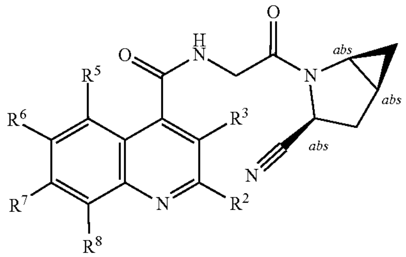

and pharmaceutically acceptable salts thereof, wherein:

$R^2$ is selected from the group consisting of hydrogen, halogen, and methyl;

$R^3$ is hydrogen or halogen;

$R^5$ is selected from the group consisting of hydrogen, hydroxy, halogen, methyl, and methoxy;

one of $R^6$ and $R^7$ is hydrogen and the other of $R^6$ and $R^7$ is selected from the group consisting of:

(a) halogen;

(b) $C_{1-6}$-alkyl, wherein the $C_{1-6}$-alkyl is optionally substituted with one or more substituents independently selected from the group consisting of halogen, hydroxy, $C_{1-6}$-alkoxy, halo-$C_{1-6}$-alkoxy, $C_{3-6}$-cycloalkyl, and $C_{3-6}$-cycloalkoxy;

(c) cyclopropyl, wherein the cyclopropyl is optionally substituted with one or more substituents independently selected from the group consisting of cyano, fluoro, $C_{1-6}$-alkyl, halo-$C_{1-6}$-alkyl, and $C_{1-6}$-alkoxy;

(d) $C_{1-6}$-alkoxy, wherein the $C_{1-6}$-alkoxy is optionally substituted with one or more substituents independently selected from the group consisting of halogen and cyclopropyl; and (e) $C_{3-6}$-cycloalkoxy, wherein the $C_{3-6}$-cycloalkoxy is optionally substituted with one or more substituents independently selected from the group consisting of halogen and $C_{1-3}$-alkyl; and $R^8$ is selected from the group consisting of hydrogen, halogen, and methyl.

In another aspect, the present disclosure provides compounds having the structure of Formula (II-A), (II-B), (II-C), (III-A), (III-B), or (III-C) as further defined herein, and pharmaceutically acceptable salts thereof.

In another aspect, the present disclosure provides pharmaceutical compositions comprising a therapeutically-effective amount of a compound having the structure of Formula (I), (II-A), (II-B), (II-C), (III-A), (III-B), or (III-C) as further defined herein, or a pharmaceutically acceptable salt thereof, and a pharmaceutically acceptable carrier.

In another aspect, the present disclosure provides pharmaceutical compositions comprising therapeutically-effective amounts of a compound having the structure of Formula (I), (II-A), (II-B), (II-C), (III-A), (III-B), or (III-C) as further defined herein, or a pharmaceutically acceptable salt thereof; a second pharmacological agent; and a pharmaceutically acceptable carrier.

In another aspect, the present disclosure provides methods for treating or preventing an FAP-mediated condition by administering a therapeutically effective amount of a compound having the structure of Formula (I), (II-A), (II-B), (II-C), (III-A), (III-B), or (III-C) as further defined herein, or pharmaceutically acceptable salt thereof, to a subject in need thereof. In one aspect, the FAP-mediated condition is selected from the group consisting of liver disease, type 2 diabetes mellitus, cardiovascular conditions, obesity, obesity-related conditions, fibrosis, keloid disorder, inflammation, and cancer. In another aspect, the FAP-mediated condition is liver disease, particularly nonalcoholic steatohepatitis (NASH).

In another aspect, the present disclosure provides compounds having the structure of Formula (I), (II-A), (II-B), (II-C), (III-A), (III-B), or (III-C) as further defined herein, or pharmaceutically acceptable salts thereof, for use as medicaments for treating or preventing an FAP-mediated condition.

In another aspect, the present disclosure provides use of compounds having the structure of Formula (I), (II-A), (II-B), (II-C), (III-A), (III-B), or (III-C) as further defined herein, or pharmaceutically acceptable salts thereof, to prepare medicaments for treating or preventing an FAP-mediated condition.

In another aspect, the present disclosure provides kits comprising a compound having the structure of Formula (I), (II-A), (II-B), (II-C), (III-A), (III-B), or and (III-C) as further defined herein, or pharmaceutically acceptable salt thereof.

In another aspect, the present disclosure provides methods for preparing compounds having the structure of Formula (I), (II-A), (II-B), (II-C), (III-A), (III-B), or (III-C) as further defined herein, or pharmaceutically acceptable salts thereof.

DETAILED DESCRIPTION

Many embodiments are detailed throughout the specification and will be apparent to a reader skilled in the art. The specification is not to be interpreted as being limited to any particular embodiment(s) described herein.

I. DEFINITIONS

With respect to the embodiments disclosed in this specification, the following terms have the meanings set forth below:

Reference to "a" or "an" means "one or more." Throughout, the plural and singular should be treated as interchangeable, other than the indication of number.

Unless the context requires otherwise, the words "comprise" or "comprises" or "comprising" are used on the basis and clear understanding that they are to be interpreted inclusively, rather than exclusively, and that Applicants intend each of those words to be so interpreted in construing this patent, including the claims below.

The term "halogen" (alone or in combination with another term(s)) means a fluorine radical (which may be depicted as —F), chlorine radical (which may be depicted as —Cl), bromine radical (which may be depicted as —Br), or iodine radical (which may be depicted as —I).

The term "hydroxy" (alone or in combination with another term(s)) means —OH.

The term "cyano" (alone or in combination with another term(s)) means —CN.

The term "alkyl" (alone or in combination with another term(s)) means a straight- or branched-chain saturated hydrocarbyl substituent (i.e., a substituent containing only carbon and hydrogen). Alkyl typically contains from 1 to about 20 carbon atoms, more typically from 1 to about 12 carbon atoms, even more typically from 1 to about 8 carbon atoms, and still even more typically from 1 to about 6 carbon atoms. Examples of such substituents include methyl, ethyl, propyl (including n-propyl and isopropyl), butyl (including n-butyl, isobutyl, sec-butyl, and tert-butyl), pentyl (including n-pentyl, iso-amyl, and 2,2-dimethylpropyl), and hexyl.

The term "cycloalkyl" (alone or in combination with another term(s)) means a saturated carbocyclyl substituent containing from 3 to about 14 carbon ring atoms, more typically from 3 to about 12 carbon ring atoms, and even more typically from 3 to about 8 carbon ring atoms. A cycloalkyl includes a single carbon ring, which typically contains from 3 to 6 carbon ring atoms. Examples of single-ring cycloalkyls include cyclopropyl, cyclobutyl, cyclopentyl, and cyclohexyl.

The term "alkoxy" (alone or in combination with another term(s)) means an alkylether substituent, i.e., alkyl-O—. Examples of alkoxy include methoxy ($CH_3$—O—), ethoxy, n-propoxy, iso-propoxy, n-butoxy, iso-butoxy, sec-butoxy, and tert-butoxy. Thus, for example:

(i) the term "alkoxyalkyl" (alone or in combination with another term(s)) means alkyl substituted with alkoxy such as "methoxymethyl" which may be depicted as:

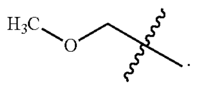

(ii) the term "cycloalkylalkoxy" (alone or in combination with another term(s)) means alkoxy substituted with cycloalkyl such as "cyclopropylmethoxy" which may be depicted as:

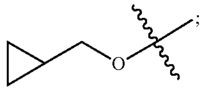 [SMILES: *OCC1CC1]

The term "cycloalkoxy" (alone or in combination with another term(s)) means a cycloalkylether substituent, i.e., cycloalkyl-O—. Examples of cycloalkoxy include cyclopropoxy, cyclobutoxy, cyclopentoxy, and cyclohexoxy. Thus, for example, the term "alkylcycloalkoxy" (alone or in combination with another term(s)) means cycloalkoxy substituted with alkyl such as "methylcyclopropoxy" which may be depicted as:

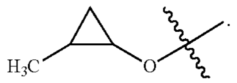

In some instances, the number of carbon atoms in a substituent (e.g., alkyl, cycloalkyl, etc.) is indicated by the prefix "$C_{x-y}$-", wherein x is the minimum and y is the maximum number of carbon atoms in the substituent. Thus, for example, "$C_{1-6}$-alkyl" refers to an alkyl substituent containing from 1 to 6 carbon atoms. Illustrating further, $C_{3-6}$-cycloalkyl refers to a cycloalkyl substituent containing from 3 to 6 carbon ring atoms.

The prefix "halo" indicates that the substituent to which the prefix is attached is substituted with one or more independently selected halogen radicals. For example, haloalkyl means an alkyl substituent wherein at least one hydrogen radical is replaced with a halogen radical. Where more than one hydrogen is replaced with a halogen, the halogens may be the identical or different. Examples of haloalkyls include fluoromethyl, difluoromethyl, trifluoromethyl, difluoroethyl, 1,1,1-trifluoroethyl, pentafluoroethyl, difluoropropyl, heptafluoropropyl, chloromethyl, dichloromethyl, trichloromethyl, difluorochloromethyl, dichlorofluoromethyl, and dichloropropyl. Similarly, "haloalkoxy" means an alkoxy substituent wherein at least one hydrogen radical is replaced by a halogen radical. Where more than one hydrogen is replaced with a halogen, the halogens may be the identical or different. Examples of haloalkoxy substituents include fluoromethoxy, difluoromethoxy, trifluoromethoxy (also known as "perfluoromethyloxy"), 1,1,1-trifluoroethoxy, and chloromethoxy.

A substituent is "substitutable" if it comprises at least one carbon or nitrogen atom that is bonded to one or more hydrogen atoms. Thus, for example, hydrogen, halogen, and cyano do not fall within this definition.

If a substituent is described as being "substituted", a non-hydrogen radical is in the place of a hydrogen radical on a carbon or nitrogen of the substituent. Thus, for example, a substituted alkyl substituent is an alkyl substituent wherein at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitutions on a substituent, each non-hydrogen radical may be identical or different (unless otherwise stated).

If a substituent is described as being "optionally substituted", the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent.

If substituents are described as being "independently selected" from a group, each substituent is selected independent of the other. Each substituent therefore may be identical to or different from the other substituent(s).

The term "pharmaceutically acceptable" is used adjectivally in this specification to mean that the modified noun is appropriate for use as a pharmaceutical product or as a part of a pharmaceutical product. For example, "pharmaceutically acceptable salts" are salts that are suitable for use in mammals, particularly humans, and include salts with an inorganic base, organic base, inorganic acid, organic acid, or basic or acidic amino acid that are suitable for use in mammals, particularly humans.

A "therapeutically effective amount" of a pharmacological agent is an amount that is sufficient to effect beneficial or desired results, including clinical results, and, as such, will depend upon the situation in which it is being administered. Where the pharmacological agent is being administered to treat liver disease, for example, a therapeutically effective amount of the agent is an amount of the agent that is sufficient, either alone or in combination with additional therapies, to provide an anti-liver disease effect in a subject as compared to the response obtained without administration of the agent.

The term "preventing" is readily understood by an ordinarily skilled physician and, with respect to treatment of a particular condition, can include is intended to have its normal meaning and includes primary prophylaxis to prevent the development of the condition and secondary prophylaxis whereby the condition has already developed and the patient is temporarily or permanently protected against exacerbation or worsening of the disease or the development of new symptoms associated with the condition.

The terms "treating" is readily understood by an ordinarily skilled physician and, with respect to treatment of a particular condition, can include (1) diminishing the extent or cause of the condition being treated, and/or (2) alleviating or ameliorating one or more symptoms associated with that condition. Treatment of liver disease, for example, can include stabilizing (i.e., not worsening), delaying, or slowing the spread or progression of the liver disease; prolonging survival as compared to expected survival if not receiving treatment; and/or otherwise ameliorating or palliating the cancer or the severity of the liver disease, in whole or in part.

II. COMPOUNDS

A. Compounds of Formula (I)

In one embodiment, the present disclosure provides compounds having the structure of Formula (I):

(I)

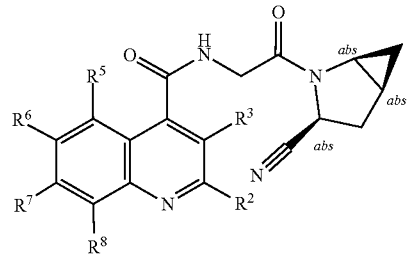

and pharmaceutically acceptable salts thereof, wherein:

$R^2$ is selected from the group consisting of hydrogen, halogen, and methyl;

$R^3$ is hydrogen or halogen;

$R^5$ is selected from the group consisting of hydrogen, hydroxy, halogen, methyl, and methoxy;

one of $R^6$ and $R^7$ is hydrogen and the other of $R^6$ and $R^7$ is selected from the group consisting of:

(a) halogen;

(b) $C_{1-6}$-alkyl, wherein the $C_{1-6}$-alkyl is optionally substituted with one or more substituents independently selected from the group consisting of halogen, hydroxy, $C_{1-6}$-alkoxy, halo-$C_{1-6}$-alkoxy, $C_{3-6}$-cycloalkyl, and $C_{3-6}$-cycloalkoxy;

(c) cyclopropyl, wherein the cyclopropyl is optionally substituted with one or more substituents independently selected from the group consisting of cyano, fluoro, $C_{1-6}$-alkyl, halo-$C_{1-6}$-alkyl, and $C_{1-6}$-alkoxy;

(d) $C_{1-6}$-alkoxy, wherein the $C_{1-6}$-alkoxy is optionally substituted with one or more substituents independently selected from the group consisting of halogen and cyclopropyl; and (e) $C_{3-6}$-cycloalkoxy, wherein the $C_{3-6}$-cycloalkoxy is optionally substituted with one or more substituents independently selected from the group consisting of halogen and $C_{1-3}$-alkyl; and $R^8$ is selected from the group consisting of hydrogen, halogen, and methyl.

In some embodiments, $R^2$ is selected from the group consisting of hydrogen, chloro, fluoro, and methyl. In one aspect, $R^2$ is selected from the group consisting of hydrogen, chloro, and methyl. In another aspect, $R^2$ is selected from the group consisting of hydrogen, fluoro, and methyl. In another aspect, $R^2$ is hydrogen or halogen. In another aspect, $R^2$ is hydrogen or chloro. In another aspect, $R^2$ is hydrogen or fluoro. In another aspect, $R^2$ is hydrogen or methyl. In another aspect, $R^2$ is hydrogen. In another aspect, $R^2$ is halogen. In another aspect, $R^2$ is chloro. In another aspect, $R^2$ is fluoro. In another aspect, $R^2$ is methyl.

In some embodiments, $R^3$ is selected from the group consisting of hydrogen, chloro, and fluoro. In one aspect, $R^3$ is hydrogen or chloro. In another aspect, $R^3$ is hydrogen or fluoro. In another aspect, $R^3$ is hydrogen. In another aspect, $R^3$ is halogen. In another aspect, $R^3$ is chloro. In another aspect, $R^3$ is fluoro.

In some embodiments, $R^5$ is selected from the group consisting of hydrogen, hydroxy, chloro, fluoro, methyl, and methoxy. In one aspect, $R^5$ is selected from the group consisting of hydrogen, chloro, and methyl. In another aspect, $R^5$ is selected from the group consisting of hydrogen, fluoro, and methyl. In another aspect, $R^5$ is hydrogen or halogen. In another aspect, $R^5$ is hydrogen or chloro. In another aspect, $R^5$ is hydrogen or fluoro. In another aspect, $R^5$ is hydrogen or methyl. In another aspect, $R^5$ is hydrogen. In another aspect, $R^5$ is hydroxy. In another aspect, $R^5$ is halogen. In another aspect, $R^5$ is chloro. In another aspect, $R^5$ is fluoro. In another aspect, $R^5$ is methyl. In another aspect, $R^5$ is methoxy.

In some embodiments, $R^8$ is selected from the group consisting of hydrogen, chloro, fluoro, and methyl. In one aspect, $R^8$ is hydrogen or chloro. In another aspect, $R^8$ is hydrogen or fluoro. In another aspect, $R^8$ is hydrogen or methyl. In another aspect, $R^8$ is hydrogen. In another aspect, $R^8$ is halogen. In another aspect, $R^8$ is chloro. In another aspect, $R^8$ is fluoro. In another aspect, $R^8$ is methyl.

In some embodiments, $R^2$ is selected from the group consisting of hydrogen, chloro, fluoro, and methyl; $R^3$ is selected from the group consisting of hydrogen, chloro, and fluoro; $R^5$ is selected from the group consisting of hydrogen, hydroxy, chloro, fluoro, methyl, and methoxy; and $R^8$ is selected from the group consisting of hydrogen, chloro, fluoro, and methyl.

In some embodiments, $R^2$ is selected from the group consisting of hydrogen, chloro, fluoro, and methyl; $R^3$ is selected from the group consisting of hydrogen, chloro, and fluoro; $R^5$ is selected from the group consisting of hydrogen, chloro, and fluoro; and $R^8$ is selected from the group consisting of hydrogen, chloro, and fluoro.

In some embodiments, $R^2$ is selected from the group consisting of hydrogen, fluoro, and methyl; $R^3$ is hydrogen or fluoro; $R^5$ is hydrogen or fluoro; and $R^8$ is hydrogen or fluoro.

In some embodiments, $R^2$ is hydrogen or methyl; $R^3$ is selected from the group consisting of hydrogen, chloro, and fluoro; $R^5$ is selected from the group consisting of hydrogen, chloro, and fluoro; and $R^8$ is selected from the group consisting of hydrogen, chloro, and fluoro.

In some embodiments, $R^2$, $R^3$, $R^5$, and $R^8$ are independently selected from hydrogen and fluoro.

In some embodiments, two of the $R^2$, $R^3$, $R^5$, and $R^8$ substituents is other than hydrogen, and the remaining $R^2$, $R^3$, $R^5$, and $R^8$ substituents are all hydrogen.

In some embodiments, one of the $R^2$, $R^3$, $R^5$, and $R^8$ substituents is other than hydrogen, and the remaining $R^2$, $R^3$, $R^5$, and $R^8$ substituents are all hydrogen.

In some embodiments, the $R^2$, $R^3$, $R^5$, and $R^8$ substituents are all hydrogen.

In some embodiments, one of $R^6$ and $R^7$ is other than hydrogen and the other of $R^6$ and $R^7$ is hydrogen. In one aspect, $R^6$ is other than hydrogen and $R^7$ is hydrogen. In another aspect, $R^6$ is hydrogen and $R^7$ is other than hydrogen.

In some embodiments, one of $R^6$ and $R^7$ is hydrogen and the other is halogen. In one aspect, one of $R^6$ and $R^7$ is hydrogen and the other is chloro. In another aspect, one of $R^6$ and $R^7$ is hydrogen and the other is fluoro. In another aspect, one of $R^6$ and $R^7$ is hydrogen and the other is bromo. In another aspect, one of $R^6$ and $R^7$ is hydrogen and the other is iodo.

In some embodiments, one of $R^6$ and $R^7$ is hydrogen and the other is $C_{1-6}$-alkyl, wherein the $C_{1-6}$-alkyl is optionally substituted with one or more substituents independently selected from the group consisting of halogen, hydroxy, $C_{1-6}$-alkoxy, halo-$C_{1-6}$-alkoxy, $C_{3-6}$-cycloalkyl, and $C_{3-6}$-cycloalkoxy. In one aspect, one of $R^6$ and $R^7$ is hydrogen and the other is $C_{1-3}$-alkyl, wherein the $C_{1-3}$-alkyl is optionally substituted with one or more substituents independently selected from the group consisting of halogen, hydroxy, $C_{1-3}$-alkoxy, halo-$C_{1-3}$-alkoxy, $C_{3-6}$-cycloalkyl, and $C_{3-6}$-cycloalkoxy. In another aspect, one of $R^6$ and $R^7$ is hydrogen and the other is $C_{1-3}$-alkyl, wherein the $C_{1-3}$-alkyl is optionally substituted with one or more substituents independently selected from the group consisting of halogen, hydroxy, methoxy, and halomethoxy. In another aspect, one of $R^6$ and $R^7$ is hydrogen and the other is $C_{1-3}$-alkyl, wherein the $C_{1-3}$-alkyl is optionally substituted with one or more substituents independently selected from the group consisting of fluoro, hydroxy, methoxy, and fluoromethoxy. In another aspect, one of $R^6$ and $R^7$ is hydrogen and the other is $C_{1-3}$-alkyl, wherein the $C_{1-3}$-alkyl is optionally substituted with one or more substituents independently selected from the group consisting of fluoro and methoxy. In another aspect, one of $R^6$ and $R^7$ is hydrogen and the other is $C_{1-6}$-alkyl, wherein the $C_{1-6}$-alkyl is optionally substituted with one or more substituents independently selected from the group consisting of halogen and $C_{1-6}$-alkoxy. In another aspect, one of $R^6$ and $R^7$ is hydrogen and the other is $C_{1-3}$-alkyl, wherein the $C_{1-3}$-alkyl is optionally substituted with one or more substituents independently selected from the group consisting of halogen and $C_{1-3}$-alkoxy.

In some embodiments, one of $R^6$ and $R^7$ is hydrogen and the other is $C_{1-6}$-alkyl. In one aspect, one of $R^6$ and $R^7$ is hydrogen and the other is $C_{1-3}$-alkyl. In another aspect, one of $R^6$ and $R^7$ is hydrogen and the other is methyl.

In some embodiments, one of $R^6$ and $R^7$ is hydrogen and the other is $C_{1-6}$-alkyl, wherein the $C_{1-6}$-alkyl is optionally substituted with one or more halogen. In one aspect, one of $R^6$ and $R^7$ is hydrogen and the other is $C_{1-3}$-alkyl, wherein the $C_{1-3}$-alkyl is optionally substituted with one or more fluoro.

In some embodiments, one of $R^6$ and $R^7$ is hydrogen and the other is $C_{1-6}$-alkyl, wherein the $C_{1-6}$-alkyl is optionally substituted with one or more hydroxy. In one aspect, one of $R^6$ and $R^7$ is hydrogen and the other is $C_{1-3}$-alkyl, wherein the $C_{1-3}$-alkyl is optionally substituted with one or more hydroxy.

In some embodiments, one of $R^6$ and $R^7$ is hydrogen and the other is $C_{1-6}$-alkyl, wherein the $C_{1-6}$-alkyl is optionally substituted with one or more $C_{1-6}$-alkoxy. In one aspect, one of $R^6$ and $R^7$ is hydrogen and the other is $C_{1-3}$-alkyl, wherein the $C_{1-3}$-alkyl is optionally substituted with one or more $C_{1-3}$-alkoxy.

In some embodiments, one of $R^6$ and $R^7$ is hydrogen and the other is $C_{1-6}$-alkyl, wherein the $C_{1-6}$-alkyl is optionally substituted with one or more halo-$C_{1-6}$-alkoxy. In one aspect, one of $R^6$ and $R^7$ is hydrogen and the other is $C_{1-3}$-alkyl, wherein the $C_{1-3}$-alkyl is optionally substituted with one or more halo-$C_{1-3}$-alkoxy. In another aspect, one of $R^6$ and $R^7$ is hydrogen and the other is $C_{1-3}$-alkyl, wherein the $C_{1-3}$-alkyl is optionally substituted with one or more fluoro-$C_{1-3}$-alkoxy.

In some embodiments, one of $R^6$ and $R^7$ is hydrogen and the other is $C_{1-6}$-alkyl, wherein the $C_{1-6}$-alkyl is optionally substituted with one or more $C_{3-6}$-cycloalkyl. In one aspect, one of $R^6$ and $R^7$ is hydrogen and the other is $C_{1-3}$-alkyl, wherein the $C_{1-3}$-alkyl is optionally substituted with one or more $C_{3-6}$-cycloalkyl.

In some embodiments, one of $R^6$ and $R^7$ is hydrogen and the other is $C_{1-6}$-alkyl, wherein the $C_{1-6}$-alkyl is optionally substituted with one or more $C_{3-6}$-cycloalkoxy. In one aspect, one of $R^6$ and $R^7$ is hydrogen and the other is $C_{1-3}$-alkyl, wherein the $C_{1-3}$-alkyl is optionally substituted with one or more $C_{3-6}$-cycloalkoxy.

In some embodiments, one of $R^6$ and $R^7$ is hydrogen and the other is selected from the group consisting of methyl, ethyl, fluoromethyl, difluoromethyl, trifluoromethyl, fluoropropyl, hydroxyethyl, hydroxypropyl, methoxyethyl, methoxypropyl, trifluoromethoxymethyl, and trifluoromethoxyethyl. In one aspect, one of $R^6$ and $R^7$ is hydrogen and the other is selected from the group consisting of methyl, ethyl, fluoromethyl, difluoromethyl, trifluoromethyl, fluoropropyl, methoxyethyl, and methoxypropyl.

In some embodiments, one of $R^6$ and $R^7$ is hydrogen and the other is cyclopropyl, wherein the cyclopropyl is optionally substituted with one or more substituents independently selected from the group consisting of cyano, fluoro, $C_{1-6}$-alkyl, halo-$C_{1-6}$-alkyl, and $C_{1-6}$-alkoxy. In one aspect, one of $R^6$ and $R^7$ is hydrogen and the other is cyclopropyl, wherein the cyclopropyl is optionally substituted with one or more substituents independently selected from the group consisting of cyano, fluoro, $C_{1-3}$-alkyl, halo-$C_{1-3}$-alkyl, and $C_{1-3}$-alkoxy. In another aspect, one of $R^6$ and $R^7$ is hydrogen and the other is cyclopropyl, wherein the cyclopropyl is optionally substituted with one or more substituents independently selected from the group consisting of cyano, $C_{1-3}$-alkyl, fluoro-$C_{1-3}$-alkyl, and $C_{1-3}$-alkoxy.

In some embodiments, one of $R^6$ and $R^7$ is hydrogen and the other is cyclopropyl.

In some embodiments, one of $R^6$ and $R^7$ is hydrogen and the other is cyclopropyl, wherein the cyclopropyl is optionally substituted with one or more cyano.

In some embodiments, one of $R^6$ and $R^7$ is hydrogen and the other is cyclopropyl, wherein the cyclopropyl is optionally substituted with one or more fluoro.

In some embodiments, one of $R^6$ and $R^7$ is hydrogen and the other is cyclopropyl, wherein the cyclopropyl is optionally substituted with one or $C_{1-6}$-alkyl. In one aspect, one of $R^6$ and $R^7$ is hydrogen and the other is cyclopropyl, wherein the cyclopropyl is optionally substituted with one or more $C_{1-3}$-alkyl.

In some embodiments, one of $R^6$ and $R^7$ is hydrogen and the other is cyclopropyl, wherein the cyclopropyl is optionally substituted with one or more halo-$C_{1-6}$-alkyl. In one aspect, one of $R^6$ and $R^7$ is hydrogen and the other is cyclopropyl, wherein the cyclopropyl is optionally substituted with one or more halo-$C_{1-3}$-alkyl. In another aspect, one of $R^6$ and $R^7$ is hydrogen and the other is cyclopropyl, wherein the cyclopropyl is optionally substituted with one or more fluoro-$C_{1-3}$-alkyl.

In some embodiments, one of $R^6$ and $R^7$ is hydrogen and the other is cyclopropyl, wherein the cyclopropyl is optionally substituted with one or more $C_{1-6}$-alkoxy. In another aspect, one of $R^6$ and $R^7$ is hydrogen and the other is cyclopropyl, wherein the cyclopropyl is optionally substituted with one or more $C_{1-3}$-alkoxy.

In some embodiments, one of $R^6$ and $R^7$ is hydrogen and the other is cyclopropyl, wherein the cyclopropyl is optionally substituted with one or more substituents independently selected from the group consisting of cyano, methyl, trifluoromethyl, and ethoxy.

In some embodiments, one of $R^6$ and $R^7$ is hydrogen and the other is $C_{1-6}$-alkoxy, wherein the $C_{1-6}$-alkoxy is optionally substituted with one or more substituents independently selected from the group consisting of halogen and cyclopropyl. In one aspect, one of $R^6$ and $R^7$ is hydrogen and the other is $C_{1-3}$-alkoxy, wherein the $C_{1-3}$-alkoxy is optionally substituted with one or more substituents independently selected from the group consisting of halogen and cyclopropyl.

In some embodiments, one of $R^6$ and $R^7$ is hydrogen and the other is $C_{1-6}$-alkoxy. In one aspect, one of $R^6$ and $R^7$ is hydrogen and the other is $C_{1-3}$-alkoxy.

In some embodiments, one of $R^6$ and $R^7$ is hydrogen and the other is $C_{1-6}$-alkoxy, wherein the $C_{1-6}$-alkoxy is optionally substituted with one or more halogen. In one aspect, one of $R^6$ and $R^7$ is hydrogen and the other is $C_{1-3}$-alkoxy, wherein the $C_{1-3}$-alkoxy is optionally substituted with one or more halogen. In another aspect, one of $R^6$ and $R^7$ is hydrogen and the other is $C_{1-3}$-alkoxy, wherein the $C_{1-3}$-alkoxy is optionally substituted with one or more fluoro.

In some embodiments, one of $R^6$ and $R^7$ is hydrogen and the other is $C_{1-6}$-alkoxy, wherein the $C_{1-6}$-alkoxy is optionally substituted with one or more cyclopropyl. In one aspect, one of $R^6$ and $R^7$ is hydrogen and the other is $C_{1-3}$-alkoxy, wherein the $C_{1-3}$-alkoxy is optionally substituted with one or more cyclopropyl.

In some embodiments, one of $R^6$ and $R^7$ is hydrogen and the other is selected from the group consisting of methoxy, propoxy, trifluoroethoxy, and cyclopropylmethoxy.

In some embodiments, one of $R^6$ and $R^7$ is hydrogen and the other is $C_{3-6}$-cycloalkoxy, wherein the $C_{3-6}$-cycloalkoxy is optionally substituted with one or more $C_{1-3}$-alkyl.

In some embodiments, one of $R^6$ and $R^7$ is hydrogen and the other is $C_{3-6}$-cycloalkoxy, wherein the $C_{3-6}$-cycloalkoxy is optionally substituted with one or more halogen. In one aspect, one of $R^6$ and $R^7$ is hydrogen and the other is $C_{3-6}$-cycloalkoxy, wherein the $C_{3-6}$-cycloalkoxy is optionally substituted with one or more fluoro. In another aspect, one of $R^6$ and $R^7$ is hydrogen and the other is cyclohexyloxy, wherein the cyclohexyloxy is optionally substituted with one or more halogen. In another aspect, one of $R^6$ and $R^7$ is hydrogen and the other is cyclohexyloxy, wherein the cyclohexyloxy is optionally substituted with one or more fluoro. In another aspect, one of $R^6$ and $R^7$ is hydrogen and the other is cyclopropoxy, wherein the cyclopropoxy is optionally substituted with one or more halogen. In another aspect, one of $R^6$ and $R^7$ is hydrogen and the other is cyclopropoxy, wherein the cyclopropoxy is optionally substituted with one or more fluoro.

In some embodiments, one of $R^6$ and $R^7$ is hydrogen and the other is $C_{3-6}$-cycloalkoxy. In one aspect, one of $R^6$ and $R^7$ is hydrogen and the other is cyclopropoxy. In another aspect, one of $R^6$ and $R^7$ is hydrogen and the other is cyclohexyloxy.

In some embodiments, the compounds, and pharmaceutically acceptable salts thereof, have the structure of Formula (II-A):

(II-A)

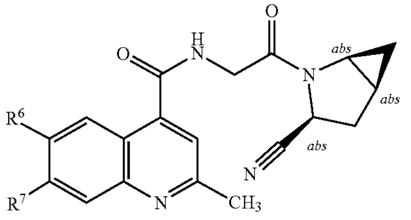

wherein $R^6$ and $R^7$ are as defined in the various embodiments of this specification.

In some embodiments, the compounds, and pharmaceutically acceptable salts thereof, have the structure of Formula (II-B):

(II-B)

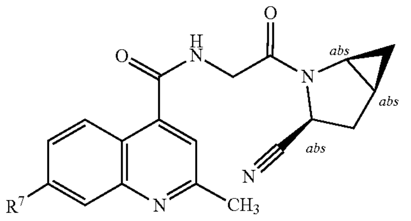

wherein $R^7$ is as defined in the various embodiments of this specification.

In some embodiments, the compounds, and pharmaceutically acceptable salts thereof, have the structure of Formula (II-C):

(II-C)

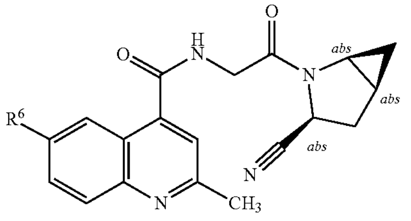

wherein $R^6$ is as defined in the various embodiments of this specification.

In some embodiments, the compounds, and pharmaceutically acceptable salts thereof, have the structure of Formula (III-A):

(III-A)

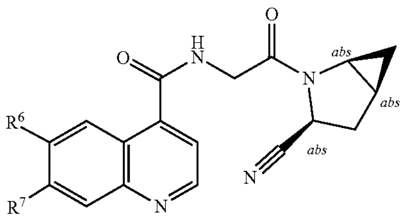

wherein $R^6$ and $R^7$ are as defined in the various embodiments of this specification.

In some embodiments, the compounds, and pharmaceutically acceptable salts thereof, have the structure of Formula (III-B):

(III-B)

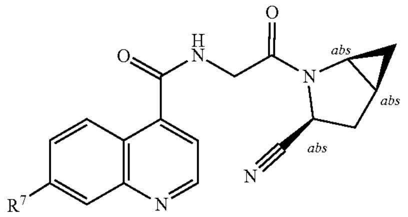

wherein $R^7$ is as defined in the various embodiments of this specification.

In some embodiments, the compounds, and pharmaceutically acceptable salts thereof, have the structure of Formula (III-C):

(III-C)

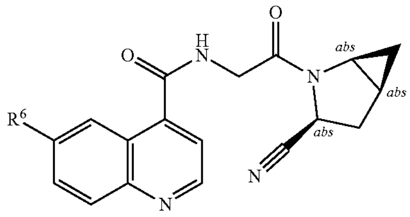

wherein $R^6$ is as defined in the various embodiments of this specification.

B. Embodiments

Embodiment 1: Compounds having the structure of Formula (I), or pharmaceutically acceptable salts thereof, wherein one of $R^6$ and $R^7$ is hydrogen and the other of $R^6$ and $R^7$ is selected from the group consisting of:

(a) halogen;

(b) $C_{1-6}$-alkyl, wherein the $C_{1-6}$-alkyl is optionally substituted with one or more substituents independently selected from the group consisting of halogen, hydroxy, $C_{1-6}$-alkoxy, halo-$C_{1-6}$-alkoxy, $C_{3-6}$-cycloalkyl, and $C_{3-6}$-cycloalkoxy; and (c) cyclopropyl, wherein the cyclopropyl is optionally substituted with one or more substituents independently selected from the group consisting of cyano, fluoro, $C_{1-6}$-alkyl, halo-$C_{1-6}$-alkyl, and $C_{1-6}$-alkoxy.

Embodiment 2: Compounds having the structure of Formula (I), or pharmaceutically acceptable salts thereof, wherein:

$R^2$ is selected from the group consisting of hydrogen, halogen, and methyl;

$R^3$ is hydrogen or halogen;

$R^5$ is selected from the group consisting of hydrogen, hydroxy, halogen, methyl, and methoxy;

one of $R^6$ and $R^7$ is hydrogen and the other of $R^6$ and $R^7$ is selected from the group consisting of:

(a) halogen;

(b) $C_{1-6}$-alkyl, wherein the $C_{1-6}$-alkyl is optionally substituted with one or more substituents independently selected from the group consisting of halogen, hydroxy, $C_{1-6}$-alkoxy, and halo-$C_{1-6}$-alkoxy; and (c) cyclopropyl, wherein the cyclopropyl is optionally substituted with one or more substituents independently selected from the group consisting of cyano, $C_{1-6}$-alkyl, halo-$C_{1-6}$-alkyl, and $C_{1-6}$-alkoxy; and $R^8$ is hydrogen or halogen.

Embodiment 3: Compounds having the structure of Formula (I), or pharmaceutically acceptable salts thereof, wherein:

$R^2$ is selected from the group consisting of hydrogen, chloro, fluoro, and methyl;

$R^3$ is selected from the group consisting of hydrogen, chloro, and fluoro;

$R^5$ is selected from the group consisting of hydrogen, hydroxy, chloro, fluoro, methyl, and methoxy;

one of $R^6$ and $R^7$ is hydrogen and the other of $R^6$ and $R^7$ is selected from the group consisting of:

(a) halogen;

(b) $C_{1-6}$-alkyl, wherein the $C_{1-6}$-alkyl is optionally substituted with one or more substituents independently selected from the group consisting of halogen, hydroxy, $C_{1-6}$-alkoxy, and halo-$C_{1-6}$-alkoxy; and (c) cyclopropyl, wherein the cyclopropyl is optionally substituted with one or more substituents independently selected from the group consisting of cyano, $C_{1-6}$-alkyl, halo-$C_{1-6}$-alkyl, and $C_{1-6}$-alkoxy; and $R^8$ is selected from the group consisting of hydrogen, chloro, and fluoro.

Embodiment 4: Compounds having the structure of Formula (I), or pharmaceutically acceptable salts thereof, wherein:

$R^2$ is selected from the group consisting of hydrogen, chloro, and methyl;

$R^3$ is hydrogen or chloro;

$R^5$ is hydrogen or chloro;

one of $R^6$ and $R^7$ is hydrogen and the other of $R^6$ and $R^7$ is selected from the group consisting of:

(a) halogen;

(b) $C_{1-6}$-alkyl, wherein the $C_{1-6}$-alkyl is optionally substituted with one or more substituents independently selected from the group consisting of halogen, hydroxy, $C_{1-6}$-alkoxy, and halo-$C_{1-6}$-alkoxy; and (c) cyclopropyl, wherein the cyclopropyl is optionally substituted with one or more substituents independently selected from the group consisting of cyano, $C_{1-6}$-alkyl, halo-$C_{1-6}$-alkyl, and $C_{1-6}$-alkoxy; and $R^8$ is hydrogen or chloro.

Embodiment 5: Compounds having the structure of Formula (I), or pharmaceutically acceptable salts thereof, wherein:

$R^2$ is selected from the group consisting of hydrogen, fluoro, and methyl;

$R^3$ is hydrogen or fluoro;

$R^5$ is hydrogen or fluoro;

one of $R^6$ and $R^7$ is hydrogen and the other of $R^6$ and $R^7$ is selected from the group consisting of:

(a) halogen;

(b) $C_{1-6}$-alkyl, wherein the $C_{1-6}$-alkyl is optionally substituted with one or more substituents independently selected from the group consisting of halogen, hydroxy, $C_{1-6}$-alkoxy, and halo-$C_{1-6}$-alkoxy; and (c) cyclopropyl, wherein the cyclopropyl is optionally substituted with one or more substituents independently selected from the group consisting of cyano, $C_{1-6}$-alkyl, halo-$C_{1-6}$-alkyl, and $C_{1-6}$-alkoxy; and $R^8$ is hydrogen or fluoro.

Embodiment 6: Compounds having the structure of Formula (I), or pharmaceutically acceptable salts thereof, wherein one of $R^6$ and $R^7$ is hydrogen and the other of $R^6$ and $R^7$ is selected from the group consisting of:

(a) halogen;

(b) $C_{1-3}$-alkyl, wherein the $C_{1-3}$-alkyl is optionally substituted with one or more substituents independently selected from the group consisting of halogen, hydroxy, $C_{1-3}$-alkoxy, and halo-$C_{1-3}$-alkoxy; and (c) cyclopropyl, wherein the cyclopropyl is optionally substituted with one or more substituents independently selected from the group consisting of cyano, $C_{1-3}$-alkyl, halo-$C_{1-3}$-alkyl, and $C_{1-3}$-alkoxy.

Embodiment 7: Compounds of any of Embodiments 1 to 6, or pharmaceutically acceptable salts thereof, wherein one of $R^6$ and $R^7$ is hydrogen and the other is halogen.

Embodiment 8: Compounds of any of Embodiments 1 to 6, or pharmaceutically acceptable salts thereof, wherein one of $R^6$ and $R^7$ is hydrogen and the other is chloro.

Embodiment 9: Compounds of any of Embodiments 1 to 6, or pharmaceutically acceptable salts thereof, wherein one of $R^6$ and $R^7$ is hydrogen and the other is fluoro.

Embodiment 10: Compounds of any of Embodiments 1 to 6, or pharmaceutically acceptable salts thereof, wherein one of $R^6$ and $R^7$ is hydrogen and the other is bromo.

Embodiment 11: Compounds of any of Embodiments 1 to 6, or pharmaceutically acceptable salts thereof, wherein one of $R^6$ and $R^7$ is hydrogen and the other is iodo.

Embodiment 12: Compounds of any of Embodiments 1 to 5, or pharmaceutically acceptable salts thereof, wherein one of $R^6$ and $R^7$ is hydrogen and the other is $C_{1-6}$-alkyl, wherein the $C_{1-6}$-alkyl is optionally substituted with one or more substituents independently selected from the group consisting of halogen, hydroxy, $C_{1-6}$-alkoxy, and halo-$C_{1-6}$-alkoxy.

Embodiment 13: Compounds of any of Embodiments 1 to 6, or pharmaceutically acceptable salts thereof, wherein one of $R^6$ and $R^7$ is hydrogen and the other is $C_{1-3}$-alkyl, wherein the $C_{1-3}$-alkyl is optionally substituted with one or more substituents independently selected from the group consisting of halogen, hydroxy, $C_{1-3}$-alkoxy, and halo-$C_{1-3}$-alkoxy.

Embodiment 14: Compounds of any of Embodiments 1 to 6, or pharmaceutically acceptable salts thereof, wherein one of $R^6$ and $R^7$ is hydrogen and the other is $C_{1-3}$-alkyl, wherein the $C_{1-3}$-alkyl is optionally substituted with one or more substituents independently selected from the group consisting of halogen, hydroxy, methoxy, and halomethoxy.

Embodiment 15: Compounds of any of Embodiments 1 to 6, or pharmaceutically acceptable salts thereof, wherein one of $R^6$ and $R^7$ is hydrogen and the other is $C_{1-3}$-alkyl, wherein the $C_{1-3}$-alkyl is optionally substituted with one or more substituents independently selected from the group consisting of fluoro, hydroxy, methoxy, and fluoromethoxy.

Embodiment 16: Compounds of any of Embodiments 1 to 6, or pharmaceutically acceptable salts thereof, wherein one of $R^6$ and $R^7$ is hydrogen and the other is $C_{1-3}$-alkyl, wherein the $C_{1-3}$-alkyl is optionally substituted with one or more substituents independently selected from the group consisting of fluoro and methoxy.

Embodiment 17: Compounds of any of Embodiments 1 to 5, or pharmaceutically acceptable salts thereof, wherein one of $R^6$ and $R^7$ is hydrogen and the other is $C_{1-6}$-alkyl, wherein the $C_{1-6}$-alkyl is optionally substituted with one or more substituents independently selected from the group consisting of halogen and $C_{1-6}$-alkoxy.

Embodiment 18: Compounds of any of Embodiments 1 to 6, or pharmaceutically acceptable salts thereof, wherein one of $R^6$ and $R^7$ is hydrogen and the other is $C_{1-3}$-alkyl, wherein the $C_{1-3}$-alkyl is optionally substituted with one or more substituents independently selected from the group consisting of halogen and $C_{1-3}$-alkoxy.

Embodiment 19: Compounds of any of Embodiments 1 to 5, or pharmaceutically acceptable salts thereof, wherein one of $R^6$ and $R^7$ is hydrogen and the other is $C_{1-6}$-alkyl.

Embodiment 20: Compounds of any of Embodiments 1 to 6, or pharmaceutically acceptable salts thereof, wherein one of $R^6$ and $R^7$ is hydrogen and the other is $C_{1-3}$-alkyl.

Embodiment 21: Compounds of any of Embodiments 1 to 6, or pharmaceutically acceptable salts thereof, wherein one of $R^6$ and $R^7$ is hydrogen and the other is methyl.

Embodiment 22: Compounds of any of Embodiments 1 to 5, or pharmaceutically acceptable salts thereof, wherein one of $R^6$ and $R^7$ is hydrogen and the other is $C_{1-6}$-alkyl, wherein the $C_{1-6}$-alkyl is optionally substituted with one or more halogen.

Embodiment 23: Compounds of any of Embodiments 1 to 6, or pharmaceutically acceptable salts thereof, wherein one of $R^6$ and $R^7$ is hydrogen and the other is $C_{1-3}$-alkyl, wherein the $C_{1-3}$-alkyl is optionally substituted with one or more fluoro.

Embodiment 24: Compounds of any of Embodiments 1 to 5, or pharmaceutically acceptable salts thereof, wherein one of $R^6$ and $R^7$ is hydrogen and the other is $C_{1-6}$-alkyl, wherein the $C_{1-6}$-alkyl is optionally substituted with one or more hydroxy.

Embodiment 25: Compounds of any of Embodiments 1 to 6, or pharmaceutically acceptable salts thereof, wherein one of $R^6$ and $R^7$ is hydrogen and the other is $C_{1-3}$-alkyl, wherein the $C_{1-3}$-alkyl is optionally substituted with one or more hydroxy.

Embodiment 26: Compounds of any of Embodiments 1 to 5, or pharmaceutically acceptable salts thereof, wherein one of $R^6$ and $R^7$ is hydrogen and the other is $C_{1-6}$-alkyl, wherein the $C_{1-6}$-alkyl is optionally substituted with one or more $C_{1-6}$-alkoxy.

Embodiment 27: Compounds of any of Embodiments 1 to 6, or pharmaceutically acceptable salts thereof, wherein one of $R^6$ and $R^7$ is hydrogen and the other is $C_{1-3}$-alkyl, wherein the $C_{1-3}$-alkyl is optionally substituted with one or more $C_{1-3}$-alkoxy.

Embodiment 28: Compounds of any of Embodiments 1 to 5, or pharmaceutically acceptable salts thereof, wherein one of $R^6$ and $R^7$ is hydrogen and the other is $C_{1-6}$-alkyl, wherein the $C_{1-6}$-alkyl is optionally substituted with one or more halo-$C_{1-6}$-alkoxy.

Embodiment 29: Compounds of any of Embodiments 1 to 6, or pharmaceutically acceptable salts thereof, wherein one of $R^6$ and $R^7$ is hydrogen and the other is $C_{1-3}$-alkyl, wherein the $C_{1-3}$-alkyl is optionally substituted with one or more halo-$C_{1-3}$-alkoxy.

Embodiment 30: Compounds of any of Embodiments 1 to 6, or pharmaceutically acceptable salts thereof, wherein one of $R^6$ and $R^7$ is hydrogen and the other is $C_{1-3}$-alkyl, wherein the $C_{1-3}$-alkyl is optionally substituted with one or more fluoro-$C_{1-3}$-alkoxy.

Embodiment 31: Compounds of any of Embodiments 1 to 6, or pharmaceutically acceptable salts thereof, wherein one of $R^6$ and $R^7$ is hydrogen and the other is selected from the group consisting of methyl, ethyl, fluoromethyl, difluoromethyl, trifluoromethyl, fluoropropyl, hydroxyethyl, hydroxypropyl, methoxyethyl, methoxypropyl, trifluoromethoxymethyl, and trifluoromethoxyethyl.

Embodiment 32: Compounds of any of Embodiments 1 to 6, or pharmaceutically acceptable salts thereof, wherein one of $R^6$ and $R^7$ is hydrogen and the other is selected from the group consisting of methyl, ethyl, fluoromethyl, difluoromethyl, trifluoromethyl, fluoropropyl, methoxyethyl, and methoxypropyl.

Embodiment 33: Compounds of any of Embodiments 1 to 5, or pharmaceutically acceptable salts thereof, wherein one of $R^6$ and $R^7$ is hydrogen and the other is cyclopropyl, wherein the cyclopropyl is optionally substituted with one or more substituents independently selected from the group consisting of cyano, $C_{1-6}$-alkyl, halo-$C_{1-6}$-alkyl, and $C_{1-6}$-alkoxy.

Embodiment 34: Compounds of any of Embodiments 1 to 6, or pharmaceutically acceptable salts thereof, wherein one of $R^6$ and $R^7$ is hydrogen and the other is cyclopropyl, wherein the cyclopropyl is optionally substituted with one or more substituents independently selected from the group consisting of cyano, $C_{1-3}$-alkyl, halo-$C_{1-3}$-alkyl, and $C_{1-3}$-alkoxy.

Embodiment 35: Compounds of any of Embodiments 1 to 6, or pharmaceutically acceptable salts thereof, wherein one of $R^6$ and $R^7$ is hydrogen and the other is cyclopropyl, wherein the cyclopropyl is optionally substituted with one or more substituents independently selected from the group consisting of cyano, $C_{1-3}$-alkyl, fluoro-$C_{1-3}$-alkyl, and $C_{1-3}$-alkoxy.

Embodiment 36: Compounds of any of Embodiments 1 to 6, or pharmaceutically acceptable salts thereof, wherein one of $R^6$ and $R^7$ is hydrogen and the other is cyclopropyl.

Embodiment 37: Compounds of any of Embodiments 1 to 6, or pharmaceutically acceptable salts thereof, wherein one of $R^6$ and $R^7$ is hydrogen and the other is cyclopropyl, wherein the cyclopropyl is optionally substituted with one or more cyano.

Embodiment 38: Compounds of any of Embodiments 1 to 5, or pharmaceutically acceptable salts thereof, wherein one of $R^6$ and $R^7$ is hydrogen and the other is cyclopropyl, wherein the cyclopropyl is optionally substituted with one or $C_{1-6}$-alkyl.

Embodiment 39: Compounds of any of Embodiments 1 to 6, or pharmaceutically acceptable salts thereof, wherein one of $R^6$ and $R^7$ is hydrogen and the other is cyclopropyl, wherein the cyclopropyl is optionally substituted with one or more $C_{1-3}$-alkyl.

Embodiment 40: Compounds of any of Embodiments 1 to 5, or pharmaceutically acceptable salts thereof, wherein one of $R^6$ and $R^7$ is hydrogen and the other is cyclopropyl, wherein the cyclopropyl is optionally substituted with one or more halo-$C_{1-6}$-alkyl.

Embodiment 41: Compounds of any of Embodiments 1 to 6, or pharmaceutically acceptable salts thereof, wherein one of $R^6$ and $R^7$ is hydrogen and the other is cyclopropyl, wherein the cyclopropyl is optionally substituted with one or more halo-$C_{1-3}$-alkyl.

Embodiment 42: Compounds of any of Embodiments 1 to 6, or pharmaceutically acceptable salts thereof, wherein one of $R^6$ and $R^7$ is hydrogen and the other is cyclopropyl, wherein the cyclopropyl is optionally substituted with one or more fluoro-$C_{1-3}$-alkyl.

Embodiment 43: Compounds of any of Embodiments 1 to 5, or pharmaceutically acceptable salts thereof, wherein one of $R^6$ and $R^7$ is hydrogen and the other is cyclopropyl, wherein the cyclopropyl is optionally substituted with one or more $C_{1-6}$-alkoxy.

Embodiment 44: Compounds of any of Embodiments 1 to 6, or pharmaceutically acceptable salts thereof, wherein one of $R^6$ and $R^7$ is hydrogen and the other is cyclopropyl, wherein the cyclopropyl is optionally substituted with one or more $C_{1-3}$-alkoxy.

Embodiment 45: Compounds of any of Embodiments 1 to 6, or pharmaceutically acceptable salts thereof, wherein one of $R^6$ and $R^7$ is hydrogen and the other is cyclopropyl, wherein the cyclopropyl is optionally substituted with one or more substituents independently selected from the group consisting of cyano, methyl, trifluoromethyl, and ethoxy.

Embodiment 46: Compounds of any of Embodiments 1 to 6, or pharmaceutically acceptable salts thereof, wherein one of $R^6$ and $R^7$ is hydrogen and the other of $R^6$ and $R^7$ is selected from the group consisting of:

(a) the group consisting of chloro, fluoro, bromo, and iodo;

(b) $C_{1-3}$-alkyl, wherein the $C_{1-3}$-alkyl is optionally substituted with one or more substituents independently selected from the group consisting of halogen, hydroxy, $C_{1-3}$-alkoxy, and halo-$C_{1-3}$-alkoxy; and (c) cyclopropyl, wherein the cyclopropyl is optionally substituted with one or more substituents independently selected from the group consisting of cyano, $C_{1-3}$-alkyl, halo-$C_{1-3}$-alkyl, and $C_{1-3}$-alkoxy.

Embodiment 47: Compounds of any of Embodiments 1 to 6, or pharmaceutically acceptable salts thereof, wherein one of $R^6$ and $R^7$ is hydrogen and the other of $R^6$ and $R^7$ is selected from the group consisting of:

(a) the group consisting of chloro, fluoro, bromo, and iodo;

(b) $C_{1-3}$-alkyl, wherein the $C_{1-3}$-alkyl is optionally substituted with one or more substituents independently selected from the group consisting of halogen, hydroxy, methoxy, and halomethoxy; and (c) cyclopropyl, wherein the cyclopropyl is optionally substituted with one or more substituents independently selected from the group consisting of cyano, $C_{1-3}$-alkyl, halo-$C_{1-3}$-alkyl, and $C_{1-3}$-alkoxy.

Embodiment 48: Compounds of any of Embodiments 1 to 5, or pharmaceutically acceptable salts thereof, wherein one of $R^6$ and $R^7$ is hydrogen and the other of $R^6$ and $R^7$ is selected from the group consisting of:

(a) the group consisting of chloro, fluoro, bromo, and iodo;

(b) $C_{1-6}$-alkyl, wherein the $C_{1-6}$-alkyl is optionally substituted with one or more substituents independently selected from the group consisting of halogen and $C_{1-6}$-alkoxy; and (c) cyclopropyl, wherein the cyclopropyl is optionally substituted with one or more substituents independently selected from the group consisting of cyano, $C_{1-3}$-alkyl, halo-$C_{1-3}$-alkyl, and $C_{1-3}$-alkoxy.

Embodiment 49: Compounds of any of Embodiments 1 to 6, or pharmaceutically acceptable salts thereof, wherein one of $R^6$ and $R^7$ is hydrogen and the other of $R^6$ and $R^7$ is selected from the group consisting of:

(a) the group consisting of chloro, fluoro, bromo, and iodo;

(b) $C_{1-3}$-alkyl, wherein the $C_{1-3}$-alkyl is optionally substituted with one or more substituents independently selected from the group consisting of halogen and $C_{1-3}$-alkoxy; and (c) cyclopropyl, wherein the cyclopropyl is optionally substituted with one or more substituents independently selected from the group consisting of cyano, $C_{1-3}$-alkyl, halo-$C_{1-3}$-alkyl, and $C_{1-3}$-alkoxy.

Embodiment 50: Compounds of any of Embodiments 1 to 6, or pharmaceutically acceptable salts thereof, wherein one of $R^6$ and $R^7$ is hydrogen and the other of $R^6$ and $R^7$ is selected from the group consisting of:

(a) the group consisting of chloro, fluoro, bromo, and iodo;

(b) $C_{1-3}$-alkyl, wherein the $C_{1-3}$-alkyl is optionally substituted with one or more substituents independently selected from the group consisting of halogen, hydroxy, $C_{1-3}$-alkoxy, and halo-$C_{1-3}$-alkoxy; and (c) cyclopropyl, wherein the cyclopropyl is optionally substituted with one or more substituents independently selected from the group consisting of cyano, methyl, trifluoromethyl, and ethoxy.

Embodiment 51: Compounds of any of Embodiments 1 to 6, or pharmaceutically acceptable salts thereof, wherein one of $R^6$ and $R^7$ is hydrogen and the other of $R^6$ and $R^7$ is selected from the group consisting of:

(a) the group consisting of chloro, fluoro, bromo, and iodo;

(b) $C_{1-3}$-alkyl, wherein the $C_{1-3}$-alkyl is optionally substituted with one or more substituents independently selected from the group consisting of halogen and $C_{1-3}$-alkoxy; and (c) cyclopropyl, wherein the cyclopropyl is optionally substituted with one or more substituents independently selected from the group consisting of cyano, methyl, trifluoromethyl, and ethoxy.

Embodiment 52: Compounds of any of Embodiments 1 to 6, or pharmaceutically acceptable salts thereof, wherein one of $R^6$ and $R^7$ is hydrogen and the other of $R^6$ and $R^7$ is selected from the group consisting of:

(a) the group consisting of chloro and fluoro;

(b) $C_{1-3}$-alkyl, wherein the $C_{1-3}$-alkyl is optionally substituted with one or more substituents independently selected from the group consisting of halogen, hydroxy, methoxy, and halomethoxy; and (c) cyclopropyl, wherein the cyclopropyl is optionally substituted with one or more substituents independently selected from the group consisting of cyano, methyl, trifluoromethyl, and ethoxy.

Embodiment 53: Compounds of any of Embodiments 1 to 6, or pharmaceutically acceptable salts thereof, wherein one of $R^6$ and $R^7$ is hydrogen and the other of $R^6$ and $R^7$ is selected from the group consisting of:

(a) the group consisting of chloro and fluoro;

(b) $C_{1-3}$-alkyl, wherein the $C_{1-3}$-alkyl is optionally substituted with one or more substituents independently selected from the group consisting of fluoro, hydroxy, methoxy, and fluoromethoxy; and (c) cyclopropyl, wherein the cyclopropyl is optionally substituted with one or more substituents independently selected from the group consisting of cyano, methyl, trifluoromethyl, and ethoxy.

Embodiment 54: Compounds of any of Embodiments 1 to 6, or pharmaceutically acceptable salts thereof, wherein one of $R^6$ and $R^7$ is hydrogen and the other of $R^6$ and $R^7$ is selected from the group consisting of:

(a) the group consisting of chloro and fluoro;

(b) $C_{1-3}$-alkyl, wherein the $C_{1-3}$-alkyl is optionally substituted with one or more substituents independently selected from the group consisting of methyl, ethyl, propyl, fluoromethyl, difluoromethyl, trifluoromethyl, fluoropropyl, hydroxyethyl, hydroxypropyl, methoxyethyl, methoxypropyl, trifluoromethoxymethyl, and trifluoromethoxyethyl; and (c) cyclopropyl, wherein the cyclopropyl is optionally substituted with one or more substituents independently selected from the group consisting of cyano, methyl, trifluoromethyl, and ethoxy.

Embodiment 55: Compounds of any of Embodiments 1 to 6, or pharmaceutically acceptable salts thereof, wherein one of $R^6$ and $R^7$ is hydrogen and the other of $R^6$ and $R^7$ is selected from the group consisting of:

(a) the group consisting of chloro and fluoro;

(b) $C_{1-3}$-alkyl, wherein the $C_{1-3}$-alkyl is optionally substituted with one or more substituents independently selected from the group consisting of methyl, ethyl, propyl, fluoromethyl, difluoromethyl, trifluoromethyl, fluoropropyl, methoxyethyl, and methoxypropyl; and (c) cyclopropyl, wherein the cyclopropyl is optionally substituted with one or more substituents independently selected from the group consisting of cyano, methyl, trifluoromethyl, and ethoxy.

Embodiment 56: Compounds of any of Embodiments 1 to 5, or pharmaceutically acceptable salts thereof, wherein one of $R^6$ and $R^7$ is hydrogen and the other of $R^6$ and $R^7$ is selected from the group consisting of:

(a) the group consisting of chloro and fluoro;

(b) $C_{1-6}$-alkyl, wherein the $C_{1-6}$-alkyl is optionally substituted with one or more substituents independently selected from the group consisting of chloro, fluoro, and methoxy; and (c) cyclopropyl, wherein the cyclopropyl is optionally substituted with one or more cyano.

Embodiment 57: Compounds of any of Embodiments 1 to 56, or pharmaceutically acceptable salts thereof, wherein $R^6$ is hydrogen.

Embodiment 58: Compounds of any of Embodiments 1 to 56, or pharmaceutically acceptable salts thereof, wherein $R^7$ is hydrogen.

Embodiment 59: Compounds of any of Embodiments 1 to 6, or pharmaceutically acceptable salts thereof, wherein the compounds have the structure of Formula (II-A).

Embodiment 60: Compounds of any of Embodiments 1 to 6, or pharmaceutically acceptable salts thereof, wherein the compounds have the structure of Formula (II-B).

Embodiment 61: Compounds of any of Embodiments 1 to 6, or pharmaceutically acceptable salts thereof, wherein the compounds have the structure of Formula (II-C).

Embodiment 62: Compounds of any of Embodiments 1 to 6, or pharmaceutically acceptable salts thereof, wherein the compounds have the structure of Formula (III-A).

Embodiment 63: Compounds of any of Embodiments 1 to 6, or pharmaceutically acceptable salts thereof, wherein the compounds have the structure of Formula III-B).

Embodiment 64: Compounds of any of Embodiments 1 to 6, or pharmaceutically acceptable salts thereof, wherein the compounds have the structure of Formula III-C) as further defined herein, and pharmaceutically acceptable salts thereof.

Embodiment 65: Compounds of Formula (I), or pharmaceutically acceptable salts thereof, wherein the compound is selected from the group consisting of:

6-Bromo-N-(2-((1S,3S,5S)-3-cyano-2-azabicyclo[3.1.0]hexan-2-yl)-2-oxoethyl)quinoline-4-carboxamide (Example 1);

7-Chloro-N-(2-((1S,3S,5S)-3-cyano-2-azabicyclo[3.1.0]hexan-2-yl)-2-oxoethyl)quinoline-4-carboxamide (Example 2);

7-Bromo-N-(2-((1S,3S,5S)-3-cyano-2-azabicyclo[3.1.0]hexan-2-yl)-2-oxoethyl)quinoline-4-carboxamide (Example 3);

N-(2-((1S,3S,5S)-3-Cyano-2-azabicyclo[3.1.0]hexan-2-yl)-2-oxoethyl)-6-fluoro-2-methylquinoline-4-carboxamide (Example 4);

6-Chloro-N-(2-((1S,3S,5S)-3-cyano-2-azabicyclo[3.1.0]hexan-2-yl)-2-oxoethyl)-2-methylquinoline-4-carboxamide (Example 5);

6-Bromo-N-(2-((1S,3S,5S)-3-cyano-2-azabicyclo[3.1.0]hexan-2-yl)-2-oxoethyl)-2-methylquinoline-4-carboxamide (Example 6);

N-(2-((1S,3S,5S)-3-Cyano-2-azabicyclo[3.1.0]hexan-2-yl)-2-oxoethyl)-6-iodo-2-methylquinoline-4-carboxamide (Example 7); and N-(2-((1S,3S,5S)-3-Cyano-2-azabicyclo[3.1.0]hexan-2-yl)-2-oxoethyl)-7-fluoro-2-methylquinoline-4-carboxamide (Example 8).

Embodiment 66: Compounds of Formula (I), or pharmaceutically acceptable salts thereof, wherein the compound is selected from the group consisting of:

6-Bromo-N-(2-((1S,3S,5S)-3-cyano-2-azabicyclo[3.1.0]hexan-2-yl)-2-oxoethyl)quinoline-4-carboxamide (Example 1);

N-(2-((1S,3S,5S)-3-Cyano-2-azabicyclo[3.1.0]hexan-2-yl)-2-oxoethyl)-6-fluoro-2-methylquinoline-4-carboxamide (Example 4);

6-Chloro-N-(2-((1S,3S,5S)-3-cyano-2-azabicyclo[3.1.0]hexan-2-yl)-2-oxoethyl)-2-methylquinoline-4-carboxamide (Example 5);

6-Bromo-N-(2-((1S,3S,5S)-3-cyano-2-azabicyclo[3.1.0]hexan-2-yl)-2-oxoethyl)-2-methylquinoline-4-carboxamide (Example 6); and N-(2-((1S,3S,5S)-3-Cyano-2-azabicyclo[3.1.0]hexan-2-yl)-2-oxoethyl)-6-iodo-2-methylquinoline-4-carboxamide (Example 7).

Embodiment 67: Compounds of Formula (I), or pharmaceutically acceptable salts thereof, wherein the compound is selected from the group consisting of:

7-Chloro-N-(2-((1S,3S,5S)-3-cyano-2-azabicyclo[3.1.0]hexan-2-yl)-2-oxoethyl)quinoline-4-carboxamide (Example 2);

7-Bromo-N-(2-((1S,3S,5S)-3-cyano-2-azabicyclo[3.1.0]hexan-2-yl)-2-oxoethyl)quinoline-4-carboxamide (Example 3); and N-(2-((1S,3S,5S)-3-Cyano-2-azabicyclo[3.1.0]hexan-2-yl)-2-oxoethyl)-7-fluoro-2-methylquinoline-4-carboxamide (Example 8).

Embodiment 68: Compounds of Formula (I), or pharmaceutically acceptable salts thereof, wherein the compound is selected from the group consisting of:

N-(2-((1S,3S,5S)-3-Cyano-2-azabicyclo[3.1.0]hexan-2-yl)-2-oxoethyl)-6-methylquinoline-4-carboxamide (Example 9);

N-(2-((1S,3S,5S)-3-Cyano-2-azabicyclo[3.1.0]hexan-2-yl)-2-oxoethyl)-6-(trifluoromethyl)quinoline-4-carboxamide (Example 10);

N-(2-((1S,3S,5S)-3-Cyano-2-azabicyclo[3.1.0]hexan-2-yl)-2-oxoethyl)-6-(fluoromethyl)quinoline-4-carboxamide (Example 11);

N-(2-((1S,3S,5S)-3-Cyano-2-azabicyclo[3.1.0]hexan-2-yl)-2-oxoethyl)-6-(2-fluoropropan-2-yl)quinoline-4-carboxamide (Example 12);

N-(2-((1S,3S,5S)-3-Cyano-2-azabicyclo[3.1.0]hexan-2-yl)-2-oxoethyl)-6-(2-hydroxypropan-2-yl)quinoline-4-carboxamide (Example 13);

N-(2-((1S,3S,5S)-3-Cyano-2-azabicyclo[3.1.0]hexan-2-yl)-2-oxoethyl)-6-(1-hydroxyethyl)quinoline-4-carboxamide (Example 14);

N-(2-((1S,3S,5S)-3-Cyano-2-azabicyclo[3.1.0]hexan-2-yl)-2-oxoethyl)-6-(1-methoxyethyl)quinoline-4-carboxamide (Example 15);

N-(2-((1S,3S,5S)-3-Cyano-2-azabicyclo[3.1.0]hexan-2-yl)-2-oxoethyl)-6-(2-methoxypropan-2-yl)quinoline-4-carboxamide (Example 16);

N-(2-((1S,3S,5S)-3-Cyano-2-azabicyclo[3.1.0]hexan-2-yl)-2-oxoethyl)-6-((trifluoromethoxy)methyl)quinoline-4-carboxamide (Example 17);

N-(2-((1S,3S,5S)-3-Cyano-2-azabicyclo[3.1.0]hexan-2-yl)-2-oxoethyl)-6-ethyl-2-methylquinoline-4-carboxamide (Example 18);

N-(2-((1S,3S,5S)-3-Cyano-2-azabicyclo[3.1.0]hexan-2-yl)-2-oxoethyl)-2,6-dimethylquinoline-4-carboxamide (Example 19);

N-(2-((1S,3S,5S)-3-Cyano-2-azabicyclo[3.1.0]hexan-2-yl)-2-oxoethyl)-7-methylquinoline-4-carboxamide (Example 20);

N-(2-((1S,3S,5S)-3-Cyano-2-azabicyclo[3.1.0]hexan-2-yl)-2-oxoethyl)-7-(2-fluoropropan-2-yl)quinoline-4-carboxamide (Example 21);

N-(2-((1S,3S,5S)-3-Cyano-2-azabicyclo[3.1.0]hexan-2-yl)-2-oxoethyl)-7-(difluoromethyl)quinoline-4-carboxamide (Example 22);

N-(2-((1S,3S,5S)-3-Cyano-2-azabicyclo[3.1.0]hexan-2-yl)-2-oxoethyl)-7-(trifluoromethyl)quinoline-4-carboxamide (Example 23);

N-(2-((1S,3S,5S)-3-Cyano-2-azabicyclo[3.1.0]hexan-2-yl)-2-oxoethyl)-7-(fluoromethyl)quinoline-4-carboxamide (Example 24);

N-(2-((1S,3S,5S)-3-Cyano-2-azabicyclo[3.1.0]hexan-2-yl)-2-oxoethyl)-7-(1-hydroxyethyl)quinoline-4-carboxamide (Example 25);

N-(2-((1S,3S,5S)-3-Cyano-2-azabicyclo[3.1.0]hexan-2-yl)-2-oxoethyl)-7-(2-hydroxypropan-2-yl)quinoline-4-carboxamide (Example 26);

N-(2-((1S,3S,5S)-3-Cyano-2-azabicyclo[3.1.0]hexan-2-yl)-2-oxoethyl)-7-(1-methoxyethyl)quinoline-4-carboxamide (Example 27);

N-(2-((1S,3S,5S)-3-Cyano-2-azabicyclo[3.1.0]hexan-2-yl)-2-oxoethyl)-7-(2-methoxypropan-2-yl)quinoline-4-carboxamide (Example 28);

N-(2-((1S,3S,5S)-3-Cyano-2-azabicyclo[3.1.0]hexan-2-yl)-2-oxoethyl)-7-((trifluoromethoxy)methyl)quinoline-4-carboxamide (Example 29);

N-(2-((1S,3S,5S)-3-Cyano-2-azabicyclo[3.1.0]hexan-2-yl)-2-oxoethyl)-7-(1-(trifluoromethoxy)ethyl)quinoline-4-carboxamide (Example 30); and N-(2-((1S,3S,5S)-3-Cyano-2-azabicyclo[3.1.0]hexan-2-yl)-2-oxoethyl)-2,7-dimethylquinoline-4-carboxamide (Example 31).

Embodiment 69: Compounds of Formula (I), or pharmaceutically acceptable salts thereof, wherein the compound is selected from the group consisting of:

N-(2-((1S,3S,5S)-3-Cyano-2-azabicyclo[3.1.0]hexan-2-yl)-2-oxoethyl)-6-methylquinoline-4-carboxamide (Example 9);

N-(2-((1S,3S,5S)-3-Cyano-2-azabicyclo[3.1.0]hexan-2-yl)-2-oxoethyl)-6-(trifluoromethyl)quinoline-4-carboxamide (Example 10);

N-(2-((1S,3S,5S)-3-Cyano-2-azabicyclo[3.1.0]hexan-2-yl)-2-oxoethyl)-6-(fluoromethyl)quinoline-4-carboxamide (Example 11);

N-(2-((1S,3S,5S)-3-Cyano-2-azabicyclo[3.1.0]hexan-2-yl)-2-oxoethyl)-6-(2-fluoropropan-2-yl)quinoline-4-carboxamide (Example 12);

N-(2-((1S,3S,5S)-3-Cyano-2-azabicyclo[3.1.0]hexan-2-yl)-2-oxoethyl)-6-(2-hydroxypropan-2-yl)quinoline-4-carboxamide (Example 13);

N-(2-((1S,3S,5S)-3-Cyano-2-azabicyclo[3.1.0]hexan-2-yl)-2-oxoethyl)-6-(1-hydroxyethyl)quinoline-4-carboxamide (Example 14);

N-(2-((1S,3S,5S)-3-Cyano-2-azabicyclo[3.1.0]hexan-2-yl)-2-oxoethyl)-6-(1-methoxyethyl)quinoline-4-carboxamide (Example 15);

N-(2-((1S,3S,5S)-3-Cyano-2-azabicyclo[3.1.0]hexan-2-yl)-2-oxoethyl)-6-(2-methoxypropan-2-yl)quinoline-4-carboxamide (Example 16);

N-(2-((1S,3S,5S)-3-Cyano-2-azabicyclo[3.1.0]hexan-2-yl)-2-oxoethyl)-6-((trifluoromethoxy)methyl)quinoline-4-carboxamide (Example 17);

N-(2-((1S,3S,5S)-3-Cyano-2-azabicyclo[3.1.0]hexan-2-yl)-2-oxoethyl)-6-ethyl-2-methylquinoline-4-carboxamide (Example 18); and N-(2-((1S,3S,5S)-3-Cyano-2-azabicyclo[3.1.0]hexan-2-yl)-2-oxoethyl)-2,6-dimethylquinoline-4-carboxamide (Example 19).

Embodiment 70: Compounds of Formula (I), or pharmaceutically acceptable salts thereof, wherein the compound is selected from the group consisting of:

N-(2-((1S,3S,5S)-3-Cyano-2-azabicyclo[3.1.0]hexan-2-yl)-2-oxoethyl)-7-methylquinoline-4-carboxamide (Example 20);

N-(2-((1S,3S,5S)-3-Cyano-2-azabicyclo[3.1.0]hexan-2-yl)-2-oxoethyl)-7-(2-fluoropropan-2-yl)quinoline-4-carboxamide (Example 21);

N-(2-((1S,3S,5S)-3-Cyano-2-azabicyclo[3.1.0]hexan-2-yl)-2-oxoethyl)-7-(difluoromethyl)quinoline-4-carboxamide (Example 22);

N-(2-((1S,3S,5S)-3-Cyano-2-azabicyclo[3.1.0]hexan-2-yl)-2-oxoethyl)-7-(trifluoromethyl)quinoline-4-carboxamide (Example 23);

N-(2-((1S,3S,5S)-3-Cyano-2-azabicyclo[3.1.0]hexan-2-yl)-2-oxoethyl)-7-(fluoromethyl)quinoline-4-carboxamide (Example 24);

N-(2-((1S,3S,5S)-3-Cyano-2-azabicyclo[3.1.0]hexan-2-yl)-2-oxoethyl)-7-(1-hydroxyethyl)quinoline-4-carboxamide (Example 25);

N-(2-((1S,3S,5S)-3-Cyano-2-azabicyclo[3.1.0]hexan-2-yl)-2-oxoethyl)-7-(2-hydroxypropan-2-yl)quinoline-4-carboxamide (Example 26);

N-(2-((1S,3S,5S)-3-Cyano-2-azabicyclo[3.1.0]hexan-2-yl)-2-oxoethyl)-7-(1-methoxyethyl)quinoline-4-carboxamide (Example 27);

N-(2-((1S,3S,5S)-3-Cyano-2-azabicyclo[3.1.0]hexan-2-yl)-2-oxoethyl)-7-(2-methoxypropan-2-yl)quinoline-4-carboxamide (Example 28);

N-(2-((1S,3S,5S)-3-Cyano-2-azabicyclo[3.1.0]hexan-2-yl)-2-oxoethyl)-7-((trifluoromethoxy)methyl)quinoline-4-carboxamide (Example 29);

N-(2-((1S,3S,5S)-3-Cyano-2-azabicyclo[3.1.0]hexan-2-yl)-2-oxoethyl)-7-(1-(trifluoromethoxy)ethyl)quinoline-4-carboxamide (Example 30); and N-(2-((1S,3S,5S)-3-Cyano-2-azabicyclo[3.1.0]hexan-2-yl)-2-oxoethyl)-2,7-dimethylquinoline-4-carboxamide (Example 31).

Embodiment 71: Compounds of Formula (I), or pharmaceutically acceptable salts thereof, wherein the compound is selected from the group consisting of.

N-(2-((1S,3S,5S)-3-Cyano-2-azabicyclo[3.1.0]hexan-2-yl)-2-oxoethyl)-7-(1-cyanocyclopropyl)quinoline-4-carboxamide (Example 40);

N-(2-((1S,3S,5S)-3-Cyano-2-azabicyclo[3.1.0]hexan-2-yl)-2-oxoethyl)-6-cyclopropylquinoline-4-carboxamide (Example 42);

N-(2-((1S,3S,5S)-3-Cyano-2-azabicyclo[3.1.0]hexan-2-yl)-2-oxoethyl)-6-(1-methylcyclopropyl)quinoline-4-carboxamide (Example 43);

N-(2-((1S,3S,5S)-3-Cyano-2-azabicyclo[3.1.0]hexan-2-yl)-2-oxoethyl)-6-(1-(trifluoromethyl)cyclopropyl)quinoline-4-carboxamide (Example 44);

N-(2-((1S,3S,5S)-3-Cyano-2-azabicyclo[3.1.0]hexan-2-yl)-2-oxoethyl)-6-(1-ethoxycyclopropyl)quinoline-4-carboxamide (Example 45);

N-(2-((1S,3S,5S)-3-Cyano-2-azabicyclo[3.1.0]hexan-2-yl)-2-oxoethyl)-6-(1-cyanocyclopropyl)quinoline-4-carboxamide (Example 46);

N-(2-((1S,3S,5S)-3-Cyano-2-azabicyclo[3.1.0]hexan-2-yl)-2-oxoethyl)-7-cyclopropylquinoline-4-carboxamide (Example 47);

N-(2-((1S,3S,5S)-3-Cyano-2-azabicyclo[3.1.0]hexan-2-yl)-2-oxoethyl)-7-(1-methylcyclopropyl)quinoline-4-carboxamide (Example 32);

N-(2-((1S,3S,5S)-3-Cyano-2-azabicyclo[3.1.0]hexan-2-yl)-2-oxoethyl)-7-(1-(trifluoromethyl)cyclopropyl)quinoline-4-carboxamide (Example 36); and N-(2-((1S,3S,5S)-3-Cyano-2-azabicyclo[3.1.0]hexan-2-yl)-2-oxoethyl)-7-(1-ethoxycyclopropyl)quinoline-4-carboxamide (Example 39).

Embodiment 72: Compounds of Formula (I), or pharmaceutically acceptable salts thereof, wherein the compound is selected from the group consisting of:

N-(2-((1S,3S,5S)-3-Cyano-2-azabicyclo[3.1.0]hexan-2-yl)-2-oxoethyl)-6-cyclopropylquinoline-4-carboxamide (Example 42);

N-(2-((1S,3S,5S)-3-Cyano-2-azabicyclo[3.1.0]hexan-2-yl)-2-oxoethyl)-6-(1-methylcyclopropyl)quinoline-4-carboxamide (Example 43);

N-(2-((1S,3S,5S)-3-Cyano-2-azabicyclo[3.1.0]hexan-2-yl)-2-oxoethyl)-6-(1-(trifluoromethyl)cyclopropyl)quinoline-4-carboxamide (Example 44);

N-(2-((1S,3S,5S)-3-Cyano-2-azabicyclo[3.1.0]hexan-2-yl)-2-oxoethyl)-6-(1-ethoxycyclopropyl)quinoline-4-carboxamide (Example 45); and N-(2-((1S,3S,5S)-3-Cyano-2-azabicyclo[3.1.0]hexan-2-yl)-2-oxoethyl)-6-(1-cyanocyclopropyl)quinoline-4-carboxamide (Example 46).

Embodiment 73: Compounds of Formula (I), or pharmaceutically acceptable salts thereof, wherein the compound is selected from the group consisting of:

N-(2-((1S,3S,5S)-3-Cyano-2-azabicyclo[3.1.0]hexan-2-yl)-2-oxoethyl)-7-(1-cyanocyclopropyl)quinoline-4-carboxamide (Example 40);

N-(2-((1S,3S,5S)-3-Cyano-2-azabicyclo[3.1.0]hexan-2-yl)-2-oxoethyl)-7-cyclopropylquinoline-4-carboxamide (Example 47);

N-(2-((1S,3S,5S)-3-Cyano-2-azabicyclo[3.1.0]hexan-2-yl)-2-oxoethyl)-7-(1-methylcyclopropyl)quinoline-4-carboxamide (Example 32);

N-(2-((1S,3S,5S)-3-Cyano-2-azabicyclo[3.1.0]hexan-2-yl)-2-oxoethyl)-7-(1-(trifluoromethyl)cyclopropyl)quinoline-4-carboxamide (Example 36); and N-(2-((1S,3S,5S)-3-Cyano-2-azabicyclo[3.1.0]hexan-2-yl)-2-oxoethyl)-7-(1-ethoxycyclopropyl)quinoline-4-carboxamide (Example 39).

Embodiment 74: Compounds of Formula (I), or pharmaceutically acceptable salts thereof, wherein the compound is selected from the group consisting of:

N-(2-((1S,3S,5S)-3-Cyano-2-azabicyclo[3.1.0]hexan-2-yl)-2-oxoethyl)-6-(2,2,2-trifluoroethoxy)quinoline-4-carboxamide (Example 33);

N-(2-((1S,3S,5S)-3-Cyano-2-azabicyclo[3.1.0]hexan-2-yl)-2-oxoethyl)-6-isopropoxyquinoline-4-carboxamide (Example 34);

N-(2-((1S,3S,5S)-3-Cyano-2-azabicyclo[3.1.0]hexan-2-yl)-2-oxoethyl)-6-(cyclopropylmethoxy)quinoline-4-carboxamide (Example 35); and N-(2-((1S,3S,5S)-3-Cyano-2-azabicyclo[3.1.0]hexan-2-yl)-2-oxoethyl)-7-methoxy-2-methylquinoline-4-carboxamide (Example 41).

Embodiment 75: Compounds of Formula (I), or pharmaceutically acceptable salts thereof, wherein the compound is selected from the group consisting of:

N-(2-((1S,3S,5S)-3-Cyano-2-azabicyclo[3.1.0]hexan-2-yl)-2-oxoethyl)-6-(2,2,2-trifluoroethoxy)quinoline-4-carboxamide (Example 33);

N-(2-((1S,3S,5S)-3-Cyano-2-azabicyclo[3.1.0]hexan-2-yl)-2-oxoethyl)-6-isopropoxyquinoline-4-carboxamide (Example 34); and N-(2-((1S,3S,5S)-3-Cyano-2-azabicyclo[3.1.0]hexan-2-yl)-2-oxoethyl)-6-(cyclopropylmethoxy)quinoline-4-carboxamide (Example 35).

Embodiment 76: N-(2-((1S,3S,5S)-3-Cyano-2-azabicyclo[3.1.0]hexan-2-yl)-2-oxoethyl)-7-methoxy-2-methylquinoline-4-carboxamide, or a pharmaceutically acceptable salt thereof (Example 41).

Embodiment 77: Compounds of Formula (I), or pharmaceutically acceptable salts thereof, wherein the compound is selected from the group consisting of:

N-(2-((1S,3S,5S)-3-Cyano-2-azabicyclo[3.1.0]hexan-2-yl)-2-oxoethyl)-6-cyclopropoxyquinoline-4-carboxamide (Example 37); and N-(2-((1S,3S,5S)-3-Cyano-2-azabicyclo[3.1.0]hexan-2-yl)-2-oxoethyl)-6-((4,4-difluorocyclohexyl)oxy)quinoline-4-carboxamide (Example 38).

Embodiment 78: Compounds of Formula (I), or pharmaceutically acceptable salts thereof, wherein the compound is selected from the group consisting of:

N-(2-((1S,3S,5S)-3-Cyano-2-azabicyclo[3.1.0]hexan-2-yl)-2-oxoethyl)-2,7-dimethylquinoline-4-carboxamide (Example 31);

6-Bromo-N-(2-((1S,3S,5S)-3-cyano-2-azabicyclo[3.1.0]hexan-2-yl)-2-oxoethyl)-2-methylquinoline-4-carboxamide (Example 6);

N-(2-((1S,3S,5S)-3-Cyano-2-azabicyclo[3.1.0]hexan-2-yl)-2-oxoethyl)-7-fluoro-2-methylquinoline-4-carboxamide (Example 8);

N-(2-((1S,3S,5S)-3-Cyano-2-azabicyclo[3.1.0]hexan-2-yl)-2-oxoethyl)-7-methoxy-2-methylquinoline-4-carboxamide (Example 41);

N-(2-((1S,3S,5S)-3-Cyano-2-azabicyclo[3.1.0]hexan-2-yl)-2-oxoethyl)-6-ethyl-2-methylquinoline-4-carboxamide (Example 18);

N-(2-((1S,3S,5S)-3-Cyano-2-azabicyclo[3.1.0]hexan-2-yl)-2-oxoethyl)-6-iodo-2-methylquinoline-4-carboxamide (Example 7);

N-(2-((1S,3S,5S)-3-Cyano-2-azabicyclo[3.1.0]hexan-2-yl)-2-oxoethyl)-2,6-dimethylquinoline-4-carboxamide (Example 19);

6-Chloro-N-(2-((1S,3S,5S)-3-cyano-2-azabicyclo[3.1.0]hexan-2-yl)-2-oxoethyl)-2-methylquinoline-4-carboxamide (Example 5); and N-(2-((1S,3S,5S)-3-Cyano-2-azabicyclo[3.1.0]hexan-2-yl)-2-oxoethyl)-6-fluoro-2-methylquinoline-4-carboxamide (Example 4).

Embodiment A-1: A compound having the structure of Formula (I):

(I)

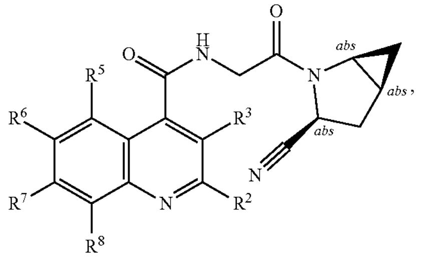

or a pharmaceutically acceptable salt thereof, wherein:

$R^2$ is selected from the group consisting of hydrogen, halogen, and methyl;

$R^3$ is hydrogen or halogen;

$R^5$ is selected from the group consisting of hydrogen, hydroxy, halogen, methyl, and methoxy;

one of $R^6$ and $R^7$ is hydrogen and the other of $R^6$ and $R^7$ is selected from the group consisting of:

(a) halogen;

(b) $C_{1-6}$-alkyl, wherein the $C_{1-6}$-alkyl is optionally substituted with one or more substituents independently selected from the group consisting of halogen, hydroxy, $C_{1-6}$-alkoxy, halo-$C_{1-6}$-alkoxy, $C_{3-6}$-cycloalkyl, and $C_{3-6}$-cycloalkoxy;

(c) cyclopropyl, wherein the cyclopropyl is optionally substituted with one or more substituents independently selected from the group consisting of cyano, fluoro, $C_{1-6}$-alkyl, halo-$C_{1-6}$-alkyl, and $C_{1-6}$-alkoxy;

(d) $C_{1-6}$-alkoxy, wherein the $C_{1-6}$-alkoxy is optionally substituted with one or more substituents independently selected from the group consisting of halogen and cyclopropyl; and (e) $C_{3-6}$-cycloalkoxy, wherein the $C_{3-6}$-cycloalkoxy is optionally substituted with one or more substituents independently selected from the group consisting of halogen and $C_{1-3}$-alkyl; and $R^8$ is selected from the group consisting of hydrogen, halogen, and methyl.

Embodiment A-2: The compound of Embodiment A-1, or a pharmaceutically acceptable salt thereof, wherein $R^2$ is selected from the group consisting of hydrogen, chloro, fluoro, and methyl.

Embodiment A-3: The compound of Embodiment A-1, or a pharmaceutically acceptable salt thereof, wherein $R^2$ is selected from the group consisting of hydrogen, chloro, and methyl.

Embodiment A-4: The compound of Embodiment A-1, or a pharmaceutically acceptable salt thereof, wherein $R^2$ is selected from the group consisting of hydrogen, fluoro, and methyl.

Embodiment A-5: The compound of Embodiment A-1, or a pharmaceutically acceptable salt thereof, wherein $R^2$ is hydrogen or halogen.

Embodiment A-6: The compound of Embodiment A-1, or a pharmaceutically acceptable salt thereof, wherein $R^2$ is hydrogen or chloro.

Embodiment A-7: The compound of Embodiment A-1, or a pharmaceutically acceptable salt thereof, wherein $R^2$ is hydrogen or fluoro.

Embodiment A-8: The compound of Embodiment A-1, or a pharmaceutically acceptable salt thereof, wherein $R^2$ is hydrogen or methyl.

Embodiment A-9: The compound of Embodiment A-1, or a pharmaceutically acceptable salt thereof, wherein $R^2$ is hydrogen.

Embodiment A-10: The compound of Embodiment A-1, or a pharmaceutically acceptable salt thereof, wherein $R^2$ is halogen.

Embodiment A-11: The compound of Embodiment A-1, or a pharmaceutically acceptable salt thereof, wherein $R^2$ is chloro.

Embodiment A-12: The compound of Embodiment A-1, or a pharmaceutically acceptable salt thereof, wherein $R^2$ is fluoro.

Embodiment A-13: The compound of Embodiment A-1, or a pharmaceutically acceptable salt thereof, wherein $R^2$ is methyl.

Embodiment A-14: The compound of any of Embodiments A-1 to A-13, or a pharmaceutically acceptable salt thereof, wherein $R^3$ is selected from the group consisting of hydrogen, chloro, and fluoro.

Embodiment A-15: The compound of any of Embodiments A-1 to A-13, or a pharmaceutically acceptable salt thereof, wherein $R^3$ is hydrogen or chloro.

Embodiment A-16: The compound of any of Embodiments A-1 to A-13, or a pharmaceutically acceptable salt thereof, wherein $R^3$ is hydrogen or fluoro.

Embodiment A-17: The compound of any of Embodiments A-1 to A-13, or a pharmaceutically acceptable salt thereof, wherein $R^3$ is hydrogen.

Embodiment A-18: The compound of any of Embodiments A-1 to A-13, or a pharmaceutically acceptable salt thereof, wherein $R^3$ is halogen.

Embodiment A-19: The compound of any of Embodiments A-1 to A-13, or a pharmaceutically acceptable salt thereof, wherein $R^3$ is chloro.

Embodiment A-20: The compound of any of Embodiments A-1 to A-13, or a pharmaceutically acceptable salt thereof, wherein $R^3$ is fluoro.

Embodiment A-21: The compound of any of Embodiments A-1 to A-20, or a pharmaceutically acceptable salt thereof, wherein $R^5$ is selected from the group consisting of hydrogen, hydroxy, chloro, fluoro, methyl, and methoxy.

Embodiment A-22: The compound of any of Embodiments A-1 to A-20, or a pharmaceutically acceptable salt thereof, wherein $R^5$ is selected from the group consisting of hydrogen, chloro, and methyl.

Embodiment A-23: The compound of any of Embodiments A-1 to A-20, or a pharmaceutically acceptable salt thereof, wherein $R^5$ is selected from the group consisting of hydrogen, fluoro, and methyl.

Embodiment A-24: The compound of any of Embodiments A-1 to A-20, or a pharmaceutically acceptable salt thereof, wherein $R^5$ is hydrogen or halogen.

Embodiment A-25: The compound of any of Embodiments A-1 to A-20, or a pharmaceutically acceptable salt thereof, wherein $R^5$ is hydrogen or chloro.

Embodiment A-26: The compound of any of Embodiments A-1 to A-20, or a pharmaceutically acceptable salt thereof, wherein $R^5$ is hydrogen or fluoro.

Embodiment A-27: The compound of any of Embodiments A-1 to A-20, or a pharmaceutically acceptable salt thereof, wherein $R^5$ is hydrogen or methyl.

Embodiment A-28: The compound of any of Embodiments A-1 to A-20, or a pharmaceutically acceptable salt thereof, wherein $R^5$ is hydrogen.

Embodiment A-29: The compound of any of Embodiments A-1 to A-20, or a pharmaceutically acceptable salt thereof, wherein $R^5$ is hydroxy.

Embodiment A-30: The compound of any of Embodiments A-1 to A-20, or a pharmaceutically acceptable salt thereof, wherein $R^5$ is halogen.

Embodiment A-31: The compound of any of Embodiments A-1 to A-20, or a pharmaceutically acceptable salt thereof, wherein $R^5$ is chloro.

Embodiment A-32: The compound of any of Embodiments A-1 to A-20, or a pharmaceutically acceptable salt thereof, wherein $R^5$ is fluoro.

Embodiment A-33: The compound of any of Embodiments A-1 to A-20, or a pharmaceutically acceptable salt thereof, wherein $R^5$ is methyl.

Embodiment A-34: The compound of any of Embodiments A-1 to A-20, or a pharmaceutically acceptable salt thereof, wherein $R^5$ is methoxy.

Embodiment A-35: The compound of any of Embodiments A-1 to A-34, or a pharmaceutically acceptable salt thereof, wherein $R^8$ is selected from the group consisting of hydrogen, chloro, fluoro, and methyl.

Embodiment A-36: The compound of any of Embodiments A-1 to A-34, or a pharmaceutically acceptable salt thereof, wherein $R^8$ is hydrogen or chloro.

Embodiment A-37: The compound of any of Embodiments A-1 to A-34, or a pharmaceutically acceptable salt thereof, wherein $R^8$ is hydrogen or fluoro.

Embodiment A-38: The compound of any of Embodiments A-1 to A-34, or a pharmaceutically acceptable salt thereof, wherein $R^8$ is hydrogen or methyl.

Embodiment A-39: The compound of any of Embodiments A-1 to A-34, or a pharmaceutically acceptable salt thereof, wherein $R^8$ is hydrogen.

Embodiment A-40: The compound of any of Embodiments A-1 to A-34, or a pharmaceutically acceptable salt thereof, wherein $R^8$ is halogen.

Embodiment A-41: The compound of any of Embodiments A-1 to A-34, or a pharmaceutically acceptable salt thereof, wherein $R^8$ is chloro.

Embodiment A-42: The compound of any of Embodiments A-1 to A-34, or a pharmaceutically acceptable salt thereof, wherein $R^8$ is fluoro.

Embodiment A-43: The compound of any of Embodiments A-1 to A-34, or a pharmaceutically acceptable salt thereof, wherein $R^8$ is methyl.

Embodiment A-44: The compound of Embodiment A-1, or a pharmaceutically acceptable salt thereof, wherein:

$R^2$ is selected from the group consisting of hydrogen, chloro, fluoro, and methyl;

$R^3$ is selected from the group consisting of hydrogen, chloro, and fluoro;

$R^5$ is selected from the group consisting of hydrogen, hydroxy, chloro, fluoro, methyl, and methoxy; and $R^8$ is selected from the group consisting of hydrogen, chloro, fluoro, and methyl.

Embodiment A-45: The compound of Embodiment A-1, or a pharmaceutically acceptable salt thereof, wherein:

$R^2$ is selected from the group consisting of hydrogen, chloro, fluoro, and methyl;

$R^3$ is selected from the group consisting of hydrogen, chloro, and fluoro;

$R^5$ is selected from the group consisting of hydrogen, chloro, and fluoro; and $R^8$ is selected from the group consisting of hydrogen, chloro, and fluoro.

Embodiment A-46: The compound of Embodiment A-1, or a pharmaceutically acceptable salt thereof, wherein:

$R^2$ is selected from the group consisting of hydrogen, fluoro, and methyl;

$R^3$ is hydrogen or fluoro;

$R^5$ is hydrogen or fluoro; and $R^8$ is hydrogen or fluoro.

Embodiment A-47: The compound of Embodiment A-1, or a pharmaceutically acceptable salt thereof, wherein:

$R^2$ is hydrogen or methyl;

$R^3$ is selected from the group consisting of hydrogen, chloro, and fluoro;

$R^5$ is selected from the group consisting of hydrogen, chloro, and fluoro; and $R^8$ is selected from the group consisting of hydrogen, chloro, and fluoro.

Embodiment A-48: The compound of Embodiment A-1, or a pharmaceutically acceptable salt thereof, wherein $R^2$, $R^3$, $R^5$, and $R^8$ are independently selected from hydrogen and fluoro.

Embodiment A-49: The compound of any of Embodiments A-1 to A-48, or a pharmaceutically acceptable salt thereof, wherein one of the $R^2$, $R^3$, $R^5$, and $R^8$ substituents is other than hydrogen, and the remaining $R^2$, $R^3$, $R^5$, and $R^8$ substituents are all hydrogen.

Embodiment A-50: The compound of any of Embodiments A-1 to A-49, or a pharmaceutically acceptable salt thereof, wherein one of $R^6$ and $R^7$ is hydrogen and the other is chloro.

Embodiment A-51: The compound of any of Embodiments A-1 to A-49, or a pharmaceutically acceptable salt thereof, wherein one of $R^6$ and $R^7$ is hydrogen and the other is fluoro.

Embodiment A-52: The compound of any of Embodiments A-1 to A-49, or a pharmaceutically acceptable salt thereof, wherein one of $R^6$ and $R^7$ is hydrogen and the other is bromo.

Embodiment A-53: The compound of any of Embodiments A-1 to A-49, or a pharmaceutically acceptable salt thereof, wherein one of $R^6$ and $R^7$ is hydrogen and the other is iodo.

Embodiment A-54: The compound of any of Embodiments A-1 to A-49, or a pharmaceutically acceptable salt thereof, wherein one of $R^6$ and $R^7$ is hydrogen and the other is $C_{1-6}$-alkyl, wherein the $C_{1-6}$-alkyl is optionally substituted with one or more substituents independently selected from the group consisting of halogen, hydroxy, $C_{1-6}$-alkoxy, halo-$C_{1-6}$-alkoxy, $C_{3-6}$-cycloalkyl, and $C_{3-6}$-cycloalkoxy.

Embodiment A-55: The compound of any of Embodiments A-1 to A-49, or a pharmaceutically acceptable salt thereof, wherein one of $R^6$ and $R^7$ is hydrogen and the other is $C_{1-3}$-alkyl, wherein the $C_{1-3}$-alkyl is optionally substituted with one or more substituents independently selected from the group consisting of halogen, hydroxy, $C_{1-3}$-alkoxy, halo-$C_{1-3}$-alkoxy, $C_{3-6}$-cycloalkyl, and $C_{3-6}$-cycloalkoxy.

Embodiment A-56: The compound of any of Embodiments A-1 to A-49, or a pharmaceutically acceptable salt thereof, wherein one of $R^6$ and $R^7$ is hydrogen and the other is $C_{1-3}$-alkyl, wherein the $C_{1-3}$-alkyl is optionally substituted with one or more substituents independently selected from the group consisting of halogen, hydroxy, methoxy, and halomethoxy.

Embodiment A-57: The compound of any of Embodiments A-1 to A-49, or a pharmaceutically acceptable salt thereof, wherein one of $R^6$ and $R^7$ is hydrogen and the other is $C_{1-3}$-alkyl, wherein the $C_{1-3}$-alkyl is optionally substituted with one or more substituents independently selected from the group consisting of fluoro, hydroxy, methoxy, and fluoromethoxy.

Embodiment A-58: The compound of any of Embodiments A-1 to A-49, or a pharmaceutically acceptable salt thereof, wherein one of $R^6$ and $R^7$ is hydrogen and the other is $C_{1-3}$-alkyl, wherein the $C_{1-3}$-alkyl is optionally substituted with one or more substituents independently selected from the group consisting of fluoro and methoxy.

Embodiment A-59: The compound of any of Embodiments A-1 to A-49, or a pharmaceutically acceptable salt thereof, wherein one of $R^6$ and $R^7$ is hydrogen and the other is $C_{1-6}$-alkyl, wherein the $C_{1-6}$-alkyl is optionally substituted with one or more substituents independently selected from the group consisting of halogen and $C_{1-6}$-alkoxy.

Embodiment A-60: The compound of any of Embodiments A-1 to A-49, or a pharmaceutically acceptable salt thereof, wherein one of $R^6$ and $R^7$ is hydrogen and the other is $C_{1-3}$-alkyl, wherein the $C_{1-3}$-alkyl is optionally substituted with one or more substituents independently selected from the group consisting of halogen and $C_{1-3}$-alkoxy.

Embodiment A-61: The compound of any of Embodiments A-1 to A-49, or a pharmaceutically acceptable salt thereof, wherein one of $R^6$ and $R^7$ is hydrogen and the other is $C_{1-6}$-alkyl.

Embodiment A-62: The compound of any of Embodiments A-1 to A-49, or a pharmaceutically acceptable salt thereof, wherein one of $R^6$ and $R^7$ is hydrogen and the other is $C_{1-3}$-alkyl.

Embodiment A-63: The compound of any of Embodiments A-1 to A-49, or a pharmaceutically acceptable salt thereof, wherein one of $R^6$ and $R^7$ is hydrogen and the other is methyl.

Embodiment A-64: The compound of any of Embodiments A-1 to A-49, or a pharmaceutically acceptable salt thereof, wherein one of $R^6$ and $R^7$ is hydrogen and the other is $C_{1-6}$-alkyl, wherein the $C_{1-6}$-alkyl is optionally substituted with one or more halogen.

Embodiment A-65: The compound of any of Embodiments A-1 to A-49, or a pharmaceutically acceptable salt thereof, wherein one of $R^6$ and $R^7$ is hydrogen and the other is $C_{1-3}$-alkyl, wherein the $C_{1-3}$-alkyl is optionally substituted with one or more fluoro.

Embodiment A-66: The compound of any of Embodiments A-1 to A-49, or a pharmaceutically acceptable salt thereof, wherein one of $R^6$ and $R^7$ is hydrogen and the other is $C_{1-6}$-alkyl, wherein the $C_{1-6}$-alkyl is optionally substituted with one or more hydroxy.

Embodiment A-67: The compound of any of Embodiments A-1 to A-49, or a pharmaceutically acceptable salt thereof, wherein one of $R^6$ and $R^7$ is hydrogen and the other is $C_{1-3}$-alkyl, wherein the $C_{1-3}$-alkyl is optionally substituted with one or more hydroxy.

Embodiment A-68: The compound of any of Embodiments A-1 to A-49, or a pharmaceutically acceptable salt thereof, wherein one of $R^6$ and $R^7$ is hydrogen and the other is $C_{1-6}$-alkyl, wherein the $C_{1-6}$-alkyl is optionally substituted with one or more $C_{1-6}$-alkoxy.

Embodiment A-69: The compound of any of Embodiments A-1 to A-49, or a pharmaceutically acceptable salt thereof, wherein one of $R^6$ and $R^7$ is hydrogen and the other is $C_{1-3}$-alkyl, wherein the $C_{1-6}$-alkyl is optionally substituted with one or more $C_{1-3}$-alkoxy.

Embodiment A-70: The compound of any of Embodiments A-1 to A-49, or a pharmaceutically acceptable salt thereof, wherein one of $R^6$ and $R^7$ is hydrogen and the other is $C_{1-6}$-alkyl, wherein the $C_{1-6}$-alkyl is optionally substituted with one or more halo-$C_{1-6}$-alkoxy.

Embodiment A-71: The compound of any of Embodiments A-1 to A-49, or a pharmaceutically acceptable salt thereof, wherein one of $R^6$ and $R^7$ is hydrogen and the other is $C_{1-3}$-alkyl, wherein the $C_{1-3}$-alkyl is optionally substituted with one or more halo-$C_{1-3}$-alkoxy.

Embodiment A-72: The compound of any of Embodiments A-1 to A-49, or a pharmaceutically acceptable salt thereof, wherein one of $R^6$ and $R^7$ is hydrogen and the other is $C_{1-3}$-alkyl, wherein the $C_{1-3}$-alkyl is optionally substituted with one or more fluoro-$C_{1-3}$-alkoxy.

Embodiment A-73: The compound of any of Embodiments A-1 to A-49, or a pharmaceutically acceptable salt thereof, wherein one of $R^6$ and $R^7$ is hydrogen and the other is $C_{1-6}$-alkyl, wherein the $C_{1-6}$-alkyl is optionally substituted with one or more $C_{3-6}$-cycloalkyl.

Embodiment A-74: The compound of any of Embodiments A-1 to A-49, or a pharmaceutically acceptable salt thereof, wherein one of $R^6$ and $R^7$ is hydrogen and the other is $C_{1-3}$-alkyl, wherein the $C_{1-3}$-alkyl is optionally substituted with one or more $C_{3-6}$-cycloalkyl.

Embodiment A-75: The compound of any of Embodiments A-1 to A-49, or a pharmaceutically acceptable salt thereof, wherein one of $R^6$ and $R^7$ is hydrogen and the other is $C_{1-6}$-alkyl, wherein the $C_{1-6}$-alkyl is optionally substituted with one or more $C_{3-6}$-cycloalkoxy.

Embodiment A-76: The compound of any of Embodiments A-1 to A-49, or a pharmaceutically acceptable salt thereof, wherein one of $R^6$ and $R^7$ is hydrogen and the other is $C_{1-3}$-alkyl, wherein the $C_{1-3}$-alkyl is optionally substituted with one or more $C_{3-6}$-cycloalkoxy.

Embodiment A-77: The compound of any of Embodiments A-1 to A-49, or a pharmaceutically acceptable salt thereof, wherein one of $R^6$ and $R^7$ is hydrogen and the other is selected from the group consisting of methyl, ethyl, fluoromethyl, difluoromethyl, trifluoromethyl, fluoropropyl, hydroxyethyl, hydroxypropyl, methoxyethyl, methoxypropyl, trifluoromethoxymethyl, and trifluoromethoxyethyl.

Embodiment A-78: The compound of any of Embodiments A-1 to A-49, or a pharmaceutically acceptable salt thereof, wherein one of $R^6$ and $R^7$ is hydrogen and the other is selected from the group consisting of methyl, ethyl, fluoromethyl, difluoromethyl, trifluoromethyl, fluoropropyl, methoxyethyl, and methoxypropyl.

Embodiment A-79: The compound of any of Embodiments A-1 to A-49, or a pharmaceutically acceptable salt thereof, wherein one of $R^6$ and $R^7$ is hydrogen and the other is cyclopropyl, wherein the cyclopropyl is optionally substituted with one or more substituents independently selected from the group consisting of cyano, fluoro, $C_{1-6}$-alkyl, halo-$C_{1-6}$-alkyl, and $C_{1-6}$-alkoxy.

Embodiment A-80: The compound of any of Embodiments A-1 to A-49, or a pharmaceutically acceptable salt thereof, wherein one of $R^6$ and $R^7$ is hydrogen and the other is cyclopropyl, wherein the cyclopropyl is optionally substituted with one or more substituents independently selected from the group consisting of cyano, fluoro, $C_{1-3}$-alkyl, halo-$C_{1-3}$-alkyl, and $C_{1-3}$-alkoxy.

Embodiment A-81: The compound of any of Embodiments A-1 to A-49, or a pharmaceutically acceptable salt thereof, wherein one of $R^6$ and $R^7$ is hydrogen and the other is cyclopropyl, wherein the cyclopropyl is optionally substituted with one or more substituents independently selected from the group consisting of cyano, $C_{1-3}$-alkyl, fluoro-$C_{1-3}$-alkyl, and $C_{1-3}$-alkoxy.

Embodiment A-82: The compound of any of Embodiments A-1 to A-49, or a pharmaceutically acceptable salt thereof, wherein one of $R^6$ and $R^7$ is hydrogen and the other is cyclopropyl.

Embodiment A-83: The compound of any of Embodiments A-1 to A-49, or a pharmaceutically acceptable salt thereof, wherein one of $R^6$ and $R^7$ is hydrogen and the other is cyclopropyl, wherein the cyclopropyl is optionally substituted with one or more cyano.

Embodiment A-84: The compound of any of Embodiments A-1 to A-49, or a pharmaceutically acceptable salt thereof, wherein one of $R^6$ and $R^7$ is hydrogen and the other is cyclopropyl, wherein the cyclopropyl is optionally substituted with one or more fluoro.

Embodiment A-85: The compound of any of Embodiments A-1 to A-49, or a pharmaceutically acceptable salt thereof, wherein one of $R^6$ and $R^7$ is hydrogen and the other is cyclopropyl, wherein the cyclopropyl is optionally substituted with one or $C_{1-6}$-alkyl.

Embodiment A-86: The compound of any of Embodiments A-1 to A-49, or a pharmaceutically acceptable salt thereof, wherein one of $R^6$ and $R^7$ is hydrogen and the other is cyclopropyl, wherein the cyclopropyl is optionally substituted with one or more $C_{1-3}$-alkyl.

Embodiment A-87: The compound of any of Embodiments A-1 to A-49, or a pharmaceutically acceptable salt thereof, wherein one of $R^6$ and $R^7$ is hydrogen and the other is cyclopropyl, wherein the cyclopropyl is optionally substituted with one or more halo-$C_{1-6}$-alkyl.

Embodiment A-88: The compound of any of Embodiments A-1 to A-49, or a pharmaceutically acceptable salt thereof, wherein one of $R^6$ and $R^7$ is hydrogen and the other is cyclopropyl, wherein the cyclopropyl is optionally substituted with one or more halo-$C_{1-3}$-alkyl.

Embodiment A-89: The compound of any of Embodiments A-1 to A-49, or a pharmaceutically acceptable salt thereof, wherein one of $R^6$ and $R^7$ is hydrogen and the other is cyclopropyl, wherein the cyclopropyl is optionally substituted with one or more fluoro-$C_{1-3}$-alkyl.

Embodiment A-90: The compound of any of Embodiments A-1 to A-49, or a pharmaceutically acceptable salt thereof, wherein one of $R^6$ and $R^7$ is hydrogen and the other is cyclopropyl, wherein the cyclopropyl is optionally substituted with one or more $C_{1-6}$-alkoxy.

Embodiment A-91: The compound of any of Embodiments A-1 to A-49, or a pharmaceutically acceptable salt thereof, wherein one of $R^6$ and $R^7$ is hydrogen and the other is cyclopropyl, wherein the cyclopropyl is optionally substituted with one or more $C_{1-3}$-alkoxy.

Embodiment A-92: The compound of any of Embodiments A-1 to A-49, or a pharmaceutically acceptable salt thereof, wherein one of $R^6$ and $R^7$ is hydrogen and the other is cyclopropyl, wherein the cyclopropyl is optionally substituted with one or more substituents independently selected from the group consisting of cyano, methyl, trifluoromethyl, and ethoxy.

Embodiment A-93: The compound of any of Embodiments A-1 to A-49, or a pharmaceutically acceptable salt thereof, wherein one of $R^6$ and $R^7$ is hydrogen and the other is $C_{1-6}$-alkoxy, wherein the $C_{1-6}$-alkoxy is optionally substituted with one or more substituents independently selected from the group consisting of halogen and cyclopropyl.

Embodiment A-94: The compound of any of Embodiments A-1 to A-49, or a pharmaceutically acceptable salt thereof, wherein one of $R^6$ and $R^7$ is hydrogen and the other is $C_{1-3}$-alkoxy, wherein the $C_{1-3}$-alkoxy is optionally substituted with one or more substituents independently selected from the group consisting of halogen and cyclopropyl.

Embodiment A-95: The compound of any of Embodiments A-1 to A-49, or a pharmaceutically acceptable salt thereof, wherein one of $R^6$ and $R^7$ is hydrogen and the other is $C_{1-6}$-alkoxy.

Embodiment A-96: The compound of any of Embodiments A-1 to A-49, or a pharmaceutically acceptable salt thereof, wherein one of $R^6$ and $R^7$ is hydrogen and the other is $C_{1-3}$-alkoxy.

Embodiment A-97: The compound of any of Embodiments A-1 to A-49, or a pharmaceutically acceptable salt thereof, wherein one of $R^6$ and $R^7$ is hydrogen and the other is $C_{1-6}$-alkoxy, wherein the $C_{1-6}$-alkoxy is optionally substituted with one or more halogen.

Embodiment A-98: The compound of any of Embodiments A-1 to A-49, or a pharmaceutically acceptable salt thereof, wherein one of $R^6$ and $R^7$ is hydrogen and the other is $C_{1-3}$-alkoxy, wherein the $C_{1-3}$-alkoxy is optionally substituted with one or more halogen.

Embodiment A-99: The compound of any of Embodiments A-1 to A-49, or a pharmaceutically acceptable salt thereof, wherein one of $R^6$ and $R^7$ is hydrogen and the other is $C_{1-3}$-alkoxy, wherein the $C_{1-3}$-alkoxy is optionally substituted with one or more fluoro.

Embodiment A-100: The compound of any of Embodiments A-1 to A-49, or a pharmaceutically acceptable salt thereof, wherein one of $R^6$ and $R^7$ is hydrogen and the other is $C_{1-6}$-alkoxy, wherein the $C_{1-6}$-alkoxy is optionally substituted with one or more cyclopropyl.

Embodiment A-101: The compound of any of Embodiments A-1 to A-49, or a pharmaceutically acceptable salt thereof, wherein one of $R^6$ and $R^7$ is hydrogen and the other is $C_{1-3}$-alkoxy, wherein the $C_{1-3}$-alkoxy is optionally substituted with one or more cyclopropyl.

Embodiment A-102: The compound of any of Embodiments A-1 to A-49, or a pharmaceutically acceptable salt thereof, wherein one of $R^6$ and $R^7$ is hydrogen and the other is selected from the group consisting of methoxy, propoxy, trifluoroethoxy, and cyclopropylmethoxy.

Embodiment A-103: The compound of any of Embodiments A-1 to A-49, or a pharmaceutically acceptable salt thereof, wherein one of $R^6$ and $R^7$ is hydrogen and the other is $C_{3-6}$-cycloalkoxy, wherein the $C_{3-6}$-cycloalkoxy is optionally substituted with one or more halogen.

Embodiment A-104: The compound of any of Embodiments A-1 to A-49, or a pharmaceutically acceptable salt thereof, wherein one of $R^6$ and $R^7$ is hydrogen and the other is $C_{3-6}$-cycloalkoxy, wherein the $C_{3-6}$-cycloalkoxy is optionally substituted with one or more $C_{1-3}$-alkyl.

Embodiment A-105: The compound of any of Embodiments A-1 to A-49, or a pharmaceutically acceptable salt thereof, wherein one of $R^6$ and $R^7$ is hydrogen and the other is $C_{3-6}$-cycloalkoxy.

Embodiment A-106: The compound of any of Embodiments A-1 to A-49, or a pharmaceutically acceptable salt thereof, wherein one of $R^6$ and $R^7$ is hydrogen and the other is cyclopropoxy.

Embodiment A-107: The compound of any of Embodiments A-1 to A-49, or a pharmaceutically acceptable salt thereof, wherein one of $R^6$ and $R^7$ is hydrogen and the other is cyclohexyloxy.

Embodiment A-108: The compound of any of Embodiments A-1 to A-49, or a pharmaceutically acceptable salt thereof, wherein one of $R^6$ and $R^7$ is hydrogen and the other is $C_{3-6}$-cycloalkoxy, wherein the $C_{3-6}$-cycloalkoxy is optionally substituted with one or more fluoro.

Embodiment A-109: The compound of any of Embodiments A-1 to A-49, or a pharmaceutically acceptable salt thereof, wherein one of $R^6$ and $R^7$ is hydrogen and the other is cyclohexyloxy, wherein the cyclohexyloxy is optionally substituted with one or more halogen.

Embodiment A-110: The compound of any of Embodiments A-1 to A-49, or a pharmaceutically acceptable salt thereof, wherein one of $R^6$ and $R^7$ is hydrogen and the other is cyclohexyloxy, wherein the cyclohexyloxy is optionally substituted with one or more fluoro.

Embodiment A-111: The compound of any of Embodiments A-1 to A-49, or a pharmaceutically acceptable salt thereof, wherein one of $R^6$ and $R^7$ is hydrogen and the other is cyclopropoxy, wherein the cyclopropoxy is optionally substituted with one or more halogen.

Embodiment A-112: The compound of Embodiment 1, or a pharmaceutically acceptable salt thereof, wherein the compound is N-(2-((1S,3S,5S)-3-Cyano-2-azabicyclo[3.1.0]hexan-2-yl)-2-oxoethyl)-7-methylquinoline-4-carboxamide.

Embodiment B-1: The compound of any of Embodiments 1 to 78 or A-1 to A-112, or a pharmaceutically acceptable salt thereof, wherein one of $R^6$ and $R^7$ is hydrogen and the other is cyclopropoxy, wherein the cyclopropoxy is optionally substituted with one or more fluoro.

Embodiment C-1: A pharmaceutical composition comprising a compound of any of Embodiments 1 to 78 or A-1 to A-112, or a pharmaceutically acceptable salt thereof, and one or more pharmaceutically acceptable excipients.

Embodiment C-2: A method of treating or preventing an FAP-mediated condition in a subject suffering from or susceptible to the FAP-mediated condition, the method comprising administering to the subject a therapeutically effective amount of a compound of any of Embodiments 1 to 78 or A-1 to A-112, or a pharmaceutically acceptable salt thereof.

Embodiment C-3: The method of Embodiment C-2, wherein the FAP-mediated condition is selected from the group consisting of liver disease, type 2 diabetes mellitus, cardiovascular conditions, obesity, obesity-related conditions, fibrosis, keloid disorder, inflammation, and cancer.

Embodiment C-4: The method of Embodiment C-3, wherein the FAP-mediated condition is liver disease.

Embodiment C-5: The method of Embodiment C-4, wherein the liver disease is nonalcoholic steatohepatitis.

Embodiment C-6: The use of a compound of any of Embodiments 1 to 78 or A-1 to A-112, or a pharmaceutically acceptable salt thereof, for the manufacture of a medicament for treating or preventing an FAP-mediated condition.

C. Combination of Embodiments

Any embodiment of the compounds described in the present disclosure can be combined with any other suitable embodiment described herein to provide additional embodiments. For example, where one embodiment individually or collectively describes possible groups for $R^2$, $R^3$, $R^5$, $R^6$, $R^7$, and/or $R^8$ and a separate embodiment describes possible groups for $R^7$, it is understood that these embodiments can be combined to provide an additional embodiment describing the possible groups described for $R^2$, $R^3$, $R^5$, $R^6$, $R^7$, and/or $R^8$ together with the possible groups described for $R^7$. In other words, for any of the embodiments of the compounds described in the present disclosure, the $R^7$ substituent can be as defined in any of the embodiments of $R^7$ described in this specification.

D. Further Embodiments

The compounds of the present disclosure have a pharmaceutically acceptable FAP inhibitory activity measured as described for the hFAP inhibition assay (tight binders) reported in the Examples below. In one aspect, the compounds have an FAP inhibitory activity at $IC_{50}$ concentrations below about 100 nM. In another aspect, the compounds have an FAP inhibitory activity at $IC_{50}$ concentrations below about 50 nM. In another aspect, the compounds have an FAP inhibitory activity at $IC_{50}$ concentrations below about 10 nM. In another aspect, the compounds have an FAP inhibitory activity at $IC_{50}$ concentrations below about 1 nM.

In some embodiments, the compounds of the present disclosure possess a pharmaceutically acceptable surface plasmon resonance (SPR) $pK_d$ value measured as described for the SPR assay reported in the Examples below. In one aspect, the compounds have a surface plasmon resonance (SPR) $pK_d$ value greater than about 6. In another aspect, the compounds have a surface plasmon resonance (SPR) $pK_d$ value greater than about 7. In another aspect, the compounds have an SPR $pK_d$ value greater than about 8. In another aspect, the compounds have an SPR $pK_d$ value greater than about 9.

In some embodiments, the compounds of the present disclosure have a pharmaceutically acceptable selectivity for FAP relative to PREP measured as described for the hFAP inhibition assay (tight binders) and the hPREP inhibition assay reported in the Examples below. In one aspect, the compounds are at least about 50 times more selective for FAP relative to PREP. In another aspect, the compounds are at least about 100 times more selective for FAP relative to PREP. In another aspect, the compounds are at least about 1,000 times more selective for FAP relative to PREP. In another aspect, the compounds are at least about 10,000 times more selective for FAP relative to PREP. In another aspect, the compounds have a PREP $IC_{50}$ value greater than about 0.1 μM. In another aspect, the compounds have a PREP $IC_{50}$ value greater than about 1.0 μM. In another aspect, the compounds have a PREP $IC_{50}$ value greater than about 10.0 μM.

In some embodiments, the compounds of the present disclosure have a pharmaceutically acceptable selectivity for FAP relative to DPP7 measured as described for the hFAP inhibition assay (tight binders) and the DPP7 selectivity assay reported in the Examples below. In one aspect, the compounds are at least about 50 times more selective for FAP relative to DPP7. In another aspect, the compounds are at least about 100 times more selective for FAP relative to DPP7. In another aspect, the compounds are at least about 1,000 times more selective for FAP relative to DPP7. In another aspect, the compounds are at least about 10,000 times more selective for FAP relative to DPP7. In another aspect, the compounds have an $IC_{50}$ value for DPP7 that is greater than about 0.1 μM. In another aspect, the compounds have an $IC_{50}$ value for DPP7 that is greater than about 1 μM. In another aspect, the compounds have an $IC_{50}$ value for DPP7 that is greater than about 10 μM.

In some embodiments, the compounds of the present disclosure have a pharmaceutically acceptable selectivity for FAP relative to DPP8 and/or DPP9 measured as described for the hFAP inhibition assay (tight binders), DPP8 selectivity assay, and DPP9 selectivity assay reported in the Examples below. In one aspect, the compounds are selective for FAP relative to DPP8. In another aspect, the compounds are selective for FAP relative to DPP9. In another aspect, the compounds are selective for FAP relative to both DPP8 and DPP9. In one aspect, the compounds are at least about 50 times more selective for FAP relative to DPP8 and/or DPP9. In another aspect, the compounds are at least about 100 times more selective for FAP relative to DPP8 and/or DPP9.

In another aspect, the compounds are at least about 500 times more selective for FAP relative to DPP8 and/or DPP9. In another aspect, the compounds are at least about 1,000 times more selective for FAP relative to DPP8 and/or DPP9. In another aspect, the compounds have an $IC_{50}$ value for DPP8 and/or DPP9 that is greater than about 0.01 μM. In another aspect, the compounds have an $IC_{50}$ value for DPP8 and/or DPP9 that is greater than about 0.1 μM. In another aspect, the compounds have an $IC_{50}$ value for DPP8 and/or DPP9 that is greater than about 0.4 μM.

In some embodiments, the compounds of the present disclosure have a pharmaceutically acceptable metabolic stability measured as described for the human liver microsomes (HLM) assay reported in the Examples below. In one aspect, the compounds have an HLM $CL_{int}$ value less than about 300 μL/min/mg. In another aspect, the compounds have an HLM $CL_{int}$ value less than about 100 μL/min/mg. In another aspect, the compounds have an HLM $CL_{int}$ value less than about 50 μL/min/mg.

In some embodiments, the compounds of the present disclosure have a pharmaceutically acceptable metabolic stability measured as described for the rat hepatocytes (rHep) assay reported in the Examples below. In one aspect, the compounds have an rHep $CL_{int}$ value less than about 300 μL/min/$10^6$ cells. In another aspect, the compounds have an rHep $CL_{int}$ value less than about 100 μL/min/$10^6$ cells. In another aspect, the compounds have an rHep $CL_{int}$ value less than about 50 μL/min/$10^6$ cells.

In some embodiments, the compounds of the present disclosure have a pharmaceutically acceptable Caco-2 AB intrinsic permeability measured as described for the Caco-2 AB intrinsic permeability assay reported in the Examples below. In one aspect, the compounds have a Caco-2 intrinsic apparent permeability of at least about $0.1\times10^{6}$ cm/s. In another aspect, the compounds have a Caco-2 intrinsic apparent permeability of at least about $0.5\times10^{6}$ cm/s. In another aspect, the compounds have a Caco-2 intrinsic apparent permeability of at least about $1\times10^{6}$ cm/s.

In some embodiments, the compounds of the present disclosure have a pharmaceutically acceptable Caco-2 bidirectional (ABBA) A to B apparent permeability measured as described for the Caco-2 bidirectional (ABBA) A to B apparent permeability assay reported in the Examples below. In one aspect, the compounds have a Caco-2 bidirectional (ABBA) A to B apparent permeability of at least about $0.1\times10^{6}$ cm/s. In another aspect, the compounds have a Caco-2 bidirectional (ABBA) A to B apparent permeability of at least about $0.25\times10^{6}$ cm/s. In another aspect, the compounds have a Caco-2 bidirectional (ABBA) A to B apparent permeability of at least about $0.5\times10^{6}$ cm/s.

In some embodiments, the compounds of the present disclosure have a pharmaceutically acceptable kinetic solubility measured as described for the kinetic solubility assay reported in the Examples below. In one aspect, the compounds have a kinetic solubility of at least about 1 μM. In another aspect, the compounds have a kinetic solubility of at least about 10 μM. In another aspect, the compounds have a kinetic solubility of at least about 25 μM. In another aspect, the compounds have a kinetic solubility of at least about 50 μM.

E. Salts

The compounds of the present disclosure may exist in salt form or in non-salt form (i.e., as a free base), and the present disclosure covers both salt forms and non-salt forms. The compounds may form acid addition salts or base addition salts. In general, an acid addition salt can be prepared using various inorganic or organic acids. Such salts can typically be formed by, for example, mixing the compound with an acid (e.g., a stoichiometric amount of an acid) using various methods known in the art. This mixing may occur in water, an organic solvent (e.g., ether, ethyl acetate, ethanol, methanol, isopropanol, or acetonitrile), or an aqueous/organic mixture. In another aspect, the acid addition salts are, for example, trifluoroacetate, formate, acetate or hydrochloric. In general, a base addition salt can be prepared using various inorganic or organic bases, for example an alkali or alkaline earth metal salt such as a sodium, calcium or magnesium salt, or other metal salts, such as potassium or zinc, or an ammonium salt, or a salt with an organic base such as methylamine, dimethylamine, trimethylamine, piperidine or morpholine. The skilled person will be aware of the general principles and techniques of preparing pharmaceutical salts, such as those described in, for example, *J. Pharm. Sci.* 1977 66, 1. Examples of pharmaceutically acceptable salts are also described in "Handbook of Pharmaceutical Salts: Properties, Selection, and Use" by Stahl and Wermuth (Wiley-VCH, Weinheim, Germany, 2002).

F. Isomers

The compounds and salts of the present disclosure may exist in one or more geometrical, optical, enantiomeric, and diastereomeric forms, including, but not limited to, cis- and trans-forms, E- and Z-forms, and R-, S- and meso-forms. Unless otherwise stated a reference to a particular compound includes all such isomeric forms, including racemic and other mixtures thereof. Where appropriate such isomers can be separated from their mixtures by the application or adaptation of known methods (e.g., chromatographic techniques and recrystallisation techniques). Where appropriate such isomers can be prepared by the application or adaptation of known methods. In some embodiments, a single stereoisomer is obtained by isolating it from a mixture of isomers (e.g., a racemate) using, for example, chiral chromatographic separation. In other embodiments, a single stereoisomer is obtained through direct synthesis from, for example, a chiral starting material.

A particular enantiomer of a compound described herein may be more active than other enantiomers of the same compound. In one embodiment, the compound, or a pharmaceutically acceptable salt thereof, is a single enantiomer being in an enantiomeric excess (% ee) of ≥90, ≥95%, ≥96%, ≥97, ≥98% or ≥99%. In one aspect, the single enantiomer is present in an enantiomeric excess (% ee) of ≥99%.

In another embodiment, the present disclosure relates to a pharmaceutical composition comprising a compound, or a pharmaceutically acceptable salt thereof, which is a single enantiomer being in an enantiomeric excess (% ee) of ≥90, ≥95%, ≥96%, ≥97, ≥98% or ≥99%, or a pharmaceutically acceptable salt thereof, in association with one or more pharmaceutically acceptable excipients. In one aspect, the single enantiomer is present in an enantiomeric excess (% ee) of ≥99%.

G. Additional Forms

The compounds and salts of the present disclosure may exist in various tautomeric forms and the specification encompasses all such tautomeric forms. "Tautomers" are structural isomers that exist in equilibrium resulting from the migration of a hydrogen atom.

The compounds of the present disclosure, and pharmaceutically acceptable salts thereof, may exist as solvates (such as a hydrates) as well as unsolvated forms, and the present specification covers all such solvates.

The compounds of the present disclosure, and pharmaceutically acceptable salts thereof, may exist in crystalline or amorphous form, and the present specification covers all such forms.

Compounds and salts of the present disclosure may be isotopically-labeled (or "radio-labeled"). In that instance, one or more atoms are replaced by an atom having an atomic mass or mass number different from the atomic mass or mass number typically found in nature. The specification encompasses isotopically-labelled forms of compounds disclosed herein. Examples of isotopes that may be incorporated include $^{2}H$ (also written as "D" for deuterium), $^{3}H$ (also written as "T" for tritium), $^{11}C$, $^{13}C$, $^{14}C$, $^{13}N$, $^{15}N$, $^{15}O$, $^{17}O$, $^{18}O$ and $^{36}Cl$. The isotope that is used will depend on the specific application of that radio-labeled derivative. For example, for in vitro receptor labeling and competition assays, 3H or $^{14}C$ are often useful. For radio-imaging applications, $^{11}C$ is often useful. In some embodiments, the radionuclide is $^{3}H$. In some embodiments, the radionuclide is $^{14}C$. In some embodiments, the radionuclide is $^{11}C$.

H. Intermediates

In some embodiments, the present disclosure provides additional compounds that are useful as intermediates for preparing the compounds of the present disclosure, and pharmaceutically acceptable salts thereof.

III. METHODS OF USE

The disclosed compounds of the present disclosure, and pharmaceutically acceptable salts thereof, are inhibitors of Prolyl endopeptidase fibroblast activation protein (FAP) activity. FAP is an endopeptidase that enzymatically cleaves substrates involved in glucose and lipid metabolism, fibrinolysis, and collagen production.

FAP is believed to cleave and inactivate human Fibroblast Growth Factor 21 (FGF-21) (*Biochem. J.* 2016, 473, 605), a protein involved in the regulation of glucose and lipid metabolism. It is hypothesized that inhibition of FAP increases endogenous FGF-21 levels and signaling, and results, for example, in decreased steatosis, improved insulin sensitivity, improved glucose tolerance, reduced body weight, and/or reduced cardiovascular disease mortality.

FAP is also believed to cleave human α2-Antiplasmin (α2AP) (*Blood* 2004 103, 3783), a protein involved in the regulation of fibrosis and fibrinolysis. Tissue repair involves coagulation which results in fibrin deposition. The fibrin of a clot is usually lysed, primarily by plasmin when converted from its inactive form (plasminogen) by plasminogen activators. Fibrinolysis is inhibited by Plasminogen Activator Inhibitor-1 (PAI-1), Plasminogen Activator Inhibitor-2 (PAI-2), and α2AP, (*Experimental & Molecular Medicine* 2020, 52, 367) all of which are induced by tissue trauma. FAP converts α2AP into a form more effectively bound to fibrin, which reduces plasmin degradation of fibrin at the site of an injury. It is hypothesized that inhibition of FAP increases fibrinolysis and improves tissue regeneration at the site of injury (*J. Thromb. Haemost.* 2013, 11, 2029; Proteomics Clin. Appl. 2014, 8, 454).

FAP is further believed to promote collagen production and deposition and to play a role in increased fibrosis through altered extracellular matrix (ECM) turnover (*J Biol Chem* 2016, 8, 291). It is hypothesized that inhibition of FAP results in a decrease in collagen deposition and a reduction in inflammation (*Inflamm. Bowel Dis.* 2018, 18, 332).

In view of the above, it is hypothesized that inhibition of FAP collectively reduces fibrosis and inflammation by decreasing hepatic stellate cell activity and increasing fibrinolysis, and further provides positive metabolic effects through increased FGF21 signaling and improved glucose tolerance.

In some embodiments, therefore, the present disclosure provides a method for treating or preventing an FAP-mediated condition in a subject in need thereof by administering to the subject a therapeutically effective amount of a compound of Formula I, or a pharmaceutically acceptable salt thereof.

In some embodiments, the present disclosure provides a method for treating or preventing a condition characterized by overexpression of FAP in a subject in need thereof by administering to the subject a therapeutically effective amount of a compound of the present disclosure, or a pharmaceutically acceptable salt thereof.

In some embodiments, the present disclosure provides a method for treating or preventing liver disease in a subject in need thereof by administering to the subject a therapeutically effective amount of a compound of the present disclosure, or a pharmaceutically acceptable salt thereof. In one aspect, the liver disease is a fatty liver disease. In another aspect, the liver disease is Nonalcoholic Fatty Liver Disease (NAFLD). In another aspect, the NAFLD is selected from the group consisting of isolated steatosis, Nonalcoholic Steatohepatitis (NASH), liver fibrosis, and cirrhosis. In another aspect, the liver disease is end stage liver disease. In another aspect, the subject is also suffering from or susceptible to one or more conditions selected from the group consisting of obesity, dyslipidemia, insulin resistance, Type 2 diabetes, and renal insufficiency.

In some embodiments, the present disclosure provides a method for treating liver disease in a subject in need thereof by administering to the subject a therapeutically effective amount of a compound of the present disclosure, or a pharmaceutically acceptable salt thereof, wherein the subject has a body mass index (BMI) of 27 $kg/m^2$ to 40 $kg/m^2$. In one aspect, the subject has a BMI of 30 $kg/m^2$ to 39.9 $kg/m^2$. In another aspect, the subject has a BMI of at least 40 $kg/m^2$. In another aspect, the subject is overweight. In another aspect, the subject is obese. In another aspect, the liver disease is NAFLD. In another aspect, the liver disease is NASH. In another aspect, the liver disease is liver fibrosis. In another aspect, the liver disease is cirrhosis.

In some embodiments, the present disclosure provides a method for treating liver disease in a subject in need thereof by administering to the subject a therapeutically effective amount of a compound of the present disclosure, or a pharmaceutically acceptable salt thereof, wherein the subject is also suffering from or susceptible to dyslipidemia. In another aspect, the liver disease is NAFLD. In another aspect, the liver disease is NASH. In another aspect, the liver disease is liver fibrosis. In another aspect, the liver disease is cirrhosis.

In some embodiments, the present disclosure provides a method for treating liver disease in a subject in need thereof by administering to the subject a therapeutically effective amount of a compound of the present disclosure, or a pharmaceutically acceptable salt thereof, wherein the subject is also suffering from or susceptible to insulin resistance. In another aspect, the liver disease is NAFLD. In another aspect, the liver disease is NASH. In another aspect, the liver disease is liver fibrosis. In another aspect, the liver disease is cirrhosis.

In some embodiments, the present disclosure provides a method for treating liver disease in a subject in need thereof by administering to the subject a therapeutically effective amount of a compound of the present disclosure, or a pharmaceutically acceptable salt thereof, wherein the subject is also suffering from or susceptible to at least one of Type 2 diabetes and renal insufficiency. In another aspect, the liver disease is NAFLD. In another aspect, the liver disease is NASH. In another aspect, the liver disease is liver fibrosis. In another aspect, the liver disease is cirrhosis.

In some embodiments, the present disclosure provides a method for treating liver disease in a subject in need thereof by administering to the subject a therapeutically effective amount of a compound of the present disclosure, or a pharmaceutically acceptable salt thereof, wherein the subject is also suffering from or susceptible to Type 2 diabetes. In another aspect, the liver disease is NAFLD. In another aspect, the liver disease is NASH. In another aspect, the liver disease is liver fibrosis. In another aspect, the liver disease is cirrhosis.

In some embodiments, the present disclosure provides a method for treating liver disease in a subject in need thereof by administering to the subject a therapeutically effective amount of a compound of the present disclosure, or a pharmaceutically acceptable salt thereof, wherein the subject is also suffering from or susceptible to renal insufficiency. In another aspect, die liver disease is NAFLD. In another aspect, the liver disease is NASH. In another aspect, the liver disease is liver fibrosis. In another aspect, the liver disease is cirrhosis.

In some embodiments, the present disclosure provides a method for reducing liver fat in a subject in need thereof by administering to the subject a therapeutically effective amount of a compound of the present disclosure, or a pharmaceutically acceptable salt thereof. In one aspect, the subject is suffering from or susceptible to NAFLD. In another aspect, the subject is suffering from or susceptible to NASH. In another aspect, the subject is suffering from or susceptible to liver fibrosis. In another aspect, the subject is suffering from or susceptible to cirrhosis. In another aspect, the subject is also suffering from or susceptible to one or more conditions selected from the group consisting of obesity, dyslipidemia, insulin resistance, Type 2 diabetes, and renal insufficiency.

In some embodiments, the present disclosure provides a method for treating or preventing Nonalcoholic Fatty Liver Disease (NAFLD) in a subject in need thereof by administering to the subject a therapeutically effective amount of a compound of the present disclosure, or a pharmaceutically acceptable salt thereof. In one aspect, the NAFLD is Stage 1 NAFLD. In another aspect, the NAFLD is Stage 2 NAFLD. In another aspect, the NAFLD is Stage 3 NAFLD. In another aspect, the NAFLD is Stage 4 NAFD. See, e.g., "The Diagnosis and Management of Nonalcoholic Fatty Liver Disease: Practice Guidance From the American Association for the Study of Liver Diseases," *Hepatology,* 2018, Vol. 67, No. 1. In another aspect, the subject is also suffering from or susceptible to one or more conditions selected from the group consisting of obesity, dyslipidemia, insulin resistance, Type 2 diabetes, and renal insufficiency.

In some embodiments, the present disclosure provides a method for treating or preventing Nonalcoholic Steatohepatitis (NASH) in a subject in need thereof by administering to the subject a therapeutically effective amount of a compound of the present disclosure, or a pharmaceutically acceptable salt thereof. In one aspect, the NASH is Stage 1 NASH. In another aspect, the NASH is Stage 2 NASH. In another aspect, the NASH is Stage 3 NASH. In another aspect, the NASH is Stage 4 NASH. In another aspect, the subject is also suffering from or susceptible to one or more conditions selected from the group consisting of obesity, dyslipidemia, insulin resistance, Type 2 diabetes, and renal insufficiency.

In some embodiments, the present disclosure provides a method for treating or preventing liver fibrosis in a subject in need thereof by administering to the subject a therapeutically effective amount of a compound of the present disclosure, or a pharmaceutically acceptable salt thereof. In one aspect, the subject is suffering from Stage 3 liver fibrosis. In another aspect, the subject is also suffering from or susceptible to one or more conditions selected from the group consisting of obesity, dyslipidemia, insulin resistance, Type 2 diabetes, and renal insufficiency.

In some embodiments, the present disclosure provides a method for treating or preventing cirrhosis in a subject in need thereof by administering to the subject a therapeutically effective amount of a compound of the present disclosure, or a pharmaceutically acceptable salt thereof. In one aspect, the subject is suffering from stage F4 cirrhosis. In another aspect, the subject is also suffering from or susceptible to one or more conditions selected from the group consisting of obesity, dyslipidemia, insulin resistance, Type 2 diabetes, and renal insufficiency.

In some embodiments, the present disclosure provides a method for treating or preventing type 2 diabetes mellitus in a subject in need thereof by administering to the subject a therapeutically effective amount of a compound of the present disclosure, or a pharmaceutically acceptable salt thereof. In one aspect, the subject is a subject is suffering from diabetic kidney disease. In another aspect, the subject is suffering from renal insufficiency. In another aspect, the administration of the compound is an adjunct to diet and exercise. In another aspect, the administration of the compound also reduces body weight and/or treats obesity. In another aspect, the subject has a BMI of 27 $kg/m^2$ to 40 $kg/m^2$. In another aspect, the subject has a BMI of 30 $kg/m^2$ to 39.9 $kg/m^2$. In another aspect, the subject has a BMI of at least 40 $kg/m^2$. In another aspect, the subject is overweight. In another aspect, the subject is obese.

In some embodiments, the present disclosure provides a method of improving glycemic control in a subject in need thereof by administering to the subject a therapeutically effective amount of a compound of the present disclosure, or a pharmaceutically acceptable salt thereof. In one aspect, the subject is a subject is suffering from type 2 diabetes. In another aspect, the subject is a subject is suffering from diabetic kidney disease. In another aspect, the subject is suffering from renal insufficiency. In another aspect, the administration of the compound is an adjunct to diet and exercise. In another aspect, the administration of the compound also reduces body weight and/or treats obesity. In another aspect, the subject has a BMI of 27 $kg/m^2$ to 40 $kg/m^2$. In another aspect, the subject has a BMI of 30 $kg/m^2$ to 39.9 $kg/m^2$. In another aspect, the subject has a BMI of at least 40 $kg/m^2$. In another aspect, the subject is overweight. In another aspect, the subject is obese.

In some embodiments, the present disclosure provides a method of improving glycemic control in a subject with type 2 diabetes and diabetic kidney disease by administering to the subject a therapeutically effective amount of a compound of the present disclosure, or a pharmaceutically acceptable salt thereof. In one aspect, the administration of the compound is an adjunct to diet and exercise. In another aspect, the administration of the compound also reduces body weight and/or treats obesity. In another aspect, the subject has a BMI of 27 $kg/m^2$ to 40 $kg/m^2$. In another aspect, the subject has a BMI of 30 $kg/m^2$ to 39.9 $kg/m^2$. In another aspect, the subject has a BMI of at least 40 $kg/m^2$. In another aspect, the subject is overweight. In another aspect, the subject is obese.

In some embodiments, the present disclosure provides a method of improving glycemic control in a subject with type 2 diabetes and renal insufficiency by administering to the subject a therapeutically effective amount of a compound of the present disclosure, or a pharmaceutically acceptable salt thereof. In one aspect, the administration of the compound is an adjunct to diet and exercise. In another aspect, the administration of the compound also reduces body weight and/or treats obesity. In another aspect, the subject has a BMI of 27 $kg/m^2$ to 40 $kg/m^2$. In another aspect, the subject has a BMI of 30 $kg/m^2$ to 39.9 $kg/m^2$. In another aspect, the subject has a BMI of at least 40 $kg/m^2$. In another aspect, the subject is overweight. In another aspect, the subject is obese.

In some embodiments, the present disclosure provides a method of treating or preventing insulin resistance in a subject thereof by administering to the subject a therapeutically effective amount of a compound of the present disclosure, or a pharmaceutically acceptable salt thereof. In another aspect, the subject is a subject is suffering from type 2 diabetes. In another aspect, the subject is a subject is suffering from diabetic kidney disease. In another aspect, the subject is suffering from renal insufficiency. Insulin resistance can be measured, for example, using the Homeostatic Model Assessment of Insulin Resistance (HOMA-IR) and/or the MATSUDA index. The HOMA-IR is explained, for example, in *Diabetologia* 1985, 28, 412, which is herein incorporated by reference in its entirety. The MATSUDA index is explained, for example, in *Diabetes Care* 1999, 22, 1462, which is herein incorporated by reference in its entirety.

In some embodiments, the present disclosure provides a method of treating or preventing glucose intolerance in a subject in need thereof by administering to the subject a therapeutically effective amount of a compound of the present disclosure, or a pharmaceutically acceptable salt thereof. In one aspect, the subject is a subject is suffering from type 2 diabetes. In another aspect, the subject is a subject is suffering from diabetic kidney disease. In another aspect, the subject is suffering from renal insufficiency.

In some embodiments, the present disclosure provides a method of treating a cardiovascular condition in a subject in need of treatment by administering to the subject a therapeutically effective amount of a compound of the present disclosure, or a pharmaceutically acceptable salt thereof. In one aspect, the cardiovascular condition is selected from the group consisting of heart failure, cardiomyopathy, atherosclerosis, venous thromboembolism, and atrial fibrillation. In one aspect, the cardiovascular condition is heart failure. In another aspect, the cardiovascular condition is heart failure with preserved ejection fraction (HFpEF). In another aspect, the cardiovascular condition is cardiomyopathy. In another aspect, the cardiomyopathy is selected from the group consisting of hypertrophic cardiomyopathy, dilated cardiomyopathy, restrictive cardiomyopathy, hypertrophic cardiomyopathy, ischemic cardiomyopathy, ischemic cardiomyopathy, dilated cardiomyopathy, and idiopathic cardiomyopathy. In another aspect, the cardiovascular condition is atherosclerosis. In another aspect, the cardiovascular condition is venous thromboembolism. In another aspect, the cardiovascular condition is atrial fibrillation.

In some embodiments, the present disclosure provides a method of treating obesity or an obesity-related condition in a subject in need thereof by administering to the subject a therapeutically effective amount of a compound of the present disclosure, or a pharmaceutically acceptable salt thereof. In one aspect, the obesity-related condition is an obesity-related metabolic condition. In another aspect, the obesity-related condition is selected from the group consisting of insulin resistance, pre-diabetes, type 2 diabetes, glucose intolerance, increased fasting glucose, and glucagonomas. In another aspect, the obesity-related condition is dyslipidemia. In another aspect, the obesity-related condition is a cardiovascular condition is selected from the group consisting of heart failure, cardiomyopathy, atherosclerosis, venous thromboembolism, and atrial fibrillation. In another aspect, the obesity-related condition is renal disease.

In some embodiments, the present disclosure provides a method of reducing body weight in a subject in need thereof by administering to the subject a therapeutically effective amount of a compound of the present disclosure, or a pharmaceutically acceptable salt thereof. In one aspect, the subject is a subject is suffering from type 2 diabetes. In another aspect, the subject is a subject is suffering from diabetic kidney disease. In another aspect, the subject is suffering from renal insufficiency. In another aspect, the administration of the compound is an adjunct to diet and exercise. In another aspect, the administration of the compound also reduces body weight and/or treats obesity. In another aspect, the subject has a BMI of 27 $kg/m^2$ to 40 $kg/m^2$. In another aspect, the subject has a BMI of 30 $kg/m^2$ to 39.9 $kg/m^2$. In another aspect, the subject has a BMI of at least 40 $kg/m^2$. In another aspect, the subject is overweight. In another aspect, the subject is obese. In another aspect, the subject's weight is reduced, for example, by at least about 5%, 10%, 15%, 20%, 25%, 30%, 35%, or 40%.

In some embodiments, the present disclosure provides a method of reducing body fat in a subject in need of treatment by administering to the subject a therapeutically effective amount of a compound of the present disclosure, or a pharmaceutically acceptable salt thereof. In another aspect, the subject is a subject is suffering from type 2 diabetes. In another aspect, the subject is a subject is suffering from diabetic kidney disease. In another aspect, the subject is suffering from renal insufficiency. In another aspect, the administration of the compound is an adjunct to diet and exercise. In another aspect, the administration of the compound also reduces body weight and/or treats obesity. In another aspect, the subject has a BMI of 27 $kg/m^2$ to 40 $kg/m^2$. In another aspect, the subject has a BMI of 30 $kg/m^2$ to 39.9 $kg/m^2$. In another aspect, the subject has a BMI of at least 40 $kg/m^2$. In another aspect, the subject is overweight. In another aspect, the subject is obese. In another aspect, the fat is liver fat.

In some embodiments, the present disclosure provides a method for treating or preventing fibrosis in a subject in need thereof by administering to the subject a therapeutically effective amount of a compound of the present disclosure, or a pharmaceutically acceptable salt thereof. In one aspect, the fibrosis is interstitial lung disease. In another aspect, the fibrosis is interstitial lung disease with progressive fibrosis. In another aspect, the interstitial lung disease is pulmonary fibrosis. In another aspect, the interstitial lung disease is idiopathic pulmonary fibrosis (IPF).

In some embodiments, the present disclosure provides a method for promoting tissue remodeling in a subject in need thereof by administering to the subject a therapeutically effective amount of a compound of the present disclosure, or a pharmaceutically acceptable salt thereof. In one aspect, the subject has suffered cardiac tissue damage due to a myocardial infarction.

In some embodiments, the present disclosure provides a method of promoting wound healing and/or reducing adhesions in a subject in need thereof by administering to the subject a therapeutically effective amount of a compound of the present disclosure, or a pharmaceutically acceptable salt thereof. In one aspect, the administration of the compound promotes wound healing and/or reduces adhesions through increased fibrinolysis.

In some embodiments, the present disclosure provides a method for treating or preventing a keloid disorder in a subject in need thereof by administering to the subject a therapeutically effective amount of a compound of the present disclosure, or a pharmaceutically acceptable salt thereof. In one aspect, the keloid disorder is selected from the group consisting of scar formation, keloid tumors, and keloid scar.

In some embodiments, the present disclosure provides a method for treating or preventing inflammation in a subject in need thereof by administering to the subject a therapeutically effective amount of a compound of the present disclosure, or a pharmaceutically acceptable salt thereof. In one aspect, the inflammation is chronic inflammation. In one aspect, the chronic inflammation is selected from the group consisting of rheumatoid arthritis, osteoarthritis, and Crohn's disease. In another aspect, the chronic inflammation is rheumatoid arthritis.

In some embodiments, the present disclosure provides a method of treating cancer in a subject in need of treatment by administering to the subject a therapeutically effective amount of a compound of the present disclosure, or a pharmaceutically acceptable salt thereof. In one aspect, the cancer is selected from the group consisting of breast cancer, pancreatic cancer, small intestine cancer, colon cancer, rectal cancer, lung cancer, head and neck cancer, ovarian cancer, hepatocellular carcinoma, esophageal cancer, hypopharynx cancer, nasopharynx cancer, larynx cancer, myeloma cells, bladder cancer, cholangiocellular carcinoma, clear cell renal carcinoma, neuroendocrine tumor, oncogenic osteomalacia, sarcoma, CUP (carcinoma of unknown primary), thymus carcinoma, desmoid tumors, glioma, astrocytoma, cervix carcinoma, and prostate cancer. In another aspect, the cancer is hepatocellular carcinoma.

The subject treated typically will be a human or non-human mammal, particularly a human. Suitable subjects can also include domestic or wild animals; companion animals (including dogs, cats, and the like); livestock (including horses, cows and other ruminants, pigs, poultry, rabbits, and the like); primates (including monkeys such as rhesus monkeys, cynomolgus (also known as crab-eating or long-tailed) monkeys, marmosets, tamarins, chimpanzees, macaques, and the like); and rodents (including rats, mice, gerbils, guinea pigs, and the like).

In some embodiments, the present disclosure provides the compounds of the present disclosure, or pharmaceutically acceptable salts thereof, for use as medicaments.

In some embodiments, the present disclosure provides for the use of the compounds of the Formula I, or pharmaceutically acceptable salts thereof, for treating or preventing an FAP-mediated condition as discussed above.

In some embodiments, the present disclosure provides for the use of the compounds of the Formula I, or pharmaceutically acceptable salts thereof, for the manufacture of medicaments for treating or preventing an FAP-mediated condition as discussed above.

IV. COMBINATION THERAPIES AND FIXED-DOSE COMBINATIONS

The compounds of the present disclosure may be used in the methods described above as either as single pharmacological agents or in combination with other pharmacological agents or techniques. Such combination therapies may be achieved by way of the simultaneous, sequential or separate dosing of the individual components of the treatment. These combination therapies (and corresponding combination products) employ the compounds of the present disclosure within the dosage ranges described in this application and the other pharmacological agent(s), typically within its approved dosage range(s).

In some embodiments, the present disclosure provides a combination suitable for use in the treatment of a condition selected from the previously discussed conditions, wherein the combination comprises a compound of the present disclosure, or a pharmaceutically acceptable salt thereof, and a sodium-glucose transport protein 2 (SGLT2) inhibitor. In one aspect, the SGLT2 inhibitor is selected from the group consisting of canagliflozin, dapagliflozin, empagliflozin, ertugliflozin, ipragliflozin, luseogliflozin, and remogliflozin. In another aspect, the SGLT2 inhibitor is dapagliflozin.

In some embodiments, the present disclosure provides a combination suitable for use in the treatment of a condition selected from the previously discussed conditions, wherein the combination comprises a compound of the present disclosure, or a pharmaceutically acceptable salt thereof, and metformin.

In some embodiments, the present disclosure provides a combination suitable for use in the treatment of a condition selected from the previously discussed conditions, wherein the combination comprises a compound of the present disclosure, or a pharmaceutically acceptable salt thereof, and a glucagon-like peptide-1 receptor (GLP1) agonist. In one aspect, the GLP1 agonist is selected from the group consisting of exenatide, liraglutide, lixisenatide, albiglutide, dulaglutide, and semaglutide.

In some embodiments, the present disclosure provides a combination suitable for use in the treatment of a condition selected from the previously discussed conditions, wherein the combination comprises a compound of the present disclosure, or a pharmaceutically acceptable salt thereof, and a dipeptidyl peptidase 4 (DPP4) inhibitor. In one aspect, the DPP4 inhibitor is selected from the group consisting of sitagliptin, vildagliptin, saxagliptin, linagliptin, gemigliptin, anagliptin, teneligliptin, alogliptin, trelagliptin, omarigliptin, evogliptin, gosogliptin, and dutogliptin.

In some embodiments, the present disclosure provides a combination suitable for use in the treatment of a condition selected from the previously discussed conditions, wherein the combination comprises a compound of the present disclosure, or a pharmaceutically acceptable salt thereof, and a peroxisome proliferator-activated receptor (PPAR) agonist. In one aspect, the PPAR agonist is a PPAR$\alpha$ agonist. In another aspect, the PPAR agonist is a PPAR$\gamma$ agonist. In another aspect, the PPAR agonist is a PPAR$\alpha/\gamma$ agonist. In another aspect, the PPAR agonist is selected from the group consisting of clofibrate, gemfibrozil, ciprofibrate, bezafibrate, and fenofibrate. In another aspect, the PPAR agonist is a thiazolidinedione. In another aspect, the thiazolidinedione is selected from the group consisting of pioglitazone, rosiglitazone, lobeglitazone, and rivoglitazone. In another aspect, the PPAR agonist stimulates liver expression of FGF21.

In some embodiments, the present disclosure provides a pharmaceutical composition comprising a compound of the present disclosure, or a pharmaceutically acceptable salt thereof, one or more pharmacological agents selected from SGLT2 inhibitors, metformin, GLP1 agonists, DPP4 inhibitors, and PPAR agonists; and a pharmaceutically acceptable diluent or carrier. Such a combination can be used for the manufacture of a medicament for use in the treatment of a condition selected from the previously discussed conditions. In one aspect, the pharmaceutical composition comprises an SGLT2 inhibitor. In another aspect, the pharmaceutical composition comprises metformin. In another aspect, the pharmaceutical composition comprises a GLP1 agonist. In another aspect, the pharmaceutical composition comprises a DPP4 inhibitor. In another aspect, the pharmaceutical composition comprises a PPAR agonist.

In some embodiments, the present disclosure provides a combination suitable for use in the treatment of cancer, wherein the combination comprises a compound of the present disclosure, or a pharmaceutically acceptable salt thereof, and an immune checkpoint inhibitor. In one aspect, the immune checkpoint inhibitor is selected from the group consisting of anti-PD-1 antibodies, anti-PD-L1 antibodies, anti-CTLA4 antibodies, TLR7 agonists, CD40 agonists, Lag-3 antagonists, and OX40 agonists. In another aspect, the immune checkpoint inhibitor is an anti-PD-1 antibody (e.g., pembrolizumab (Keytruda), nivolumab (Opdivo), cemiplimab (Libtayo), etc.). In another aspect, the immune checkpoint inhibitor is an anti-PD-L1 antibody (e.g., atezolizumab (Tecentriq), avelumab (Bavencio), durvalumab (Imfinzi), etc.). In another aspect, the immune checkpoint inhibitor is an anti-CTLA4 antibody (e.g., ipilimumab (Yervoy), tremelimumab, etc.). In another aspect, the cancer is selected from the group consisting of pancreatic cancer, colon cancer, and rectal cancer.

V. PHARMACEUTICAL COMPOSITIONS

The compounds of the present disclosure, and pharmaceutically acceptable salts thereof, may be administered as pharmaceutical compositions, comprising one or more pharmaceutically acceptable excipients. Therefore, in some embodiments the present disclosure provides pharmaceutical compositions comprising a compound of the present disclosure, or a pharmaceutically acceptable salt thereof, and at least one pharmaceutically acceptable excipient.

The excipient(s) selected for inclusion in a particular composition will depend on factors such as the mode of administration and the form of the composition provided. Suitable pharmaceutically acceptable excipients are well known to persons skilled in the art and are described, for example, in the Handbook of Pharmaceutical Excipients, Sixth Edition, Pharmaceutical Press, edited by Rowe, Ray C; Sheskey, Paul J; Quinn, Marian. Pharmaceutically acceptable excipients may function as, for example, adjuvants, diluents, carriers, stabilisers, flavourings, colorants, fillers, binders, disintegrants, lubricants, glidants, thickening agents and coating agents. As persons skilled in the art will appreciate, certain pharmaceutically acceptable excipients may serve more than one function and may serve alternative functions depending on how much of the excipient is present in the composition and what other excipients are present in the composition.

The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous or intramuscular dosing), or as a suppository for rectal dosing. The compositions may be obtained by conventional procedures using conventional pharmaceutical excipients, well known in the art. Thus, compositions intended for oral use may contain, for example, one or more coloring, sweetening, flavoring and/or preservative agents.

The total daily dose will necessarily be varied depending upon the subject treated, the particular route of administration, any therapies being co-administered, and the severity of the illness being treated, and may include single or multiple doses. Specific dosages can be adjusted, for example, depending upon the condition being treated; the age, body weight, general health condition, sex, and diet of the subject; administration routes; dose intervals; excretion rate; and other drugs being co-administered to the subject. An ordinarily skilled physician provided with the disclosure of the present application will be able to determine appropriate dosages and regimens for administration of the therapeutic agent to the subject, and to adjust such dosages and regimens as necessary during the course of treatment, in accordance with methods well-known in the therapeutic arts. The compound of the present disclosure, or a pharmaceutically acceptable salt thereof, typically will be administered to a warm-blooded animal at a unit dose within the range 2.5 to 5000 $mg/m^2$ body area of the animal, or approximately 0.05 to 100 mg/kg, and this normally provides a therapeutically effective dose.

In some embodiments, the present disclosure provides pharmaceutical compositions for use in therapy, comprising a compound of the present disclosure, or a pharmaceutically acceptable salt thereof, and at least one pharmaceutically acceptable excipient.

In some embodiments, the present disclosure provides pharmaceutical compositions for use in the treatment of an FAP-mediated condition, comprising a compound of the present disclosure, or a pharmaceutically acceptable salt thereof, and at least one pharmaceutically acceptable excipient. In one aspect, the FAP-mediated condition is selected from the group consisting of liver disease, type 2 diabetes mellitus, cardiovascular conditions, obesity, obesity-related conditions, fibrosis, keloid disorder, inflammation, and cancer.

VI. KITS

The present disclosure further provides kits comprising a unit dosage form comprising a compound of the present disclosure, or a pharmaceutically acceptable salt thereof, contained within a packaging material and a label or package insert which indicates that the unit dosage form can be used for treating one or more of the previously described conditions.

In some embodiments, the kit comprises a unit dosage form comprising a compound of the present disclosure, or a pharmaceutically acceptable salt thereof, contained within a packaging material and a label or package insert which indicates that the pharmaceutical composition can be used for treating an FAP-mediated condition. In another aspect, the FAP-mediated condition is liver disease. In another aspect, the liver disease is selected from the group consisting of fatty liver disease, end stage liver disease, and cirrhosis. In another aspect, the liver disease is selected from the group consisting of Nonalcoholic Steatohepatitis (NASH) and Nonalcoholic Fatty Liver Disease (NAFLD).

In some embodiments, kit comprises: (a) a first unit dosage form comprising a compound of the present disclosure, or a pharmaceutically acceptable salt thereof, (b) a second unit dosage form comprising a pharmacological agent selected from the group consisting of SGLT2 inhibitors, metformin, GLP1 agonists, DPP4 inhibitors, and PPAR agonists; (c) a container means for containing said first and second dosage forms; and (d) a label or package insert which indicates that the first unit dosage form and second unit dosage form can be used for treating an FAP-mediated condition.

VII. METHODS OF PREPARATION

The present disclosure further provides processes for the preparation of the compounds of Formulae (I), (II-A), (II-B), (II-C), (III-A), (III-B), or (III-C), and pharmaceutically acceptable salts thereof. Reaction schemes 1 to 30 illustrate synthetic routes to these compounds wherein, unless otherwise stated, $R^2$, $R^3$, $R^5$, $R^6$, $R^7$, and $R^8$ are as defined in Formula (I); $R^9$ is alkyl (e.g., methyl, ethyl, tert-butyl, etc.); $R^{10}$ and $R^{11}$ are hydrogen or alkyl; and $X^1$, $X^2$ and $X^3$, are leaving groups (e.g., Cl, Br, I, OTf, etc.). One of skill in the art will appreciate that these methods are representative and are not inclusive of all possible methods for preparing the compounds of the present disclosure.

Scheme 1

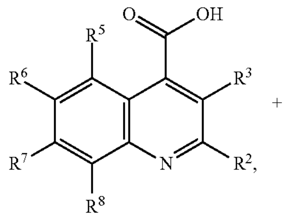

(2)

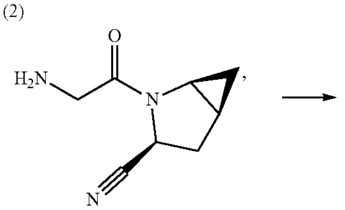

(3)

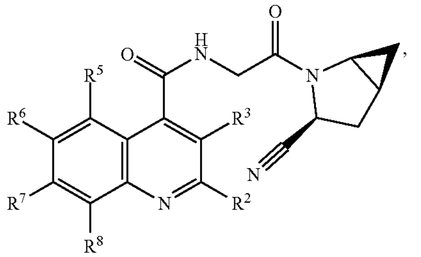

(I)

Scheme 1 illustrates a synthetic route to certain compounds of Formula (I). A compound of formula (2) may be reacted with a compound of formula (3), or salts thereof, to give a compound of Formula (I). The reaction may be performed using suitable coupling reagents (such as HATU, HOBt/EDC, T3P, etc.) in the presence of a base, typically an organic base (such as DIPEA, TEA, etc.) using a solvent (such as DCM, DMF, EtOAc, MeCN, or mixtures thereof) at temperatures ranging from typically 0° C. to 60° C.

Scheme 2

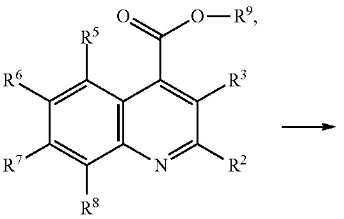

(4)

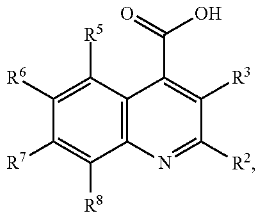

(2)

Scheme 2 illustrates a synthetic route to certain compounds of formula (2). A compound of formula (2) may be formed by reacting a compound of formula (4) with a base (such as NaOH, LiOH, etc.) in an organic solvent (such as 1,4-dioxane, THF, MeOH, or mixtures thereof) and optionally in the presence of water. The reaction may be performed in a temperature interval from 0° C. to reflux. Alternatively, for compounds of formula (4) where $R^9$=tert-butyl, the reaction may be performed with a suitable acid (such as HCl, etc.) in a solvent (such as 1,4-dioxane, EtOAc, MeOH, water, or mixtures thereof). Alternatively, the reaction may be performed using carboxylic acids (such as TFA), neat, or in a solvent (such as DCM) at temperatures ranging from typically 0° C. to 60° C.

Scheme 3

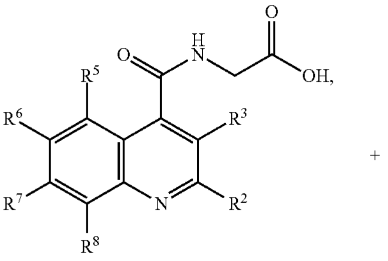

(5)

-continued

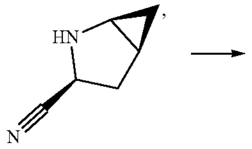

(6)

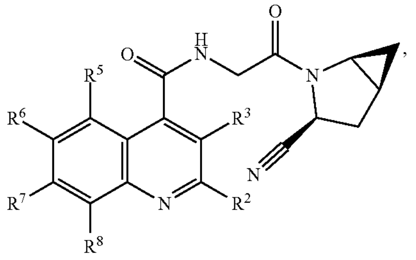

(I)

Scheme 3 illustrates a synthetic route to certain compounds of Formula (I). A compound of formula (5) may be reacted with a compound of formula (6) to give a compound of Formula (I). The reaction may be performed using suitable coupling reagents (such as HATU, HOBt/EDC, T3P, etc.) in the presence of a base, typically an organic base (such as DIPEA, TEA, etc.) using a solvent (such as DCM, DMF, EtOAc, MeCN, or mixtures thereof) at temperatures ranging from typically 0° C. to 60° C.

Scheme 4

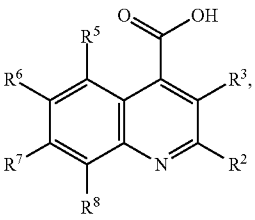

(2)

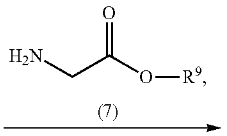

(7)

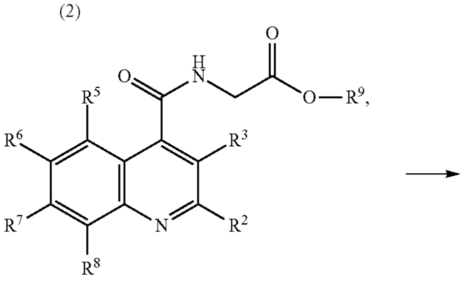

(8)

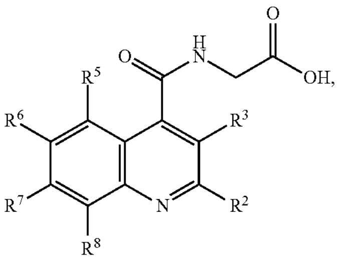

(5)

Scheme 4 illustrates a synthetic route to certain compounds of formula (5). A compound of formula (2) may be reacted with a compound of formula (7) to give a compound of formula (8). The reaction may be performed using suitable coupling reagents (such as HATU, HOBt/EDC, T3P, etc.) in the presence of a base, typically an organic base (such as DIPEA, TEA, etc.) using a solvent (such as DCM, DMF, EtOAc, MeCN, or mixtures thereof) at temperatures ranging from typically 0° C. to 120° C.

A compound of formula (5) may be formed by reacting a compound of formula (8) with a base (such as NaOH, LiOH, etc.) in an organic solvent (such as 1,4-dioxane, THF, MeOH, or mixtures thereof) and optionally in the presence of water. The reaction may be performed in a temperature interval from 0° C. to reflux. Alternatively, for compounds of formula (8) where $R^9$=tert-butyl, the reaction may be performed with a suitable acid (such as HCl, etc.) in a solvent (such as 1,4-dioxane, EtOAc, MeOH, water, or mixtures thereof). Alternatively, the reaction may be performed using carboxylic acids (such as TFA), neat, or in a solvent (such as DCM) at temperatures ranging from typically 0° C. to 60° C.

Scheme 5

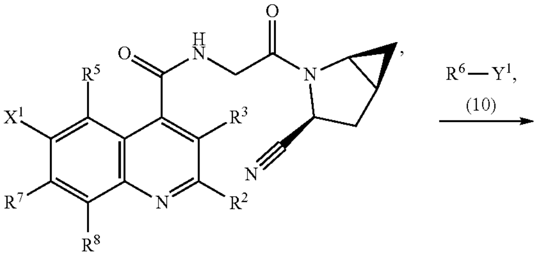

(9)

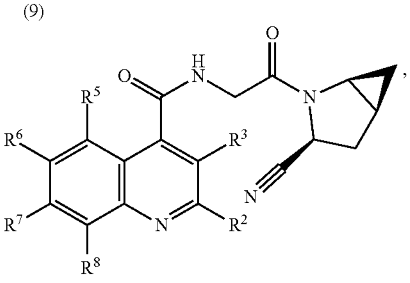

(I)

Scheme 5 illustrates synthetic routes to certain compounds of Formula (I). A compound of formula (9) may be transformed into a compound of Formula (I) by reaction with alkylzinc reagents of formula (10), wherein $R^6$ is as defined in Formula (I) group (b) and (c), and $Y^1$ is a mono-alkyl or halide derivative of zinc (such as diethylzinc, etc.). The reaction may be catalyzed by a Pd-catalyst (such as $PdCl_2$(dppf)·DCM, etc.) in a suitable solvent (such as 1,4-dioxane, THF, etc.) at a temperature ranging from typically 20° C. to reflux.

Alternatively, a compound of formula (9) may be transformed into a compound of Formula (I) by reaction with alkylboron reagents of formula (10), wherein $R^6$ is as defined in Formula (I) group (b) and (c) and $Y^1$ is boron, or a derivative thereof (such as trimethylboroxine, etc.). The reaction may be catalyzed by a Pd-catalyst (such as $PdCl_2$(dppf)·DCM, etc.) in the presence of a base (such as $K_2CO_3$, $Na_2CO_3$, etc.) in a suitable solvent (such as 1,4-dioxane, THF, etc.) at a temperature ranging from typically 20° C. to reflux.

Alternatively, a compound of formula (9) may be transformed into a compound of Formula (I) by reaction with an alkyl halide of formula (10), wherein $R^6$ is as defined in Formula (I) group (b) and (c), and $Y^1$ is a halogen, typically an alkyl bromide. The reaction may be catalyzed with a Ni-catalyst (such as $NiCl_2 \cdot DCM$, etc.) and a suitable ligand (such as bbbpy, etc.), as well as a suitable photoredox catalyst (such as $Ir[dF(CF_3)ppy]_2(dtbbpy)PF_6$, etc.) in the presence of $HSi(SiMe_3)_3$ and a base (such as $Na_2CO_3$, etc.) in a suitable solvent (such as DME, etc.), typically at 20° C. while irradiated with blue light LED.

Alternatively, a compound of formula (9) may be transformed into a compound of Formula (I) by reaction with an alcohol of formula (10), wherein $R^6$ is as defined in Formula (I) group (d) and (e), and $Y^1$ is a hydrogen. The reaction may be catalyzed with a suitable Pd-reagent (such as $Pd(OAc)_2$, etc.) with a suitable phosphine ligand (such as XPhos, t-BuXPhos, etc.) in the presence of a base (such as $K_3PO_4$, etc.) in a suitable solvent (such as toluene, 1,4-dioxane, etc.) and performed at elevated temperatures.

Alternatively, a compound of formula (9) may be transformed into a compound of Formula (I) by reaction with an alcohol of formula (10), wherein $R^6$ is as defined in Formula (I) group (d) and (e), and $Y^1$ is a hydrogen. The reaction may be promoted with a suitable Cu-reagent (such as CuBr, etc.) in the presence of a base (such as $K_2CO_3$, $Cs_2CO_3$, etc.) and a radical initiator (such as AIBN, etc.) in a suitable solvent (such as DMF) and performed at elevated temperatures.

Alternatively, a compound of formula (9) may be transformed into a compound of Formula (I) by reaction with an alcohol of formula (10), wherein $R^6$ is as defined in Formula (I) group (d) and (e), and $Y^1$ is a hydrogen. The reaction may be catalyzed with a Ni-catalyst (such as $NiCl_2 \cdot DCM$, etc.) and a suitable ligand (such as bbbpy, etc.) as well as a suitable photoredox catalyst (such as $Ir[dF(CF_3)ppy]_2(dtbbpy)PF_6$, etc.) in the presence of quinuclidine and a base (such as $K_2CO_3$, etc.) in a suitable solvent (such as acetonitrile, etc.), typically at 20° C. while irradiated with blue light LED.

Scheme 6

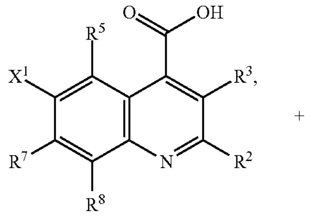

(11)

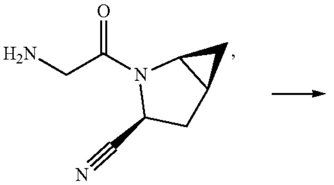

(3)

-continued

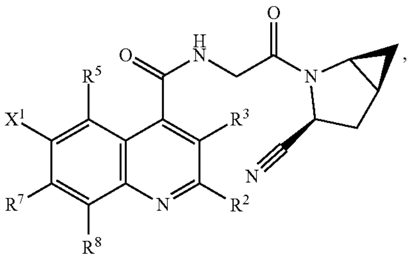

(9)

Scheme 6 illustrates a synthetic route to certain compounds of formula (9). A compound of formula (11) may be reacted with a compound of formula (3) to give a compound of formula (9). The reaction may be performed under conditions described for the analogous reaction described in Scheme 1.

Scheme 7

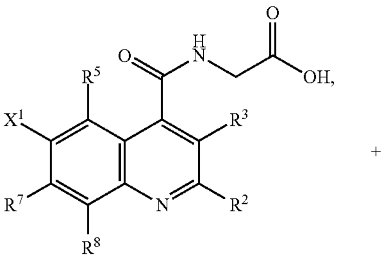

(12)

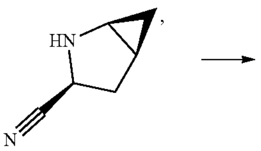

(6)

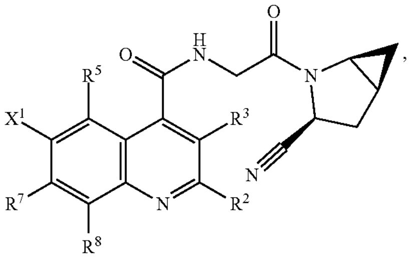

(9)

Scheme 7 illustrates a synthetic route to certain compounds of formula (9). A compound of formula (12) may be reacted with a compound of formula (6) to give a compound of formula (9). The reaction may be performed under conditions described for the analogous reaction described in Scheme 3.

Scheme 8

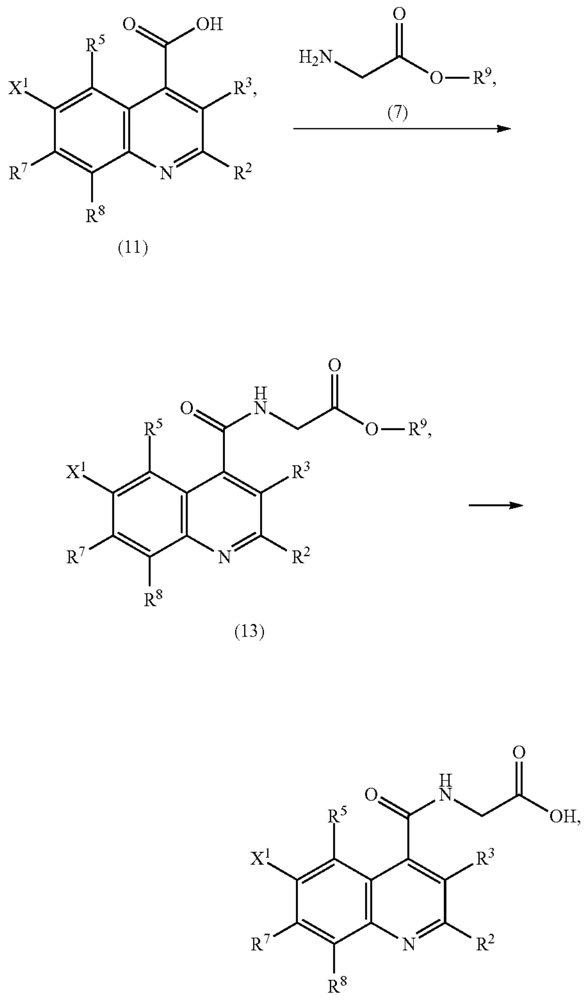

(11)

(13)

(12)

Scheme 8 illustrates a synthetic route to certain compounds of formula (12). A compound of formula (11) may be reacted with a compound of formula (7) to give a compound of formula (13). A compound of formula (12) may be formed from a compound of formula (13). The reactions may be performed under conditions described for the analogous reactions described in Scheme 4.

Scheme 9

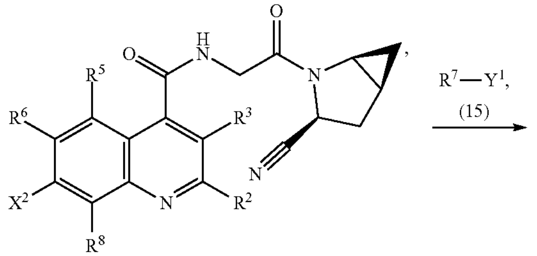

(14)

-continued

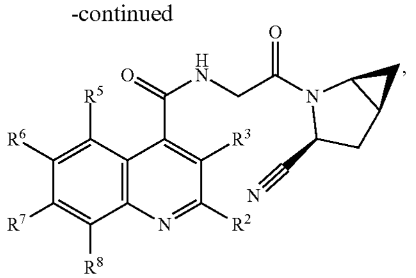

(I)

Scheme 9 illustrates synthetic routes to certain compounds of Formula (I). A compound of formula (14) may be transformed into a compound of Formula (I) by reaction with alkylzinc reagents of formula (15), wherein $R^7$ is as defined in Formula (I) group (b) and (c), and $Y^1$ is a mono-alkyl or halide derivative of zinc (such as diethylzinc, etc.). The reaction may be catalyzed by a Pd-catalyst (such as $PdCl_2$(dppf)·DCM, etc.) in a suitable solvent (such as 1,4-dioxane, THF, etc.) at a temperature ranging from typically 20° C. to reflux.

Alternatively, a compound of formula (14) may be transformed into a compound of Formula (I) by reaction with alkylboron reagents of formula (15), wherein $R^7$ is as defined in Formula (I) group (b) and (c) and $Y^1$ is boron, or a derivative thereof (such as trimethylboroxine, etc.). The reaction may be catalyzed by a Pd-catalyst (such as $PdCl_2$(dppf)·DCM, etc.) in the presence of a base (such as $K_2CO_3$, $Na_2CO_3$, etc.) in a suitable solvent (such as 1,4-dioxane, THF, etc.) at a temperature ranging from typically 20° C. to reflux.

Alternatively, a compound of formula (14) may be transformed into a compound of Formula (I) by reaction with an alkyl halide of formula (15), wherein $R^7$ is as defined in Formula (I) group (b) and (c), and $Y^1$ is a halogen, typically an alkyl bromide. The reaction may be catalyzed with a Ni-catalyst (such as $NiCl_2$·DCM, etc.) and a suitable ligand (such as bbbpy, etc.), as well as a suitable photoredox catalyst (such as $Ir[dF(CF_3)ppy]_2(dtbbpy)PF_6$, etc.) in the presence of $HSi(SiMe_3)_3$ and a base (such as $Na_2CO_3$, etc.) in a suitable solvent (such as DME, etc.), typically at 20° C. while irradiated with blue light LED.

Alternatively, a compound of formula (14) may be transformed into a compound of Formula (I) by reaction with an alcohol of formula (15), wherein $R^7$ is as defined in Formula (I) group (d) and (e), and $Y^1$ is a hydrogen. The reaction may be catalyzed with a suitable Pd-reagent (such as $Pd(OAc)_2$, etc.) with a suitable phosphine ligand (such as XPhos, t-BuXPhos, etc.) in the presence of a base (such as $K_3PO_4$, etc.) in a suitable solvent (such as toluene, 1,4-dioxane, etc.) and performed at elevated temperatures.

Alternatively, a compound of formula (14) may be transformed into a compound of Formula (I) by reaction with an alcohol of formula (15), wherein $R^7$ is as defined in Formula (I) group (d) and (e), and $Y^1$ is a hydrogen. The reaction may be promoted with a suitable Cu-reagent (such as CuBr, etc.) in the presence of a base (such as $K_2CO_3$, $Cs_2CO_3$, etc.) and a radical initiator (such as AIBN, etc.) in a suitable solvent (such as DMF, etc.) and performed at elevated temperatures.

Alternatively, a compound of formula (14) may be transformed into a compound of Formula (I) by reaction with an alcohol of formula (15), wherein $R^7$ is as defined in Formula (I) group (d) and (e), and $Y^1$ is a hydrogen. The reaction may be catalyzed with a Ni-catalyst (such as $NiCl_2$·DCM, etc.)

and a suitable ligand (such as bbbpy, etc.), as well as a suitable photoredox catalyst (such as $Ir[dF(CF_3)ppy]_2(dtbbpy)PF_6$, etc.) in the presence of quinuclidine and a base (such as $K_2CO_3$, etc.) in a suitable solvent (such as acetonitrile, etc.), typically at 20° C. while irradiated with blue light LED.

Scheme 10

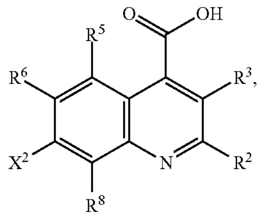

(16)

+

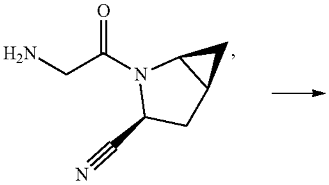

(3)

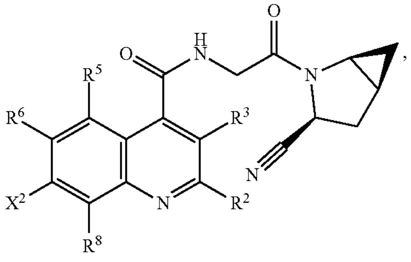

(14)

Scheme 10 illustrates a synthetic route to certain compounds of formula (14). A compound of formula (14) may be formed from compounds of formula (16) and formula (3). The reaction may be performed under conditions described for the analogous reaction described in Scheme 1.

Scheme 11

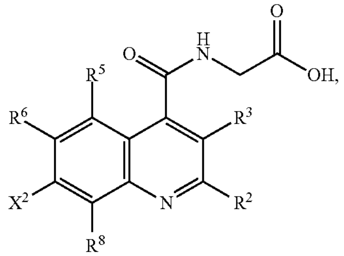

(17)

+

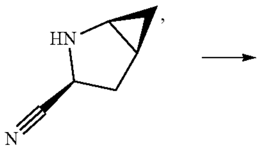

(6)

-continued

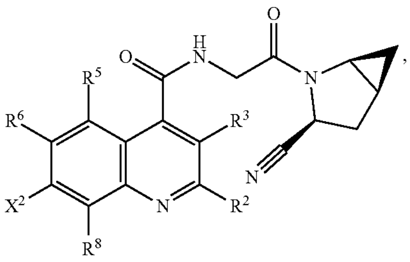

(14)

Scheme 11 illustrates a synthetic route to certain compounds of formula (14). A compound of formula (14) may be formed from compounds of formula (17) and formula (6). The reaction may be performed under conditions described for the analogous reaction described in Scheme 3.

Scheme 12

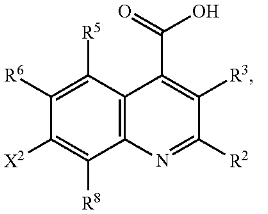

(16)

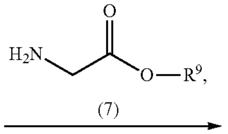

(7)

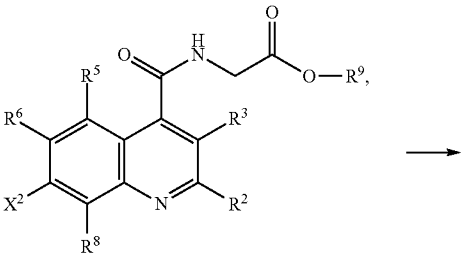

(18)

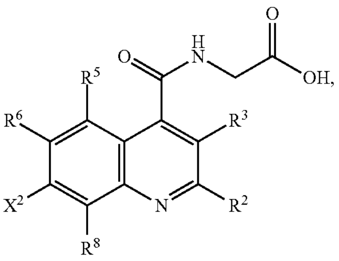

(17)

Scheme 12 illustrates a synthetic route to certain compounds of formula (17). A compound of formula (16) may be reacted with a compound of formula (7) to give a compound of formula (18). A compound of formula (17) may be formed from a compound of formula (18). The reactions may be performed under conditions described for the analogous reactions described in Scheme 4.

Scheme 13

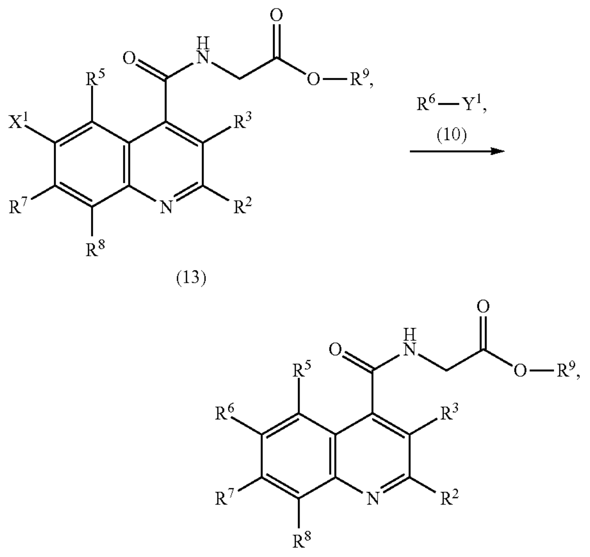

(13)
(8)

Scheme 13 illustrates synthetic routes to certain compounds of formula (8). A compound of formula (13) may be transformed into a compound of formula (8) by reaction with compounds of formula (10), wherein $R^6$ is as defined in Formula (I) group (b) (c), (d) and (e) and $Y^1$ is as defined in Scheme 5. The reactions may be performed under conditions described for the analogous reactions described in Scheme 5.

Scheme 14

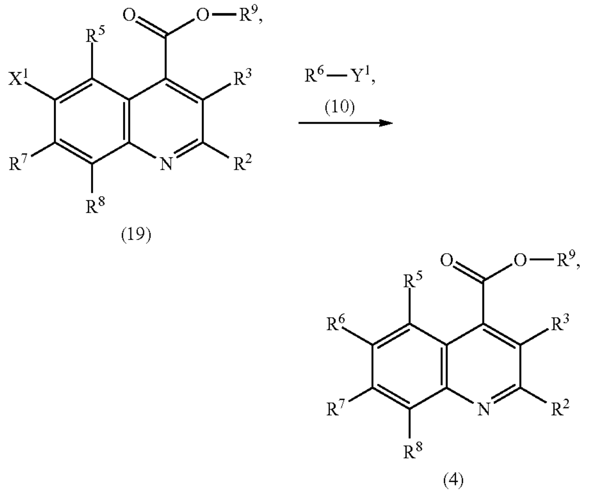

(19)
(4)

Scheme 14 illustrates synthetic routes to certain compounds of formula (4). A compound of formula (19) may be transformed into a compound of formula (4) by reaction with compounds of formula (10), wherein $R^6$ is as defined in Formula (I) group (b) (c), (d) and (e) and $Y^1$ is as defined in Scheme 5. The reactions may be performed under conditions described for the analogous reactions described in Scheme 5.

Scheme 15

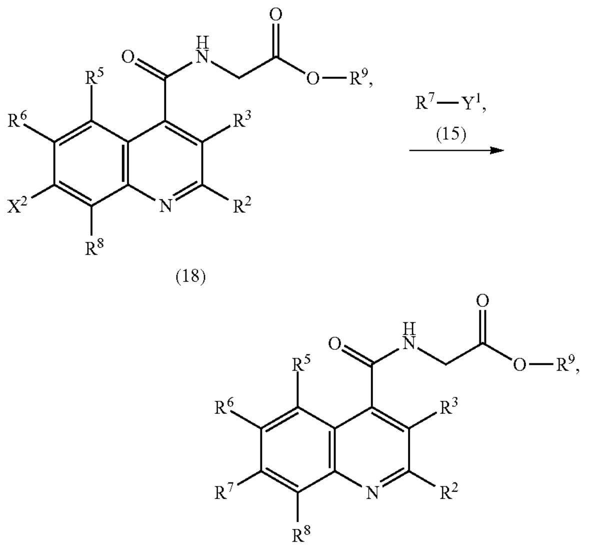

(18)
(8)

Scheme 15 illustrates synthetic routes to certain compounds of formula (8). A compound of formula (18) may be transformed into a compound of formula (8) by reaction with compounds of formula (15), wherein $R^7$ is as defined in Formula (I) group (b) (c), (d) and (e) and $Y^1$ is as defined in Scheme 9. The reactions may be performed under conditions described for the analogous reactions described in Scheme 9.

Scheme 16

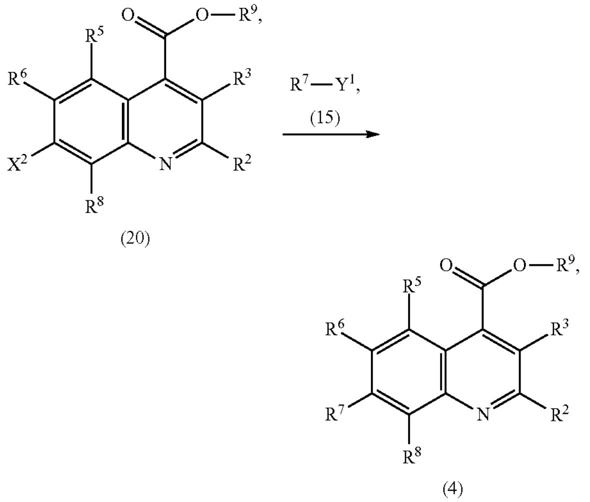

(20)
(4)

Scheme 16 illustrates synthetic routes to certain compounds of formula (4). A compound of formula (20) may be transformed into a compound of formula (4) by reaction with compounds of formula (15), wherein $R^7$ is as defined in Formula (I) group (b) (c), (d) and (e) and $Y^1$ is as defined in Scheme 9. The reactions may be performed under conditions described for the analogous reactions described in Scheme 9.

Scheme 17

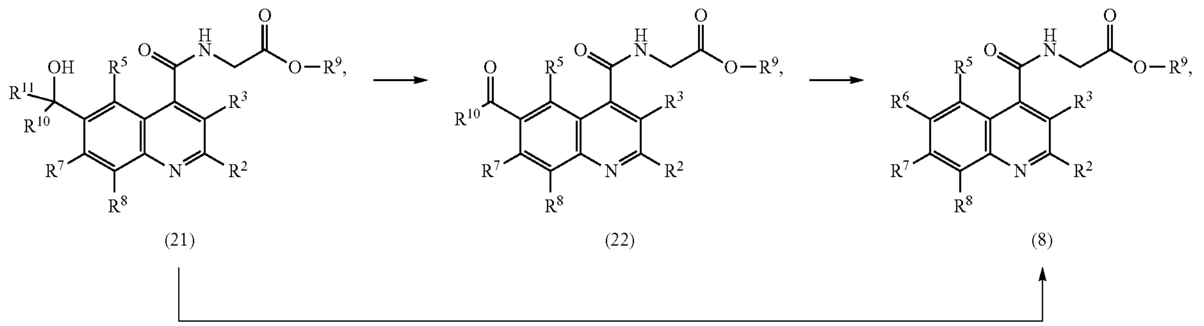

Scheme 17 illustrates a synthetic route to certain compounds of formula (8). A compound of formula (22) in which $R^{10}$ is a hydrogen or alkyl may be formed from a compound of formula (21) in which $R^{10}$ is a hydrogen or alkyl, and $R^{11}$ is a hydrogen, by reaction with an oxidation reagent (such as Dess-Martin periodinane, etc.). The reaction may be performed in a suitable solvent (such as DCM, etc.), typically at temperatures ranging from 0° C. to 40° C.

A compound of formula (8) in which $R^6$ is as defined in Formula (I) group (b) may be formed by reacting a compound of formula (22) with a fluorinating reagent (such as DAST, etc.) in a suitable solvent (such as DCM, THF, etc.) at temperatures ranging from typically 0° C. to 60° C.

Alternatively, a compound of formula (8) in which $R^6$ is as defined in Formula (I) group (b) may be formed from a compound of formula (22) by reduction with a reducing agent (such as sodium borohydride, etc.). The reaction may be performed in a solvent (such as methanol, etc.) at a temperature typically ranging from 0° C. to 40° C.

Alternatively, a compound of formula (8) in which $R^6$ is as defined in Formula (I) group (b) may be formed from a compound of formula (22) by reaction with a Grignard reagent (such as $CH_3MgCl$, $CH_3MgBr$, etc.). The reaction may be performed in a suitable solvent (such as diethyl ether, THF, etc.) at a temperature typically ranging from −78° C. to 40° C.

Alternatively, a compound of formula (8) in which $R^6$ is as defined in Formula (I) group (b) may be formed by reacting a compound of formula (21) with a fluorinating reagent (such as DAST, etc.) in a suitable solvent (such as DCM, THF, etc.) at temperatures ranging from typically 0° C. to 60° C.

Alternatively, a compound of formula (8) in which $R^6$ is as defined in Formula (I) group (b) may be formed by reacting a compound of formula (21) with (trifluoromethyl) trimethylsilane. The reaction may be performed in the presence of KF, AgOTf, Selectfluor, and 2-fluoropyridine, in a suitable solvent (such as EtOAc, etc.) at temperatures ranging from typically 0° C. to 25° C.

Alternatively, a compound of formula (8) in which $R^6$ is as defined in Formula (I) group (b) may be formed from a compound of formula (21) by reaction with an alkyl halide (such as MeI, etc.) or another alkylating agent (such as an alkyl sulfonate, alkyl triflate, etc.). The reaction may be performed using a base (such as NaH, etc.) in a suitable solvent (such as THF, DMF, etc.) at temperatures ranging from typically 0° C. to 25° C.

Scheme 18

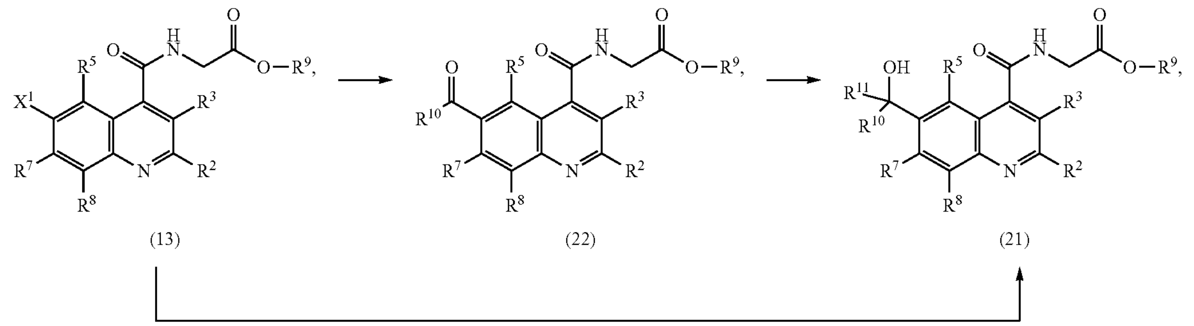

Scheme 18 illustrates synthetic routes to certain compounds of formula (21). A compound of formula (22) in which $R^{10}$ is alkyl (such as methyl, etc.) may be formed by reacting a compound of formula (13) with a trialkyl(1-alkoxyvinyl)tin reagent (such as tributyl(1-ethoxyvinyl)tin, etc.). The reaction may be catalyzed by a Pd-reagent (such as $PdCl_2(dppf)\cdot DCM$, $Pd(PPh_3)_4$, etc.) in a suitable solvent (such as toluene, 1,4-dioxane, etc.) and at a temperature ranging from typically 80° C. to reflux.

Alternatively, a compound of formula (22) in which $R^{10}$ is a hydrogen may be formed by reacting a compound of formula (13) with formic acid and acetic acid anhydride. The reaction may be performed with a Pd-reagent (such as $Pd(OAc)_2$, etc.) with a suitable ligand (such as butyl-1-adamantylphosphine, etc.) with $NaHCO_3$ and TEA, in a suitable solvent (such as DMF, etc.) and at a temperature ranging from typically 80° C. to 120° C.

A compound of formula (21) in which $R^{10}$ and $R^{11}$ are hydrogen may be formed by reacting a compound of formula (13) with a (trialkylstannyl)methanol reagent (such as (tributylstannyl)methanol, etc.). The reaction may be catalyzed by a Pd-reagent (such as $PdCl_2$(dppf)·DCM, $Pd(PPh_3)_4$, etc.) in a suitable solvent (such as toluene, 1,4-dioxane, etc.) and at a temperature ranging from typically 80° C. to reflux.

Alternatively, a compound of formula (21) in which $R^{10}$ is alkyl and $R^{11}$ is a hydrogen may be formed from a compound of formula (22) by reduction with a reducing agent (such as sodium borohydride, etc.). The reaction may be performed in a solvent (such as methanol, etc.) at a temperature typically ranging from 0° C. to 40° C.

Alternatively, a compound of formula (21) in which $R^{10}$ and $R^{11}$ are alkyl may be formed from a compound of formula (22) by reaction with a Grignard reagent (such as $CH_3MgCl$, $CH_3MgBr$, etc.). The reaction may be performed in a suitable solvent (such as diethyl ether, THF, etc.) at a temperature typically ranging from −78° C. to 40° C.

Scheme 19

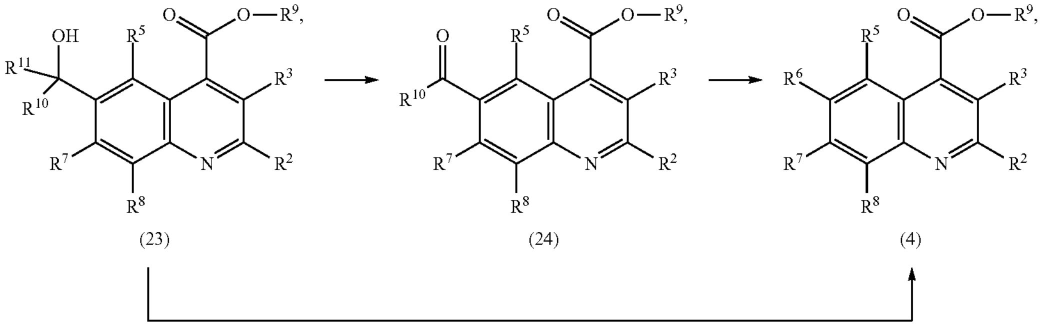

Scheme 19 illustrates a synthetic route to certain compounds of formula (4). A compound of formula (4) in which $R^6$ is as defined in Formula (I) group (b) may be formed from a compound of formula (23) or formula (24), wherein $R^{10}$ and $R^{11}$ are as defined in Scheme 17. The reactions may be performed under conditions described for the analogous reactions described in Scheme 17.

Scheme 20

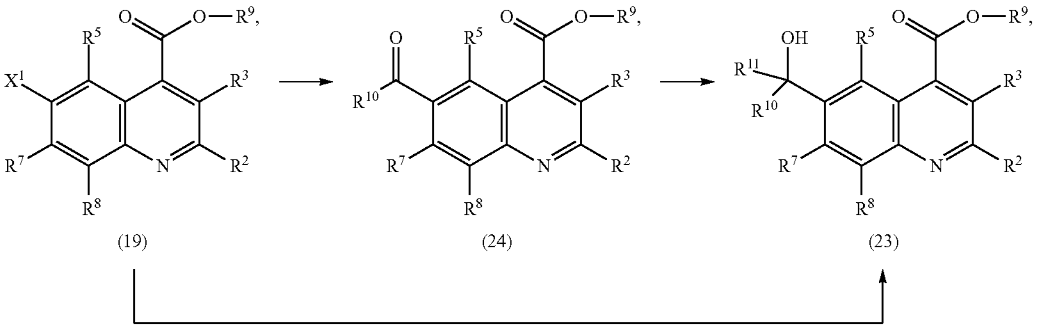

Scheme 20 illustrates synthetic routes to certain compounds of formula (23). A compound of formula (23) may be formed from a compound of formula (19) or formula (24), wherein $R^{10}$ and $R^{11}$ are as defined in Scheme 18. The reactions may be performed under conditions described for the analogous reactions described in Scheme 18.

Scheme 21

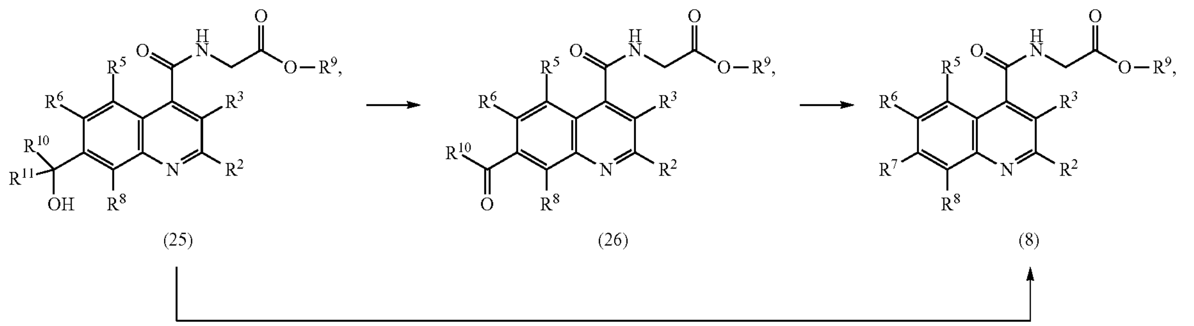

(25) (26) (8)

Scheme 21 illustrates synthetic routes to certain compounds of formula (8). A compound of formula (8) in which $R^7$ is as defined in Formula (I) group (b) may be formed from a compound of formula (25) or formula (26) wherein $R^{10}$ and $R^{11}$ are as defined in Scheme 17. The reactions may be performed under conditions described for the analogous reactions described in Scheme 17.

Scheme 22

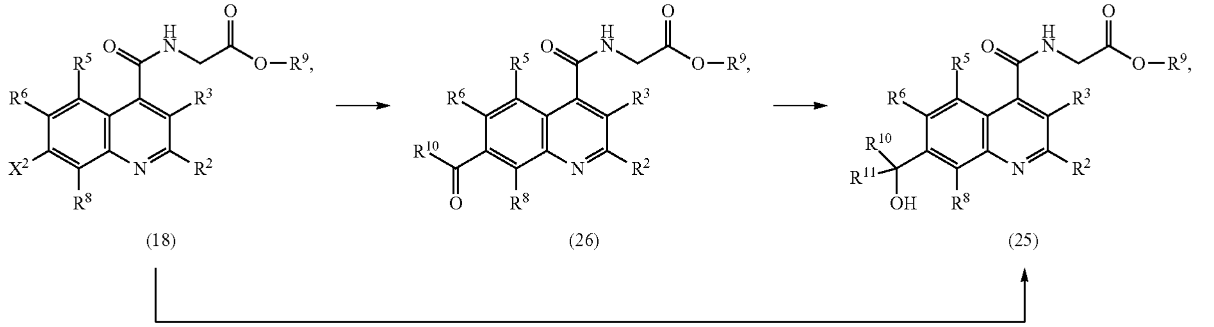

(18) (26) (25)

Scheme 22 illustrates synthetic routes to certain compounds of formula (25). A compound of formula (25) may be formed from a compound of formula (18) or formula (26), wherein $R^{10}$ and $R^{11}$ are as defined in Scheme 18. The reactions may be performed under conditions described for the analogous reactions described in Scheme 18.

Scheme 23

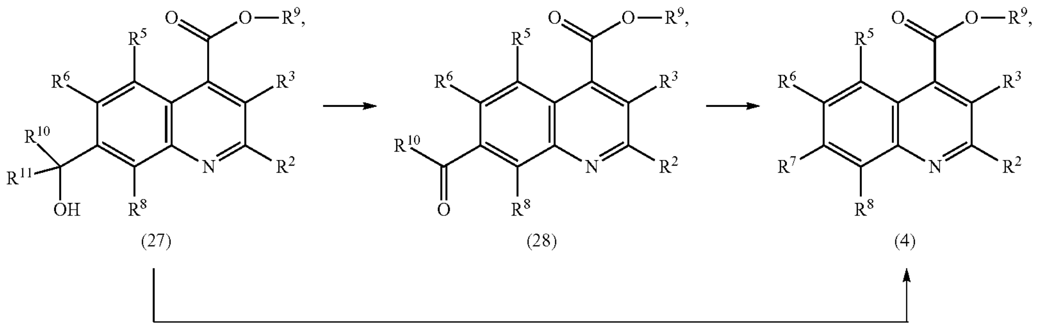

(27) (28) (4)

Scheme 23 illustrates synthetic routes to certain compounds of formula (4). A compound of formula (4) in which $R^7$ is as defined in Formula (I) group (b) may be formed from a compound of formula (27) or (28), wherein $R^{10}$ and $R^{11}$ are as defined in Scheme 17. The reactions may be performed under conditions described for the analogous reactions described in Scheme 17.

Scheme 24

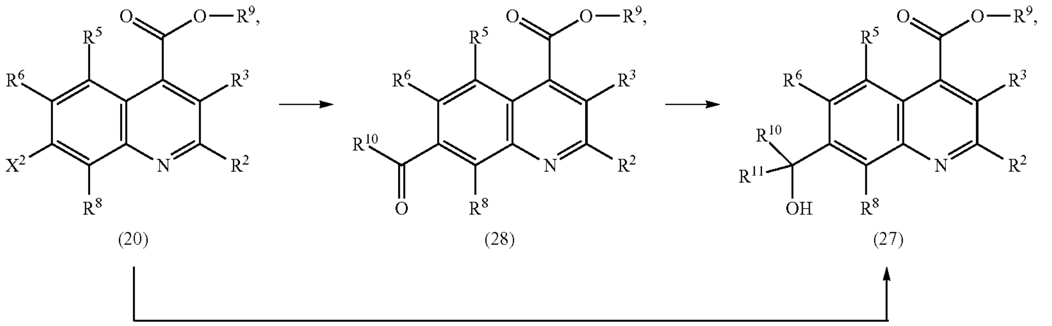

(20) (28) (27)

Scheme 24 illustrates synthetic routes to certain compounds of formula (27). A compound of formula (27) may be formed from a compound of formula (20) or (28), wherein $R^{10}$ and $R^{11}$ are as defined in Scheme 18. The reactions may be performed under conditions described for the analogous reactions described in Scheme 18.

Scheme 25

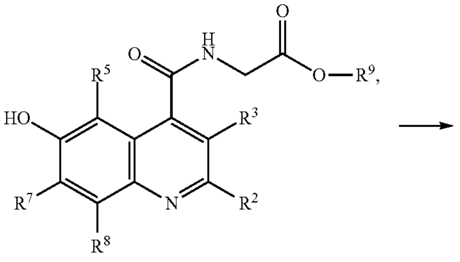

(29)

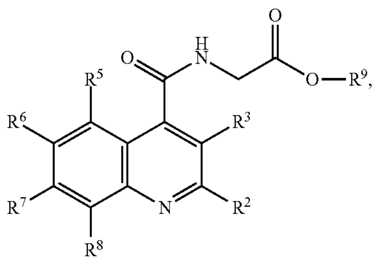

(8)

Scheme 25 illustrates synthetic routes to certain compounds of formula (8). A compound of formula (29) may be transformed into a compound of formula (8), wherein $R^6$ is as defined in Formula (I) group (d) and (e) by reaction with an alkyl halide, alkyl sulfonate, or an alkyl triflate. The reaction may be promoted by a base (such as NaOH, $K_2CO_3$, etc.) in a suitable solvent (such as DMF, etc.) and at a temperature ranging from typically 20° C. to reflux.

Scheme 26

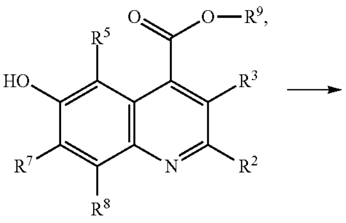

(30)

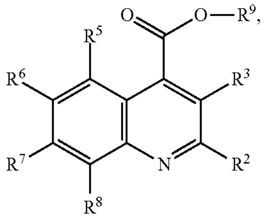

(4)

Scheme 26 illustrates synthetic routes to certain compounds of formula (4). A compound of formula (4) wherein $R^6$ is as defined in Formula (I) group (d) and (e) may be formed from a compound of formula (30). The reactions may be performed under conditions described for the analogous reaction described in Scheme 25.

Scheme 27

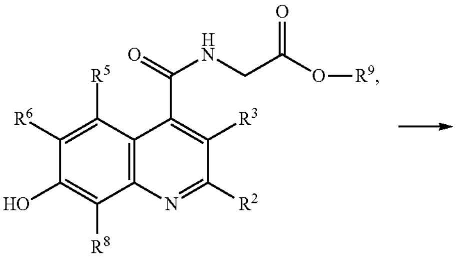

(31)

-continued

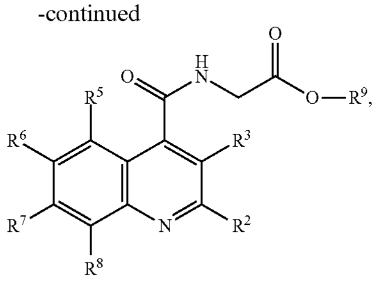

(8)

Scheme 27 illustrates synthetic routes to certain compounds of formula (8). A compound of formula (8) wherein $R^7$ is as defined in Formula (I) group (d) and (e) may be formed from a compound of formula (31). The reactions may be performed under conditions described for the analogous reaction described in Scheme 25.

Scheme 28

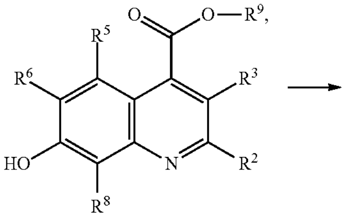

(32)

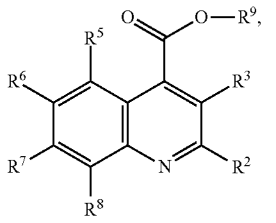

(4)

Scheme 28 illustrates synthetic routes to certain compounds of formula (4). A compound of formula (4) wherein $R^7$ is as defined in Formula (I) group (d) and (e) may be formed from a compound of formula (32). The reactions may be performed under conditions described for the analogous reaction described in Scheme 25.

Scheme 29

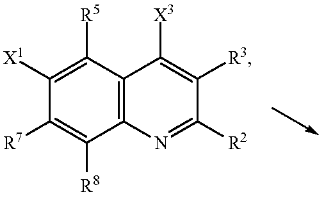

(33)

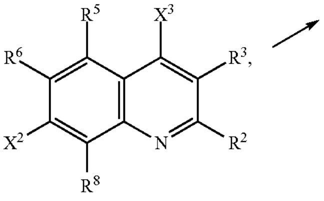

(34)

-continued

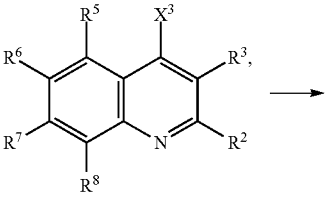

(35)

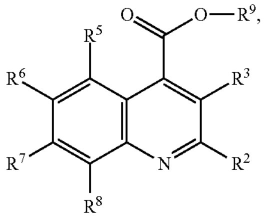

(4)

Scheme 29 illustrates synthetic routes to certain compounds of formula (4). A compound of formula (35) wherein $R^6$ and $R^7$ are as defined in Formula (I) may be formed from either a compound of formula (33) or from a compound of formula (34) using synthetic methodology performed under conditions described for the analogous reactions described in Schemes 5, 9, 17, and 18.

A compound of formula (4) may be formed by reacting a compound of formula (35) with carbon monoxide, typically at a pressure of 10 atm at a temperature ranging from typically 80° C. to 120° C. in a sealed vessel. The reaction may be catalyzed with a suitable Pd-reagent (such as $Pd(dppf)Cl_2DCM$, etc.) in the presence of a base (such as TEA, etc.) in the presence of a suitable alcohol (such as MeOH, EtOH, etc.) in a suitable solvent, or using the alcohol as solvent.

Scheme 30

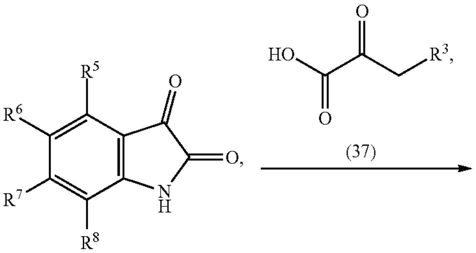

(36)

(37)

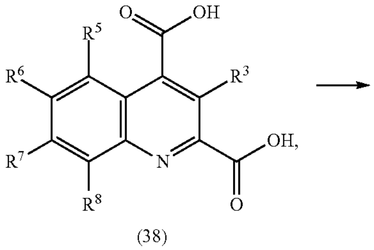

(38)

-continued

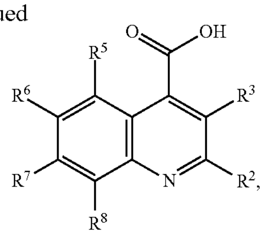

(2)

Scheme 30 illustrates a synthetic route to certain compounds of formula (2). A compound of formula (38) may be formed by reacting a compound of formula (36) with a 2-ketocarboxylic acid of formula (37), or a salt thereof (such as a sodium salt, etc.), in the presence of a base (such as NaOH, etc.) in water at reflux temperature, or at elevated temperatures ranging from typically 100° C. to 160° C. in a sealed vessel, or in a sealed tube in a microwave reactor.

A compound of formula (2) may be formed by heating a compound of formula (38), either neat, or in a suitable solvent (such as water, etc.) at elevated temperatures ranging from typically 150° C. to 250° C. in a sealed vessel, or in sealed tube in a microwave oven.

It should be understood that: (i) the organic reactions described in this disclosure are performed according to laboratory practice known to person skilled in the art; (ii) some of the reactions described in this disclosure may optionally be performed in different orders than laid out herein; (iii) chiral isomers of compounds in this disclosure can be resolved at any stage in the synthetic process using chiral resolving agents described in the literature and known to person skilled in the art, using chiral chromatography methods described in the literature and known to person skilled in the art, or as otherwise described further in the Examples; (iv) additional and/or other protective groups may optionally be needed in some of the steps described above; and (v) deprotection steps therefore optionally may be performed using methods described in the literature and known to person skilled in the art. The protection and deprotection of functional groups are described, for example, in "*Protective Groups in Organic Synthesis*" $3^{rd}$ Ed, T. W. Greene and P. G. M. Wutz, Wiley-Interscience (1999), which publication is incorporated herein by reference.

VIII. EXAMPLES

The following descriptions of experiments, procedures, examples, and intermediates are intended to exemplify embodiments of the disclosure. They are in no way intended to be limiting. Other compounds of this disclosure may be prepared using the methods illustrated in these examples, either alone or in combination with techniques generally known in the art.

A. General Conditions

Unless otherwise stated:

(i) operations were carried out at room temperature (rt), i.e., in the range 17 to 25° C., and under an atmosphere of an inert gas such as $N_2$;

(ii) where reactions refer to the use of a microwave reactor, one of the following microwave reactors was used: Biotage Initiator, Personal Chemistry Emrys Optimizer, Personal Chemistry Smith Creator, or CEM Explorer;

(iii) where reactions refer to the use of irradiation with LED, a commercial, standardized EvoluChem™ PhotoRedOx Box Photoreactor from HepatoChem equipped with a Kessil H150 blue LED (456 nm, 34 W) or a commercial standardized Photoreactor m2 from Penn Photon Devices equipped with a LED module (365 nm) was used;

(iv) in general, the course of reactions was followed by thin layer chromatography (TLC) and/or analytical high performance liquid chromatography (HPLC or UPLC) which was usually coupled to a mass spectrometer (LCMS);

(v) when necessary, organic solutions were dried over anhydrous $MgSO_4$ or $Na_2SO_4$, or by using ISOLUTE® Phase Separator, and work-up procedures were carried out using traditional phase separating techniques;

(vi) evaporations were carried out either by rotary evaporation in vacuo or in a Genevac HT-4/EZ-2 or Biotage V10;

(vii) unless otherwise stated, flash column chromatography was performed on straight phase silica, using either Merck Silica Gel (Art. 9385) or prep-packed cartridges such as Biotage® SNAP cartridges (40-63 m silica, 4-330 g), Biotage® Sfar Silica HC D cartridges (20 μm, 10-100 g), Interchim puriFlash™ cartridges (25 μm, 4-120 g), Interchim puriFlash™ cartridges (50 μm, 25-330 g), Grace™ GraceResolv™ Silica Flash Cartridges (4-120 g), or Agela Flash Colum Silica-CS cartridges (80-330 g), or on reversed phase silica using Agela Technologies C-18, spherical cartridges (20-35 μm, 100 A, 80-330 g), manually or automated using a Grace Reveleris®x2 Flash system or similar system;

(viii) preparative reverse phase HPLC and preparative reverse phase SFC were performed using standard HPLC and SFC instruments, respectively, equipped with either a MS and/or UV triggered fraction collecting instrument, using either isocratic or a gradient of the mobile phase as described in the experimental section, and one of the following methods as described below:

HPLC Prep Methods: PrepMethod A: The compound was purified by preparative HPLC on a Kromasil $C_8$ column (10 μm, 250×50 mm ID) using a gradient of MeCN in $H_2O$/MeCN/FA (95/5/0.2) as mobile phase; PrepMethod B: The compound was purified by preparative HPLC on a XSelect CSH OBD column (5 μm, 150×30 mm ID) using a gradient of MeCN in $H_2O$/TFA (0.05%) as mobile phase; PrepMethod C: The compound was purified by preparative HPLC on a XSelect CSH OBD column (5 μm, 150×30 mm ID) using a gradient of MeCN in $H_2O$/FA (0.1%) as mobile phase; PrepMethod D: The compound was purified by preparative SFC on a Waters™ BEH 2-EP column (5 μm, 250×30 mm ID) using MeOH/$H_2O$ ($NH_3$ 20 mM) in $CO_2$ as mobile phase; PrepMethod E: The compound was purified by preparative SFC on a Phenomenex Luna Hilic column (5 μm, 250×30 mm ID) using MeOH/$H_2O$ ($NH_3$ 20 mM) in $CO_2$ as mobile phase; PrepMethod F: The compound was purified by preparative HPLC on a XBridge™ OBD C18 column (5 μm, 150×30 mm ID) using a gradient of MeCN in $H_2O$/$NH_3$ (0.05%) as mobile phase; PrepMethod G: The compound was purified by preparative HPLC on a Atlantis Prep T3 OBD column (10 μm, 250×19 mm ID)

using a gradient of MeCN in $H_2O$/TFA (0.05%) as mobile phase; PrepMethod H: The compound was purified by preparative HPLC on a XBridge™ OBD C18 column (5 μm, 250×19 mm ID) using a gradient of MeCN in $H_2O$/FA (0.1%) as mobile phase; PrepMethod I: The compound was purified by preparative HPLC on a XBridge™ OBD C18 column (5 μm, 150×30 mm ID) using a gradient of MeCN in $H_2O$/FA (0.1%) as mobile phase; PrepMethod J: The compound was purified by preparative HPLC on a XBridge™ OBD C18 column (5 μm, 250×19 mm ID) using a gradient of MeCN in $H_2O/NH_3$ (0.05%) as mobile phase; PrepMethod K: The compound was purified by preparative HPLC on a XBridge™ C18 OBD column (5 μm, 150×19 mm ID) using a gradient of MeCN in a $H_2O/NH_4HCO_3$ (10 mM)/$NH_3$ (0.1%, aq) buffer system as mobile phase; PrepMethod L: The compound was purified by preparative HPLC on a XBridge™ C18 OBD column (5 μm, 150×30 mm ID) using a gradient of MeCN in a $H_2O/NH_4HCO_3$ (10 mM) as mobile phase; PrepMethod M: The compound was purified by preparative HPLC on a XBridge™ C18 OBD column (5 μm, 250×19 mm ID) using a gradient of MeCN in a $H_2O/NH_4HCO_3$ (10 mM)/$NH_3$ (0.1%, aq) buffer system as mobile phase; PrepMethod N: The compound was purified by preparative HPLC on a XBridge™ C18 OBD column (5 μm, 150×30 mm ID) using a gradient of MeCN in a $H_2O/NH_4HCO_3$ (10 mM)/$NH_3$ (0.1%, aq) buffer system as mobile phase; PrepMethod O: The compound was purified by preparative SFC on a Waters™ Acquity UPC2 BEH 2-EP column, (3.5 μm, 100×3 mm ID) using MeOH/$H_2O$ ($NH_3$ 20 mM) in $CO_2$ as mobile phase; PrepMethod P: The compound was purified by preparative SFC on a Waters™ BEH column (5 μm, 250×30 mm ID) using MeOH/$H_2O$ ($NH_3$ 20 mM) in $CO_2$ as mobile phase; PrepMethod R: The compound was purified by preparative HPLC on a Waters™ Sunfire™ C18 OBD column (5 μm, 150×30 mm ID) using a gradient of MeCN in $H_2O$/FA (0.1 M) as mobile phase; PrepMethod S: The compound was purified by preparative HPLC on a XBridge™ OBD C18 column (5 μm, 150×30 mm ID) using a gradient of MeCN in $H_2O$ (pH 10) as mobile phase; and PrepMethod T: The compound was purified by preparative SFC on a CHIRAL ART amylose-SA, (5 μm, 250×20 mm ID) using MeOH/$H_2O$ in $CO_2$ as mobile phase;

Relevant fractions were collected, combined, and freeze-dried to give the purified compound, or relevant fractions were collected, combined, and concentrated at reduced pressure, extracted with DCM or EtOAc, and the organic phase was dried either over $Na_2SO_4$ or by using a phase-separator, and then concentrated at reduced pressure to give the purified compound;

(ix) chiral preparative chromatography was carried out using HPLC or SFC on a standard HPLC or SFC instruments, respectively, and using either isocratic or gradient run with mobile phase as described in the experimental section;

(x) yields, where present, are not necessarily the maximum attainable, and when necessary, reactions were repeated if a larger amount of the reaction product was required;

(xi) where certain compounds were obtained as an acid-addition salt (for example, a mono-hydrochloride salt or a di-hydrochloride salt), the stoichiometry of the salt was based on the number and nature of the basic groups in the compound, the exact stoichiometry of the salt was generally not determined, for example by means of elemental analysis data;

(xii) in general, the structures of the end-products of the Formula (I) were confirmed by nuclear magnetic resonance (NMR) and/or mass spectral techniques; proton NMR chemical shift values were measured on the delta scale using Bruker Avance III 300, 400, 500 and 600 spectrometers, operating at $^1H$ frequencies of 300, 400, 500 and 600 MHz, respectively. The experiments were typically recorded at 25° C. Chemical shifts are given in ppm with the solvent as internal standard. Protons on heteroatoms such as NH and OH protons are only reported when detected in NMR and can therefore be missing. In certain instances, protons can be masked or partially masked by solvent peaks and will therefore either be missing and not reported or reported as multiplets overlapping with solvent. The following abbreviations have been used (and derivatives thereof, e.g., dd, doublet of doublets, etc.): s, singlet; d, doublet; t, triplet; q, quartet; m, multiplet; br, broad; qn, quintet; and p, pentet. In some cases, the structures of the end-products of the Formula (I) might appear as rotamers in the NMR-spectrum, in which instances only peaks of the major rotamer are reported. Electrospray mass spectral data were obtained using a Waters Acquity UPLC coupled to a Waters single quadrupole mass spectrometer or similar equipment, acquiring both positive and negative ion data, and generally, only ions relating to the parent structure are reported; high resolution electrospray mass spectral data were obtained using a Waters XEVO qToF mass spectrometer or similar equipment, coupled to a Waters Acquity UPLC, acquiring either positive and negative ion data, and generally, only ions relating to the parent structure are reported;

(xiii) intermediates were not necessarily fully purified but their structures and purity were assessed by TLC, analytical HPLC/UPLC, and/or NMR analysis and/or mass spectrometry;

(xiv) unless stated otherwise, compounds containing an asymmetric carbon and/or sulfur atom were not resolved;

(xv) in general, Examples and Intermediate compounds are named using ChemDraw Professional version 19.0.0.22 or 20.0.2.51 from PerkinElmer. ChemDraw Professional version 19.0.0.22 and 20.0.2.51 generates the names of chemical structures using the Cahn-Ingold-Prelog (CIP) rules for stereochemistry and follows IUPAC rules as closely as possible when generating chemical names. Stereoisomers are differentiated from each other by stereodescriptors cited in names and assigned in accordance with the CIP rules.

ChemDraw is optionally using labels in the graphical representation of stereocenters such as '&' and 'or' to describe the configuration of the stereochemical centers present in the structure. In general, chemical structures of Examples and Intermediates containing the label '&' at a stereocenter means the configuration of such Example or Intermediate at that stereocenter is a mixture of both (R) and (S); and a label 'or' means the configuration of such Example or Intermediate at that stereocenter is either (S) or (R). Absolute, unspecified, '&', and 'or' stereocenters can all be present in a single structure.

In general, for structures of Examples and Intermediates where all of the stereocenters are designated as '&', the structure is named with a "rac-" prefix. For structures of Examples and Intermediates where all of the stereocenters are designated as 'or', the structure is named with a "rel-" prefix.

In general, Examples and Intermediate compounds are named using the descriptors (RS) and (SR) to denote general '&' centers for chemical structures with multiple chiral centers where only some are designated as '&'. The descriptors (R*) and (S*) are used to denote the general 'or' centers for chemical structures with multiple chiral centers where only some are designated as 'or'.

In general, the descriptors (r) and (s) are used to describe the absolute configuration of any pseudo-asymmetric centers in the structures of Examples and Intermediates.

In general, the label "Isomer 1" corresponds to the first eluted isomer, and "Isomer 2" corresponds to the second eluted isomer, on a given chiral TIPLC column and eluent, and are used to distinguish two isomers containing one or more stereocenters with absolute unknown configuration at one or more stereocenters;

(xvi) where reactions refer to being degassed or purged, this can be performed for example by purging the reaction solvent with a constant flow of nitrogen for a suitable period of time (for example, 5 to 10 min);

(xvii) where reactions refer to applying an evacuate-refill cycle, this can be performed by evacuating the reaction vessel by applying vacuum to the reaction vessel and then refilling with an inert gas, typically $N_2$ or Argon. The process is generally repeated, typically three times; and (xvii) in addition to the ones mentioned above, the following abbreviations have been used:

| | | | |
|---|---|---|---|
| AgOTf | Silver trifluoromethane-sulfonate | $Ir[dF(CF_3)ppy]_2(dtbbpy)PF_6$ | [4,4'-Bis(1,1-dimethylethyl)-2,2'-bipyridine-N1,N1']bis-[3,5-difluoro-2-[5-(trifluoromethyl)-2-pyridinyl-N]phenyl-C]Iridium(III) hexafluorophosphate CAS Number 870987-63-6 |
| AIBN | 2,2'-Azobis(2-methyl-propionitrile), 2-(azo(1-cyano-1-methylethyl))-2-methylpropane nitrile | LC | liquid chromatography |
| Ala | alanine | LED | light emitting diode |
| AMC | 7-amino-4-methylcoumarin | MeCN | acetonitrile |
| Aq | aqueous | MeI | Methyl iodide |
| bbbpy | 4,4'-di-tert-butyl-2,2'-dipyridyl | MeOH | methanol |
| Bis(pinacolato) diboron | 4,4,4',4',5,5,5',5'-octamethyl-2,2'-bi-(1,3,2-dioxaborolane) | MS | mass spectrometry |
| BSA | bovine serum albumin | MW | molecular weight |
| t-BuXPhos | di-tert-butyl(2',4',6'-triisopropyl-[1,1'-biphenyl]-2-yl)-phosphane | m/z | mass spectrometry peak(s) |
| calcd | calculated | $NiCl_2$•DME | Nickel(II) chloride 2-methoxyethyl ether complex |
| $CL_{int}$ | intrinsic clearance | NMR | nuclear magnetic resonance |
| Chaps | (3-((3-cholamidopropyl) dimethylammonio)-1-propanesulfonate) | OTf | triflate |
| CR | concentration response | $P_{app}$ | apparent permeability coefficient |
| DAST | diethylaminosulfur trifluoride | PBS | phosphate buffered saline |
| DCM | dichloromethane | PCR | polymerase chain reaction |
| Dess-Martin periodinane | 3-oxo-1$\lambda^5$-benzo[d][1,2]iodaoxole-1,1,1(3H)-triyl triacetate | $Pd_2(dba)_3$•$CHCl_3$ | (tris(dibenzylideneacetone) dipalladium(0) chloroform adduct |
| DIPEA | N-ethyl-N-isopropyl-propan-2-amine | $Pd(dppf)Cl_2$•DCM | 1,1'-Bis(diphenylphosphino)-ferrocenedichloropalladium (II) complex with dichloromethane (1:1) |
| DME | dimethyl ether | $Pd(OAc)_2$ | Palladium(II) acetate |
| DMF | N,N-dimethylformamide | $Pd(PPh_3)_4$ | Tetrakis(triphenylphosphine) palladium(0) |
| DMSO | dimethyl sulfoxide | PK | pharmacokinetics |
| dtbbpy | 4-tert-butyl-2-(4-tert-butylpyridin-2-yl)-pyridine | PREP | prolyl oligopeptidase |
| EDC | 3-(ethylimino-methylene-amino)-N,N-dimethyl-propan-1-amine; hydrochloride | Pro | proline |
| ESI | electrospray ionization | Quinuclidine | 1-azabicyclo[2.2.2]octane |
| EtOAc | ethyl acetate | $RhCl(PPh_3)_3$ | tris(triphenylphosphine) rhodium(I) chloride [CAS Number 14694-95-2] |
| EtOH | ethanol | rt | room temperature |

-continued

| | | | |
|---|---|---|---|
| $Et_2Zn$ | diethyl zinc | RU | response unit |
| FA | formic acid | sat | saturated |
| FAC | final assay concentration | SD | standard deviation |
| FAP | prolyl endopeptidase fibroblast activation protein | Selectfluor | 1-(chloromethyl)-4-fluoro-1,4-diazabicyclo[2.2.2]-octane-1,4-diium tetrafluoroborate |
| (g) | gas | SFC | supercritical fluid chromatography |
| gly | glycine | TBAF | tetra-n-butylammonium fluoride |
| HATU | (1-(Bis(dimethylamino)-methylene]-1H-1,2,3-triazolo[4,5-b]-pyridinium-3-oxo hexafluoro-phosphate | TCEP | tris(2-carboxyethyl)-phosphine hydrochloride |
| hDPP7 | human dipeptidylpeptidase VII | TEA | triethylamine |
| hDPP8 | human dipeptidylpeptidase VIII | TFA | trifluoro acetic acid |
| hDPP9 | human dipeptidylpeptidase IX | THF | tetrahydrofuran |
| HEPES | (4-(2-hydroxyethyl)-1-piperazineethane-sulfonic acid) | TLC | thin layer chromatography |
| hFAP | human prolyl endopeptidase fibroblast activation protein | TMB | 2,4,6-trimethyl-1,3,5,2,4,6-trioxatriborinane |
| HFIP | 1,1,1,3,3,3-hexafluoro-propan-2-ol | T3P | propanephosphonic acid anhydride |
| his | histidine | Tris HCl | tris(hydroxymethyl)amino-methane hydrochloride |
| HOBt | 1-hydroxybenzotriazole; hydrate | Triton X-100 | t-octylphenoxypolyethoxy-ethanol |
| HPLC | high performance liquid chromatography | (Trimethylsilyl) acetonitrile | $(CH_3)_3SiCH_2CN$ |
| hPREP | human prolyl oligopeptidase | Tris(trimethylsilyl) silane | 1,1,1,3,3,3-hexamethyl-2-(trimethylsilyl)trisilane |
| HRMS | high resolution mass spectrometry | UPLC | ultra performance liquid chromatography |
| $HSi(SiMe_3)_3$ | 1,1,1,3,3,3-hexamethyl-2-(trimethylsilyl)-trisilane | UV | ultraviolet |
| $IC_{50}$ | half-maximum inhibitory concentration | XantPhos | (9,9-dimethyl-9H-xanthene-4,5-diyl)bis(diphenyl-phosphane) |
| ID | inter diameter | XPhos | Dicyclohexyl[2',4',6'-tris(propan-2-y1)[1,1'-biphenyl]-2-yl]phosphane |

| UNITS | |
|---|---|
| A | Angström |
| C | Celcius |
| DA | Dalton |
| g | gram |
| h | hour(s) |
| M | Molar |
| MHz | megahertz |
| mg | milligram |
| min | minute(s) |
| mL | milliliter |
| mm | millimeter |
| mmol | millimole |
| μL | microliter |
| μm | micrometer |
| μmol | micromole |
| nm | nanometer |
| rpm | revolution per minute |
| v/v | volume by volume |
| W | watt |

Intermediate 1: tert-Butyl (2-((1S,3S,5S)-3-cyano-2-azabicyclo[3.1.0]hexan-2-yl)-2-oxoethyl)carbamate

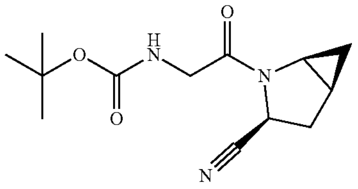 [SMILES: CC(C)(C)OC(=O)NCC(=O)N1[C@H](C#N)C[C@@H]2C[C@@H]21]

DIPEA (3.0 mL, 17 mmol) and HATU (2.28 g, 5.99 mmol) was added to a solution of (tert-butoxycarbonyl) glycine (1.0 g, 5.7 mmol) in DMF (17.2 mL) at 0° C. and the reaction mixture was stirred at rt for 15 min. A solution of (1S,3S,5S)-2-azabicyclo[3.1.0]hexane-3-carbonitrile 4-methylbenzenesulfonate WO2007029086 (1.6 g, 5.7 mmol) in DMF (11.5 mL) was added and the reaction mixture was stirred at rt overnight. The reaction mixture was diluted with EtOAc and the organic phase was washed sequentially with 1 M citric acid (aq, containing 0.5 mL brine) and 1 M citric acid (aq), then three times with sat $NaHCO_3$ (aq). The organic phase was dried using a phase separator and evaporated in vacuo. The crude product was purified by straight phase flash chromatography on silica (gradient: 10-100% EtOAc in heptane). The compound containing fractions were collected, concentrated in vacuo and purified by straight phase flash chromatography on silica (gradient: 0-100% EtOAc in heptane) to give the title compound (1.24 g, 82%): $^1$H NMR (400 MHz, $CD_3OD$) δ 5.03 (dd, 1H), 4.22-4.12 (m, 1H), 3.99 (d, 1H), 3.66 (s, 1H), 2.71-2.54 (m, 1H), 2.31 (dd, 1H), 1.97-1.80 (m, 1H), 1.46 (s, 9H), 1.11-0.98 (m, 1H), 0.98-0.82 (m, 1H).

Intermediate 2: (1S,3S,5S)-2-Glycyl-2-azabicyclo[3.1.0]hexane-3-carbonitrile 4-methylbenzene-sulfonate

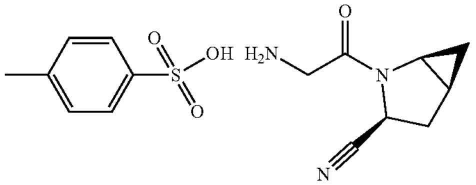

tert-Butyl (2-((1S,3S,5S)-3-cyano-2-azabicyclo[3.1.0]hexan-2-yl)-2-oxoethyl)carbamate Intermediate 1 (1.24 g, 4.67 mmol) was dissolved in MeCN (12 mL) and the reaction mixture was cooled on an ice-bath. 4-Methylbenzenesulfonic acid hydrate (1.24 g, 6.54 mmol) was added and the reaction mixture was stirred at 0° C. for 15 min and then allowed to attain rt and stirred at rt for 29 h. The reaction mixture was evaporated in vacuo and the residue was twice suspended in DCM and evaporated to give a brown beige meringue. The residue was suspended in cold EtOAc, while kept on an ice-bath. The solids were allowed to settle and the EtOAc was removed using a pasteur pipette. The solids were suspended once more in cold EtOAc, allowed to settle, and the organic phase was removed. The solids were dried in vacuo to give the title compound (1.51 g) as a beige foam: MS (ESI) m/z $[M+H]^+$ 166.2.

Intermediate 3: (1S,3S,5S)-2-Glycyl-2-azabicyclo[3.1.0]hexane-3-carbonitrile hydrochloride

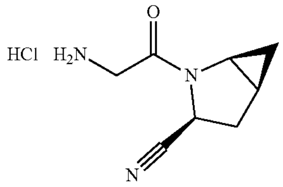 [SMILES: Cl ; N#C[C@@H]1C[C@@H]2C[C@@H]2N1C(=O)CN]

12 M HCl (aq, 1.13 mL, 13.6 mmol) was added to a solution of tert-butyl (2-((1S,3S,5S)-3-cyano-2-azabicyclo[3.1.0]hexan-2-yl)-2-oxoethyl)carbamate Intermediate 1 (1.2 g, 4.5 mmol) in MeOH (10.2 mL) and the clear colorless solution was stirred at rt for 20 h. The reaction mixture was concentrated in vacuo to give the title compound (0.80 g, 88%) as a beige foam; $^1$H NMR (500 MHz, $CD_3OD$) δ 5.11 (dd, 1H), 4.26-3.97 (m, 2H), 3.65 (td, 1H), 2.68 (ddd, 1H), 2.35 (dd, 1H), 1.97 (dq, 1H), 1.12-1.04 (m, 1H), 0.98-0.90 (m, 1H).

Intermediate 4: (1S,3S,5S)-2-Glycyl-2-azabicyclo[3.1.0]hexane-3-carbonitrile

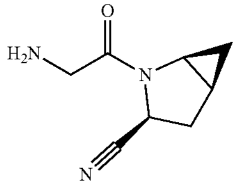 [SMILES: N#C[C@@H]1C[C@@H]2C[C@@H]2N1C(=O)CN]

tert-Butyl (2-((1S,3S,5S)-3-cyano-2-azabicyclo[3.1.0]hexan-2-yl)-2-oxoethyl)carbamate Intermediate 1 (3.0 g, 11 mmol) and TFA (0.87 mL, 11 mmol) were dissolved in DCM (300 mL) and the reaction mixture was stirred at 20° C. for 2 h. The reaction mixture was concentrated in vacuo and the crude product was purified by reversed phase flash chromatography on a C18 column (gradient: 0-50% MeCN in water) to give the title compound (1.50 g, 80%); MS (ESI) m/z $[M+H]^+$ 166; $^1$H NMR (300 MHz, $CD_3OD$) δ 5.12 (dd, 1H), 4.21 (d, 1H), 4.05 (d, 1H), 3.65 (td, 1H), 2.78-2.62 (m, 1H), 2.38 (dd, 1H), 1.99 (dq, 1H), 1.18-0.89 (m, 2H).

Intermediate 5: tert-Butyl (6-bromoquinoline-4-carbonyl)glycinate

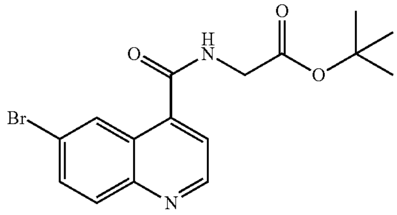 [SMILES: CC(C)(C)OC(=O)CNC(=O)c1ccnc2ccc(Br)cc12]

DIPEA (2.08 mL, 11.9 mmol) was added to a mixture of 6-bromoquinoline-4-carboxylic acid (1.0 g, 4.0 mmol), tert-butyl glycinate hydrochloride (0.80 g, 4.8 mmol), EDC (0.913 g, 4.76 mmol) and HOBt (0.729 g, 4.76 mmol) in DMF (10 mL) at 20° C. and the reaction mixture was stirred at 20° C. for 16 h. The reaction mixture was quenched with sat $NaHCO_3$ (aq, 20 mL) and water (20 mL) and the suspension was filtered. The solid was washed with water and dried under vacuum to give the title compound (1.40 g, 97%); MS (ESI) m/z $[M+H]^+$ 365/367.

Intermediate 6: (6-Bromoquinoline-4-carbonyl)glycine

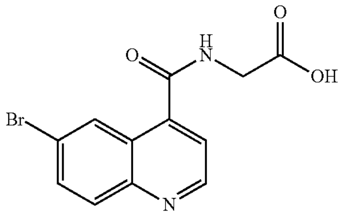 [SMILES: O=C(O)CNC(=O)c1ccnc2ccc(Br)cc12]

TFA (1.0 mL, 13 mmol) was added to a solution of tert-butyl (6-bromoquinoline-4-carbonyl)glycinate Intermediate 5 (0.25 g, 0.68 mmol) in DCM (1 mL) at 20° C. and the reaction mixture was stirred at 20° C. for 4 h. The solvent was removed under reduced pressure. The residue was dissolved in water and basified with sat $NaHCO_3$ (aq) to pH=5-6. The reaction mixture was filtered, and the solid was washed with water and dried under vacuum to give the title compound (0.130 g, 61%); MS (ESI) m/z $[M+H]^+$ 309/311.

Intermediate 7: tert-Butyl (7-bromoquinoline-4-carbonyl)glycinate

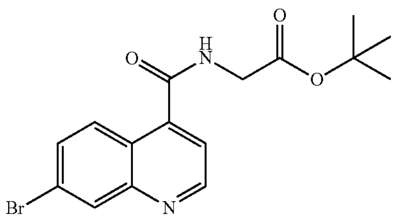 [SMILES: CC(C)(C)OC(=O)CNC(=O)c1ccnc2cc(Br)ccc12]

A solution of 7-bromoquinoline-4-carboxylic acid (4.50 g, 17.9 mmol), tert-butyl glycinate hydrochloride (4.49 g, 26.8 mmol), EDC (5.13 g, 26.8 mmol), HOBt (3.62 g, 26.8 mmol) and DIPEA (9.35 mL, 53.6 mmol) in THE (80 mL) was stirred at 30° C. for 15 h. The solvent was removed under reduced pressure and the reaction mixture was diluted with EtOAc (80 mL). The organic phase was washed sequentially with sat $NaHCO_3$ (aq, 2×35 mL), and water (35 mL). The organic layer was dried over $Na_2SO_4$, filtered and evaporated. The crude product was purified by straight phase flash chromatography on silica (gradient: 5-55% EtOAc in petroleum ether) to give the title compound (6.0 g, 92%); MS (ESI) m/z $[M+H]^+$ 365.

Intermediate 8: (7-Bromoquinoline-4-carbonyl)glycine

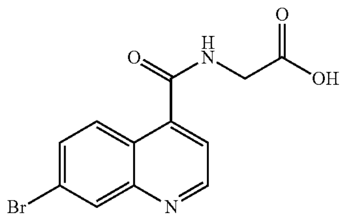 [SMILES: O=C(O)CNC(=O)c1ccnc2cc(Br)ccc12]

TFA (40.5 mL, 526 mmol) was added to a solution of tert-butyl (7-bromoquinoline-4-carbonyl)glycinate Intermediate 7 (1.20 g, 3.29 mmol) in DCM (5 mL), and the reaction mixture was stirred at rt for 2 h. The solvent was removed under reduced pressure to give the title compound (1.0 g, 98%); MS (ESI) m/z $[M+H]^+$ 311.

Intermediate 9: tert-Butyl (6-(trifluoromethyl)quinoline-4-carbonyl)glycinate

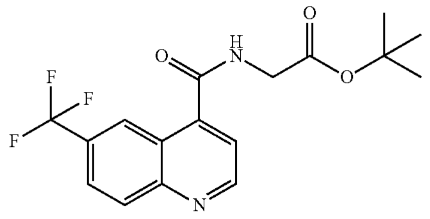 [SMILES: CC(C)(C)OC(=O)CNC(=O)c1ccnc2ccc(C(F)(F)F)cc12]

DIPEA (0.39 mL, 2.2 mmol) was added to a suspension of 6-(trifluoromethyl)quinoline-4-carboxylic acid (0.18 g, 0.75 mmol), tert-butyl glycinate hydrochloride (0.15 g, 0.90 mmol), EDC (0.215 g, 1.12 mmol) and HOBt (0.171 g, 1.12 mmol) in DMF (2 mL), and the reaction mixture was stirred at 20° C. for 4 h. The reaction mixture was quenched with sat $NaHCO_3$ (aq, 20 mL), and the reaction mixture was filtered. The solid was dried under vacuum to give the title compound (0.220 g, 83%); MS (ESI) m/z $[M+H]^+$ 335.

Intermediate 10: (6-(Trifluoromethyl)quinoline-4-carbonyl)glycine

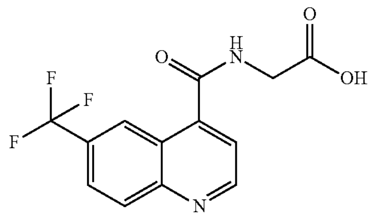 [SMILES: O=C(O)CNC(=O)c1ccnc2ccc(C(F)(F)F)cc12]

TFA (0.478 mL, 6.21 mmol) was added to a solution of tert-butyl (6-(trifluoromethyl)quinoline-4-carbonyl)glycinate Intermediate 9 (220 mg, 0.62 mmol) in DCM (1 mL) at 0° C., and the reaction mixture was stirred at 20° C. for 4 h. The solvent was removed under reduced pressure to give the crude title compound (120 mg); MS (ESI) m/z $[M+H]^+$ 299.

Intermediate 11: tert-Butyl (6-(hydroxymethyl)quinoline-4-carbonyl)glycinate

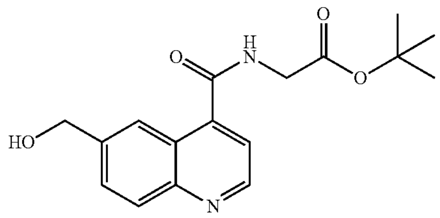 [SMILES: CC(C)(C)OC(=O)CNC(=O)c1ccnc2ccc(CO)cc12]

(Tributylstannyl)methanol (0.527 g, 1.64 mmol) was added to a mixture of tert-butyl (6-bromoquinoline-4-carbonyl)glycinate Intermediate 5 (0.50 g, 1.4 mmol) and $Pd(PPh_3)_4$ (0.158 g, 0.14 mmol) in degassed 1,4-dioxane (5 mL) at 20° C. and under an atmosphere of $N_2$ (g), and the reaction mixture was stirred at 80° C. for 18 h. The reaction was quenched with water (20 mL), and the mixture was extracted with EtOAc (3×20 mL). The combined organic layer was dried over $Na_2SO_4$, filtered and evaporated at reduced pressure. The residue was purified by preparative TLC (DCM:MeOH, 10:1) to give the title compound (0.350 g, 81%) as a pale yellow oil; MS (ESI) m/z $[M+H]^+$ 317.

Intermediate 12: tert-Butyl (6-(fluoromethyl)quinoline-4-carbonyl)glycinate

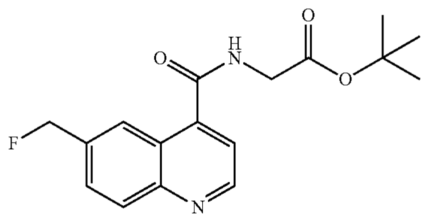 [SMILES: CC(C)(C)OC(=O)CNC(=O)c1ccnc2ccc(CF)cc12]

DAST (0.125 mL, 0.95 mmol) was added to a solution of tert-butyl (6-(hydroxymethyl)quinoline-4-carbonyl)glycinate Intermediate 11 (0.15 g, 0.47 mmol) in DCM (3 mL) and the reaction mixture was stirred at 18° C. for 4 h. The solvent was removed under reduced pressure and the residue was purified by preparative TLC (DCM:MeOH, 10:1) to give the title compound (0.077 g, 51%) as an orange gum; MS (ESI) m/z $[M+H]^+$ 319.

Intermediate 13: (6-(Fluoromethyl)quinoline-4-carbonyl)glycine

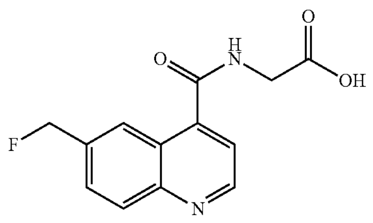 [SMILES: O=C(O)CNC(=O)c1ccnc2ccc(CF)cc12]

4 M HCl in 1,4-dioxane (1.20 mL, 4.84 mmol) was added dropwise to tert-butyl (6-(fluoromethyl)quinoline-4-carbonyl)glycinate Intermediate 12 (77 mg, 0.24 mmol) at 20° C. and under an atmosphere of $N_2$ (g), and the reaction mixture was stirred at 20° C. for 20 h. The solvent was removed under reduced pressure and the crude product was dissolved in MeOH (2 mL) and water (0.67 mL). LiOH (30 mg, 1.3 mmol) was added to the reaction mixture and it was stirred at 20° C. for 4 h. The solvent was removed under reduced pressure, and the residue was dissolved in water (5 mL), and the mixture was acidified with 3 M HCl (aq) to pH 6-7. The aqueous layer was washed with DCM and then concentrated in vacuo to give the crude title compound (103 mg); MS (ESI) m/z $[M+H]^+$ 263.

Intermediate 14: tert-Butyl (6-acetylquinoline-4-carbonyl)glycinate

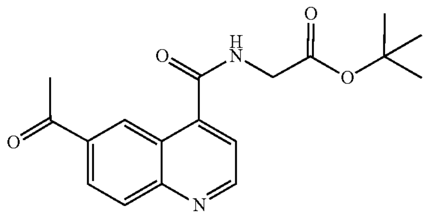 [SMILES: CC(=O)c1ccc2nccc(C(=O)NCC(=O)OC(C)(C)C)c2c1]

Tributyl(1-ethoxyvinyl)stannane (0.593 g, 1.64 mmol) was added to a mixture of tert-butyl (6-bromoquinoline-4-carbonyl)glycinate Intermediate 5 (0.50 g, 1.4 mmol) and $Pd(dppf)Cl_2$·DCM (0.112 g, 0.14 mmol) in degassed toluene (5 mL) at 20° C. and under an atmosphere of $N_2$ (g), and the reaction mixture was stirred at 100° C. for 18 h. The reaction mixture was diluted with MeCN (5 mL). 6 M HCl (aq, 0.1 mL) was added and the reaction mixture was stirred for 20 min. The reaction was quenched with water (15 mL) and extracted with EtOAc (3×15 mL). The combined organic layer was dried over $Na_2SO_4$, filtered and evaporated at reduced pressure. The residue was purified by preparative TLC (DCM:MeOH, 10:1), to give the title compound (0.430 g, 96%) as an orange gum; MS (ESI) m/z $[M+H]^+$ 329.

Intermediate 15: tert-Butyl (6-(2-hydroxypropan-2-yl)quinoline-4-carbonyl)glycinate

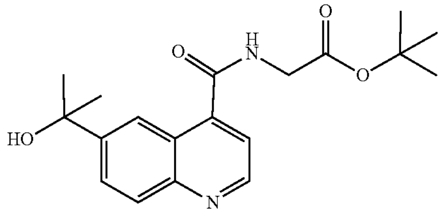 [SMILES: CC(C)(C)OC(=O)CNC(=O)c1ccnc2ccc(C(C)(C)O)cc12]

$CH_3MgCl$ in THE (3 M in THF, 0.51 mL, 1.5 mmol) was added to a solution of tert-butyl (6-acetylquinoline-4-carbonyl)glycinate Intermediate 14 (0.20 g, 0.61 mmol) in THE (5 mL) at 0° C. and under an atmosphere of $N_2$ (g), and the reaction mixture was stirred at 0° C. for 3 h. The reaction was quenched with sat $NH_4Cl$ (aq, 20 mL), and extracted with DCM (3×20 mL). The combined organic layer was dried over $Na_2SO_4$, filtered and evaporated at reduced pressure. The residue was purified by preparative TLC (DCM:MeOH, 10:1), to give the title compound (0.070 g, 33%) as an orange gum; MS (ESI) m/z $[M+H]^+$ 345.

Intermediate 16: tert-Butyl (6-(2-fluoropropan-2-yl) quinoline-4-carbonyl)glycinate

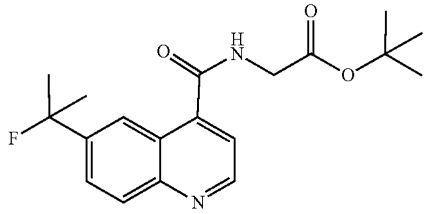 [SMILES: CC(C)(C)OC(=O)CNC(=O)c1ccnc2ccc(C(C)(C)F)cc12]

DAST (0.153 mL, 1.16 mmol) was added to a solution of tert-butyl (7-(2-hydroxypropan-2-yl)quinoline-4-carbonyl) glycinate Intermediate 15 (100 mg, 0.29 mmol) in DCM (2 mL) at 19° C., and the reaction mixture was stirred at 20° C. for 19 h. The solvent was removed under reduced pressure and the residue was purified by preparative TLC (DCM: MeOH, 10:1), to give the title compound (30 mg, crude) as a pale yellow gum; MS (ESI) m/z $[M+H]^+$ 347.

Intermediate 17: (6-(2-Fluoropropan-2-yl)quinoline-4-carbonyl)glycine

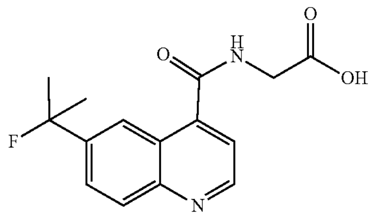 [SMILES: CC(C)(F)c1ccc2nccc(C(=O)NCC(=O)O)c2c1]

TFA (0.267 mL, 3.46 mmol) was added to a solution of crude tert-butyl (6-(2-fluoropropan-2-yl)quinoline-4-carbonyl)glycinate Intermediate 16 (30 mg) in DCM (0.5 mL) at 20° C., and the reaction mixture was stirred at 20° C. for 4 h. The solvent was removed under reduced pressure, and the residue was dried under vacuum to give the crude title compound (30 mg) as orange gum; MS (ESI) m/z $[M+H]^+$ 291.

Intermediate 18: (6-(2-Hydroxypropan-2-yl)quinoline-4-carbonyl)glycine

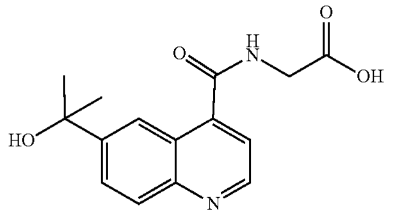 [SMILES: CC(C)(O)c1ccc2nccc(C(=O)NCC(=O)O)c2c1]

TFA (0.215 mL, 2.79 mmol) was added to a solution of tert-butyl (7-(2-hydroxypropan-2-yl)quinoline-4-carbonyl) glycinate Intermediate 15 (48 mg, 0.14 mmol) in DCM (0.5 mL) at 20° C., and the reaction mixture was stirred at 20° C. for 3 h. The solvent was removed under reduced pressure, and the residue was dried under vacuum to give the crude title compound (50 mg, 89%) as pale orange gum; $^1H$ NMR (400 MHz, $CD_3OD$) δ 9.12 (d, 1H), 8.62 (d, 1H), 8.31 (dd, 1H), 8.19 (d, 1H), 7.93 (d, 1H), 4.26 (s, 2H), 1.67 (s, 6H).

Intermediate 19: tert-Butyl (6-(1-hydroxyethyl)quinoline-4-carbonyl)glycinate

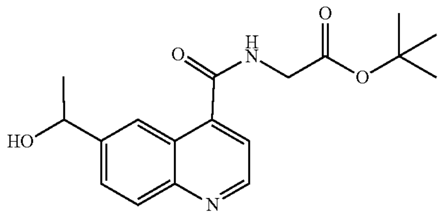 [SMILES: CC(O)c1ccc2nccc(C(=O)NCC(=O)OC(C)(C)C)c2c1]

$NaBH_4$ (42 mg, 1.1 mmol) was added to a solution of tert-butyl (6-acetylquinoline-4-carbonyl)glycinate Intermediate 14 (120 mg, 0.37 mmol) in THE (1 mL) and the reaction mixture was stirred at 20° C. for 4 h. The reaction was quenched with water (10 mL) and extracted with EtOAc (3×10 mL). The combined organic layer was dried over $Na_2SO_4$, filtered and concentrated in vacuo and the residue was purified by preparative TLC (DCM:MeOH, 10:1) to give the title compound (90 mg, 74%); MS (ESI) m/z $[M+H]^+$ 331.

Intermediate 20: (6-(1-Hydroxyethyl)quinoline-4-carbonyl)glycine

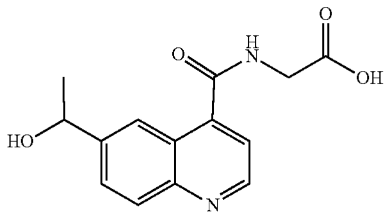 [SMILES: CC(O)c1ccc2nccc(C(=O)NCC(=O)O)c2c1]

TFA (0.117 mL, 1.51 mmol) was added to a solution of tert-butyl (6-(1-hydroxyethyl)quinoline-4-carbonyl)glycinate Intermediate 19 (100 mg, 0.30 mmol) in DCM (1 mL) and the reaction mixture was stirred at 20° C. for 4 h. The solvent was removed under reduced pressure to give the crude title compound (100 mg); MS (ESI) m/z $[M+H]^+$ 289.1.

Intermediate 21: Methyl 6-acetylquinoline-4-carboxylate

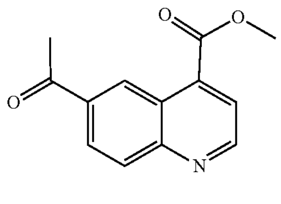 [SMILES: COC(=O)c1ccnc2ccc(C(C)=O)cc12]

Tributyl(1-ethoxyvinyl)stannane (1.63 g, 4.51 mmol) was added in one portion to a suspension of methyl 6-bromo-quinoline-4-carboxylate (0.80 g, 3.0 mmol) and Pd(dppf) $Cl_2$·DCM (0.22 g, 0.30 mmol) in toluene (10 mL) at 20° C. and under an atmosphere of $N_2$ (g), and the reaction mixture was stirred at 100° C. for 4 h. The reaction mixture was diluted with 4 M HCl in 1,4-dioxane and stirred at 20° C. for 30 min. The reaction mixture was concentrated in vacuo and the crude product was purified by preparative TLC (EtOAc: petroleum ether, 1:1), to give the title compound (610 mg, 89%); MS (ESI) m/z $[M+H]^+$ 229.

Intermediate 22: Methyl 6-(1-hydroxyethyl)quinoline-4-carboxylate

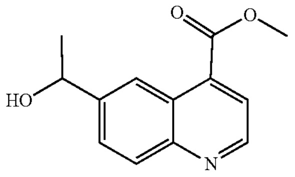 [SMILES: COC(=O)c1ccnc2ccc(C(C)O)cc12]

$NaBH_4$ (27 mg, 0.65 mmol) was added to a solution of methyl 6-acetylquinoline-4-carboxylate Intermediate 21 (300 mg, 1.31 mmol) in MeOH (5 mL), and the reaction mixture was stirred at 25° C. for 2 h. The reaction mixture was concentrated in vacuo and the crude product was purified by preparative TLC (EtOAc:pentane, 1:1) to give the title compound (200 mg, 66%); MS (ESI) m/z $[M+H]^+$ 232.

Intermediate 23: Methyl 6-(1-methoxyethyl)quinoline-4-carboxylate

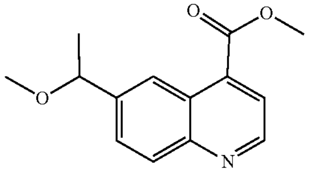

NaH (60% in oil, 42 mg, 1.0 mmol) was added to a solution of methyl 6-(1-hydroxyethyl)quinoline-4-carboxylate Intermediate 22 (120 mg, 0.52 mmol) in DMF (3 mL) at 0° C., and the reaction mixture was stirred at 0° C. for 10 min. $CH_3I$ (110 mg, 0.78 mmol) was added to the reaction mixture and it was stirred at 0° C. for 1 h. The solvent was removed under reduced pressure, and the residue was purified by preparative TLC (EtOAc:petroleum ether, 1:1), to give the title compound (80 mg, 63%); MS (ESI) m/z $[M+H]^+$ 246.

Intermediate 24: 6-(1-Methoxyethyl)quinoline-4-carboxylic acid

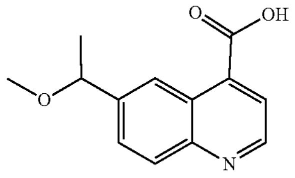 [SMILES: COC(C)c1ccc2nccc(C(=O)O)c2c1]

LiOH (12 mg, 0.49 mmol) was added to a solution of methyl 6-(1-methoxyethyl)quinoline-4-carboxylate Intermediate 23 (30 mg, 0.12 mmol) in MeOH (0.9 mL) and water (0.3 mL) and the reaction mixture was stirred at 20° C. for 3 h. The solvent was removed under reduced pressure and the residue was acidified with 2 M HCl (aq) to pH-6-7. The aqueous phase was washed with DCM, and concentrated in vacuo to give the crude title compound (30 mg); MS (ESI) m/z $[M+H]^+$ 232.

Intermediate 25: Methyl 6-(2-hydroxypropan-2-yl)quinoline-4-carboxylate

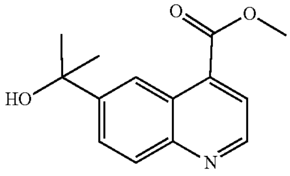 [SMILES: COC(=O)c1ccnc2ccc(C(C)(C)O)cc12]

$CH_3MgCl$ (3 M in THF, 0.87 mL, 2.6 mmol) was added dropwise to a solution of methyl 6-acetylquinoline-4-carboxylate Intermediate 21 (0.30 g, 1.3 mmol) in THE (3 mL) at 0° C. and under an atmosphere of $N_2$ (g), and the reaction mixture was stirred at 0° C. for 3 h. The reaction was quenched with sat $NH_4Cl$ (aq, 20 mL), and the mixture was extracted with DCM (3x20 mL). The combined organic layer was dried over $Na_2SO_4$, filtered and evaporated under reduced pressure. The residue was purified by preparative TLC (DCM:MeOH, 10:1), to give the title compound (0.20 g, 62%) as an orange gum; MS (ESI) m/z $[M+H]^+$ 246.

Intermediate 26: Methyl 6-(2-methoxypropan-2-yl)quinoline-4-carboxylate

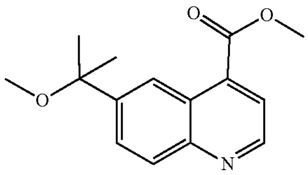

NaH (60% in oil, 24 mg, 0.61 mmol) was added to a solution of methyl 6-(2-hydroxypropan-2-yl)quinoline-4-carboxylate Intermediate 25 (100 mg, 0.41 mmol) in DMF (1 mL), and the reaction mixture was stirred at 20° C. for 30 min. $CH_3I$ (0.051 mL, 0.82 mmol) was added to the reaction mixture and it was stirred at rt for 16 h. An additional batch was prepared as described above using (70 mg, 0.29 mmol) of Intermediate 25. The reaction mixtures from both batches were combined and the reaction was quenched with water (10 mL) and extracted with EtOAc (3×10 mL). The combined organic layer was dried over $Na_2SO_4$, filtered and evaporated. The residue was purified by preparative TLC (DCM:MeOH, 10:1), to give the title compound (70 mg, 48%) as a brown gum; MS (ESI) m/z $[M+H]^+$ 260.1.

Intermediate 27: 6-(2-Methoxypropan-2-yl)quinoline-4-carboxylic acid

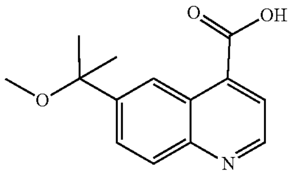 [SMILES: COC(C)(C)c1ccc2nccc(C(=O)O)c2c1]

LiOH (9 mg, 0.4 mmol) was added to a solution of methyl 6-(2-methoxypropan-2-yl)quinoline-4-carboxylate Intermediate 26 (50 mg, 0.19 mmol) in MeOH (0.9 mL) and water (0.3 mL) and the reaction mixture was stirred at 20° C. for 4 h. The reaction mixture was acidified with 2 M HCl (aq) to pH-5-6, and the reaction mixture was concentrated to dryness to give the crude title compound (60 mg); MS (ESI) m/z $[M+H]^+$ 246.

Intermediate 28: Methyl 6-(hydroxymethyl)quinoline-4-carboxylate

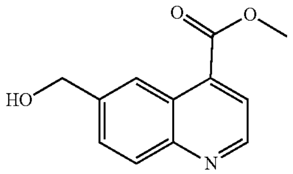 [SMILES: COC(=O)c1ccnc2ccc(CO)cc12]

(Tributylstannyl)methanol (1.45 g, 4.51 mmol) was added to a suspension of methyl 6-bromoquinoline-4-carboxylate (1.0 g, 3.8 mmol) and $Pd(PPh_3)_4$ (0.43 g, 0.38 mmol) in degassed toluene (25 mL) at 20° C. and under an atmosphere of $N_2$ (g), and the reaction mixture was stirred at 80° C. for 18 h. The solvent was removed under reduced pressure and the residue was purified by preparative TLC (EtOAc:pentane 3:2), to give the title compound (0.62 g, 76%); MS (ESI) m/z $[M+H]^+$ 218.

Intermediate 29: Methyl 6-((trifluoromethoxy) methyl)quinoline-4-carboxylate

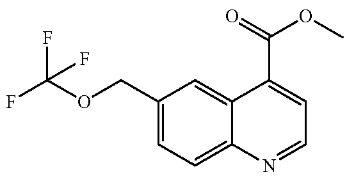 [SMILES: COC(=O)c1ccnc2ccc(COC(F)(F)F)cc12]

AgOTf (1.04 g, 4.05 mmol), Selectfluor (1.08 g, 3.04 mmol) and 2-fluoropyridine (393 mg, 4.05 mmol) were added to a solution of methyl 6-(hydroxymethyl)-quinoline-4-carboxylate Intermediate 28 (440 mg, 2.03 mmol), $(CH_3)_3SiCF_3$ (576 mg, 4.05 mmol) and KF (353 mg, 6.08 mmol) in EtOAc (9.4 mL) at 25° C., under an atmosphere of $N_2$ (g), and the reaction mixture was stirred at 25° C. for 12 h. The reaction mixture was concentrated in vacuo and the residue was purified by preparative TLC (EtOAc:petroleum ether, 1:2) to give the title compound (240 mg, 42%); MS (ESI) m/z $[M+H]^+$ 285.

Intermediate 30: 6-((Trifluoromethoxy)methyl)quinoline-4-carboxylic acid

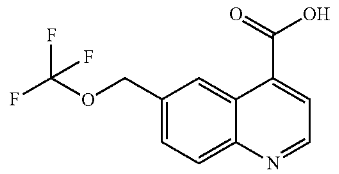 [SMILES: O=C(O)c1ccnc2ccc(COC(F)(F)F)cc12]

NaOH (194 mg, 4.84 mmol) was added to a solution of methyl 6-((trifluoromethoxy)methyl)-quinoline-4-carboxylate Intermediate 29 (230 mg, 0.81 mmol) in MeOH (4 mL) and water (1 mL) and the reaction mixture was stirred at 25° C. for 2 h. The reaction mixture was concentrated in vacuo and the residue was purified by preparative TLC (EtOAc: petroleum ether, 1:1) to give the title compound (170 mg, 78%); MS (ESI) m/z $[M+H]^+$271.

Intermediate 31: Methyl 7-acetylquinoline-4-carboxylate

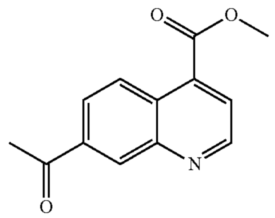 [SMILES: COC(=O)c1ccnc2cc(C(C)=O)ccc12]

$Pd(PPh_3)_4$ (1.18 g, 1.02 mmol) was added to a solution of methyl 7-bromoquinoline-4-carboxylate (2.72 g, 10.2 mmol) and tributyl(1-ethoxyvinyl)stannane (4.81 g, 13.3 mmol) in 1,4-dioxane (50 mL) under an atmosphere of $N_2$ (g) and the reaction mixture was stirred at 80° C. for 16 h. The reaction mixture was cooled and diluted with MeCN (20 mL). 2 M HCl (aq, 10 mL) was added and the reaction mixture was stirred for 30 min. The reaction mixture was poured into water (50 mL) and the mixture was extracted with EtOAc (3×60 mL). The combined organic phase was dried over $Na_2SO_4$, filtered and concentrated under reduced pressure. The crude product was purified straight phase flash chromatography on silica (gradient: 0-50% EtOAc in petroleum ether) to give the title compound (2.1 g, 89%); MS (ESI) m/z $[M+H]^+$ 230.

Intermediate 32: Methyl 7-(2-hydroxypropan-2-yl)quinoline-4-carboxylate

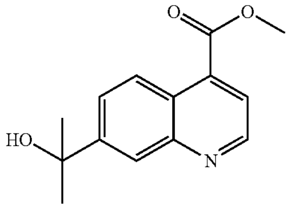 [SMILES: COC(=O)c1ccnc2cc(C(C)(C)O)ccc12]

MeMgBr (3.2 M in THF, 1.64 mL, 5.23 mmol) was added dropwise to a solution of methyl 7-acetylquinoline-4-carboxylate Intermediate 31 (300 mg, 1.31 mmol) in THE (5 mL) and the reaction mixture was stirred at 0° C. for 4 h. The reaction was quenched with sat $NH_4Cl$ (aq, 5 mL), and the mixture was extracted with EtOAc (3×20 mL). The combined organic layer was dried over $Na_2SO_4$, filtered and evaporated at reduced pressure. The crude product was purified by preparative TLC (DCM:MeOH, 10:1) to give the title compound (120 mg, 37%); $^1H$ NMR (400 MHz, $CD_3OD$) δ 8.97 (d, 1H), 8.73 (dd, 1H), 8.23 (dd, 1H), 7.96 (d, 1H), 7.89 (dd, 1H), 4.06 (s, 3H), 1.66 (s, 6H).

Intermediate 33: Methyl 7-(2-fluoropropan-2-yl)quinoline-4-carboxylate

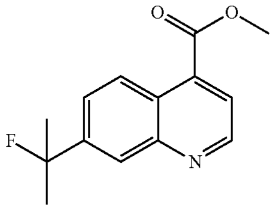 [SMILES: COC(=O)c1ccnc2cc(C(C)(C)F)ccc12]

DAST (0.404 mL, 3.06 mmol was added to a solution of methyl 7-(2-hydroxypropan-2-yl)quinoline-4-carboxylate Intermediate 32 (150 mg, 0.61 mmol) in DCM (2 mL), and the reaction mixture was stirred at 20° C. for 16 h. The mixture was quenched with water (20 mL) and the mixture was extracted with EtOAc (2×50 mL). The combined organic layer was dried over $Na_2SO_4$, filtered and concentrated in vacuo and the crude product was purified by preparative TLC (DCM:MeOH, 20:1) to give the title compound (60 mg, 40%); MS (ESI) m/z $[M+H]^+$ 248.

Intermediate 34: 7-(2-Fluoropropan-2-yl)quinoline-4-carboxylic acid

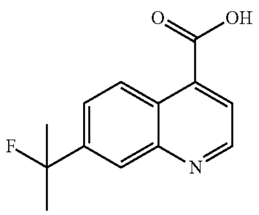 [SMILES: CC(C)(F)c1ccc2c(C(=O)O)ccnc2c1]

Methyl 7-(2-fluoropropan-2-yl)quinoline-4-carboxylate Intermediate 33 (60 mg, 0.24 mmol) and NaOH (48 mg, 1.2 mmol) was dissolved in a mixture of MeOH (2 mL) and water (0.5 mL), and the reaction mixture was stirred at 35° C. for 3 h. The pH of the reaction mixture was adjusted to 5 using 2 M HCl (aq, 1 mL). The mixture was diluted with EtOAc (20 mL) and washed sequentially with sat brine (2×10 mL). The organic layer was dried over $Na_2SO_4$, filtered and evaporated in vacuo to give the crude title compound (30 mg); MS (ESI) m/z $[M+H]^+$ 234.

Intermediate 35: tert-Butyl (7-(hydroxymethyl)quinoline-4-carbonyl)glycinate

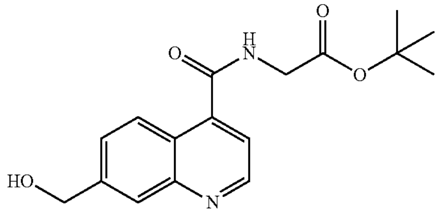 [SMILES: CC(C)(C)OC(=O)CNC(=O)c1ccnc2cc(CO)ccc12]

Pd(dppf)$Cl_2$DCM (112 mg, 0.14 mmol) was added in one portion to a solution of tert-butyl (7-bromoquinoline-4-carbonyl)glycinate Intermediate 7 (500 mg, 1.37 mmol) and (tributylstannyl)methanol (484 mg, 1.51 mmol) in 1,4-dioxane (5 mL) at 20° C., under an atmosphere of $N_2$ (g), and the reaction mixture was stirred at 80° C. for 16 h. The reaction mixture was concentrated in vacuo and the crude product was purified by preparative TLC (EtOAc:petroleum ether, 1:1) to give the title compound (350 mg, 81%); $^1H$ NMR (400 MHz, $CD_3OD$) δ 8.93 (d, 1H), 8.35 (d, 1H), 8.10 (s, 1H), 7.69 (dd, 1H), 7.61 (d, 1H), 4.12 (s, 2H), 3.36 (m, overlapping with solvent), 1.56 (s, 9H).

Intermediate 36: tert-Butyl (7-difluoromethyl)quinoline-4-carbonyl)glycinate

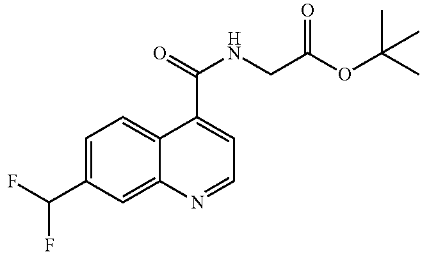 [SMILES: CC(C)(C)OC(=O)CNC(=O)c1ccnc2cc(C(F)F)ccc12]

Step a) tert-Butyl (7-formylquinoline-4-carbonyl)glycinate

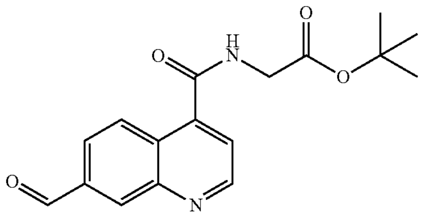 [SMILES: CC(C)(C)OC(=O)CNC(=O)c1ccnc2cc(C=O)ccc12]

Dess-Martin periodinane (1488 mg, 3.51 mmol) was added portion-wise to a solution of tert-butyl (7-(hydroxymethyl)quinoline-4-carbonyl)glycinate Intermediate 35 (370 mg, 1.17 mmol) in DCM (6 mL) and the reaction mixture was stirred at 35° C. for 5 h. The reaction mixture was diluted with EtOAc (100 mL) and washed with water (2×100 mL). The organic layer was dried over $Na_2SO_4$, filtered and evaporated in vacuo and the residue was purified by preparative TLC (EtOAc:petroleum ether, 1:1) to give the Step a) subtitle compound (250 mg, crude).

Step b) tert-Butyl (7-(difluoromethyl)quinoline-4-carbonyl)glycinate

DAST (0.841 mL, 6.36 mmol) was added dropwise to a solution of tert-butyl (7-formylquinoline-4-carbonyl)glycinate Intermediate Step a) (250 mg, 0.80 mmol) in DCM (5 mL), and the reaction mixture was stirred at 0° C. for 16 h. The reaction mixture was diluted with EtOAc (20 mL), and washed with sat brine (2×20 mL). The organic layer was dried over $Na_2SO_4$, filtered and evaporated in vacuo and the crude product was purified by preparative TLC (EtOAc: petroleum ether, 1:1) to give the title compound (100 mg, 37%) as a yellow liquid; MS (ESI) m/z $[M+H]^+$ 337.

Intermediate 37: (7-(Difluoromethyl)quinoline-4-carbonyl)glycine

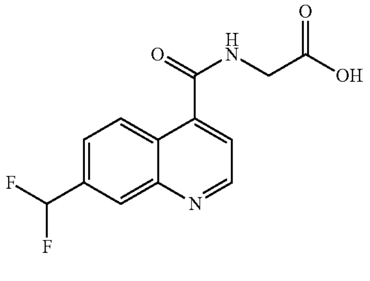 [SMILES: O=C(O)CNC(=O)c1ccnc2cc(C(F)F)ccc12]

4 M HCl in 1,4-dioxane (0.037 mL, 1.5 mmol) was added dropwise to a solution of tert-butyl (7-(difluoromethyl) quinoline-4-carbonyl)glycinate Intermediate 36 (100 mg, 0.30 mmol) in 1.4-dioxane (2 mL) and the reaction mixture was stirred at 35° C. for 2 h. The reaction mixture was concentrated in vacuo to give the crude title compound (50 mg); MS (ESI) m/z $[M+H]^+$ 284.

Intermediate 38: tert-Butyl (7-(trifluoromethyl)quinoline-4-carbonyl)glycinate

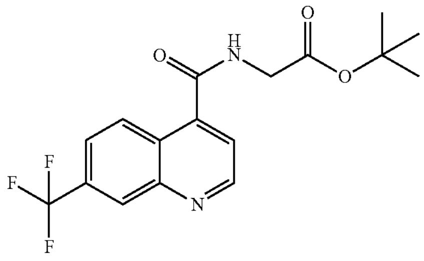 [SMILES: CC(C)(C)OC(=O)CNC(=O)c1ccnc2cc(C(F)(F)F)ccc12]

DIPEA (0.369 mL, 2.11 mmol) was added to a solution of 7-(trifluoromethyl)-quinoline-4-carboxylic acid (0.17 g, 0.70 mmol), tert-butyl glycinate hydrochloride (0.142 g, 0.85 mmol), EDC (0.203 g, 1.06 mmol) and HOBt (0.162 g, 1.06 mmol) in DMF (2 mL), and the reaction mixture was stirred at 20° C. for 4 h. The reaction was quenched with sat $NaHCO_3$ (aq, 20 mL) and extracted with EtOAc (3×20 mL). The combined organic layer was dried over $Na_2SO_4$, filtered and evaporated at reduced pressure. The residue was purified by preparative TLC (EtOAc:petroleum ether, 1:2), to give the title compound (0.150 g, 60%); MS (ESI) m/z $[M+H]^+$ 355.

Intermediate 39: (7-(Trifluoromethyl)quinoline-4-carbonyl)glycine

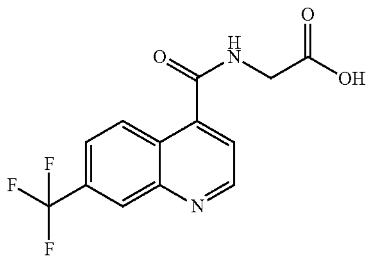 [SMILES: O=C(O)CNC(=O)c1ccnc2cc(C(F)(F)F)ccc12]

4 M HCl in 1.4-dioxane (1.06 mL, 4.23 mmol) was added to a solution of tert-butyl (7-(trifluoromethyl)quinoline-4-carbonyl)glycinate Intermediate 38 (150 mg, 0.42 mmol) in DCM (1 mL) at 0° C., and the reaction mixture was stirred at 20° C. for 4 h. The solvent was removed under reduced pressure to give the crude title compound (0.180 g); MS (ESI) m/z $[M+H]^+$ 299.

Intermediate 40: tert-Butyl (7-(fluoromethyl)quinoline-4-carbonyl)glycinate

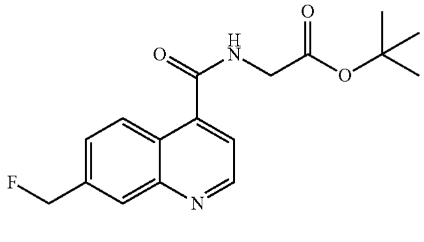 [SMILES: CC(C)(C)OC(=O)CNC(=O)c1ccnc2cc(CF)ccc12]

DAST (550 mg, 3.41 mmol) was added to a solution of tert-butyl (7-(hydroxymethyl)quinoline-4-carbonyl)glycinate Intermediate 35 (540 mg, 1.71 mmol) in DCM (10 mL) at 0° C., and the reaction mixture was stirred at 25° C. for 4 h. The reaction mixture was poured into sat $NaHCO_3$ (aq, 100 mL) and the mixture was extracted with DCM (3×50 mL). The combined organic layer was dried over $Na_2SO_4$, filtered and evaporated in vacuo, and the residue was purified by preparative TLC (EtOAc:petroleum ether, 1:1) to give the title compound (250 mg, 46%); MS (ESI) m/z $[M+H]^+$ 318.

Intermediate 41: (7-(Fluoromethyl)quinoline-4-carbonyl)glycine

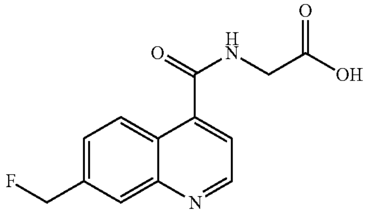 [SMILES: O=C(O)CNC(=O)c1ccnc2cc(CF)ccc12]

4 M HCl in 1,4-dioxane (2.0 mL, 2.5 mmol) was added to a solution of tert-butyl (7-(fluoromethyl)quinoline-4-carbonyl)glycinate Intermediate 40 (200 mg, 0.63 mmol) in 1,4-dioxane (2 mL), and the reaction mixture was stirred at 25° C. for 3 h. The reaction mixture was concentrated in vacuo to give the crude title compound (105 mg); MS (ESI) m/z $[M+H]^+$ 262.

Intermediate 42: tert-Butyl (7-acetylquinoline-4-carbonyl)glycinate

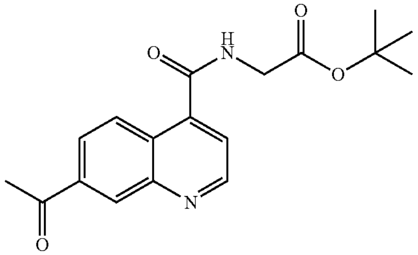 [SMILES: CC(=O)c1ccc2c(C(=O)NCC(=O)OC(C)(C)C)ccnc2c1]

tert-Butyl (7-bromoquinoline-4-carbonyl)glycinate Intermediate 7 (800 mg, 2.19 mmol), tributyl(1-ethoxyvinyl) stannane (949 mg, 2.63 mmol) and $Pd(dppf)Cl_2 \cdot DCM$ (160 mg, 0.22 mmol) were suspended in toluene (10 mL) under an atmosphere of $N_2$ (g), and the reaction mixture was stirred at 100° C. for 12 h. The reaction mixture was acidified with 2 M HCl (aq) to pH 6, and the mixture was concentrated at reduced pressure. The residue was purified by preparative TLC (EtOAc:petroleum ether, 2:1) to give the title compound (400 mg, 56%); MS (ESI) m/z $[M+H]^+$ 329.

Intermediate 43: tert-Butyl (7-(1-hydroxyethyl)quinoline-4-carbonyl)glycinate

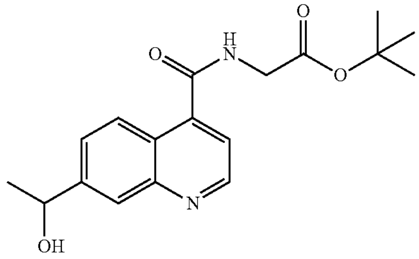 [SMILES: CC(O)c1ccc2c(C(=O)NCC(=O)OC(C)(C)C)ccnc2c1]

$NaBH_4$ (28 mg, 0.73 mmol) was added to a solution of tert-butyl (7-acetylquinoline-4-carbonyl)glycinate Intermediate 42 (120 mg, 0.37 mmol) in THE (1 mL) and the reaction mixture was stirred at 20° C. for 2 h. The reaction mixture was diluted with EtOAc (10 mL) and washed sequentially with sat $NaHCO_3$ (aq), sat NaCl (aq), and water. The organic layer was dried over $Na_2SO_4$, filtered and concentrated at reduced pressure. The residue was purified by preparative TLC (EtOAc:petroleum ether, 3:2), to give the title compound (98 mg, 81%); MS (ESI) m/z $[M+H]^+$ 331.

Intermediate 44: (7-(1-Hydroxyethyl)quinoline-4-carbonyl)glycine

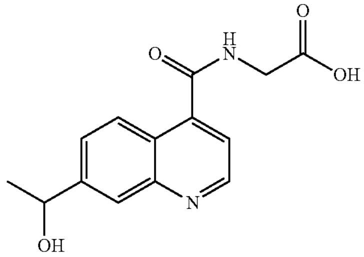 [SMILES: CC(O)c1ccc2c(C(=O)NCC(=O)O)ccnc2c1]

TFA (0.069 mL, 0.89 mmol) was added to a solution of tert-butyl (7-(1-hydroxyethyl)quinoline-4-carbonyl)glycinate Intermediate 43 (98 mg, 0.30 mmol) in DCM (1 mL) and the reaction mixture was stirred at 20° C. for 4 h. The solvent was removed under reduced pressure to give crude title compound (100 mg); MS (ESI) m/z $[M+H]^+$ 275.

Intermediate 45: tert-Butyl (7-(2-hydroxypropan-2-yl)quinoline-4-carbonyl)glycinate

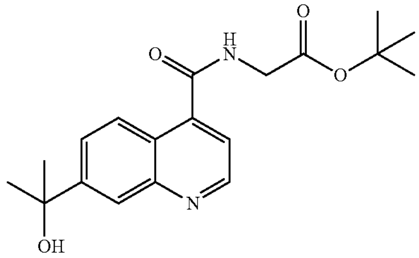 [SMILES: CC(C)(C)OC(=O)CNC(=O)c1ccnc2cc(C(C)(C)O)ccc12]

MeMgCl (3 M in THF, 0.25 mL, 0.76 mmol) was added to a solution of tert-butyl (6-acetylquinoline-4-carbonyl) glycinate Intermediate 42 (100 mg, 0.30 mmol) in THE (1 mL) at 0° C. and under an atmosphere of $N_2$ (g), and the reaction mixture was stirred at 0° C. for 3 h. The reaction was quenched with sat $NH_4Cl$ (aq, 10 mL), and the mixture was extracted with EtOAc (3×10 mL). The combined organic layer was dried over $Na_2SO_4$, filtered and evaporated at reduced pressure. The residue was purified by preparative TLC (DCM:MeOH, 10:1), to give the title compound (6.0 mg, 57%) as an orange gum; MS (ESI) m/z $[M+H]^+$ 345.

Intermediate 46: (7-(2-Hydroxypropan-2-yl)quinoline-4-carbonyl)glycine

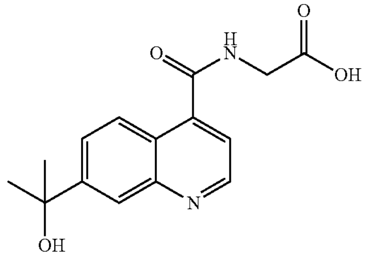 [SMILES: CC(C)(O)c1ccc2c(C(=O)NCC(=O)O)ccnc2c1]

TFA (5.0 mL, 65 mmol) was added slowly to a solution of tert-butyl (7-(2-hydroxypropan-2-yl)quinoline-4-carbonyl)glycinate Intermediate 45 (110 mg, 0.32 mmol) in DCM (1 mL) and the reaction mixture was stirred at 25° C. for 2 h. The reaction mixture was concentrated at reduced pressure to give the crude title compound (75 mg); MS (ESI) m/z $[M+H]^+$ 289.

Intermediate 47: Methyl 7-(1-hydroxyethyl)quinoline-4-carboxylate

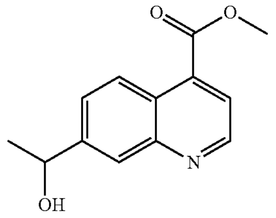 [SMILES: COC(=O)c1ccnc2cc(C(C)O)ccc12]

$NaBH_4$ (136 mg, 3.60 mmol) was added to a solution of methyl 7-acetylquinoline-4-carboxylate Intermediate 31 (550 mg, 2.40 mmol) in MeOH (10 mL) at 0° C., and the reaction mixture was stirred at rt for 2 h. The reaction mixture was diluted with water (50 mL) and extracted with EtOAc (3×50 mL). The organic layer was dried over $Na_2SO_4$, filtered and evaporated at reduced pressure. The residue was purified by preparative TLC (DCM:MeOH, 10:1), to give the title compound (420 mg, 76%) as a yellow oil; MS (ESI) m/z $[M+H]^+$ 232.

Intermediate 48: Methyl 7-(1-methoxyethyl)quinoline-4-carboxylate

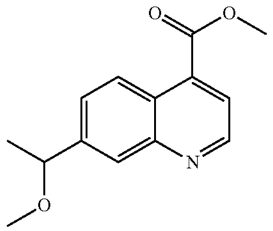 [SMILES: COC(=O)c1ccnc2cc(C(C)OC)ccc12]

NaH (60% in oil, 26 mg, 0.65 mmol) was added to a solution of methyl 7-(1-hydroxyethyl)quinoline-4-carboxylate Intermediate 47 (100 mg, 0.43 mmol) in DMF (1.5 mL) at 0° C. and under an atmosphere of $N_2$ (g), and the reaction mixture was stirred at 20° C. for 30 min. The reaction mixture was cooled to 0° C. and $CH_3I$ (0.054 mL, 0.86 mmol) was added and the reaction mixture was slowly warmed up to rt and then stirred at rt for 2 h. The reaction was quenched with water (10 mL), and the mixture was extracted with EtOAc (3×10 mL). The combined organic layer was dried over $Na_2SO_4$, filtered and evaporated at reduced pressure. The residue was purified by preparative TLC (DCM:MeOH, 10:1), to give the title compound (60 mg, 57%) as a pale yellow gum; MS (ESI) m/z $[M+H]^+$ 246.

Intermediate 49: 7-(1-Methoxyethyl)quinoline-4-carboxylic acid

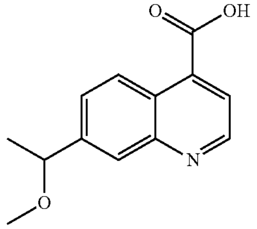 [SMILES: COC(C)c1ccc2c(C(=O)O)ccnc2c1]

LiOH (18 mg, 0.73 mmol) was added to a solution of methyl 7-(1-methoxyethyl)quinoline-4-carboxylate Intermediate 48 (60 mg, 0.24 mmol) in MeOH (0.9 mL) and water (0.3 mL) under an atmosphere of $N_2$ (g) and the reaction mixture was stirred at 20° C. for 3 h. The solvent was removed under reduced pressure, and the residue was dissolved in water and acidified with 2 M HCl (aq) to pH-5-6. The mixture was washed with DCM and the aqueous layer was concentrated at reduced pressure to give the crude title compound (60 mg); MS (ESI) m/z $[M+H]^+$ 232.

Intermediate 50: Methyl 7-(2-methoxypropan-2-yl)quinoline-4-carboxylate

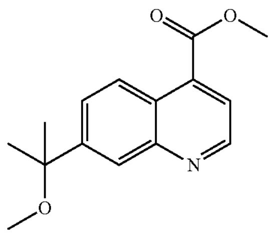 [SMILES: COC(=O)c1ccnc2cc(C(C)(C)OC)ccc12]

NaH (60% in oil, 42 mg, 1.06 mmol) was added portion wise to a solution of methyl 7-(2-hydroxypropan-2-yl)quinoline-4-carboxylate Intermediate 32 (130 mg, 0.53 mmol) in DMF (4 mL) at 0° C., and the reaction mixture was stirred at 0° C. for 30 min. $CH_3I$ (226 mg, 1.59 mmol) was added, and the reaction mixture was stirred at 20° C. for 2 h. The reaction mixture was diluted with EtOAc (20 mL), and washed with sat $NH_4Cl$ (aq, 2×20 mL). The organic layer was dried over $Na_2SO_4$, filtered and evaporated at reduced pressure to give the title compound (80 mg, 58%); $^1H$ NMR (400 MHz, $CD_3OD$) δ 8.99 (d, 1H), 8.77 (dd, 1H), 8.12 (d, 1H), 7.99 (d, 1H), 7.85 (dd, 1H), 4.06 (s, 3H), 3.15 (s, 3H), 1.66 (s, 6H).

Intermediate 51: 7-(2-Methoxypropan-2-yl)quinoline-4-carboxylic acid

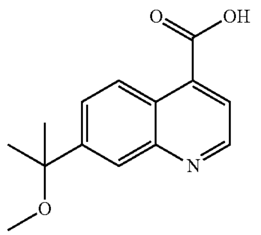 [SMILES: COC(C)(C)c1ccc2c(C(=O)O)ccnc2c1]

Methyl 7-(2-methoxypropan-2-yl)quinoline-4-carboxylate Intermediate 50 (100 mg, 0.39 mmol) and NaOH (77 mg, 1.9 mmol) was dissolved in MeOH (4 mL) and water (1 mL), and the reaction mixture was stirred at 20° C. for 1 h. The mixture was concentrated in vacuo to give the crude title compound (60 mg); MS (ESI) m/z $[M+H]^+$ 246.

Intermediate 52: Methyl 7-(hydroxymethyl)quinoline-4-carboxylate

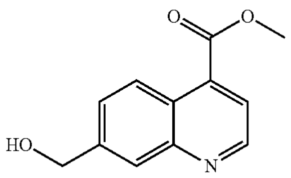 [SMILES: COC(=O)c1ccnc2cc(CO)ccc12]

Methyl 7-bromoquinoline-4-carboxylate (600 mg, 2.25 mmol), (tributylstannyl)-methanol (1.08 g, 3.38 mmol) and $Pd(PPh_3)_4$ (261 mg, 0.23 mmol) were suspended in 1,4-dioxane (10 mL) at 20° C., and the reaction mixture was stirred at 80° C. for 16 h. The reaction mixture was concentrated in vacuo and the residue was purified by preparative TLC (EtOAc) to give the title compound (450 mg, 92%); MS (ESI) m/z $[M+H]^+$ 218.

Intermediate 53: Methyl 7-((trifluoromethoxy) methyl)quinoline-4-carboxylate

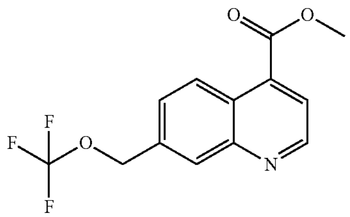 [SMILES: COC(=O)c1ccnc2cc(COC(F)(F)F)ccc12]

AgOTf (710 mg, 2.76 mmol), Selectfluor (734 mg, 2.07 mmol), KF (241 mg, 4.14 mmol) and methyl 7-(hydroxymethyl)quinoline-4-carboxylate Intermediate 52 (300 mg, 1.38 mmol) were dissolved in EtOAc (4 mL) under an atmosphere of $N_2$ (g) and the reaction mixture was stirred at rt for 2 min. 2-Fluoropyridine (268 mg, 2.76 mmol) and $(CH_3)_3SiCF_3$ 393 mg, 2.76 mmol) were added and the reaction mixture was stirred at 20° C. for 12 h. The reaction mixture was filtered through celite. The filtrate was concentrated in vacuo and the residue was purified by preparative TLC (EtOAc:petroleum ether, 1:1) to give the title compound (200 mg, 51%); MS (ESI) m/z $[M+H]^+$ 286.

Intermediate 54: Methyl 7-(1-(trifluoromethoxy) ethyl)quinoline-4-carboxylate

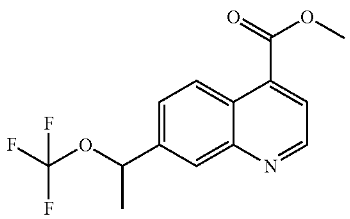 [SMILES: COC(=O)c1ccnc2cc(C(C)OC(F)(F)F)ccc12]

$(CH_3)_3SiCF_3$ (1.48 g, 10.4 mmol) was added to a solution of methyl 7-(1-hydroxyethyl)quinoline-4-carboxylate Intermediate 47 (800 mg, 3.46 mmol), Selectfluor (1.84 g, 5.19 mmol), AgOTf (2.67 g, 10.4 mmol), 2-fluoropyridine (0.892 mL, 10.4 mmol), 2,6-di-tert-butylphenol (357 mg, 1.73 mmol), and KF (804 mg, 13.8 mmol) in EtOAc (100 mL) at 20° C. and under an atmosphere of $N_2$ (g) and the reaction mixture was stirred at 20° C. for 96 h. The reaction mixture was filtered through celite. The filtrate was washed with water (2×60 mL), and the organic layer was dried over $Na_2SO_4$, and concentrated under vacuum. The residue was purified by preparative TLC (EtOAc:petroleum ether, 1:2) to give the title compound (152 mg, 15%); MS (ESI) m/z $[M+H]^+$ 300.

Intermediate 55: 7-(1-(Trifluoromethoxy)ethyl)quinoline-4-carboxylic acid

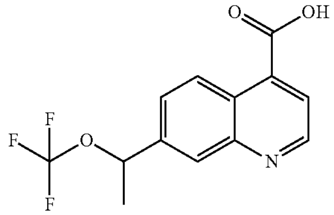

NaOH (40 mg, 1.0 mmol) was added to a solution of methyl 7-(1-(trifluoromethoxy)ethyl)quinoline-4-carboxylate Intermediate 54 (150 mg, 0.50 mmol) in EtOH (20 mL), and the reaction mixture was stirred at 40° C. for 3 h. The solvent was removed under vacuum to give the crude title compound (150 mg); MS (ESI) m/z $[M+H]^+$ 286.

Intermediate 56: tert-Butyl (7-(1-ethoxyvinyl)quinoline-4-carbonyl)glycinate

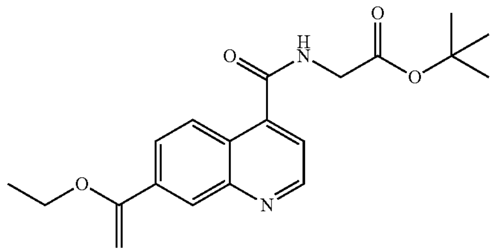 [SMILES: C=C(OCC)c1ccc2c(C(=O)NCC(=O)OC(C)(C)C)ccnc2c1]

Pd(dppf)$Cl_2$·DCM (112 mg, 0.14 mmol) was added in one portion to a solution of tert-butyl (7-bromoquinoline-4-carbonyl)glycinate Intermediate 7 (500 mg, 1.37 mmol) and tributyl(1-ethoxyvinyl)stannane (593 mg, 1.64 mmol) in toluene (8 mL) at 19° C. and under an atmosphere of $N_2$ (g), and the reaction mixture was stirred at 100° C. for 8 h. The reaction mixture was concentrated in vacuo and the residue was diluted with EtOAc (100 mL). The organic layer was washed with sat brine (2×100 mL), dried over $Na_2SO_4$, filtered and concentrated under reduced pressure. The crude product was purified by preparative TLC (EtOAc:petroleum ether, 1:1) to give the title compound (350 mg, 72%). $^1H$ NMR (400 MHz, $CD_3OD$) δ 8.93 (d, 1H), 8.38-8.28 (m, 2H), 7.97 (dd, 1H), 7.60 (d, 1H), 5.01 (d, 1H), 4.51 (d, 1H), 4.12 (s, 2H), 4.04 (q, 2H), 1.56 (s, 9H), 1.50 (t, 3H).

Intermediate 57: tert-Butyl (7-(1-ethoxycyclopropyl)quinoline-4-carbonyl)glycinate

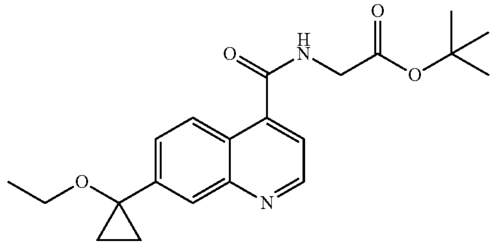 [SMILES: CCOC1(c2ccc3c(C(=O)NCC(=O)OC(C)(C)C)ccnc3c2)CC1]

A solution of $CH_2I_2$ (451 mg, 1.68 mmol) in DCM (1 mL) was added to a solution of $Et_2Zn$ (15 wt % in hexane, 693 mg, 0.84 mmol) in DCM (4 mL) at −78° C. and under an atmosphere of $N_2$ (g), and the reaction mixture was stirred at −15° C. for 30 min. A solution of TFA (65 μL, 0.84 mmol) in DCM (1 mL) was added, and the reaction mixture was stirred at −15° C. for 30 min. A solution of tert-butyl (7-(1-ethoxyvinyl)quinoline-4-carbonyl)glycinate Intermediate 56 (300 mg, 0.84 mmol) in DCM (0.5 mL) was added at −15° C., and the reaction mixture was stirred at rt for 3 h. The reaction mixture was diluted with DCM (50 mL) and washed with sat $NH_4Cl$ (4×20 mL). The organic layer was dried over $Na_2SO_4$, filtered and evaporated at reduced pressure to give the crude title product (200 mg): MS (ESI) m/z $[M+H]^+$371.

Intermediate 58: (7-(1-Ethoxycyclopropyl)quinoline-4-carbonyl)glycine

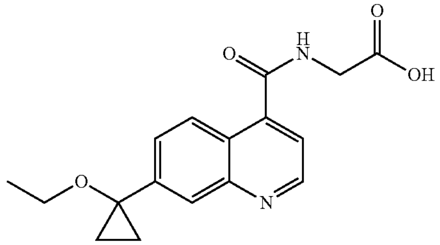 [SMILES: CCOC1(c2ccc3c(C(=O)NCC(=O)O)ccnc3c2)CC1]

4 M HCl in 1,4-dioxane (4.0 mL, 16 mmol) was added to tert-butyl (7-(1-ethoxycyclopropyl)quinoline-4-carbonyl) glycinate Intermediate 57 (200 mg, 0.54 mmol), and the reaction mixture was stirred at 35° C. for 3 h. The reaction mixture was concentrated in vacuo to give the crude title compound (100 mg); MS (ESI) m/z $[M+H]^+$ 315.

Intermediate 59: tert-Butyl (6-(1-methylcyclopropyl)quinoline-4-carbonyl)glycinate

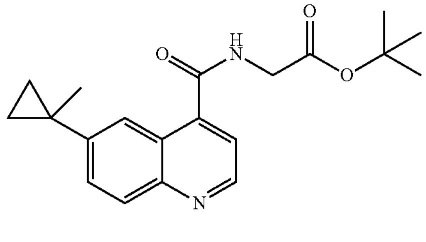 [SMILES: CC(C)(C)OC(=O)CNC(=O)c1ccnc2ccc(C3(C)CC3)cc12]

Dtbbpy (0.022 g, 0.08 mmol) was added to a mixture of $NiCl_2$·DME (0.012 g, 0.05 mmol) in degassed DME (12 mL) at 20° C. and under an atmosphere of $N_2$ (g), and the resulting mixture was stirred at 20° C. for 30 min. Tris (trimethylsilyl)silane (0.272 g, 1.10 mmol), tert-butyl (6-bromoquinoline-4-carbonyl)glycinate Intermediate 5 (0.20 g, 0.55 mmol), 1-bromo-1-methylcyclopropane (0.148 g, 1.10 mmol), $Na_2CO_3$ (0.174 g, 1.64 mmol) and [Ir{dF $(CF_3)$ppy}$_2$(dtbbpy)]$PF_6$ (0.012 g, 11 μmol) were added and the reaction mixture was stirred under a 34 W blue LEDs light irradiation under an atmosphere of $N_2$(g) at rt for 20 h. The reaction was quenched with water (20 mL), and the mixture was extracted with EtOAc (3×20 mL). The organic layer was dried over $Na_2SO_4$, filtered and evaporated. The residue was purified twice by preparative TLC (DCM: MeOH, 10:1), to give the title compound (0.21 g) as a light orange gum: MS (ESI) m/z $[M+H]^+$ 341.

Intermediate 60: (6-(1-Methylcyclopropyl)quinoline-4-carbonyl)glycine

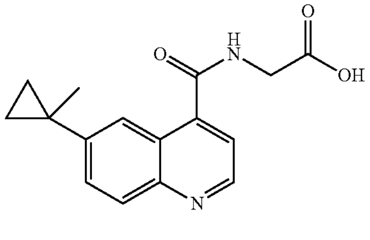 [SMILES: CC1(c2ccc3nccc(C(=O)NCC(=O)O)c3c2)CC1]

TFA (0.905 mL, 11.8 mmol) was added to a solution of tert-butyl (6-(1-methylcyclopropyl)quinoline-4-carbonyl) glycinate Intermediate 59 (0.20 g, 0.59 mmol) in DCM (2 mL) at 20° C., and the reaction mixture was stirred at 20° C. for 3 h. The solvent was removed under reduced pressure, and the crude product was purified by preparative HPLC, PrepMethod B, (gradient: 13-23%), to give the title compound (0.045 g, 27%): MS (ESI) m/z $[M+H]^+$ 285.

Intermediate 61: Methyl 6-formylquinoline-4-carboxylate

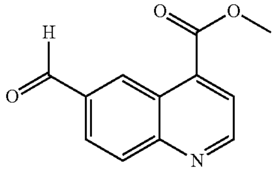 [SMILES: COC(=O)c1ccnc2ccc(C=O)cc12]

Dess-Martin periodinane (4.64 g, 10.9 mmol) was added to a solution of methyl 6-(hydroxymethyl)quinoline-4-carboxylate Intermediate 28 (950 mg, 4.37 mmol) in DCM (20 mL), and the reaction mixture was stirred at 25° C. for 2 h. The reaction mixture was concentrated in vacuo and the crude product was purified by preparative TLC (EtOAc: petroleum ether, 1:1) to give the title compound (850 mg, 90%): MS (ESI) m/z $[M+H]^+$ 215.

Intermediate 62: Methyl 6-(3-(trimethylsilyl)propanoyl)quinoline-4-carboxylate

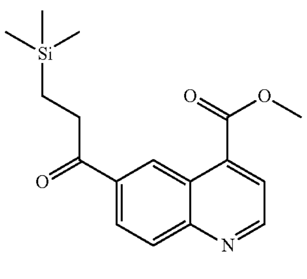

$RhCl(PPh_3)_3$ (344 mg, 0.37 mmol) and benzoic acid (91 mg, 0.74 mmol) were added to a solution of methyl 6-formylquinoline-4-carboxylate Intermediate 61 (800 mg, 3.72 mmol), 3-methylpyridin-2-amine (402 mg, 3.72 mmol) and trimethyl(vinyl)silane (3.73 mg, 37.2 mmol) in toluene (10 mL) at 25° C. and under an atmosphere of $N_2$ (g), and the reaction mixture was heated at 150° C. for 2 h. The reaction mixture was concentrated in vacuo and the residue was purified by preparative TLC (EtOAc:petroleum ether, 1:2) to give the title compound (700 mg, 60%): MS (ESI) m/z $[M+H]^+$ 315.

Intermediate 63: Methyl 6-(1,1,1-trifluoro-2-hydroxy-4-(trimethylsilyl)butan-2-yl)quinoline-4-carboxylate

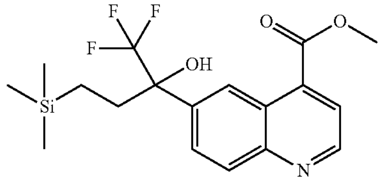

$(CH_3)_3SiCF_3$ (0.793 g, 5.58 mmol) was added to a solution of methyl 6-(3-(trimethylsilyl)propanoyl)quinoline-4-carboxylate Intermediate 62 (1.1 g, 3.5 mmol) and CsF (0.026 g, 0.17 mmol) in THE (15 mL), and the reaction mixture was stirred at 25° C. for 4 h. Water (0.377 g, 20.9 mmol) and TBAF (1 M in THF, 0.697 mL, 0.70 mmol) were added and the reaction mixture was stirred at 25° C. for 12 h. The reaction mixture was poured into sat brine (50 mL), extracted with EtOAc (3×50 mL), and the combined organic layer was dried over $Na_2SO_4$, filtered and evaporated at reduced pressure. The residue was purified by preparative TLC (EtOAc:petroleum ether, 1:2) to give the title compound (450 mg, 33%); MS (ESI) m/z $[M+H]^+$ 386.15.

Intermediate 64: Methyl 6-(1,1,1-trifluoro-2-((methylsulfonyl)oxy)-4-(trimethylsilyl)butan-2-yl)quinoline-4-carboxylate

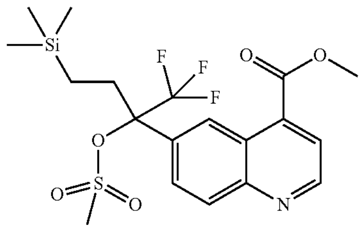

Methanesulfonyl chloride (61 mg, 0.53 mmol) was added to a solution of methyl 6-(1,1,1-trifluoro-2-hydroxy-4-(trimethylsilyl)butan-2-yl)quinoline-4-carboxylate Intermediate 63 (170 mg, 0.44 mmol) and TEA (89 mg, 0.88 mmol) in DCM (5 mL) at 0° C., and the reaction mixture was stirred at 0° C. for 20 min, and then at 25° C. for 2 h. The reaction mixture was concentrated in vacuo and the residue was purified by preparative TLC (EtOAc:petroleum ether, 1:1) to give the title compound (90 mg, 44%): MS (ESI) m/z $[M+H]^+$ 463.

Intermediate 65: 6-(1-(Trifluoromethyl)cyclopropyl) quinoline-4-carboxylic acid

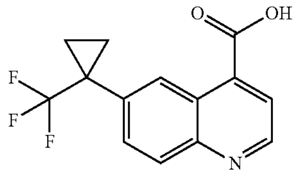 [SMILES: O=C(O)c1ccnc2ccc(C3(C(F)(F)F)CC3)cc12]

Step a) Methyl 6-(1-(trifluoromethyl)cyclopropyl) quinoline-4-carboxylate

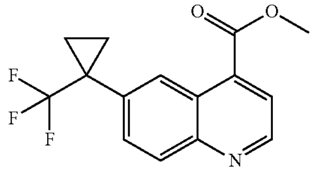 [SMILES: COC(=O)c1ccnc2ccc(C3(C(F)(F)F)CC3)cc12]

Pyridine (61 mg, 0.78 mmol) was added to a solution of methyl 6-(1,1,1-trifluoro-2-((methylsulfonyl)oxy)-4-(trimethylsilyl)butan-2-yl)quinoline-4-carboxylate Intermediate 64 (180 mg, 0.39 mmol) in HFIP (2 mL), and the reaction mixture was stirred at 25° C. for 2 h. The reaction mixture was poured into 0.5 M citric acid (aq, 50 mL) and extracted with EtOAc (3×50 mL). The combined organic layer was dried over $Na_2SO_4$, filtered and evaporated to give the title compound (100 mg, 87%) as a yellow oil; MS (ESI) m/z $[M+H]^+$ 296.1.

Step b) 6-(1-(Trifluoromethyl)cyclopropyl)quinoline-4-carboxylic acid

NaOH (12 mg, 0.30 mmol) was added to a solution of methyl 6-(1-(trifluoromethyl)cyclopropyl)quinoline-4-carboxylate Step a) (90 mg, 0.30 mmol) in MeOH (3 mL) and water (0.75 mL) at 25° C., and the reaction mixture was heated at 40° C. for 2 h. The reaction mixture was poured into water (50 mL), the pH was adjusted to pH 3 with 2 M HCl (aq), and the mixture was extracted with EtOAc (3×50 mL). The combined organic layer was dried over $Na_2SO_4$, filtered and evaporated to afford the title compound (80 mg, 93%) as a yellow oil; MS (ESI) m/z $[M+H]^+$ 282.0.

Intermediate 66: Methyl 6-(1-ethoxyvinyl)quinoline-4-carboxylate

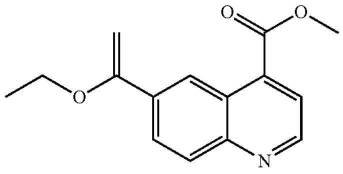 [SMILES: C=C(OCC)c1ccc2nccc(C(=O)OC)c2c1]

A solution of methyl 6-bromoquinoline-4-carboxylate (400 mg, 1.50 mmol), tributyl(1-ethoxyvinyl)stannane (651 mg, 1.80 mmol) and Pd(dppf)$_2$·DCM (123 mg, 0.15 mmol) in 1,4-dioxane (15 mL) was stirred at 80° C. for 15 h. The solvent was removed under reduced pressure and the residue was dried under vacuum. The residue was purified by preparative TLC (EtOAc:pentane, 1:4), to give the title compound (300 mg, 78%): MS (ESI) m/z $[M+H]^+$ 258.

Intermediate 67: Methyl 6-(1-ethoxycyclopropyl)quinoline-4-carboxylate

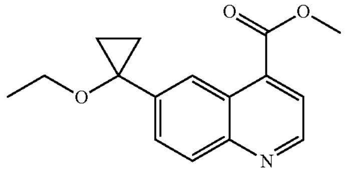 [SMILES: CCOC1(c2ccc3nccc(C(=O)OC)c3c2)CC1]

A solution of $CH_2I_2$ (1.25 g, 4.66 mmol) in DCM (1 mL) was added to a solution of $Et_2Zn$ (15 wt % in hexane, 288 mg, 2.33 mmol) in DCM (4 mL) at −78° C. and under an atmosphere of $N_2$ (g). After complete addition the reaction mixture was stirred at −15° C. for 30 min. A solution of TFA (0.180 mL, 2.33 mmol) in DCM (1 mL) was added at −15° C., and the reaction mixture was stirred at −15° C. for 30 min. A solution of methyl 6-(1-ethoxyvinyl)-quinoline-4-carboxylate Intermediate 66 (300 mg, 1.17 mmol) in DCM (0.5 mL) was added at −5° C., and the reaction mixture was stirred at 20° C. for 3 h. The reaction mixture was poured into water (50 mL), extracted with DCM (2×100 mL), and the combined organic layer was dried over $Na_2SO_4$, filtered and evaporated in vacuo. The residue was purified by preparative TLC (EtOAc:petroleum ether, 1:2) to give the title compound (120 mg, 38%): MS (ESI) m/z $[M+H]^+$272.

Intermediate 68: 6-(1-Ethoxycyclopropyl)quinoline-4-carboxylic acid

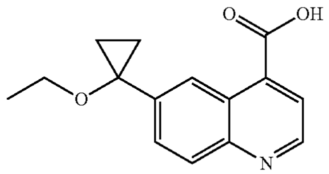 [SMILES: CCOC1(c2ccc3nccc(C(=O)O)c3c2)CC1]

Methyl 6-(1-ethoxycyclopropyl)quinoline-4-carboxylate Intermediate 67 (120 mg, 0.44 mmol) and NaOH (88 mg, 2.21 mmol) was dissolved in MeOH (2 mL) and water (0.5 mL), and the reaction mixture was stirred at 35° C. for 2 h. The pH of the reaction mixture was adjusted to 6 using 0.1 M HCl (aq) and the mixture was concentrated in vacuo to give the crude title compound (100 mg): MS (ESI) m/z $[M+H]^+$ 258.

Intermediate 69: Methyl 6-(cyanomethyl)quinoline-4-carboxylate

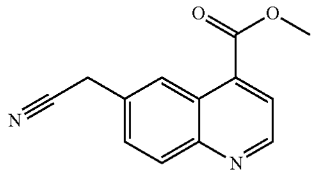 [SMILES: COC(=O)c1ccnc2ccc(CC#N)cc12]

$Pd_2(dba)_3 \cdot CHCl_3$ (194 mg, 0.19 mmol) was added in one portion to a suspension of methyl 6-bromoquinoline-4-carboxylate (500 mg, 1.88 mmol), 2-(trimethylsilyl)acetonitrile (277 mg, 2.44 mmol), $ZnF_2$ (136 mg, 1.32 mmol) and XantPhos (109 mg, 0.19 mmol) in DMF (8 mL) at 20° C. and under an atmosphere of $N_2$ (g), and the reaction mixture was stirred at 105° C. for 10 h. The reaction mixture was diluted with EtOAc (100 mL), and washed with sat brine (3×50 mL). The organic layer was dried over $Na_2SO_4$, filtered and evaporated in vacuo and the residue was purified by preparative TLC (EtOAc:petroleum ether, 1:2) to give the title compound (340 mg, 80%): MS (ESI) m/z $[M+H]^+$ 227.

Intermediate 70: Methyl 6-(1-cyanocyclopropyl)quinoline-4-carboxylate

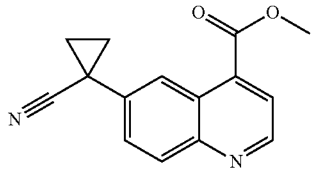 [SMILES: COC(=O)c1ccnc2ccc(C3(C#N)CC3)cc12]

NaH (60% in mineral oil, 53 mg, 1.3 mmol) was added portion wise to a solution of methyl 6-(cyanomethyl)quinoline-4-carboxylate Intermediate 69 (300 mg, 1.33 mmol) in DMF (2 mL) and the reaction mixture was stirred at rt for 1 h. 1,2-Dibromoethane (249 mg, 1.33 mmol) was added and the reaction mixture was stirred at 20° C. for 2 h. The reaction mixture was diluted with EtOAc (50 mL), and washed with water (2×20 mL). The organic layer was dried over $Na_2SO_4$, filtered and evaporated and the residue was purified by preparative TLC (EtOAc:petroleum ether, 1:2) to give the title compound (200 mg, 60%): MS (ESI) m/z $[M+H]^+$253.

Intermediate 71: 6-(1-Cyanocyclopropyl)quinoline-4-carboxylic acid

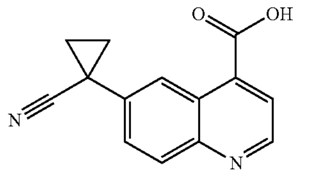 [SMILES: N#CC1(c2ccc3nccc(C(=O)O)c3c2)CC1]

A solution of methyl 6-(1-cyanocyclopropyl)quinoline-4-carboxylate Intermediate 70 (130 mg, 0.52 mmol) and LiOH (25 mg, 1.0 mmol) in THE (6 mL) and water (1 mL) was stirred at rt for 2 h. The solvent was removed under reduced pressure. The reaction mixture was acidified with 2 M HCl (aq) and the precipitate was collected by filtration, washed with water to give the crude title compound (70 mg). MS (ESI) m/z $[M+H]^+$ 239.

Intermediate 72: tert-Butyl (7-(1-methylcyclopropyl)quinoline-4-carbonyl)glycinate

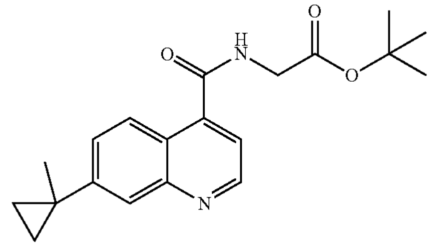 [SMILES: CC(C)(C)OC(=O)CNC(=O)c1ccnc2cc(C3(C)CC3)ccc12]

Dtbbpy (0.022 g, 0.08 mmol) was added to a solution of $NiCl_2 \cdot DME$ (0.012 g, 0.05 mmol) in degassed DME (12 mL) at 20° C. under an atmosphere of $N_2$ (g) and the mixture was stirred at 20° C. for 30 min. Tris(trimethylsilyl)silane (0.272 g, 1.10 mmol), tert-butyl (7-bromoquinoline-4-carbonyl)glycinate Intermediate 7 (0.20 g, 0.55 mmol), 1-bromo-1-methylcyclopropane (0.148 g, 1.10 mmol), $Na_2CO_3$ (0.174 g, 1.64 mmol) and $[Ir\{dF(CF_3)ppy\}_2(dtbbpy)]PF_6$ (0.012 g, 11 μmol) were added and the reaction mixture was stirred under a 34 W blue LEDs light irradiation at rt and under an atmosphere of $N_2$(g) for 20 h. The reaction was quenched with water (20 mL), extracted with DCM (3×20 mL), and the organic layer was dried over $Na_2SO_4$, filtered and evaporated at reduced pressure. The residue was purified by preparative TLC (EtOAc:petroleum ether, 1:1), to give the title compound (0.045 g, 24%) as a pale yellow gum: MS (ESI) m/z $[M+H]^+$ 341.

Intermediate 73: (7-(1-Methylcyclopropyl)quinoline-4-carbonyl)glycine

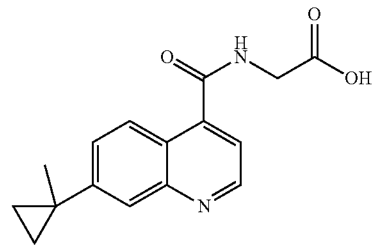 [SMILES: CC1(c2ccc3c(C(=O)NCC(=O)O)ccnc3c2)CC1]

TFA (0.362 mL, 4.70 mmol) was added to tert-butyl (7-(1-methylcyclopropyl)-quinoline-4-carbonyl)glycinate Intermediate 72 (40 mg, 0.12 mmol) in DCM (0.5 mL) at 20° C., and the reaction mixture was stirred at 20° C. for 4 h. The solvent was removed under reduced pressure, and the residue was dried under vacuum to give the crude title compound (40 mg) as pale orange gum; MS (ESI) m/z $[M+H]^+$ 285.

Intermediate 74: Methyl 7-formylquinoline-4-carboxylate

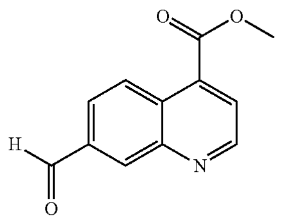 [SMILES: COC(=O)c1ccnc2cc(C=O)ccc12]

Dess-Martin periodinane 2.93 g, 6.91 mmol was added in portions to a solution of methyl 7-(hydroxymethyl)quinoline-4-carboxylate Intermediate 52 (600 mg, 2.76 mmol) in DCM (10 mL) at 25° C., and the reaction mixture was stirred at 25° C. for 3 h. The reaction mixture was concentrated in vacuo and the residue was purified by preparative TLC (petroleum ether:EtOAc, 1:1) to give the title compound (510 mg, 86%); MS (ESI) m/z $[M+H]^+$ 215.

Intermediate 75: Methyl 7-(3-(trimethylsilyl)propanoyl)quinoline-4-carboxylate

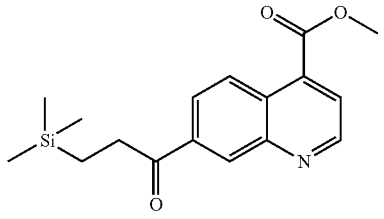

$RhCl(PPh_3)_3$ (365 mg, 0.39 mmol) and trimethyl(vinyl) silane (3.96 g, 39.5 mmol) were added to a solution of benzoic acid (96 mg, 0.79 mmol), methyl 7-formylquinoline-4-carboxylate Intermediate 74 (850 mg, 3.95 mmol) and 3-methylpyridin-2-amine (427 mg, 3.95 mmol) in toluene (10 mL) at 25° C. under an atmosphere of $N_2$ (g), and the reaction mixture was stirred at 150° C. for 2 h. The reaction mixture was concentrated in vacuo and the residue was purified by preparative TLC (petroleum ether:EtOAc, 2:1) to give the title compound (700 mg, 56%): MS (ESI) m/z $[M+H]^+$ 315.

Intermediate 76: Methyl 7-(1,1,1-trifluoro-2-hydroxy-4-(trimethylsilyl)butan-2-yl)quinoline-4-carboxylate

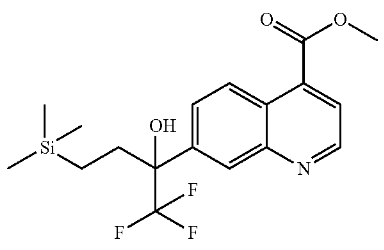

$(CH_3)_3SiCF_3$ (176 mg, 1.24 mmol) and CsF (7 mg, 0.05 mmol) were added to a mixture of methyl 7-(3-(trimethylsilyl)propanoyl)quinoline-4-carboxylate Intermediate 75 (300 mg, 0.95 mmol), TBAF (50 mg, 0.19 mmol) and water (103 mg, 5.71 mmol) in THE (10 mL) at 25° C., and under an atmosphere of $N_2$ (g). The reaction mixture was stirred at 25° C. for 12 h, and then concentrated in vacuo. The residue was purified by preparative TLC (petroleum ether:EtOAc, 2:1) to give the title compound (110 mg, 29%): MS (ESI) m/z $[M+H]^+$386.2.

Intermediate 77: Methyl 7-(1,1,1-trifluoro-2-((methylsulfonyl)oxy)-4-(trimethylsilyl)butan-2-yl)quinoline-4-carboxylate

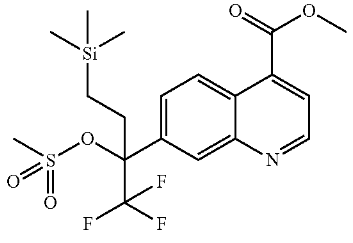

Methanesulfonyl chloride (96 mg, 0.84 mmol) was added to a solution of methyl 7-(1,1,1-trifluoro-2-hydroxy-4-(trimethylsilyl)butan-2-yl)quinoline-4-carboxylate Intermediate 76 (270 mg, 0.70 mmol) and TEA (142 mg, 1.40 mmol) in DCM (10 mL) and the reaction mixture was stirred at 25° C. for 2 h. The reaction mixture was poured into sat $NaHCO_3$ (aq, 50 mL) and extracted with DCM (3×50 mL). The combined organic layer was dried over $Na_2SO_4$, filtered and evaporated at reduced pressure to give the title product (300 mg, 92%) as a yellow oil; MS (ESI) m/z $[M+H]^+$ 464.1.

Intermediate 78: Methyl 7-(1-(trifluoromethyl)cyclopropyl)quinoline-4-carboxylate

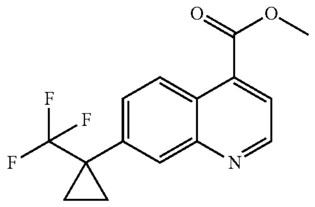 [SMILES: COC(=O)c1ccnc2cc(C3(C(F)(F)F)CC3)ccc12]

Pyridine (63 mg, 0.80 mmol) was added to a solution of methyl 7-(1,1,1-trifluoro-2-((methylsulfonyl)oxy)-4-(trimethylsilyl)butan-2-yl)quinoline-4-carboxylate Intermediate 77 (185 mg, 0.40 mmol) in HFIP (2 mL) and the reaction mixture was stirred at 25° C. for 2 h. The reaction mixture was poured into 0.5 M citric acid (aq, 50 mL), and extracted with EtOAc (3×50 mL). The combined organic layer was dried over $Na_2SO_4$, filtered and evaporated at reduced pressure to give the title compound (170 mg) as a crude; MS (ESI) m/z $[M+H]^+$ 296.1.

Intermediate 79: 7-(1-(Trifluoromethyl)cyclopropyl) quinoline-4-carboxylic acid

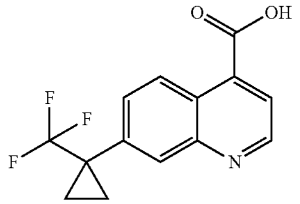 [SMILES: O=C(O)c1ccnc2cc(C3(C(F)(F)F)CC3)ccc12]

NaOH (22 mg, 0.56 mmol) was added to a solution of methyl 7-(1-(trifluoromethyl)-cyclopropyl)quinoline-4-carboxylate Intermediate 78 (165 mg, 0.56 mmol) in MeOH (2 mL) and water (0.5 mL) at 25° C., and the reaction mixture was stirred at 40° C. for 2 h. The reaction mixture was poured into water (50 mL), and the pH was adjusted to 3 with 2 M HCl (aq). The mixture was extracted with EtOAc (3×50 mL) and the combined organic layer was dried over $Na_2SO_4$, filtered and evaporated at reduced pressure to give the title compound (150 mg, 95%); MS (ESI) m/z $[M+H]^+$ 282.0.

Intermediate 80: Methyl 7-(1-cyanocyclopropyl)quinoline-4-carboxylate

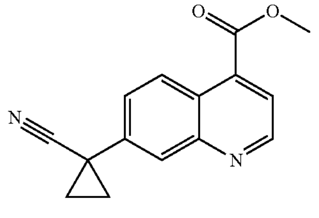 [SMILES: COC(=O)c1ccnc2cc(C3(C#N)CC3)ccc12]

A solution of methyl 7-bromoquinoline-4-carboxylate (500 mg, 1.88 mmol), bis(pinacolato)diboron (716 mg, 2.82 mmol), $Pd(dppf)Cl_2$·DCM (153 mg, 0.19 mmol) and potassium acetate (369 mg, 3.76 mmol) in 1,4-dioxane (8 mL) was stirred at 80° C. for 2 h, under an atmosphere of $N_2$ (g). 1-Bromocyclopropane-1-carbonitrile (549 mg, 3.76 mmol), $K_2CO_3$ (519 mg, 3.76 mmol) and water (2 mL) was added and the reaction mixture was stirred at 80° C. overnight under an atmosphere of $N_2$ (g). The solid was filtered out, and the filtrate was concentrated under vacuum. The residue was purified by preparative TLC (petroleum ether:EtOAc, 3:2), to give the title compound (240 mg, 51%): MS (ESI) m/z $[M+H]^+$ 253.

Intermediate 81: 7-(1-Cyanocyclopropyl)quinoline-4-carboxylic acid

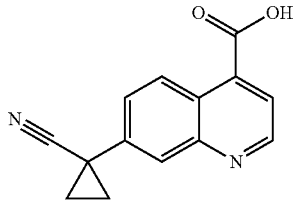 [SMILES: N#CC1(c2ccc3c(C(=O)O)ccnc3c2)CC1]

A solution of methyl 7-(1-cyanocyclopropyl)quinoline-4-carboxylate Intermediate 80 (300 mg, 1.19 mmol) and LiOH (85 mg, 3.6 mmol) in THE (8 mL) and water (2 mL) was stirred at rt for 2 h. The reaction mixture was concentrated under reduced pressure, and the residue was diluted with water. The pH of the mixture was adjusted to 6 with 2 M HCl (aq). The precipitate was collected by filtration, and washed with water to give the crude title compound (200 mg): MS (ESI) m/z $[M+H]^+$ 239.

C. Final Compounds

Example 1: 6-Bromo-N-(2-((1S,3S,5S)-3-cyano-2-azabicyclo[3.1.0]hexan-2-yl)-2-oxoethyl)quinoline-4-carboxamide

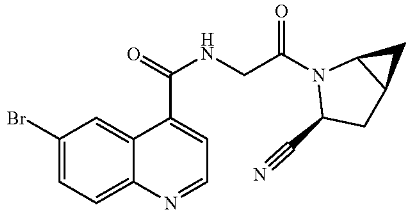 [SMILES: N#C[C@@H]1C[C@@H]2C[C@@H]2N1C(=O)CNC(=O)c1ccnc2ccc(Br)cc12]

DIPEA (0.12 mL, 0.68 mmol) was added to a solution of (1S,3S,5S)-2-azabicyclo[3.1.0]hexane-3-carbonitrile 4-methylbenzenesulfonate WO2007029086 (95 mg, 0.34 mmol), Intermediate 6 (6-bromoquinoline-4-carbonyl)glycine (70 mg, 0.23 mmol), EDC (65 mg, 0.34 mmol) and HOBt (52 mg, 0.34 mmol) in DMF (1 mL) at 20° C. and the reaction mixture was stirred at 20° C. for 18 h. The reaction was quenched with sat $NaHCO_3$ (aq, 10 mL) and extracted with EtOAc (3×15 mL). The combined organic layer was dried over $Na_2SO_4$, filtered and evaporated. The crude product was purified by preparative HPLC, PrepMethod C (gradient: 28-38%), to give the title compound (38 mg, 42%); HRMS (ESI) m/z $[M+H]^+$ calcd for $C_{18}H_{16}BrN_4O_2$: 399.0452, found: 399.0454; $^1H$ NMR (400 MHz, DMSO-$d_6$) δ 9.20 (t, 1H), 9.04 (d, 1H), 8.60 (d, 1H), 8.05 (d, 1H), 7.96 (dd, 1H), 7.65 (d, 1H), 5.18 (dd, 1H), 4.58 (dd, 1H), 4.23 (dd, 1H), 3.87 (td, 1H), 2.65-2.53 (m, 1H), 2.25 (dd, 1H), 1.96-1.85 (m, 1H), 1.07-0.94 (m, 1H), 0.84-0.76 (m, 1H).

Example 2: 7-Chloro-N-(2-((1S,3S,5S)-3-cyano-2-azabicyclo[3.1.0]hexan-2-yl)-2-oxoethyl)quinoline-4-carboxamide

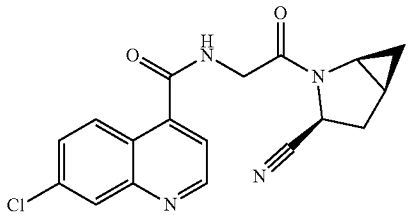

HATU (0.063 g, 0.17 mmol) and DIPEA (0.105 mL, 0.60 mmol) were added to a suspension of 7-chloroquinoline-4-carboxylic acid (0.033 g, 0.16 mmol) and (1S,3S,5S)-2-glycyl-2-azabicyclo[3.1.0]hexane-3-carbonitrile hydrochloride Intermediate 3 (0.030 g, 0.15 mmol) in a mixture of DCM (1 mL) and MeCN (0.2 mL) and the reaction mixture was stirred at rt overnight. The mixture was diluted with DCM and washed with sat $NaHCO_3$ (aq). The water phase was extracted twice with EtOAc, and the combined organic phase was dried using a phase separator and evaporated in vacuo. The crude product was purified by preparative SFC, PrepMethod D (gradient: 15-20%), to give the title compound (20 mg, 38%); HRMS (ESI) m/z $[M+H]^+$ calcd for $C_{15}H_{16}ClN_4O_2$: 355.0956, found: 355.0934; $^1H$ NMR (600 MHz, DMSO-$d_6$) δ 9.19 (t, 1H), 9.05 (d, 1H), 8.41 (d, 1H), 8.17 (d, 1H), 7.76 (dd, 1H), 7.63 (d, 1H), 5.17 (dd, 1H), 4.57 (dd, 1H), 4.23 (dd, 1H), 3.87 (td, 1H), 2.64-2.55 (m, 1H), 2.26 (dd, 1H), 1.94-1.87 (m, 1H), 1.05-0.99 (m, 1H), 0.83-0.77 (m, 1H).

Example 3: 7-Bromo-N-(2-((1S,3S,5S)-3-cyano-2-azabicyclo[3.1.0]hexan-2-yl)-2-oxoethyl)quinoline-4-carboxamide

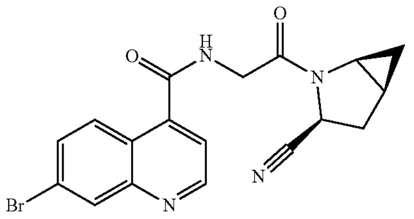 [SMILES: N#C[C@@H]1C[C@@H]2C[C@@H]2N1C(=O)CNC(=O)c1ccnc2cc(Cl)ccc12]

DIPEA (0.17 mL, 0.97 mmol) was added to a solution of (1S,3S,5S)-2-azabicyclo[3.1.0]hexane-3-carbonitrile 4-methylbenzenesulfonate WO2007029086 (136 mg, 0.49 mmol), (7-bromoquinoline-4-carbonyl)glycine Intermediate 8 (100 mg, 0.32 mmol), EDC (93 mg, 0.49 mmol) and HOBt (74 mg, 0.49 mmol) in DMF (1 mL) at 20° C., and the reaction mixture was stirred at 20° C. for 18 h. The reaction was quenched with sat $NaHCO_3$ (aq, 10 mL) and extracted with EtOAc (3×15 mL). The organic layer was dried over $Na_2SO_4$, filtered and evaporated. The crude product was purified by preparative HPLC, PrepMethod C (gradient: 25-36%), to give the title compound (74 mg, 57%); HRMS (ESI) m/z $[M+H]^+$ calcd for $C_{18}H_{16}BrN_4O_2$: 399.0452, found: 399.0454; $^1H$ NMR (400 MHz, DMSO-$d_6$) δ 9.18 (t, 1H), 9.03 (d, 1H), 8.35-8.28 (m, 2H), 7.86 (dd, 1H), 7.64 (d, 1H), 5.16 (dd, 1H), 4.57 (dd, 1H), 4.23 (dd, 1H), 3.87 (td, 1H), 2.66-2.54 (m, 1H), 2.25 (dd, 1H), 1.96-1.85 (m, 1H), 1.06-0.96 (m, 1H), 0.84-0.76 (m, 1H).

Example 4: N-(2-((1S,3S,5S)-3-Cyano-2-azabicyclo[3.1.0]hexan-2-yl)-2-oxoethyl)-6-fluoro-2-methylquinoline-4-carboxamide

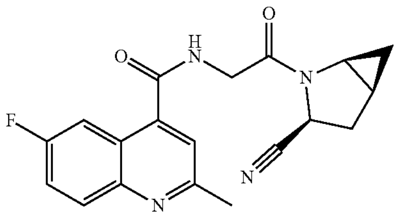 [SMILES: Cc1cc(C(=O)NCC(=O)N2[C@H](C#N)C[C@@H]3C[C@@H]32)c2cc(F)ccc2n1]

HATU (59 mg, 0.15 mmol) was added to a suspension of 6-fluoro-2-methylquinoline-4-carboxylic acid (29 mg, 0.14 mmol) in DCM (1 mL) and the reaction mixture was stirred at rt for 15 min. (1S,3S,5S)-2-Glycyl-2-azabicyclo[3.1.0]hexane-3-carbonitrile hydrochloride Intermediate 3 (28 mg, 0.14 mmol) and DIPEA (0.073 mL, 0.42 mmol) were added followed by MeCN (0.2 mL) and the reaction mixture was stirred at rt overnight. The mixture was diluted with DCM and washed with sat $NaHCO_3$ (aq). The organic phase was dried using a phase separator and evaporated in vacuo. The crude product was purified by preparative SFC, PrepMethod D (gradient: 12-17%), to give the title compound (25 mg, 51%); HRMS (ESI) m/z $[M+H]^+$ calcd for $C_{19}H_{18}FN_4O_2$: 353.1408, found: 353.1402; $^1H$ NMR (600 MHz, DMSO-$d_6$) δ 9.12 (t, 1H), 8.09 (dd, 1H), 8.05 (dd, 1H), 7.69 (ddd, 1H), 7.55 (s, 1H), 5.17 (dd, 1H), 4.54 (dd, 1H), 4.21 (dd, 1H), 3.86 (td, 1H), 2.69 (s, 3H), 2.63-2.55 (m, 1H), 2.25 (dd, 1H), 1.94-1.86 (m, 1H), 1.06-0.93 (m, 1H), 0.82-0.75 (m, 1H).

Example 5: 6-Chloro-N-(2-((1S,3S,5S)-3-cyano-2-azabicyclo[3.1.0]hexan-2-yl)-2-oxoethyl)-2-methylquinoline-4-carboxamide

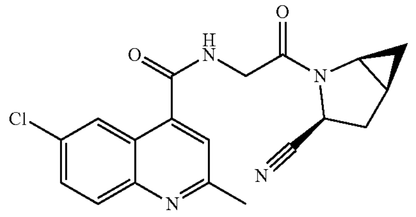 [SMILES: Cc1cc(C(=O)NCC(=O)N2[C@H](C#N)C[C@@H]3C[C@@H]32)c2cc(Cl)ccc2n1]

HATU (59 mg, 0.15 mmol) was added to a suspension of 6-chloro-2-methylquinoline-4-carboxylic acid (31 mg, 0.14 mmol) in DCM (1 mL) and the reaction mixture was stirred at rt for 15 min. (1S,3S,5S)-2-Glycyl-2-azabicyclo[3.1.0]hexane-3-carbonitrile hydrochloride Intermediate 3 (28 mg, 0.14 mmol) and DIPEA (0.073 mL, 0.42 mmol) were added followed by DCM (0.5 mL) and MeCN (0.2 mL) and the reaction mixture was stirred at rt overnight. The reaction mixture was diluted with DCM and washed with sat $NaHCO_3$ (aq). The organic phase was dried using a phase separator and evaporated in vacuo. The crude product was purified by preparative SFC, PrepMethod D (gradient: 15-20%), to give the title compound (29 mg, 57%); HRMS (ESI) m/z $[M+H]^+$ calcd for $C_{19}H_{18}ClN_4O_2$: 369.1112, found: 369.1118; $^1H$ NMR (600 MHz, DMSO-$d_6$) δ 9.16 (t, 1H), 8.37 (d, 1H), 8.00 (d, 1H), 7.79 (dd, 1H), 7.56 (s, 1H), 5.17 (dd, 1H), 4.55 (dd, 1H), 4.22 (dd, 1H), 3.86 (td, 1H), 2.70 (s, 3H), 2.63-2.56 (m, 1H), 2.24 (dd, 1H), 1.94-1.87 (m, 1H), 1.06-0.91 (m, 1H), 0.85-0.75 (m, 1H).

Example 6: 6-Bromo-N-(2-((1S,3S,5S)-3-cyano-2-azabicyclo[3.1.0]hexan-2-yl)-2-oxoethyl)-2-methylquinoline-4-carboxamide

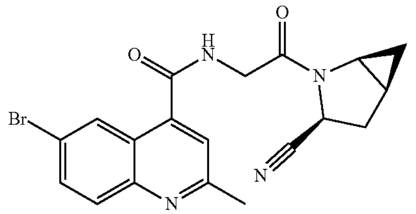

HATU (59 mg, 0.15 mmol) and DIPEA (0.073 mL, 0.42 mmol) were added to a suspension of 6-bromo-2-methylquinoline-4-carboxylic acid (37 mg, 0.14 mmol) in DCM (1 mL) and the reaction mixture was stirred at rt for 15 min. A solution of (1S,3S,5S)-2-glycyl-2-azabicyclo[3.1.0]hexane-3-carbonitrile hydrochloride Intermediate 3 (28 mg, 0.14 mmol) in DCM (1 mL) was added followed by MeCN (0.2 mL) and the reaction mixture was stirred at rt for 2 h. The reaction mixture was diluted with DCM and washed with sat $NaHCO_3$ (aq). The organic phase was dried using a phase separator and evaporated in vacuo. The crude product was purified by preparative SFC, PrepMethod E (gradient: 15-20%) to give the title compound (15 mg, 26%); HRMS (ESI) m/z $[M+H]^+$ calcd for $C_{19}H_{18}BrN_4O_2$: 413.0608, found: 413.0630; $^1$H NMR (600 MHz, DMSO-$d_6$) δ 9.16 (t, 1H), 8.51 (d, 1H), 8.02-7.83 (m, 2H), 7.55 (s, 1H), 5.17 (dd, 1H), 4.55 (dd, 1H), 4.22 (dd, 1H), 3.86 (td, 1H), 2.69 (s, 3H), 2.62-2.55 (m, 1H), 2.24 (dd, 1H), 1.94-1.86 (m, 1H), 1.05-0.99 (m, 1H), 0.79 (ddd, 1H).

Example 7: N-(2-((1S,3S,5S)-3-Cyano-2-azabicyclo[3.1.0]hexan-2-yl)-2-oxoethyl)-6-iodo-2-methylquinoline-4-carboxamide

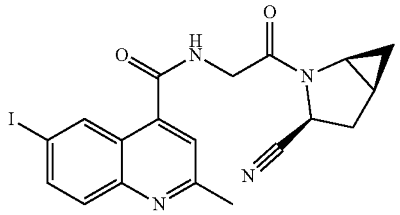 [SMILES: Cc1cc(C(=O)NCC(=O)N2[C@H](C#N)C[C@@H]3C[C@@H]32)c2cc(I)ccc2n1]

HATU (59 mg, 0.15 mmol) was added to a suspension of 6-iodo-2-methylquinoline-4-carboxylic acid (44 mg, 0.14 mmol) in DCM (1 mL) and the reaction mixture was stirred at rt for 15 min. (1S,3S,5S)-2-Glycyl-2-azabicyclo[3.1.0]hexane-3-carbonitrile hydrochloride Intermediate 3 (28 mg, 0.14 mmol) and DIPEA (0.073 mL, 0.42 mmol) were added to the reaction mixture, followed by DCM (0.5 mL) and MeCN (0.2 mL). The reaction mixture was stirred at rt overnight. The reaction mixture was diluted with DCM and washed with sat $NaHCO_3$ (aq), and the organic phase was dried using a phase separator and evaporated in vacuo. The crude product was purified by preparative SFC, PrepMethod D (gradient: 15-20%), to give the title compound (33 mg, 52%); HRMS (ESI) m/z $[M+H]^+$ calcd for $C_{19}H_{15}IN_4O_2$: 461.0468, found: 461.0460; $^1$H NMR (600 MHz, DMSO-$d_6$) δ 9.14 (t, 1H), 8.67 (d, 1H), 8.02 (dd, 1H), 7.76 (d, 1H), 7.52 (s, 1H), 5.16 (dd, 1H), 4.55 (dd, 1H), 4.21 (dd, 1H), 3.85 (td, 1H), 2.68 (s, 3H), 2.63-2.56 (m, 1H), 2.24 (dd, 1H), 1.94-1.86 (m, 1H), 1.06-0.93 (m, 1H), 0.85-0.73 (m, 1H).

Example 8: N-(2-((1S,3S,5S)-3-Cyano-2-azabicyclo[3.1.0]hexan-2-yl)-2-oxoethyl)-7-fluoro-2-methylquinoline-4-carboxamide

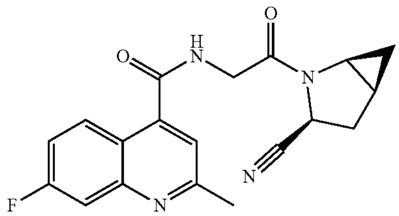 [SMILES: Cc1cc(C(=O)NCC(=O)N2[C@H](C#N)C[C@@H]3C[C@@H]32)c2ccc(F)cc2n1]

HATU (59 mg, 0.15 mmol) was added to a suspension of 7-fluoro-2-methylquinoline-4-carboxylic acid (29 mg, 0.14 mmol) in DCM (1 mL) and the reaction mixture was stirred at rt for 15 min. (1S,3S,5S)-2-Glycyl-2-azabicyclo[3.1.0]hexane-3-carbonitrile hydrochloride Intermediate 3 (28 mg, 0.14 mmol) and DIPEA (0.073 mL, 0.42 mmol) were added followed by DCM (0.5 mL) and MeCN (0.2 mL) and the reaction mixture was stirred at rt overnight. The reaction mixture was diluted with DCM and washed with sat $NaHCO_3$ (aq), and the organic phase was dried using a phase separator and evaporated in vacuo. The crude product was purified by preparative SFC, PrepMethod D (gradient: 12-17%), to give the title compound (29 mg, 58%); HRMS (ESI) m/z $[M+H]^+$ calcd for $C_{19}H_{18}FN_4O_2$: 353.1408, found: 353.1406; $^1$H NMR (600 MHz, DMSO-$d_6$) δ 9.12 (t, 1H), 8.38 (dd, 1H), 7.72 (dd, 1H), 7.55 (td, 1H), 7.48 (s, 1H), 5.15 (dd, 1H), 4.54 (dd, 1H), 4.21 (dd, 1H), 3.86 (td, 1H), 2.70 (s, 3H), 2.62-2.55 (m, 1H), 2.25 (dd, 1H), 1.94-1.86 (m, 1H), 1.07-0.89 (m, 1H), 0.84-0.66 (m, 1H).

Example 9: N-(2-((1S,3S,5S)-3-Cyano-2-azabicyclo[3.1.0]hexan-2-yl)-2-oxoethyl)-6-methylquinoline-4-carboxamide

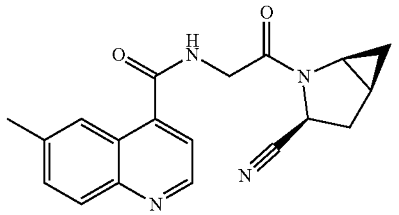 [SMILES: Cc1ccc2nccc(C(=O)NCC(=O)N3[C@H](C#N)C[C@@H]4C[C@@H]43)c2c1]

$Pd(dppf)_2$·DCM (12 mg, 0.02 mmol) was added to a suspension of 6-bromo-N-(2-((1S,3S,5S)-3-cyano-2-azabicyclo[3.1.0]hexan-2-yl)-2-oxoethyl)quinoline-4-carboxamide Example 1 (120 mg, 0.30 mmol), TMB (113 mg, 0.90 mmol), and $K_2CO_3$ (125 mg, 0.90 mmol) in 1,4-dioxane (2 mL), and the reaction mixture was stirred at 80° C. for 4 h. The reaction mixture was diluted with EtOAc (10 mL) and the mixture was washed sequentially with sat $NaHCO_3$ (aq), sat NaCl (aq), and $H_2O$. The organic layer was dried over $Na_2SO_4$, filtered and concentrated in vacuo, and the residue was purified by preparative TLC (MeOH:DCM, 1:10). The crude product was purified by preparative HPLC, Prep- Method F (gradient: 15-40%), to give the title compound (50 mg, 50%); HRMS (ESI) m/z $[M+H]^+$ calcd for $C_{19}H_{19}N_4O_2$: 335.1502, found: 335.1506; $^1H$ NMR (400 MHz, $CD_3OD$) δ 8.87 (d, 1H), 8.22-8.15 (m, 1H), 8.00 (d, 1H), 7.69 (dd, 1H), 7.64 (d, 1H), 5.12 (dd, 1H), 4.64 (d, 1H), 4.42 (d, 1H), 3.82 (td, 1H), 2.76-2.65 (m, 1H), 2.57 (s, 3H), 2.38 (dd, 1H), 2.03-1.91 (m, 1H), 1.15-1.07 (m, 1H), 1.05-0.95 (m, 1H).

Example 10: N-(2-((1S,3S,5S)-3-Cyano-2-azabicyclo[3.1.0]hexan-2-yl)-2-oxoethyl)-6-(trifluoromethyl)quinoline-4-carboxamide

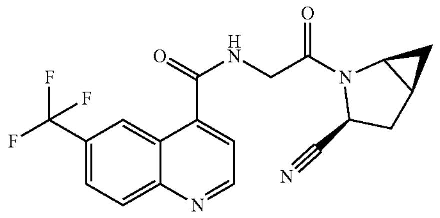 [SMILES: N#C[C@@H]1C[C@@H]2C[C@@H]2N1C(=O)CNC(=O)c1ccnc2ccc(C(F)(F)F)cc12]

EDC (85 mg, 0.44 mmol) and DIPEA (0.14 mL, 0.80 mmol) were added to a solution of HOBt (68 mg, 0.44 mmol), (1S,3S,5S)-2-azabicyclo[3.1.0]hexane-3-carbonitrile 4-methylbenzenesulfonate WO2007029086 (124 mg, 0.44 mmol), and (6-(trifluoromethyl)-quinoline-4-carbonyl) glycine Intermediate 10 (120 mg, 0.40 mmol) in DMF (2 mL) at 0° C., The reaction mixture was stirred at 20° C. for 4 h. The reaction mixture was diluted with EtOAc (10 mL) and washed sequentially with sat $NaHCO_3$ (aq), sat NaCl (aq), and water. The organic layer was dried over $Na_2SO_4$, filtered and concentrated in vacuo. The crude product was purified by preparative HPLC, PrepMethod F (gradient: 15-40%), to give the title compound (50 mg, 32%); HRMS (ESI) m/z $[M+H]^+$ calcd for $C_{19}H_{16}F_3N_4O_2$: 389.1220, found: 389.1224; $^1H$ NMR (300 MHz, $CD_3OD$) δ 9.11 (d, 1H), 8.85-8.78 (m, 1H), 8.41-8.25 (m, 1H), 8.04 (dd, 1H), 7.84 (d, 1H), 5.12 (dd, 1H), 4.67 (d, 1H), 4.44 (d, 1H), 3.81 (td, 1H), 2.77-2.61 (m, 1H), 2.36 (dd, 1H), 2.05-1.90 (m, 1H), 1.25-0.93 (m, 2H).

Example 11: N-(2-((1S,3S,5S)-3-Cyano-2-azabicyclo[3.1.0]hexan-2-yl)-2-oxoethyl)-6-(fluoromethyl) quinoline-4-carboxamide

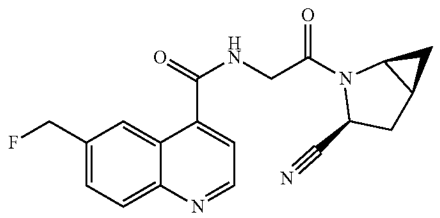 [SMILES: N#C[C@@H]1C[C@@H]2C[C@@H]2N1C(=O)CNC(=O)c1ccnc2ccc(CF)cc12]

DIPEA (0.174 mL, 1.00 mmol) was added to a solution of (1S,3S,5S)-2-azabicyclo[3.1.0]hexane-3-carbonitrile 4-methylbenzenesulfonate WO2007029086 (70 mg, 0.25 mmol), (6-(fluoromethyl)quinoline-4-carbonyl)glycine Intermediate 13 (103 mg) and T3P (50% in EtOAc, 477 mg, 0.75 mmol) in EtOAc (1 mL) at 20° C. and the reaction mixture was stirred at 20° C. for 4 h. The reaction mixture was quenched with sat $NaHCO_3$ (aq, 15 mL) and extracted with DCM (3×15 mL). The combined organic layer was dried over $Na_2SO_4$, filtered and evaporated at reduced pressure. The crude product was purified by preparative HPLC, PrepMethod F (isocratic 34%), to give the title compound (6.5 mg, 5%); HRMS (ESI) m/z $[M+H]^+$ calcd for $C_{19}H_{18}FN_4O_2$: 353.1408, found: 353.1388; $^1H$ NMR (400 MHz, $CD_3OD$) δ 9.03 (d, 1H), 8.51-8.43 (m, 1H), 8.17 (d, 1H), 7.94 (dd, 1H), 7.81 (d, 1H), 5.62 (d, 2H), 5.13 (dd, 1H), 4.65 (d, 1H), 4.45 (d, 1H), 3.81 (td, 1H), 2.78-2.63 (m, 1H), 2.37 (dd, 1H), 2.06-1.90 (m, 1H), 1.17-1.06 (m, 1H), 1.05-0.96 (m, 1H).

Example 12: N-(2-((1S,3S,5S)-3-Cyano-2-azabicyclo[3.1.0]hexan-2-yl)-2-oxoethyl)-6-(2-fluoropropan-2-yl)quinoline-4-carboxamide

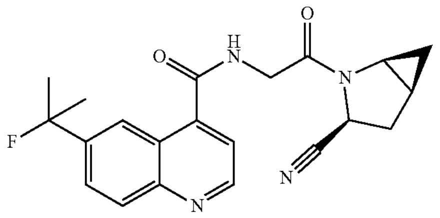 [SMILES: CC(C)(F)c1ccc2nccc(C(=O)NCC(=O)N3[C@H](C#N)C[C@@H]4C[C@@H]43)c2c1]

DIPEA (0.072 mL, 0.41 mmol) was added to a solution of (6-(2-fluoropropan-2-yl)quinoline-4-carbonyl)glycine Intermediate 17 (30 mg, 0.10 mmol), (1S,3S,5S)-2-azabicyclo [3.1.0]hexane-3-carbonitrile 4-methylbenzenesulfonate WO2007029086 (43 mg, 0.16 mmol), EDC (40 mg, 0.21 mmol) and HOBt (32 mg, 0.21 mmol) in DMF (1 mL) at 20° C., and the reaction mixture was stirred at 30° C. for 20 h. The reaction was quenched with sat $NaHCO_3$ (aq, 10 mL), extracted with DCM (3×10 mL), and the combined organic layer was dried over $Na_2SO_4$, filtered and evaporated at reduced pressure. The crude product was purified by preparative HPLC, PrepMethod H (gradient 45-47%), and then by preparative HPLC, PrepMethod I (gradient 10-50%), to give the title compound (8 mg, 20%); HRMS (ESI) m/z $[M+H]^+$ calcd for $C_{21}H_{22}FN_4O_2$: 381.1722, found: 381.1722; $^1H$ NMR (400 MHz, $CD_3OD$) δ 8.94 (d, 1H), 8.51-8.45 (m, 1H), 8.10 (d, 1H), 7.94 (dd, 1H), 7.69 (d, 1H), 5.12 (dd, 1H), 4.64 (d, 1H), 4.43 (d, 1H), 3.80 (td, 1H), 2.78-2.64 (m, 1H), 2.36 (dd, 1H), 2.03-1.92 (m, 1H), 1.79 (d, 6H), 1.15-1.05 (m, 1H), 1.05-0.97 (m, 1H).

Example 13: N-(2-((1S,3S,5S)-3-Cyano-2-azabicyclo[3.1.0]hexan-2-yl)-2-oxoethyl)-6-(2-hydroxypropan-2-yl)quinoline-4-carboxamide

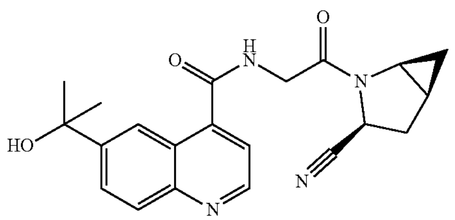 [SMILES: CC(C)(O)c1ccc2nccc(C(=O)NCC(=O)N3[C@H](C#N)C[C@@H]4C[C@@H]43)c2c1]

DIPEA (0.091 mL, 0.52 mmol) was added to a solution of (6-(2-hydroxypropan-2-yl)quinoline-4-carbonyl)glycine Intermediate 18 (50 mg, 0.17 mmol), (1S,3S,5S)-2-azabicyclo[3.1.0]hexane-3-carbonitrile 4-methylbenzenesulfonate WO2007029086 (53 mg, 0.19 mmol), EDC (50 mg, 0.26 mmol) and HOBt (40 mg, 0.26 mmol) in DMF (1 mL) at 20° C., and the reaction mixture was stirred at 20° C. for 20 h. The reaction mixture was quenched with sat $NaHCO_3$ (aq, 20 mL), extracted with DCM (3×20 mL), and the combined organic layer was dried over $Na_2SO_4$, filtered and evaporated at reduced pressure. The crude product was purified by preparative HPLC, PrepMethod B (gradient: 13-23%) and then by preparative HPLC, PrepMethod B (gradient: 10-21%), to give the title compound (6 mg, 9%); HRMS (ESI) m/z $[M+H]^+$ calcd for $C_{21}H_{23}N_4O_3$: 379.1764, found: 379.1760; $^1H$ NMR (300 MHz, $CD_3OD$) δ 9.04 (d, 1H), 8.59 (d, 1H), 8.19 (dd, 1H), 8.13 (d, 1H), 7.86 (d, 1H), 5.12 (dd, 1H), 4.67 (d, 1H), 4.46 (d, 1H), 3.81 (td, 1H), 2.83-2.64 (m, 1H), 2.37 (dd, 1H), 2.08-1.92 (m, 1H), 1.66 (s, 6H), 1.20-1.06 (m, 1H), 1.05-0.94 (m, 1H).

Example 14: N-(2-((1S,3S,5S)-3-Cyano-2-azabicyclo[3.1.0]hexan-2-yl)-2-oxoethyl)-6-(1-hydroxyethyl)quinoline-4-carboxamide

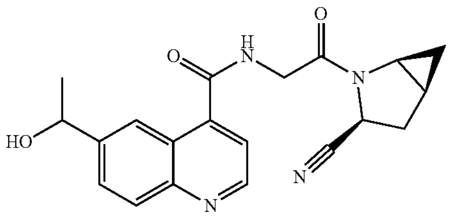 [SMILES: CC(O)c1ccc2nccc(C(=O)NCC(=O)N3[C@H](C#N)C[C@@H]4C[C@@H]43)c2c1]

EDC (77 mg, 0.40 mmol) and DIPEA (0.191 mL, 1.09 mmol) were added to a solution of (1S,3S,5S)-2-azabicyclo[3.1.0]hexane-3-carbonitrile 4-methylbenzenesulfonate WO2007029086 (112 mg, 0.40 mmol), (6-(1-hydroxyethyl)quinoline-4-carbonyl)glycine Intermediate 20 (100 mg, 0.36 mmol), and HOBt (61 mg, 0.40 mmol) in DMF (1 mL) and the reaction mixture was stirred at 20° C. for 16 h. The reaction mixture was diluted with EtOAc (10 mL), and washed with sat $NaHCO_3$ (aq), sat NaCl (aq), and water. The organic layer was dried over $Na_2SO_4$, filtered and concentrated at reduced pressure. The crude product was purified by preparative HPLC, PrepMethod B (gradient: 8-18%) to give the title compound (10 mg, 8%); HRMS (ESI) m/z $[M+H]^+$ calcd for $C_{20}H_{21}N_4O_3$: 365.1608, found: 365.1596; $^1H$ NMR (300 MHz, $CD_3OD$) δ 9.03 (d, 1H), 8.43 (d, 1H), 8.15 (d, 1H), 8.04 (dd, 1H), 7.86 (d, 1H), 5.21-5.03 (m, 2H), 4.66 (d, 1H), 4.46 (d, 1H), 3.80 (td, 1H), 2.79-2.59 (m, 1H), 2.36 (dd, 1H), 2.09-1.86 (m, 1H), 1.54 (d, 3H), 1.17-1.06 (m, 1H), 1.06-0.95 (m, 1H).

Example 15: N-(2-((1S,3S,5S)-3-Cyano-2-azabicyclo[3.1.0]hexan-2-yl)-2-oxoethyl)-6-(1-methoxyethyl)quinoline-4-carboxamide

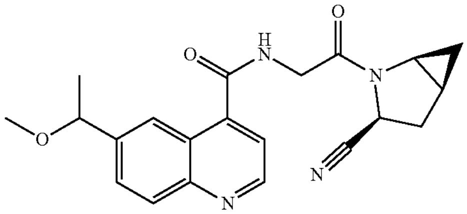 [SMILES: COC(C)c1ccc2nccc(C(=O)NCC(=O)N3[C@H](C#N)C[C@@H]4C[C@@H]43)c2c1]

DIPEA (0.068 mL, 0.39 mmol) was added to a solution of 6-(1-methoxyethyl)quinoline-4-carboxylic acid Intermediate 24 (30 mg, 0.13 mmol), (1S,3S,5S)-2-glycyl-2-azabicyclo[3.1.0]hexane-3-carbonitrile Intermediate 4 (26 mg, 0.16 mmol), EDC (37 mg, 0.19 mmol) and HOBt (30 mg, 0.19 mmol) in DMF (2 mL) and the reaction mixture was stirred at 20° C. for 18 h. The reaction was quenched with sat $NaHCO_3$ (aq, 10 mL) and extracted with DCM (3×10 mL). The combined organic layer was dried over $Na_2SO_4$, filtered and concentrated in vacuo. The crude product was purified by preparative HPLC, PrepMethod B (gradient: 17-27%), to give the title compound (33 mg, 67%); HRMS (ESI) m/z $[M+H]^+$ calcd for $C_{21}H_{23}N_4O_3$: 379.1764, found: 379.1764; $^1H$ NMR (300 MHz, $CD_3OD$) δ 9.07 (d, 1H), 8.48-8.42 (m, 1H), 8.18 (d, 1H), 8.00 (dd, 1H), 7.90 (d, 1H), 5.13 (dd, 1H), 4.72-4.56 (m, 2H), 4.47 (dd, 1H), 3.80 (td, 1H), 3.28 (d, 3H), 2.78-2.62 (m, 1H), 2.37 (dd, 1H), 2.06-1.90 (m, 1H), 1.50 (dd, 3H), 1.18-1.07 (m, 1H), 1.06-0.96 (m, 1H).

Example 16: N-(2-((1S,3S,5S)-3-Cyano-2-azabicyclo[3.1.0]hexan-2-yl)-2-oxoethyl)-6-(2-methoxypropan-2-yl)quinoline-4-carboxamide

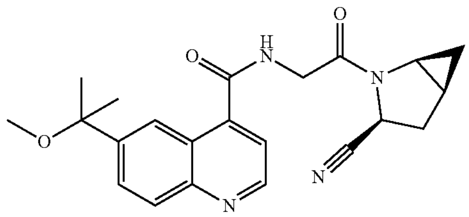 [SMILES: COC(C)(C)c1ccc2nccc(C(=O)NCC(=O)N3[C@H](C#N)C[C@@H]4C[C@@H]43)c2c1]

DIPEA (0.085 mL, 0.49 mmol) was added to a solution of 6-(2-methoxypropan-2-yl)quinoline-4-carboxylic acid Intermediate 27 (40 mg, 0.16 mmol), (1S,3S,5S)-2-glycyl-2-azabicyclo[3.1.0]hexane-3-carbonitrile Intermediate 4 (27 mg, 0.16 mmol), EDC (47 mg, 0.24 mmol) and HOBt (38 mg, 0.24 mmol) in DMF (1 mL) and the reaction mixture was stirred at 30° C. for 20 h. The reaction was quenched with sat $NaHCO_3$ (aq, 10 mL) and extracted with DCM (3×10 mL). The combined organic layer was dried over $Na_2SO_4$, filtered and evaporated at reduced pressure. The crude product was purified by preparative HPLC, PrepMethod I (gradient: 18-28%), to give the title compound (37 mg, 58%); HRMS (ESI) m/z $[M+H]^+$ calcd for $C_{22}H_{25}N_4O_3$: 393.1922, found: 393.1934; $^1H$ NMR (400 MHz, $CD_3OD$) δ 8.92 (d, 1H), 8.42 (d, 1H), 8.09 (d, 1H), 7.97 (dd, 1H), 7.68 (d, 1H), 5.11 (dd, 1H), 4.64 (d, 1H), 4.43 (d, 1H), 3.80 (td, 1H), 3.11 (s, 3H), 2.78-2.64 (m, 1H), 2.36 (dd, 1H), 2.03-1.92 (m, 1H), 1.64 (s, 6H), 1.17-1.06 (m, 1H), 1.05-0.97 (m, 1H).

Example 17: N-(2-((1S,3S,5S)-3-Cyano-2-azabicyclo[3.1.0]hexan-2-yl)-2-oxoethyl)-6-((trifluoromethoxy)methyl)quinoline-4-carboxamide

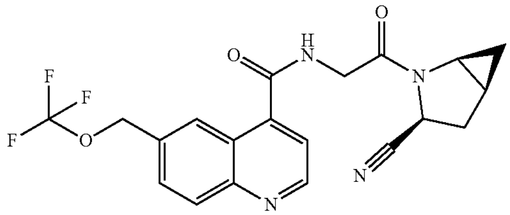 [SMILES: N#C[C@@H]1C[C@@H]2C[C@@H]2N1C(=O)CNC(=O)c1ccnc2ccc(COC(F)(F)F)cc12]

(1S,3S,5S)-2-Glycyl-2-azabicyclo[3.1.0]hexane-3-carbonitrile Intermediate 4 (97 mg, 0.59 mmol), EDC (226 mg, 1.18 mmol) and HOBt (159 mg, 1.18 mmol) were added to a solution of 6-((trifluoromethoxy)methyl)quinoline-4-carboxylic acid Intermediate 30 (160 mg, 0.59 mmol) and DIPEA (305 mg, 2.36 mmol) in DMF (4 mL) under an atmosphere of $N_2$ (g), and the reaction mixture was stirred at 38° C. for 2 h. The reaction mixture was concentrated in vacuo and the residue was purified by preparative HPLC, PrepMethod J, (gradient: 30-60%), to give the title compound (33 mg, 14%); HRMS (ESI) m/z $[M+H]^+$ calcd for $C_{20}H_{18}F_3N_4O_3$: 419.1326, found: 419.1326; $^1H$ NMR (400 MHz, $CD_3OD$) δ 9.00 (d, 1H), 8.48-8.42 (m, 1H), 8.15 (d, 1H), 7.88 (dd, 1H), 7.73 (d, 1H), 5.31 (s, 2H), 5.12 (dd, 1H), 4.64 (d, 1H), 4.44 (d, 1H), 3.81 (td, 1H), 2.76-2.63 (m, 1H), 2.37 (dd, 1H), 2.04-1.92 (m, 1H), 1.16-1.06 (m, 1H), 1.05-0.97 (m, 1H).

Example 18: N-(2-((1S,3S,5S)-3-Cyano-2-azabicyclo[3.1.0]hexan-2-yl)-2-oxoethyl)-6-ethyl-2-methylquinoline-4-carboxamide

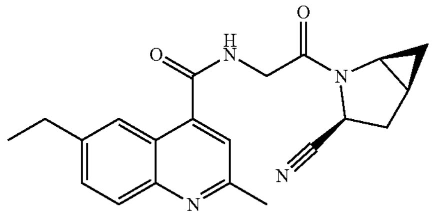 [SMILES: CCc1ccc2nc(C)cc(C(=O)NCC(=O)N3[C@H](C#N)C[C@@H]4C[C@@H]43)c2c1]

HATU (59 mg, 0.15 mmol) was added to a suspension of 6-ethyl-2-methylquinoline-4-carboxylic acid (30 mg, 0.14 mmol) in DCM (1 mL) and the reaction mixture was stirred at rt for 15 min. (1S,3S,5S)-2-Glycyl-2-azabicyclo[3.1.0] hexane-3-carbonitrile hydrochloride Intermediate 3 (28 mg, 0.14 mmol) and DIPEA (0.073 mL, 0.42 mmol) were added to the reaction mixture, followed by DCM (0.5 mL) and MeCN (0.2 mL) and the reaction mixture was stirred at rt overnight. The reaction mixture was diluted with DCM and washed with sat $NaHCO_3$ (aq). The organic layer was dried using a phase separator and evaporated at reduced pressure to give a yellow oil. The residue was dissolved in MeCN, filtered through a syringe filter and purified by preparative SFC, PrepMethod D (gradient: 12-17%), to give the title compound (25 mg, 49%); HRMS (ESI) m/z $[M+H]^+$ calcd for $C_{21}H_{23}N_4O_2$: 363.1816, found: 363.1814; $^1H$ NMR (600 MHz, DMSO-$d_6$) δ 9.03 (t, 1H), 8.07 (d, 1H), 7.89 (d, 1H), 7.64 (dd, 1H), 7.43 (s, 1H), 5.15 (dd, 1H), 4.52 (dd, 1H), 4.23 (dd, 1H), 3.85 (td, 1H), 2.78 (q, 2H), 2.67 (s, 3H), 2.62-2.56 (m, 1H), 2.24 (dd, 1H), 1.93-1.86 (m, 1H), 1.27 (t, 3H), 1.04-0.98 (m, 1H), 0.83-0.73 (m, 1H).

Example 19: N-(2-((1S,3S,5S)-3-Cyano-2-azabicyclo[3.1.0]hexan-2-yl)-2-oxoethyl)-2,6-dimethylquinoline-4-carboxamide

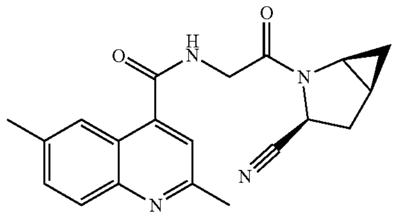 [SMILES: Cc1ccc2nc(C)cc(C(=O)NCC(=O)N3[C@H](C#N)C[C@@H]4C[C@@H]43)c2c1]

HATU (59 mg, 0.15 mmol) was added to a suspension of 2,6-dimethylquinoline-4-carboxylic acid (28 mg, 0.14 mmol) in DCM (1 mL) and the reaction mixture was stirred at rt for 15 min. (1S,3S,5S)-2-Glycyl-2-azabicyclo[3.1.0] hexane-3-carbonitrile hydrochloride Intermediate 3 (28 mg, 0.14 mmol) and DIPEA (0.073 mL, 0.42 mmol) were added to the reaction mixture, followed by DCM (0.5 mL) and MeCN (0.2 mL), and the reaction mixture was stirred at rt overnight. The reaction mixture was diluted with DCM and washed with sat $NaHCO_3$ (aq). The organic layer was dried using a phase separator and evaporated at reduced pressure. The residue was dissolved in MeCN, filtered through a syringe filter and purified by preparative SFC, PrepMethod D (gradient; 12-17%), to give the title compound (25 mg, 52%); HRMS (ESI) m/z $[M+H]^+$ calcd for $C_{20}H_{21}N_4O_2$: 349.1658, found: 349.1650; $^1H$ NMR (600 MHz, DMSO-$d_6$) δ 9.03 (t, 1H), 8.06-8.02 (m, 1H), 7.87 (d, 1H), 7.60 (dd, 1H), 7.43 (s, 1H), 5.15 (dd, 1H), 4.52 (dd, 1H), 4.22 (dd, 1H), 3.85 (td, 1H), 2.67 (s, 3H), 2.63-2.55 (m, 1H), 2.48 (s, 3H), 2.24 (dd, 1H), 1.94-1.86 (m, 1H), 1.07-0.91 (m, 1H), 0.85-0.68 (m, 1H).

Example 20: N-(2-((1S,3S,5S)-3-Cyano-2-azabicyclo[3.1.0]hexan-2-yl)-2-oxoethyl)-7-methylquinoline-4-carboxamide

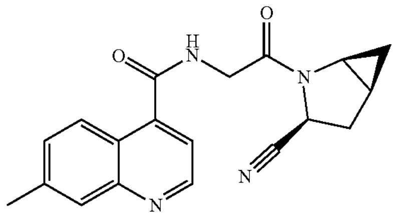 [SMILES: Cc1ccc2c(C(=O)NCC(=O)N3[C@H](C#N)C[C@@H]4C[C@@H]43)ccnc2c1]

Pd(dppf)$Cl_2$·DCM (15 mg, 0.02 mmol) was added to a suspension of 7-bromo-N-(2-((1S,3S,5S)-3-cyano-2-azabicyclo[3.1.0]hexan-2-yl)-2-oxoethyl)quinoline-4-carboxamide Example 3 (150 mg, 0.38 mmol), $K_2CO_3$ (156 mg, 1.13 mmol), and TMB (141 mg, 1.13 mmol) in 1,4-dioxane (2 mL) under an atmosphere of $N_2$ (g), and the reaction mixture was stirred at 80° C. for 4 h. The reaction mixture was diluted with EtOAc (10 mL), and washed sequentially with sat $NaHCO_3$ (aq), sat NaCl (aq), and water. The organic layer was dried over $Na_2SO_4$, filtered and concentrated at reduced pressure. The residue was purified by preparative TLC (MeOH:DCM, 1:10). The crude product was purified by preparative HPLC, PrepMethod B, (gradient: 11-21%), to give the title compound (80 mg, 64%); HRMS (ESI) m/z $[M+H]^+$ calcd for $C_{19}H_{19}N_4O_2$: 335.1508, found: 335.1507; $^1H$ NMR (400 MHz, $CD_3OD$) δ 9.09 (d, 1H), 8.48 (d, 1H), 8.01-7.96 (m, 1H), 7.89 (d, 1H), 7.76 (dd, 1H), 5.13 (dd, 1H), 4.67 (d, 1H), 4.47 (d, 1H), 3.81 (td, 1H), 2.78-2.66 (m, 4H), 2.38 (dd, 1H), 2.07-1.94 (m, 1H), 1.16-1.08 (m, 1H), 1.07-0.99 (m, 1H).

Example 21: N-(2-((1S,3S,5S)-3-Cyano-2-azabicyclo[3.1.0]hexan-2-yl)-2-oxoethyl)-7-(2-fluoropropan-2-yl)quinoline-4-carboxamide

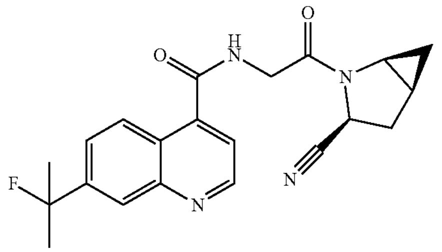 [SMILES: CC(C)(F)c1ccc2c(C(=O)NCC(=O)N3[C@H](C#N)C[C@@H]4C[C@@H]43)ccnc2c1]

DIPEA (0.060 mL, 0.34 mmol) was added dropwise to a solution of 7-(2-fluoropropan-2-yl)quinoline-4-carboxylic acid Intermediate 34 (20 mg, 0.09 mmol), (1S,3S,5S)-2-glycyl-2-azabicyclo[3.1.0]hexane-3-carbonitrile Intermediate 4 (17 mg, 0.10 mmol), EDC (33 mg, 0.17 mmol) and HOBt (26 mg, 0.17 mmol) in DMF (2 mL), and the reaction mixture was stirred at 35° C. for 4 h. The reaction mixture was concentrated in vacuo and the residue was purified by preparative HPLC, PrepMethod K (gradient: 29-30%) to give the title compound (5 mg, 15%); HRMS (ESI) m/z $[M+H]^+$ calcd for $C_{21}H_{22}FN_4O_2$: 381.1722, found: 381.1724; $^1H$ NMR (400 MHz, $CD_3OD$) δ 8.97 (d, 1H), 8.44 (d, 1H), 8.13 (d, 1H), 7.75 (dd, 1H), 7.69 (d, 1H), 5.13 (dd, 1H), 4.65 (d, 1H), 4.44 (d, 1H), 3.82 (td, 1H), 2.75-2.64 (m, 1H), 2.38 (dd, 1H), 2.05-1.93 (m, 1H), 1.79 (d, 6H), 1.17-1.06 (m, 1H), 1.05-0.98 (m, 1H).

Example 22: N-(2-((1S,3S,5S)-3-Cyano-2-azabicyclo[3.1.0]hexan-2-yl)-2-oxoethyl)-7-(difluoromethyl)quinoline-4-carboxamide

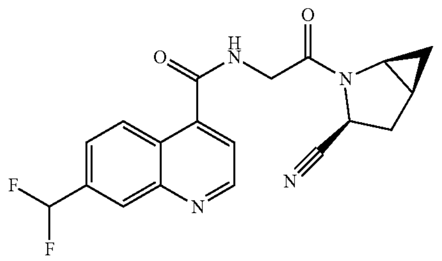 [SMILES: N#C[C@@H]1C[C@@H]2C[C@@H]2N1C(=O)CNC(=O)c1ccnc2cc(C(F)F)ccc12]

DIPEA (0.125 mL, 0.71 mmol) was added dropwise to a solution of (7-(difluoromethyl)quinoline-4-carbonyl)glycine Intermediate 37 (50 mg, 0.18 mmol), (1S,3S,5S)-2-azabicyclo[3.1.0]hexane-3-carbonitrile 4-methylbenzenesulfonate WO2007029086 (75 mg, 0.27 mmol), EDC (68 mg, 0.36 mmol) and HOBt (55 mg, 0.36 mmol) in DMF (2 mL), and the reaction mixture was stirred at 35° C. for 4 h. The reaction mixture was concentrated in vacuo and the crude product was purified by preparative HPLC, PrepMethod K (isocratic: 27%), to give the title compound (15 mg, 23%); HRMS (ESI) m/z $[M+H]^+$ calcd for $C_{19}H_{17}F_2N_4O_2$: 371.1320, found: 371.1304; $^1H$ NMR (400 MHz, $CD_3OD$) δ 9.04 (d, 1H), 8.55 (d, 1H), 8.26 (d, 1H), 7.83 (dd, 1H), 7.78 (d, 1H), 7.04 (t, 1H), 5.12 (dd, 1H), 4.64 (d, 1H), 4.43 (d, 1H), 3.81 (td, 1H), 2.77-2.62 (m, 1H), 2.37 (dd, 1H), 2.04-1.89 (m, 1H), 1.17-1.06 (m, 1H), 1.05-0.97 (m, 1H).

Example 23: N-(2-((1S,3S,5S)-3-Cyano-2-azabicyclo[3.1.0]hexan-2-yl)-2-oxoethyl)-7-(trifluoromethyl)quinoline-4-carboxamide

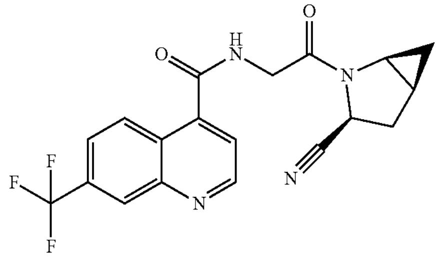 [SMILES: N#C[C@@H]1C[C@@H]2C[C@@H]2N1C(=O)CNC(=O)c1ccnc2cc(C(F)(F)F)ccc12]

EDC (139 mg, 0.72 mmol) and DIPEA (0.316 mL, 1.81 mmol) were added to a solution of (1S,3S,5S)-2-azabicyclo[3.1.0]hexane-3-carbonitrile 4-methylbenzenesulfonate WO2007029086 (203 mg, 0.72 mmol), (7-(trifluoromethyl)quinoline-4-carbonyl)glycine Intermediate 39 (180 mg, 0.60 mmol), and HOBt (98 mg, 0.72 mmol) in DMF (1 mL), and the reaction mixture was stirred at 20° C. for 4 h. The reaction mixture was diluted with EtOAc (20 mL) and washed with sat $NaHCO_3$ (aq), sat NaCl (aq), and water. The organic layer was dried over $Na_2SO_4$, filtered and concentrated at reduced pressure. The crude product was purified by preparative HPLC, PrepMethod L (isocratic: 35%) to give the title compound (80 mg, 34%); HRMS (ESI) m/z $[M+H]^+$ calcd for $C_{19}H_{16}F_3N_4O_2$: 389.1220, found: 389.1224; $^1H$ NMR (300 MHz, $CD_3OD$) δ 9.10 (d, 1H), 8.68-8.58 (m, 1H), 8.44-8.37 (m, 1H), 7.90 (dd, 1H), 7.83 (d, 1H), 5.12 (dd, 1H), 4.64 (d, 1H), 4.45 (d, 1H), 3.80 (td, 1H), 2.78-2.62 (m, 1H), 2.37 (dd, 1H), 2.05-1.90 (m, 1H), 1.22-0.96 (m, 2H).

Example 24: N-(2-((1S,3S,5S)-3-Cyano-2-azabicyclo[3.1.0]hexan-2-yl)-2-oxoethyl)-7-(fluoromethyl)quinoline-4-carboxamide

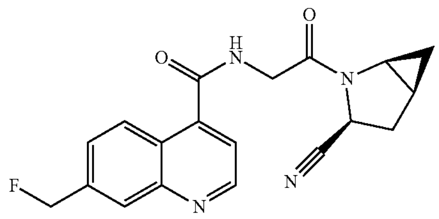 [SMILES: N#C[C@@H]1C[C@@H]2C[C@@H]2N1C(=O)CNC(=O)c1ccnc2cc(CF)ccc12]

HOBt (129 mg, 0.95 mmol) and EDC (146 mg, 0.76 mmol) were added to a solution of (7-(fluoromethyl)quinoline-4-carbonyl)glycine Intermediate 41 (100 mg, 0.38 mmol), (1S,3S,5S)-2-azabicyclo[3.1.0]hexane-3-carbonitrile 4-methylbenzenesulfonate WO2007029086 (128 mg, 0.46 mmol), and DIPEA (197 mg, 1.53 mmol) in DMF (5 mL) and the reaction mixture was stirred at 80° C. for 24 h. The reaction mixture was concentrated in vacuo and the residue was purified by preparative HPLC, PrepMethod F (gradient: 23-30%), to give the title compound (21 mg, 15%); HRMS (ESI) m/z $[M+H]^+$ calcd for $C_{19}H_{18}FN_4O_2$: 353.1408, found: 353.1400; $^1H$ NMR (400 MHz, $CD_3OD$) δ 8.97 (d, 1H), 8.45 (d, 1H), 8.14-8.05 (m, 1H), 7.76-7.66 (m, 2H), 5.64 (d, 2H), 5.12 (dd, 1H), 4.63 (d, 1H), 4.42 (d, 1H), 3.80 (td, 1H), 2.77-2.62 (m, 1H), 2.37 (dd, 1H), 2.03-1.91 (m, 1H), 1.16-1.05 (m, 1H), 1.05-0.96 (m, 1H).

Example 25: N-(2-((1S,3S,5S)-3-Cyano-2-azabicyclo[3.1.0]hexan-2-yl)-2-oxoethyl)-7-(1-hydroxyethyl)quinoline-4-carboxamide

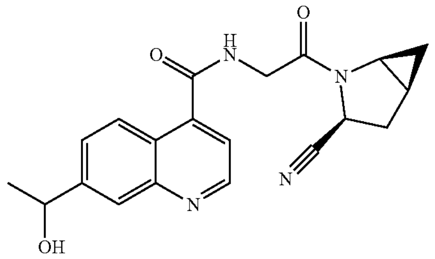 [SMILES: CC(O)c1ccc2c(C(=O)NCC(=O)N3[C@H](C#N)C[C@@H]4C[C@@H]43)ccnc2c1]

DIPEA (0.172 mL, 0.98 mmol) and EDC (69 mg, 0.36 mmol) were added to a solution of (1S,3S,5S)-2-azabicyclo[3.1.0]hexane-3-carbonitrile 4-methylbenzenesulfonate WO2007029086 (101 mg, 0.36 mmol), HOBt (55 mg, 0.36 mmol), and (7-(1-hydroxyethyl)-quinoline-4-carbonyl)glycine Intermediate 44 (90 mg, 0.33 mmol) in DMF (1 mL) and the reaction mixture was stirred at 20° C. for 6 h. The reaction mixture was diluted with EtOAc (10 mL), and washed sequentially with sat $NaHCO_3$ (aq), sat NaCl (aq), and water. The organic layer was dried over $Na_2SO_4$, filtered and concentrated in vacuo. The crude product was purified by preparative HPLC, PrepMethod M (isocratic 20%) to give the title compound (10 mg, 8%); HRMS (ESI) m/z $[M+H]^+$ calcd for $C_{20}H_{21}N_4O_3$: 365.1608, found: 365.1610; $^1H$ NMR (400 MHz, $CD_3OD$) δ 8.93 (d, 1H), 8.38 (d, 1H), 8.11-8.06 (m, 1H), 7.73 (dd, 1H), 7.66 (d, 1H), 5.24-5.02 (m, 2H), 4.63 (d, 1H), 4.42 (d, 1H), 3.81 (td, 1H), 2.75-2.64 (m, 1H), 2.37 (dd, 1H), 2.04-1.92 (m, 1H), 1.55 (d, 3H), 1.15-1.05 (m, 1H), 1.05-0.97 (m, 1H).

Example 26: N-(2-((1S,3S,5S)-3-Cyano-2-azabicyclo[3.1.0]hexan-2-yl)-2-oxoethyl)-7-(2-hydroxypropan-2-yl)quinoline-4-carboxamide

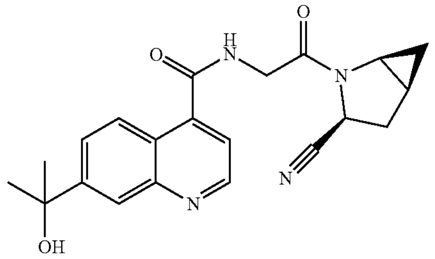 [SMILES: CC(C)(O)c1ccc2c(C(=O)NCC(=O)N3[C@H](C#N)C[C@@H]4C[C@@H]43)ccnc2c1]

DIPEA (0.197 mL, 1.13 mmol) was added dropwise to a solution of (7-(2-hydroxypropan-2-yl)quinoline-4-carbonyl)glycine Intermediate 46 (65 mg, 0.23 mmol), (1S,3S,5S)-2-azabicyclo[3.1.0]hexane-3-carbonitrile (37 mg, 0.34 mmol), EDC (86 mg, 0.45 mmol) and HOBt (69 mg, 0.45 mmol) in DMF (2 mL) and the reaction mixture was stirred at 25° C. for 4 h. The reaction mixture was concentrated in vacuo and the residue was purified by preparative TLC (DCM:MeOH, 10:1). The crude product was purified by preparative HPLC, PrepMethod N, (gradient 18-35%) to give the title compound (25 mg, 29%); HRMS (ESI) m/z $[M+H]^+$ calcd for $C_{21}H_{23}N_4O_3$: 377.1608, found: 377.1620; $^1H$ NMR (400 MHz, $CD_3OD$) δ 8.93 (d, 1H), 8.38 (d, 1H), 8.22 (d, 1H), 7.87 (dd, 1H), 7.67 (d, 1H), 5.13 (dd, 1H), 4.64 (d, 1H), 4.43 (d, 1H), 3.82 (td, 1H), 2.76-2.64 (m, 1H), 2.38 (dd, 1H), 2.07-1.93 (m, 1H), 1.66 (s, 6H), 1.17-1.06 (m, 1H), 1.05-0.97 (m, 1H).

Example 27: N-(2-((1S,3S,5S)-3-Cyano-2-azabicyclo[3.1.0]hexan-2-yl)-2-oxoethyl)-7-(1-methoxyethyl)quinoline-4-carboxamide

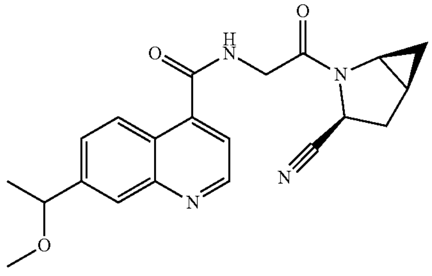 [SMILES: COC(C)c1ccc2c(C(=O)NCC(=O)N3[C@H](C#N)C[C@@H]4C[C@@H]43)ccnc2c1]

DIPEA (0.038 mL, 0.22 mmol) was added to a solution of 7-(1-methoxyethyl)quinoline-4-carboxylic acid Intermediate 49 (50 mg, 0.22 mmol), (1S,3S,5S)-2-glycyl-2-azabicyclo[3.1.0]hexane-3-carbonitrile Intermediate 4 (36 mg, 0.22 mmol), EDC (41 mg, 0.22 mmol) and HOBt (33 mg, 0.22 mmol) in DMF (1 mL) at 20° C., and the reaction mixture was stirred at 40° C. for 18 h. The reaction was quenched with sat $NaHCO_3$ (aq, 10 mL) and extracted with DCM (3×10 mL). The organic layer was dried over $Na_2SO_4$, filtered and evaporated at reduced pressure, and the crude product was purified by preparative HPLC, PrepMethod B, (gradient: 16-26%), to give the title compound (25 mg, 31%); HRMS (ESI) m/z $[M+H]^+$ calcd for $C_{21}H_{23}N_4O_3$: 379.1764, found: 379.1748; $^1H$ NMR (300 MHz, $CD_3OD$) δ 9.09 (d, 1H), 8.55 (d, 1H), 8.13-8.06 (m, 1H), 7.92-7.86 (m, 1H), 7.83 (dd, 1H), 5.17-5.07 (m, 1H), 4.73-4.58 (m, 2H), 4.53-4.38 (m, 1H), 3.88-3.73 (m, 1H), 3.33 (s, 3H), 2.78-2.65 (m, 1H), 2.37 (dd, 1H), 2.07-1.88 (m, 1H), 1.51 (d, 3H), 1.20-0.92 (m, 2H).

Example 28: N-(2-((1S,3S,5S)-3-Cyano-2-azabicyclo[3.1.0]hexan-2-yl)-2-oxoethyl)-7-(2-methoxypropan-2-yl)quinoline-4-carboxamide

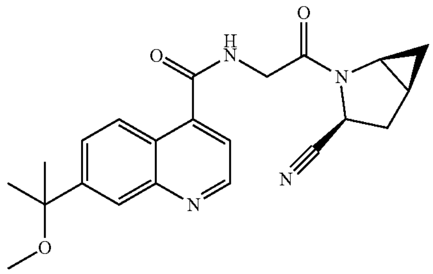 [SMILES: COC(C)(C)c1ccc2c(C(=O)NCC(=O)N3[C@H](C#N)C[C@@H]4C[C@@H]43)ccnc2c1]

DIPEA (0.285 mL, 1.63 mmol) was added in one portion to a solution of 7-(2-methoxypropan-2-yl)quinoline-4-carboxylic acid Intermediate 51 (100 mg, 0.41 mmol), (1S,3S,5S)-2-glycyl-2-azabicyclo[3.1.0]hexane-3-carbonitrile Intermediate 4 (101 mg, 0.61 mmol), EDC (156 mg, 0.82 mmol) and HOBt (125 mg, 0.82 mmol) in DMF (1 mL) and the reaction mixture was stirred at 35° C. for 3 h. The reaction mixture was concentrated in vacuo and the residue was purified by preparative HPLC, PrepMethod N (gradient: 20-38%), to give the title compound (30 mg, 19%); HRMS (ESI) m/z $[M+H]^+$ calcd for $C_{22}H_{25}N_4O_3$: 393.1922, found: 393.1928; $^1H$ NMR (300 MHz, $CD_3OD$) δ 8.94 (d, 1H), 8.40 (d, 1H), 8.09 (d, 1H), 7.82 (dd, 1H), 7.68 (d, 1H), 5.12 (dd, 1H), 4.64 (d, 1H), 4.42 (d, 1H), 3.81 (td, 1H), 3.14 (s, 3H), 2.78-2.62 (m, 1H), 2.37 (dd, 1H), 2.05-1.90 (m, 1H), 1.65 (s, 6H), 1.19-0.96 (m, 2H).

Example 29: N-(2-((1S,3S,5S)-3-Cyano-2-azabicyclo[3.1.0]hexan-2-yl)-2-oxoethyl)-7-((trifluoromethoxy)methyl)quinoline-4-carboxamide

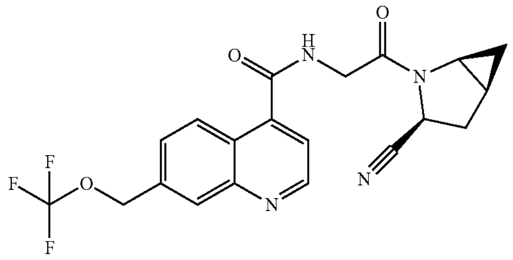 [SMILES: N#C[C@@H]1C[C@@H]2C[C@@H]2N1C(=O)CNC(=O)c1ccnc2cc(COC(F)(F)F)ccc12]

Step a) 7-((Trifluoromethoxy)methyl)quinoline-4-carboxylic acid

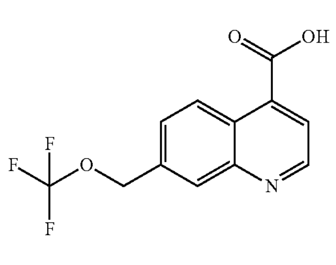 [SMILES: O=C(O)c1ccnc2cc(COC(F)(F)F)ccc12]

Methyl 7-((trifluoromethoxy)methyl)quinoline-4-carboxylate Intermediate 53 (220 mg, 0.77 mmol) and NaOH (30.9 mg, 0.77 mmol) was dissolved in MeOH (4 mL) and water (1 mL), and the reaction mixture was stirred at 20° C. for 2 h. The mixture was concentrated in vacuo to give the subtitle compound as a crude product.

Step b) N-(2-((1S,3S,5S)-3-Cyano-2-azabicyclo[3.1.0]hexan-2-yl)-2-oxoethyl)-7-((trifluoromethoxy)methyl)quinoline-4-carboxamide DIPEA (0.322 mL, 1.84 mmol) was added dropwise to a solution of 7-((trifluoromethoxy)methyl)quinoline-4-carboxylic acid Example 29 Step a) (150 mg, 0.55 mmol), (1S,3S,5S)-2-glycyl-2-azabicyclo[3.1.0]hexane-3-carbonitrile Intermediate 4 (76 mg, 0.46 mmol), EDC (177 mg, 0.92 mmol), and HOBt (141 mg, 0.92 mmol) in DMF (5 mL), and the reaction mixture was stirred at 38° C. for 3 h. The reaction mixture was concentrated in vacuo and the residue was purified by preparative HPLC, PrepMethod F (gradient: 34-39%), to give the title compound (50 mg, 26%); HRMS (ESI) m/z $[M+H]^+$ calcd for $C_{20}H_{18}F_3N_4O_3$: 419.1326, found: 419.1308; $^1H$ NMR (400 MHz, $CD_3OD$) δ 9.00 (d, 1H), 8.48 (d, 1H), 8.14 (d, 1H), 7.77-7.68 (m, 2H), 5.36 (s, 2H), 5.13 (dd, 1H), 4.65 (d, 1H), 4.44 (d, 1H), 3.82 (td, 1H), 2.77-2.64 (m, 1H), 2.38 (dd, 1H), 2.05-1.92 (m, 1H), 1.16-1.06 (m, 1H), 1.05-0.97 (m, 1H).

Example 30: N-(2-((1S,3S,5S)-3-Cyano-2-azabicyclo[3.1.0]hexan-2-yl)-2-oxoethyl)-7-(1-(trifluoromethoxy)ethyl)quinoline-4-carboxamide

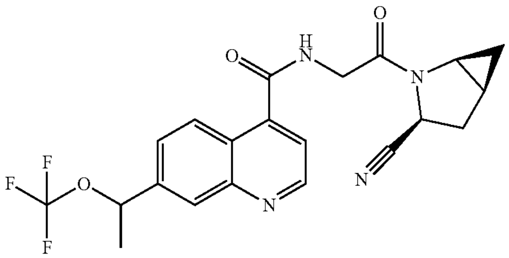 [SMILES: CC(OC(F)(F)F)c1ccc2c(C(=O)NCC(=O)N3[C@H](C#N)C[C@@H]4C[C@@H]43)ccnc2c1]

(1S,3S,5S)-2-Glycyl-2-azabicyclo[3.1.0]hexane-3-carbonitrile Intermediate 4 (87 mg, 0.53 mmol) was added to a solution of 7-(1-(trifluoromethoxy)ethyl)quinoline-4-carboxylic acid Intermediate 55 (150 mg, 0.53 mmol), T3P (50% in EtOAc, 335 mg, 1.05 mmol) in DMF (2.0 mL), and TEA (0.147 mL, 1.05 mmol) in EtOAc (8 mL), and the reaction mixture was stirred at 20° C. for 48 h. The solvent was removed under vacuum, and the residue was purified by preparative TLC (MeOH:DCM, 1:10), and then by preparative HPLC, PrepMethod F (gradient: 33-45%) to give the title compound (16 mg, 7%); HRMS (ESI) m/z $[M+H]^+$ calcd for $C_{21}H_{20}F_3N_4O_3$: 433.1482, found: 433.1488; $^1H$ NMR (400 MHz, DMSO-$d_6$) δ 9.14 (t, 1H), 9.03 (d, 1H), 8.43 (d, 1H), 8.15-8.10 (m, 1H), 7.76 (dd, 1H), 7.61 (d, 1H), 5.86 (q, 1H), 5.17 (dd, 1H), 4.57 (dd, 1H), 4.23 (dd, 1H), 3.91-3.83 (m, 1H), 2.70-2.55 (m, overlapping with solvent peak), 2.26 (dd, 1H), 1.97-1.84 (m, 1H), 1.70 (d, 3H), 1.07-0.94 (m, 1H), 0.85-0.72 (m, 1H).

Example 31: N-(2-((1S,3S,5S)-3-Cyano-2-azabicyclo[3.1.0]hexan-2-yl)-2-oxoethyl)-2,7-dimethylquinoline-4-carboxamide

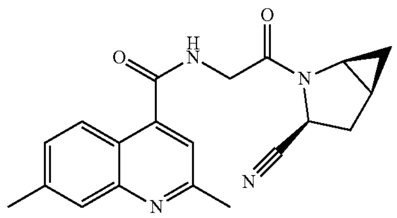 [SMILES: Cc1ccc2c(C(=O)NCC(=O)N3[C@H](C#N)C[C@@H]4C[C@@H]43)cc(C)nc2c1]

DIPEA (0.085 mL, 0.48 mmol) and HATU (0.068 g, 0.18 mmol) was added to a suspension of 2,7-dimethylquinoline-4-carboxylic acid (0.032 g, 0.16 mmol) in DCM (1 mL) and the reaction mixture was stirred at rt for 15 min. A solution of (1S,3S,5S)-2-glycyl-2-azabicyclo[3.1.0]hexane-3-carbonitrile 4-methylbenzenesulfonate Intermediate 2 (0.071 g, 0.16 mmol) in DCM (1 mL) was added followed by MeCN (0.2 mL) and the reaction mixture was stirred at rt overnight. The reaction mixture was diluted with DCM and washed with sat $NaHCO_3$ (aq.). The organic layer was dried using a phase separator and evaporated at reduced pressure. The residue was dissolved in MeCN, filtered through a syringe filter and purified by preparative SFC, PrepMethod O (gradient: 12-17%), and then by preparative SFC, PrepMethod P (gradient: 15-20%), to give the title compound (32 mg, 60%); HRMS (ESI) m/z $[M+H]^+$ calcd for $C_{20}H_{21}N_4O_2$: 349.1664, found: 349.1658; $^1H$ NMR (600 MHz, DMSO-$d_6$) δ 9.03 (t, 1H), 8.16 (d, 1H), 7.79-7.73 (m, 1H), 7.43 (dd, 1H), 7.39 (s, 1H), 5.14 (dd, 1H), 4.51 (dd, 1H), 4.20 (dd, 1H), 3.84 (td, 1H), 2.66 (s, 3H), 2.62-2.55 (m, 1H), 2.54 (s, 3H), 2.24 (dd, 1H), 1.93-1.86 (m, 1H), 1.04-0.98 (m, 1H), 0.78 (ddd, 1H).

Example 32: N-(2-((1S,3S,5S)-3-Cyano-2-azabicyclo[3.1.0]hexan-2-yl)-2-oxoethyl)-7-(1-methylcyclopropyl)quinoline-4-carboxamide

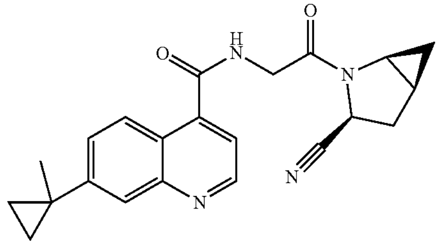 [SMILES: CC1(c2ccc3c(C(=O)NCC(=O)N4[C@H](C#N)C[C@@H]5C[C@@H]54)ccnc3c2)CC1]

DIPEA (0.074 mL, 0.42 mmol) was added to a solution of (7-(1-methylcyclopropyl)-quinoline-4-carbonyl)glycine Intermediate 73 (40 mg, 0.14 mmol), (1S,3S,5S)-2-azabicyclo[3.1.0]hexane-3-carbonitrile 4-methylbenzenesulfonate WO2007029086 (47 mg, 0.17 mmol), EDC (40 mg, 0.21 mmol) and HOBt (32 mg, 0.21 mmol) in DMF (1 mL) at 20° C., and the reaction mixture was stirred at 20° C. for 18 h. The reaction mixture was quenched with sat $NaHCO_3$ (10 mL), extracted with DCM (3×10 mL), and the organic layer was dried over $Na_2SO_4$, filtered and evaporated at reduced pressure. The crude product was purified by preparative HPLC, PrepMethod B, (gradient: 21-32%) to give the title compound (15 mg, 28%); HRMS (ESI) m/z $[M+H]^+$ calcd for $C_{22}H_{23}N_4O_2$: 375.1816, found: 375.1814; $^1H$ NMR (300 MHz, $CD_3OD$) δ 9.09 (d, 1H), 8.49 (d, 1H), 8.02 (d, 1H), 7.89 (d, 1H), 7.70 (dd, 1H), 5.11 (dd, 1H), 4.65 (d, 1H), 4.45 (d, 1H), 3.80 (td, 1H), 2.77-2.60 (m, 1H), 2.37 (dd, 1H), 2.04-1.91 (m, 1H), 1.59 (s, 3H), 1.22-0.95 (m, 6H).

Example 33: N-(2-((1S,3S,5S)-3-Cyano-2-azabicyclo[3.1.0]hexan-2-yl)-2-oxoethyl)-6-(2,2,2-trifluoroethoxy)quinoline-4-carboxamide

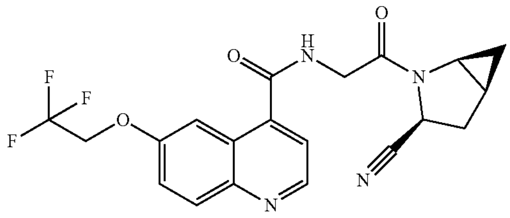 [SMILES: N#C[C@@H]1C[C@@H]2C[C@@H]2N1C(=O)CNC(=O)c1ccnc2ccc(OCC(F)(F)F)cc12]

A stock-solution A was prepared by dissolving $NiCl_2$·DME (4 mg, 18 μmol) and dtbbpy (5 mg, 0.02 mmol) in MeCN (1 mL). A stock-solution B was prepared by dissolving quinuclidine (4.2 mg, 38 μmol) in MeCN (1 mL). Stock-solution B (0.1 mL) and stock-solution A (0.1 mL) were added to a mixture of 6-bromo-N-(2-((1S,3S,5S)-3-cyano-2-azabicyclo[3.1.0]hexan-2-yl)-2-oxoethyl)quinoline-4-carboxamide Example 1 (0.015 g, 0.04 mmol), Ir[dF$(CF_3)$ppy]$_2$(dtbbpy)$PF_6$ (2.1 mg, 1.8 μmol) and $K_2CO_3$ (5.2 mg, 0.04 mmol) and an atmosphere of $N_2$ (g) was applied to the reaction vessel. 2,2,2-Trifluoroethan-1-ol (0.011 g, 0.11 mmol) was added and the reaction mixture was degassed three times by applying a evacuate-refill cycle using $N_2$ (g) as the inert gas. The reaction vessel was capped and sealed using parafilm and the reaction mixture was irradiated with blue LED (34 W, 456 nm) in a fan-cooled chamber for 24 h at rt. The reaction mixture was partitioned between EtOAc (2 mL) and water (2 mL). The aqueous phase was extracted with EtOAc (2×2 mL). The combined organic layer was washed with brine, dried using a phase separator, and then concentrated in vacuo. The residue was purified by preparative SFC, PrepMethod E, (gradient: 15-20%), to give the title compound (1.5 mg, 10%); HRMS (ESI) m/z $[M+H]^+$ calcd for $C_{20}H_{18}F_3N_4O_3$: 419.1326, found: 419.1338.

Example 34: N-(2-((1S,3S,5S)-3-Cyano-2-azabicyclo[3.1.0]hexan-2-yl)-2-oxoethyl)-6-isopropoxyquinoline-4-carboxamide

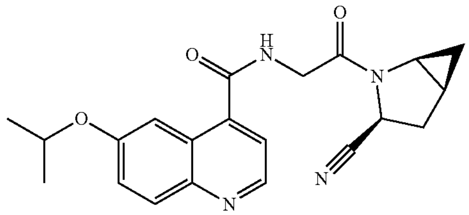 [SMILES: CC(C)Oc1ccc2nccc(C(=O)NCC(=O)N3[C@H](C#N)C[C@@H]4C[C@@H]43)c2c1]

A stock-solution A was prepared by dissolving $NiCl_2$·DME (4.2 mg, 19 μmol) and dtbbpy (5 mg, 0.02 mmol) in MeCN (1 mL). A stock-solution B was prepared by dissolving quinuclidine (4.1 mg, 37 μmol) in MeCN (1 mL).

Stock-solution B (0.1 mL) and stock-solution A (0.1 mL) were added to a mixture of 6-bromo-N-(2-((1S,3S,5S)-3-cyano-2-azabicyclo[3.1.0]hexan-2-yl)-2-oxoethyl)quinoline-4-carboxamide Example 1 (0.015 g, 0.04 mmol), Ir[dF(CF$_3$)ppy]$_2$(dtbbpy)PF$_6$ (2.1 mg, 1.9 μmol) and $K_2CO_3$ (5.2 mg, 0.04 mmol) and an atmosphere of $N_2$ (g) was applied to the reaction vessel. Propan-2-ol (8.7 μL, 0.11 mmol) was added and the reaction vessel was capped and the reaction mixture was degassed three times by applying a evacuate-refill cycle using $N_2$ (g) as the inert gas. The reaction vessel was sealed using parafilm and the reaction mixture was irradiated with blue LED (34 W, 456 nm) in a fan-cooled chamber for 24 h at rt. The reaction mixture was partitioned between EtOAc (5 mL) and water (5 mL). The aqueous phase was extracted with EtOAc. The combined organic layer was washed with brine, dried using a phase separator, and then concentrated in vacuo. The residue was purified by preparative HPLC, PrepMethod A, (gradient: 5-55%), to give the title compound (3.0 mg, 21%); HRMS (ESI) m/z $[M+H]^+$ calcd for $C_{21}H_{23}N_4O_3$: 379.1764, found: 379.1772; $^1$H NMR (500 MHz, $CD_3OD$) δ 8.74 (d, 1H), 8.01-7.92 (m, 2H), 7.58 (d, 1H), 7.41 (dd, 1H), 5.10 (dd, 1H), 4.67-4.57 (m, 2H), 4.41 (d, 1H), 3.79 (td, 1H), 2.78-2.62 (m, 1H), 2.36 (dd, 1H), 2.02-1.93 (m, 1H), 1.40 (t, 6H), 1.14-1.06 (m, 1H), 1.04-0.96 (m, 1H).

Example 35: N-(2-((1S,3S,5S)-3-Cyano-2-azabicyclo[3.1.0]hexan-2-yl)-2-oxoethyl)-6-(cyclopropylmethoxy)quinoline-4-carboxamide

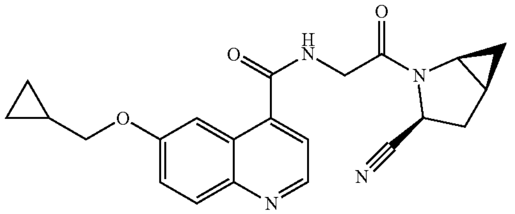 [SMILES: N#C[C@@H]1C[C@@H]2C[C@@H]2N1C(=O)CNC(=O)c1ccnc2ccc(OCC3CC3)cc12]

A stock-solution A was prepared by dissolving $NiCl_2$·DME (14 mg, 63 μmol) and dtbbpy (17 mg, 63 μmol) in MeCN (2.5 mL). A stock-solution B was prepared by dissolving quinuclidine (14 mg, 0.13 mmol) in MeCN (2 mL). Stock-solution B (0.2 mL) and stock-solution A (0.25 mL) were added to a mixture of 6-bromo-N-(2-((1S,3S,5S)-3-cyano-2-azabicyclo[3.1.0]hexan-2-yl)-2-oxoethyl)quinoline-4-carboxamide Example 1 (50 mg, 0.13 mmol), Ir[dF(CF$_3$)ppy]$_2$(dtbbpy)PF$_6$ (7.0 mg, 6.3 μmol) and $K_2CO_3$ (17 mg, 0.13 mmol) and an atmosphere of $N_2$ (g) was applied to the reaction vessel. Cyclopropyl-methanol (15 μL, 0.19 mmol) was added and the reaction vessel was capped and the reaction mixture was degassed three times by applying a evacuate-refill cycle using $N_2$ (g) as the inert gas. The reaction vessel was sealed using parafilm and the reaction mixture was irradiated with blue LED (34 W, 456 nm) in a fan-cooled chamber for 24 h at rt. The reaction mixture was partitioned between EtOAc and water. The aqueous phase was extracted with EtOAc. The combined organic layer was washed with brine, dried using a phase separator, and then concentrated in vacuo. The residue was purified by preparative HPLC, PrepMethod S, (gradient: 5-90%), to give the title compound (7 mg, 14%); HRMS (ESI) m/z $[M+H]^+$ calcd for $C_{22}H_{23}N_4O_3$: 391.1764, found: 391.1772; $^1$H NMR (600 MHz, DMSO-d$_6$) δ 9.07 (t, 1H), 8.80 (d, 1H), 7.98 (d, 1H), 7.86 (d, 1H), 7.48 (d, 1H), 7.47 (dd, 1H), 5.14 (dd, 1H), 4.54 (dd, 1H), 4.23 (dd, 1H), 4.03 (dd, 1H), 3.96 (dd, 1H), 3.86 (td, 1H), 2.65-2.57 (m, 1H), 2.26 (dd, 1H), 1.94-1.86 (m, 1H), 1.34-1.25 (m, 1H), 1.04-0.95 (m, 1H), 0.82-0.77 (m, 1H), 0.63-0.55 (m, 2H), 0.45-0.36 (m, 2H).

Example 36: N-(2-((1S,3S,5S)-3-Cyano-2-azabicyclo[3.1.0]hexan-2-yl)-2-oxoethyl)-7-(1-(trifluoromethyl)cyclopropyl)quinoline-4-carboxamide

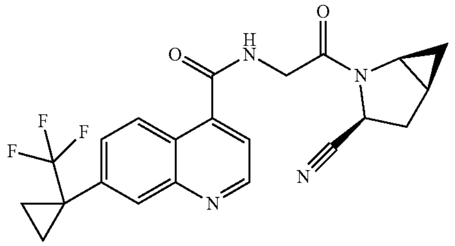 [SMILES: N#C[C@@H]1C[C@@H]2C[C@@H]2N1C(=O)CNC(=O)c1ccnc2cc(C3(C(F)(F)F)CC3)ccc12]

(1S,3S,5S)-2-Glycyl-2-azabicyclo[3.1.0]hexane-3-carbonitrile Intermediate 4 (56 mg, 0.34 mmol) and EDC (109 mg, 0.57 mmol) were added to a solution of 7-(1-(trifluoromethyl)cyclopropyl)quinoline-4-carboxylic acid Intermediate 79 (80 mg, 0.28 mmol), HOBt (87 mg, 0.57 mmol) and DIPEA (199 μL, 1.14 mmol) in DMF (2 mL) at 25° C., and the reaction mixture was stirred at 40° C. for 2 h. The reaction mixture was concentrated in vacuo and the residue was purified by preparative HPLC, PrepMethod F, (gradient: 22-37%) to give the title compound (19 mg, 16%); HRMS (ESI) m/z $[M+H]^+$ calcd for $C_{22}H_{20}F_3N_4O_2$: 429.1532, found: 429.1544; $^1$H NMR (400 MHz, $CD_3OD$) δ 8.98 (d, 1H), 8.42 (d, 1H), 8.19 (d, 1H), 7.80 (dd, 1H), 7.71 (d, 1H), 5.12 (dd, 1H), 4.63 (d, 1H), 4.42 (d, 1H), 3.80 (td, 1H), 2.75-2.63 (m, 1H), 2.37 (dd, 1H), 2.03-1.92 (m, 1H), 1.56-1.47 (m, 2H), 1.35-1.23 (m, 2H), 1.16-1.06 (m, 1H), 1.05-0.94 (m, 1H).

Example 37: N-(2-((1S,3S,5S)-3-Cyano-2-azabicyclo[3.1.0]hexan-2-yl)-2-oxoethyl)-7-cyclopropylquinoline-4-carboxamide

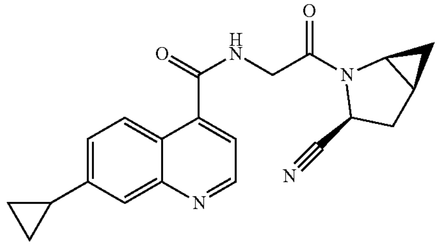 [SMILES: N#C[C@@H]1C[C@@H]2C[C@@H]2N1C(=O)CNC(=O)c1ccnc2cc(C3CC3)ccc12]

A pre-catalyst solution was made as described below. $NiCl_2$·DME (4.1 mg, 0.02 mmol) and dtbbpy (4.2 mg, 0.02 mmol) were suspended in DME (1 mL) and the catalyst mixture was sealed and purged with $N_2$ (g). DME (2 mL) was added and the solution was stirred for 5 min. (CH$_3$Si)$_3$SiH (93 mg, 0.38 mmol) and $Na_2CO_3$ (60 mg, 0.56 mmol) were added to a solution of 7-bromo-N-(2-((1S,3S,5S)-3-cyano-2-azabicyclo[3.1.0]hexan-2-yl)-2-oxoethyl)-quinoline-4-carboxamide (150 mg, 0.38 mmol) Example 3 (150 mg, 0.38 mmol), [Ir{dF(CF$_3$)ppy}$_2$(dtbbpy)]PF$_6$ (4.2 mg, 3.8 μmol), and bromocyclopropane (91 mg, 0.75 mmol) in DME (1 mL). The pre-catalyst solution (1 mL, 0.5 mol % catalyst, 2.5 μmol) was injected into the reaction mixture and the solution was degassed by sparging with $N_2$ (g), while stirring, for 10 min. The reaction mixture was sealed with Parafilm and the reaction was stirred and irradiated with 34 W blue LED at 25° C. using fan-cooling for 16 h. The reaction mixture was diluted with EtOAc (30 mL) and washed with sat $NaHCO_3$ (aq), sat NaCl (aq), and water. The organic layer was dried over $Na_2SO_4$, filtered and concentrated at reduced pressure. The residue was purified by preparative HPLC, PrepMethod B, (gradient: 13-23%) to give the title compound (8 mg, 6%); HRMS (ESI) m/z $[M+H]^+$ calcd for $C_{21}H_{21}N_4O_2$: 361.1658, found: 361.1660; $^1H$ NMR (400 MHz, DMSO-$d_6$) δ 9.09 (t, 1H), 8.95 (d, 1H), 8.27 (d, 1H), 7.79 (d, 1H), 7.51 (d, 1H), 7.41 (dd, 1H), 5.16 (dd, 1H), 4.55 (dd, 1H), 4.21 (dd, 1H), 3.86 (td, 1H), 2.69-2.53 (m, overlapping with solvent peak), 2.30-2.16 (m, 2H), 1.99-1.81 (m, 1H), 1.17-0.96 (m, 3H), 0.95-0.72 (m, 3H).

Example 38: N-(2-((1S,3S,5S)-3-Cyano-2-azabicyclo[3.1.0]hexan-2-yl)-2-oxoethyl)-6-((4,4-difluorocyclohexyl)oxy)quinoline-4-carboxamide

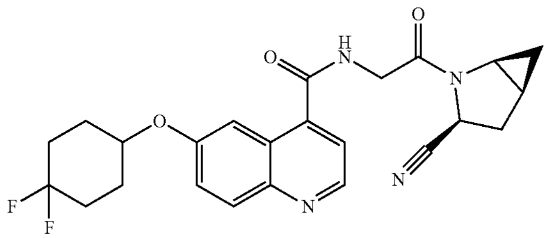 [SMILES: N#C[C@@H]1C[C@@H]2C[C@@H]2N1C(=O)CNC(=O)c1ccnc2ccc(OC3CCC(F)(F)CC3)cc12]

A stock-solution A was prepared by dissolving $NiCl_2$·DME (5.5 mg, 25 μmol) and dtbbpy (6.7 mg, 25 μmol) in MeCN (1 mL). A stock-solution B was prepared by dissolving quinuclidine (5.6 mg, 50 μmol) in MeCN (1 mL). Stock-solution B (0.1 mL) and stock-solution A (0.1 mL) were added to a mixture of 6-bromo-N-(2-((1S,3S,5S)-3-cyano-2-azabicyclo[3.1.0]hexan-2-yl)-2-oxoethyl)quinoline-4-carboxamide Example 1 (0.020 g, 0.05 mmol), Ir[dF$(CF_3)$ppy]$_2$(dtbbpy)$PF_6$ (2.8 mg, 2.5 μmol) and $K_2CO_3$ (28 mg, 0.20 mmol) and an atmosphere of $N_2$ (g) was applied to the reaction vessel. 4,4-Difluorocyclohexan-1-ol (20 mg, 0.15 mmol) was added and the reaction vessel was capped and the reaction mixture was degassed three times by applying a evacuate-refill cycle using $N_2$ (g) as the inert gas. The reaction vessel was sealed using parafilm and the reaction mixture was irradiated with blue LED (34 W, 456 nm) in a fan-cooled chamber for 24 h at rt. The reaction mixture was partitioned between EtOAc and water. The aqueous phase was extracted with EtOAc. The combined organic layer was washed with brine, dried using a phase separator, and then concentrated in vacuo. The residue was purified by preparative HPLC, PrepMethod A, (gradient: 5-60%), to give the title compound (7.3 mg, 32%); HRMS (ESI) m/z $[M+H]^+$ calcd for $C_{24}H_{25}F_2N_4O_3$: 455.1890, found: 455.1888; $^1H$ NMR (500 MHz, $CD_3OD$) 8.76 (d, 1H), 8.08 (d, 1H), 7.99 (d, 1H), 7.57 (d, 1H), 7.48 (dd, 1H), 5.08 (dd, 1H), 4.95-4.85 (m, 1H), 4.61 (d, 1H), 4.39 (d, 1H), 3.78 (td, 1H), 2.75-2.66 (m, 1H), 2.37 (dd, 1H), 2.26-1.93 (m, 9H), 1.14-1.06 (m, 1H), 1.03-0.97 (m, 1H).

Example 39: N-(2-((1S,3S,5S)-3-Cyano-2-azabicyclo[3.1.0]hexan-2-yl)-2-oxoethyl)-7-(1-ethoxycyclopropyl)quinoline-4-carboxamide

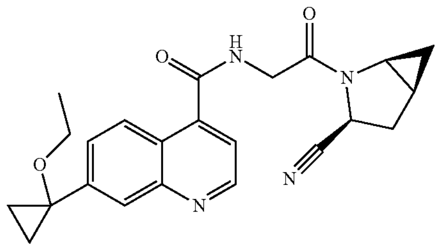 [SMILES: CCOC1(c2ccc3c(C(=O)NCC(=O)N4[C@H](C#N)C[C@@H]5C[C@@H]54)ccnc3c2)CC1]

DIPEA (0.089 mL, 0.51 mmol) was added dropwise to a solution of (7-(1-ethoxy-cyclopropyl)quinoline-4-carbonyl) glycine Intermediate 58 (40 mg, 0.13 mmol), (1S,3S,5S)-2-azabicyclo[3.1.0]hexane-3-carbonitrile 4-methylbenzenesulfonate WO2007029086 (53 mg, 0.19 mmol), EDC (49 mg, 0.25 mmol), and HOBt (39 mg, 0.25 mmol) in DMF (5 mL), and the reaction mixture was stirred at 35° C. for 3 h. The reaction mixture was diluted with EtOAc (20 mL) and washed with sat brine (3×20 mL). The organic layer was dried over $Na_2SO_4$, filtered and evaporated and the crude product was purified by preparative HPLC, PrepMethod K (gradient: 29-30%) to give the title compound (10 mg, 19%); HRMS (ESI) m/z $[M+H]^+$ calcd for $C_{23}H_{25}N_4O_3$: 405.1922, found: 405.1912; $^1H$ NMR (400 MHz, $CD_3OD$) δ 8.92 (d, 1H), 8.38 (d, 1H), 8.01 (d, 1H), 7.65 (d, 1H), 7.59 (dd, 1H), 5.11 (dd, 1H), 4.63 (d, 1H), 4.42 (d, 1H), 3.80 (td, 1H), 3.55 (q, 2H), 2.79-2.62 (m, 1H), 2.37 (dd, 1H), 2.05-1.93 (m, 1H), 1.44-1.32 (m, 2H), 1.29-1.15 (m, 5H), 1.14-1.06 (m, 1H), 1.05-0.96 (m, 1H).

Example 40: N-(2-((1S,3S,5S)-3-Cyano-2-azabicyclo[3.1.0]hexan-2-yl)-2-oxoethyl)-7-(1-cyanocyclopropyl)quinoline-4-carboxamide

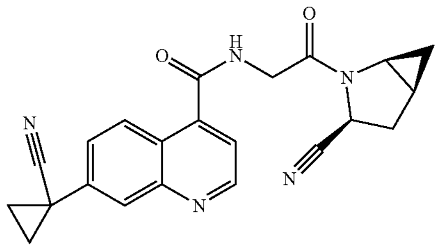 [SMILES: N#C[C@@H]1C[C@@H]2C[C@@H]2N1C(=O)CNC(=O)c1ccnc2cc(C3(C#N)CC3)ccc12]

A solution of 7-(1-cyanocyclopropyl)quinoline-4-carboxylic acid Intermediate 81 (150 mg, 0.63 mmol), (1S,3S,5S)-2-glycyl-2-azabicyclo[3.1.0]hexane-3-carbonitrile Intermediate 4 (312 mg, 1.89 mmol), EDC (181 mg, 0.94 mmol), HOBt (145 mg, 0.94 mmol) and DIPEA (0.550 mL, 3.15 mmol) in DMF (8 mL) was stirred at rt for 3 h. The reaction mixture was concentrated under reduced pressure and the residue was purified by preparative TLC (DCM:MeOH, 20:1). The crude product was purified by preparative HPLC, PrepMethod L, (gradient: 28-38%) followed by preparative SFC, PrepMethod T, (isocratic 50%) to give the title compound (55 mg, 23%); HRMS (ESI) m/z $[M+H]^+$ calcd for $C_{22}H_{20}N_5O_2$: 386.1612, found: 386.1612; $^1H$ NMR (400

MHz, $CD_3OD$) δ 8.98 (d, 1H), 8.46 (d, 1H), 8.11 (d, 1H), 7.70 (d, 1H), 7.57 (dd, 1H), 5.12 (dd, 1H), 4.64 (d, 1H), 4.43 (d, 1H), 3.81 (td, 1H), 2.75-2.63 (m, 1H), 2.36 (dd, 1H), 2.05-1.93 (m, 1H), 1.93-1.84 (m, 2H), 1.80-1.67 (m, 2H), 1.16-1.05 (m, 1H), 1.05-0.97 (m, 1H).

Example 41: N-(2-((1S,3S,5S)-3-Cyano-2-azabicyclo[3.1.0]hexan-2-yl)-2-oxoethyl)-7-methoxy-2-methylquinoline-4-carboxamide

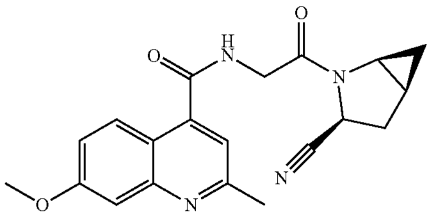 [SMILES: COc1ccc2c(C(=O)NCC(=O)N3[C@H](C#N)C[C@@H]4C[C@@H]43)cc(C)nc2c1]

HATU (59 mg, 0.15 mmol) was added to a suspension of 7-methoxy-2-methylquinoline-4-carboxylic acid (30 mg, 0.14 mmol) in DCM (1 mL) and the reaction mixture was stirred at rt for 15 min. (1S,3S,5S)-2-Glycyl-2-azabicyclo[3.1.0]hexane-3-carbonitrile hydrochloride Intermediate 3 (28 mg, 0.14 mmol) and DIPEA (0.073 mL, 0.42 mmol) were added followed by DCM (0.5 mL) and MeCN (0.2 mL), and the reaction mixture was stirred at rt overnight. The reaction mixture was diluted with DCM and washed with sat $NaHCO_3$ (aq). The organic layer was dried using a phase separator and evaporated at reduced pressure. The crude product was dissolved in MeCN, filtered through a syringe filter and purified by preparative SFC, PrepMethod D, (gradient: 15-20%), to give the title compound (26 mg, 51%); HRMS (ESI) m/z $[M+H]^+$ calcd for $C_{20}H_{21}N_4O_3$: 365.1608, found: 365.1620; $^1$H NMR (600 MHz, DMSO-$d_6$) δ 9.02 (t, 1H), 8.19 (d, 1H), 7.37 (d, 1H), 7.31 (s, 1H), 7.23 (dd, 1H), 5.14 (dd, 1H), 4.52 (dd, 1H), 4.19 (dd, 1H), 3.91 (s, 3H), 3.85 (td, 1H), 2.66 (s, 3H), 2.63-2.55 (m, 1H), 2.24 (dd, 1H), 1.93-1.86 (m, 1H), 1.03-0.98 (m, 1H), 0.82-0.73 (m, 1H).

Example 42: N-(2-((1S,3S,5S)-3-Cyano-2-azabicyclo[3.1.0]hexan-2-yl)-2-oxoethyl)-6-cyclopropylquinoline-4-carboxamide

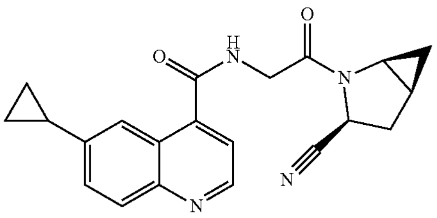 [SMILES: N#C[C@@H]1C[C@@H]2C[C@@H]2N1C(=O)CNC(=O)c1ccnc2ccc(C3CC3)cc12]

A pre-catalyst solution was made as described below. $NiCl_2 \cdot DME$ (2.7 mg, 0.01 mmol) and dtbbpy (3.4 mg, 0.02 mmol) were suspended in DME (1 mL) and the catalyst mixture was sealed and purged with $N_2$ (g). DME (2 mL) was added and the solution was stirred for 5 min.

$(CH_3Si)_3SiH$ (93 mg, 0.38 mmol) and $Na_2CO_3$ (53 mg, 0.50 mmol) were added to a solution of 6-bromo-N-(2-((1S,3S,5S)-3-cyano-2-azabicyclo[3.1.0]hexan-2-yl)-2-oxoethyl)quinoline-4-carboxamide Example 1 (150 mg, 0.38 mmol), [Ir{dF($CF_3$)ppy}2(dtbbpy)]$PF_6$ (2.8 mg, 2.5 μmol), and bromocyclopropane (45 mg, 0.38 mmol) in DME (1 mL). The pre-catalyst solution (1 mL, 0.5 mol % catalyst, 2.5 μmol) was injected into the reaction mixture and the solution was degassed by sparging with $N_2$ (g), while stirring, for 10 min. The reaction mixture was sealed with Parafilm and the reaction was stirred and irradiated with 34 W blue LED at 25° C. using fan-cooling for 16 h. The reaction mixture was diluted with EtOAc (10 mL) and washed with sat $NaHCO_3$ (aq), sat NaCl (aq), and water. The organic layer was dried over $Na_2SO_4$, filtered and concentrated at reduced pressure. The residue was purified by preparative TLC (EtOAc: petroleum ether, 1:1). The crude product was purified by preparative HPLC, PrepMethod B, (gradient: 10-40%) to give the title compound (8.0 mg, 9%); HRMS (ESI) m/z $[M+H]^+$ calcd for $C_{21}H_{21}N_4O_2$: 361.1658, found: 361.1668; $^1$H NMR (300 MHz, DMSO-$d_6$) δ 9.21 (t, 1H), 8.98 (d, 1H), 8.14 (d, 1H), 8.04 (d, 1H), 7.73-7.62 (m, 2H), 5.13 (dd, 1H), 4.52 (d, 1H), 4.28 (d, 1H), 3.86-3.75 (m, overlapping with solvent peak), 2.67-2.52 (m, overlapping with solvent peak), 2.24 (dd, 1H), 2.19-2.03 (m, 1H), 1.96-1.82 (m, 1H), 1.14-0.96 (m, 3H), 0.93-0.71 (m, 3H).

Example 43: N-(2-((1S,3S,5S)-3-Cyano-2-azabicyclo[3.1.0]hexan-2-yl)-2-oxoethyl)-6-(1-methylcyclopropyl)quinoline-4-carboxamide

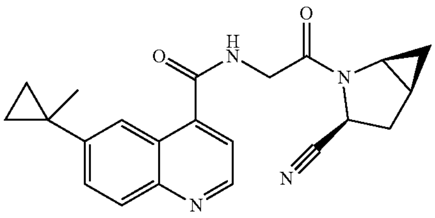 [SMILES: CC1(c2ccc3nccc(C(=O)NCC(=O)N4[C@H](C#N)C[C@@H]5C[C@@H]54)c3c2)CC1]

DIPEA (0.056 mL, 0.32 mmol) was added to a solution of (6-(1-methylcyclopropyl)quinoline-4-carbonyl)glycine Intermediate 60 (46 mg, 0.16 mmol), (1S,3S,5S)-2-azabicyclo[3.1.0]hexane-3-carbonitrile 4-methylbenzenesulfonate WO2007029086 (30 mg, 0.11 mmol), EDC (31 mg, 0.16 mmol) and HOBt (25 mg, 0.16 mmol) in DMF (0.5 mL) at 20° C., and the reaction mixture was stirred at 20° C. for 18 h. Sat $NaHCO_3$ (15 mL) was added to the reaction mixture, and the mixture was extracted with DCM (3×15 mL). The organic layer was dried over $Na_2SO_4$, filtered and evaporated. The crude product was purified by preparative HPLC, PrepMethod B, (gradient: 22-32%), to give the title compound (16 mg, 40%); HRMS (ESI) m/z $[M+H]^+$ calcd for $C_{22}H_{23}N_4O_2$: 375.1816, found: 375.1830; $^1$H NMR (300 MHz, $CD_3OD$) δ 9.04 (d, 1H), 8.43 (d, 1H), 8.10 (d, 1H), 7.97-7.86 (m, 2H), 5.12 (dd, 1H), 4.66 (d, 1H), 4.46 (d, 1H), 3.80 (td, 1H), 2.78-2.62 (m, 1H), 2.37 (dd, 1H), 2.03-1.92 (dd, 1H), 1.56 (s, 3H), 1.17-0.97 (m, 4H), 0.97-0.89 (m, 2H).

Example 44: N-(2-((1S,3S,5S)-3-Cyano-2-azabicyclo[3.1.0]hexan-2-yl)-2-oxoethyl)-6-(1-(trifluoromethyl)cyclopropyl)quinoline-4-carboxamide

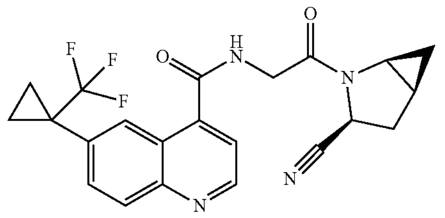 [SMILES: N#C[C@@H]1C[C@@H]2C[C@@H]2N1C(=O)CNC(=O)c1ccnc2ccc(C3(C(F)(F)F)CC3)cc12]

(1S,3S,5S)-2-Glycyl-2-azabicyclo[3.1.0]hexane-3-carbonitrile Intermediate 4 (49 mg, 0.30 mmol) and EDC (95 mg, 0.50 mmol) were added to a solution of HOBt (67 mg, 0.50 mmol), 6-(1-(trifluoromethyl)cyclopropyl)quinoline-4-carboxylic acid Intermediate 65 (70 mg, 0.25 mmol) and DIPEA (129 mg, 1.00 mmol) in DMF (2 mL) at 25° C. and the reaction mixture was stirred at 40° C. for 2 h. The reaction mixture was concentrated in vacuo and the residue was purified by preparative HPLC, PrepMethod C, (gradient: 35-47%), to give the title compound (11 mg, 10%); HRMS (ESI) m/z $[M+H]^+$ calcd for $C_{22}H_{20}F_3N_4O_2$: 429.1532, found: 429.1518; $^1H$ NMR (400 MHz, $CD_3OD$) δ 8.97 (d, 1H), 8.53 (d, 1H), 8.10 (d, 1H), 8.01-7.93 (m, 1H), 7.72 (d, 1H), 5.13 (dd, 1H), 4.65 (d, 1H), 4.43 (d, 1H), 3.80 (td, 1H), 2.76-2.64 (m, 1H), 2.37 (dd, 1H), 2.03-1.92 (m, 1H), 1.50-1.42 (m, 2H), 1.37-1.24 (m, 2H), 1.17-1.05 (m, 1H), 1.05-0.98 (m, 1H).

Example 45: N-(2-((1S,3S,5S)-3-Cyano-2-azabicyclo[3.1.0]hexan-2-yl)-2-oxoethyl)-6-(1-ethoxycyclopropyl)quinoline-4-carboxamide

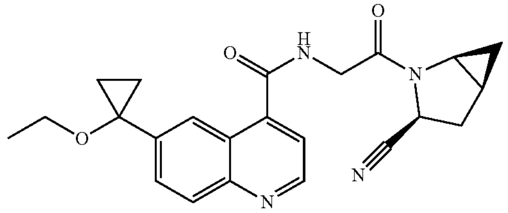 [SMILES: CCOC1(c2ccc3nccc(C(=O)NCC(=O)N4[C@H](C#N)C[C@@H]5C[C@@H]54)c3c2)CC1]

DIPEA (50 mg, 0.39 mmol) was added dropwise to a solution of 6-(1-ethoxy-cyclopropyl)quinoline-4-carboxylic acid Intermediate 68 (100 mg, 0.39 mmol), (1S,3S,5S)-2-glycyl-2-azabicyclo[3.1.0]hexane-3-carbonitrile Intermediate 4 (64 mg, 0.39 mmol), EDC (74 mg, 0.39 mmol) and HOBt (60 mg, 0.39 mmol) in DMF (4 mL) and the reaction mixture was stirred at 35° C. for 4 h. The reaction mixture was concentrated in vacuo and the residue was purified by preparative HPLC, PrepMethod N, (gradient: 20-38%), to give the title compound (30 mg, 19%); HRMS (ESI) m/z $[M+H]^+$ calcd for $C_{23}H_{25}N_4O_3$: 405.1922, found: 405.1942; $^1H$ NMR (400 MHz, $CD_3OD$) δ 8.89 (d, 1H), 8.29 (d, 1H), 8.07 (d, 1H), 7.84 (dd, 1H), 7.66 (d, 1H), 5.11 (dd, 1H), 4.63 (d, 1H), 4.42 (d, 1H), 3.80 (td, 1H), 3.51 (q, 2H), 2.77-2.64 (m, 1H), 2.36 (dd, 1H), 2.03-1.91 (m, 1H), 1.34-1.15 (m, 7H), 1.14-1.06 (m, 1H), 1.05-0.96 (m, 1H).

Example 46: N-(2-((1S,3S,5S)-3-Cyano-2-azabicyclo[3.1.0]hexan-2-yl)-2-oxoethyl)-6-(1-cyanocyclopropyl)quinoline-4-carboxamide

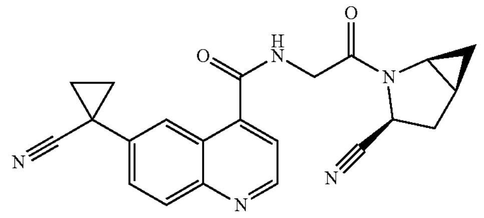 [SMILES: N#C[C@@H]1C[C@@H]2C[C@@H]2N1C(=O)CNC(=O)c1ccnc2ccc(C3(C#N)CC3)cc12]

DIPEA (0.293 mL, 1.68 mmol) was added dropwise to a solution of 6-(1-cyanocyclopropyl)quinoline-4-carboxylic acid Intermediate 71 (100 mg, 0.42 mmol), (1S,3S,5S)-2-glycyl-2-azabicyclo[3.1.0]hexane-3-carbonitrile Intermediate 4 (104 mg, 0.63 mmol), EDC (161 mg, 0.84 mmol), and HOBt (129 mg, 0.84 mmol) in DMF (1 mL) and the reaction mixture was stirred at 35° C. for 3 h. The reaction mixture was concentrated in vacuo and the residue was purified by preparative HPLC, PrepMethod C, (gradient: 20-30%) to give the title compound (30 mg, 19%); HRMS (ESI) m/z $[M+H]^+$ calcd for $C_{22}H_{20}N_5O_2$: 386.1612, found: 386.1630; $^1H$ NMR (400 MHz, $CD_3OD$) δ 9.05 (d, 1H), 8.51-8.42 (m, 1H), 8.19 (d, 1H), 8.03 (dd, 1H), 7.83 (d, 1H), 5.15 (dd, 1H), 4.67 (d, 1H), 4.45 (d, 1H), 3.81 (td, 1H), 2.77-2.63 (m, 1H), 2.37 (dd, 1H), 2.05-1.93 (m, 1H), 1.92-1.76 (m, 4H), 1.17-1.06 (m, 1H), 1.05-0.97 (m, 1H).

D. Biological Data

The hFAP protein used in the Examples was either commercially sourced or produced in insect cells as recombinant hFAP (Gp67-6HN-TEV-FAP(M39-A757), MW 89086.7 Da, or cd33-FAP (27-757)-6His, MW85926 Da). Recombinant hFAP protein was secreted from Sf21 cells in media, purified with affinity (batchmode, Ni excel resin, ÄKTA, GE Healthcare) and size exclusion chromatography (Superdex200, ÄKTA, GE Healthcare), concentrated to 19.5 mg/mL, snapfrozen in liquid $N_2$ and stored in −80° C.

Example 47: FAP Inhibition and Binding Assays

A. hFAP Inhibition Assay

Compounds were tested in a biochemical inhibition assay using hFAP enzyme at 0.24 nM FAC (Proteros, 38-760 (PR-0071)) and the substrate Ala-Pro-AMC (ARI-3144) at 20 μM FAC. 384 low volume black plates (Greiner #784076) were used. 4 μL, 0.48 nM enzyme solution (100 mM Tris HCl, 100 mM NaCl, 0.05% Chaps, pH 7.4) was added to 40 nL compounds (in DMSO) at 10 CR, 3-fold dilution series from 50 μM FAC. Plates were incubated for 15 min at rt in dark. 4 μL, 40 μM substrate solution (100 mM Tris HCl, 100 mM NaCl, 0.05% Chaps, pH 7.4) was added to each well. Plates were centrifuged at 1000 rpm and incubated for 30 min at rt in dark. The plates were read on a PHERAstar® reader with excitation 340 nm and emission 460 nm. Data were analyzed in Genedata Screener®. $IC_{50}$ values were determined by plotting % inhibition versus log compound concentration and using a one site dose response model. Raw data signals were normalized using 0.5% DMSO as 0% control and Reference Compound A (i.e., (S)—N-(2-(2-cyano-4,4-difluoropyrrolidin-1-yl)-2-oxoethyl)quinoline-4-carboxamide as reported in *J. Med. Chem.* 2014, 57, 3053) at 50 μM as 100% inhibitor control. Data for the compounds tested are reported in Table 1A.

B. hFAP Inhibition Assay (Tight Binders)

Compounds were tested in a biochemical inhibition assay using human Fibroblast activation protein alpha (hFAP) enzyme at 2.4 μM FAC (Proteros, 38-760 (PR-0071) and the substrate Ala-Pro-AMC (ARI-3144) at 20 μM FAC. 384 low volume black plates (Greiner #784076) were used. 4 μL, 4.8 μM enzyme solution (100 mM Tris HCl, 100 mM NaCl, 0.05% Chaps, pH 7.4) was added to 40 nL compounds (in DMSO) at 10 CR, 3-fold dilution series from 50 nM FAC. Plates were incubated for 15 min at rt in dark. 4 μL, 40 μM substrate solution (100 mM Tris HCl, 100 mM NaCl, 0.05% Chaps, pH 7.4) was added to each well. Plates were centrifuged at 1000 rpm and incubated for 2.5 h at rt in dark. The plates were read on a PHERAstar® reader with excitation 340 nm and emission 460 nm. Data were analyzed in Genedata Screener®. $IC_{50}$ values were determined by plotting % inhibition versus log compound concentration and using a one site dose response model. Raw data signals were normalized using 0.5% DMSO as 0% control and Reference Compound A (i.e., (S)—N-(2-(2-cyano-4,4-difluoropyrrolidin-1-yl)-2-oxoethyl)quinoline-4-carboxamide as reported in *J. Med. Chem.* 2014, 57, 3053) at 50 μM as 100% inhibitor control. Data for the compounds tested are reported in Table 1A.

TABLE 1A

| Example | hFAP inhibition assay $IC_{50}$ (nM)[1] | hFAP inhibition assay (tight binders) $IC_{50}$ (nM)[2] |
|---|---|---|
| 1 | 2 | 0.44 |
| 2 | 0.65 | 0.18 |
| 3 | 0.68 | 0.12 |
| 4 | 64 | 32 |
| 5 | 65 | 18 |
| 6 | 58 | 18 |
| 7 | 53 | 15 |
| 8 | 71 | 20 |
| 9 | <2.8 | 0.56 |
| 10 | 4.8 | |
| 11 | 2.2 | 0.40 |
| 12 | 3.8 | 0.75 |
| 13 | 3.8 | 0.86 |
| 14 | 2.6 | 0.91 |
| 15 | 16 | 1.1 |
| 16 | 4.2 | 0.81 |
| 17 | 1.7 | 0.38 |
| 18 | 80 | 25 |
| 19 | 80 | 33 |
| 20 | <1.6 | 0.48 |
| 21 | 2.8 | 0.97 |
| 22 | 1.5 | 0.51 |
| 23 | 0.81 | 0.33 |
| 24 | 1.2 | 0.30 |
| 25 | <1.8 | 0.37 |
| 26 | 2.1 | 0.70 |
| 27 | 6 | 2 |
| 28 | 4.6 | 1.3 |
| 29 | 1.3 | 0.30 |
| 30 | 3.1 | 0.41 |
| 31 | 31 | 11 |
| 32 | 2 | |
| 33 | 1.4 | |
| 34 | 4.1 | 1.2 |
| 35 | 0.64 | 0.097 |
| 36 | 3.4 | 0.58 |
| 37 | <1.7 | 0.30 |
| 38 | 1.3 | |
| 39 | 1.5 | 0.41 |
| 40 | 0.49 | 0.15 |
| 41 | 38 | |

TABLE 1A-continued

| Example | hFAP inhibition assay $IC_{50}$ (nM)[1] | hFAP inhibition assay (tight binders) $IC_{50}$ (nM)[2] |
|---|---|---|
| 42 | 5.6 | |
| 43 | 2.9 | 0.56 |
| 44 | 4.6 | 1.1 |
| 45 | 0.76 | 0.25 |
| 46 | 1.7 | 0.18 |

[1] $IC_{50}$ is reported as geometric mean for multiple measurements (n = 2-29).
[2] $IC_{50}$ is reported after single measurement (n = 1) or as geometric mean for multiple measurements (n = 5-10).

C. hFAP Binding Assay

Compounds were tested in a direct binding assay using 8K surface plasmon resonance biosensor (GE Healthcare) at 20° C. Immobilization of hFAP (M39-A757) on a CMD200M sensor chip (Xantec) was performed using standard amine coupling procedure in immobilization buffer (10 mM HEPES, 150 mM NaCl, 0.05% Tween20, pH 7.4). The surface was washed with 10 mM NaOH, 1M NaCl before being activated with EDC/NHS (GE Healthcare), followed by immobilization of hFAP (in 10 mM Acetate pH 5.0). Finally, the surface was deactivated by ethanolamine. Immobilization levels of hFAP were around 4000-6000 RU. The reference spot was treated as described, omitting the injection of hFAP. Compound concentration series were injected over the immobilized protein in increasing concentrations (2-500 nM) using single cycle kinetics in running buffer (20 mM TRIS, 150 mM NaCl, 0.05% Tween20, 1% DMSO, pH 7.4). Interaction models were fitted globally to the experimental traces, enabling determination of $k_{on}$, $k_{off}$ and $K_d$. Data for the compounds tested are reported in Table 1B.

TABLE 1B

| Example | hFAP Binding assay $K_d$ (nM)[1] | hFAP Binding assay $k_{(on)}$ ($M^{-1}s^{-1}$)[1] | hFAP Binding assay $k_{(off)}$ (1/s)[1] |
|---|---|---|---|
| 11 | 17 | 120000000 | 2 |
| 12 | 13 | 1100000 | 0.011 |
| 16 | 20 | 180000 | 0.0038 |
| 17 | 8.5 | 1500000 | 0.012 |
| 21 | 10 | 940000 | 0.0095 |
| 24 | 8.2 | 150000 | 0.0012 |
| 28 | 7.8 | 630000 | 0.0056 |
| 29 | 11 | 2500000 | 0.026 |
| 36 | 4.3 | 1100000 | 0.0048 |
| 40 | 5.5 | 1600000 | 0.0089 |
| 43 | 11 | 160000 | 0.0018 |
| 44 | 12 | 1300000 | 0.016 |
| 45 | 7.3 | 1300000 | 0.0098 |
| 46 | 25 | 13000000 | 0.32 |

[1] $K_d$ is reported after single measurement (n = 1) or as geometric mean for multiple measurements (n = 2-4). $k_{(on)}$ and $k_{(off)}$ are reported after single measurement (n = 1) or as an average for multiple measurements (n = 2-4).

D. FAP Plasma Inhibition Assay

This assay was adapted from the method described in Example 53 for detection of FAP target engagement enzyme activity in plasma. Plasma (anticoagulant K2EDTA) was used as the enzyme source: Human plasma (Pooled from AZ Biobank) and Mouse plasma (AZ AST Biobank). 384-Well black fluotrack PS plates (Greiner 781076) were used. 20 μL diluted plasma (Human plasma dilution 1:40, Mouse plasma dilution 1:67) in buffer (PBS, 0.1% BSA) was added to 0.6 μL compounds (in DMSO). Compounds were tested using 10 CR, 3-fold dilution series from 500 nM FAC. Two replicates for each assay point were run on the same plate. A fluorescence blank read was taken before substrate addition. Substrate, Ala-Pro-AMC (ARI-3144) stock solution (20 mM in DMSO) was diluted in buffer (PBS, 0.1% BSA) to 150 μM concentration and 20 μL added giving 75 μM FAC. Plates were incubated for 40 min at rt in the dark. The plates were read on a Beckman Paradigm® reader with excitation 360 nm and emission 465 nm. Data were analyzed in Excel (IDBS XLfit Add-In) using a one site dose response model (4-parameter logistic fit). $IC_{50}$ values were determined by plotting % inhibition versus log compound concentration. Raw data signals were normalized using 1.5% DMSO in diluted plasma as 0% control and 1.5% DMSO in buffer (no plasma) as 100% inhibitor control. Data for the compounds tested are reported in Table 2.

TABLE 2

| Example | FAP Human Plasma $IC_{50}$ (nM)[1] | FAP Mouse Plasma $IC_{50}$ (nM)[2] |
|---|---|---|
| 1 | 23 | 20 |
| 2 | 13 | 7.1 |
| 3 | 15 | 15 |
| 9 | 7.5 | 2.7 |
| 10 | 34 | 15 |
| 20 | 1.6 | 0.73 |
| 23 | 3.6 | 1.9 |
| 31 | 320 | |
| 37 | 5.5 | 2.4 |
| 40 | 4.1 | 2.8 |
| 41 | 380 | 300 |

[1] $IC_{50}$ is reported after single measurement (n = 1).
[2] $IC_{50}$ is reported after single measurement (n = 1).

Example 48: hPrep Inhibition Assay

Compounds were tested in a biochemical inhibition assay using Prolyl endopeptidase, Prolyl Oligopeptidase (hPREP) enzyme at 0.6 nM FAC (R&D Systems, 4308-SE) and the substrate Z-Gly-Pro-amino-methylcoumarin (Bachem, I-1145) at 50 μM FAC. 384 Low volume black plates (Greiner #784076) were used. 4 μL, 1.2 nM enzyme solution (25 mM Tris HCl, 250 mM NaCl, 0.01% Triton X-100, 5 mM Glutathione, pH 7.5) was added to 40 nL compounds (in DMSO) at 10 CR, 3-fold dilution series from 50 μM FAC. Plates were incubated for 15 min at rt in dark. 4 μL, 100 μM substrate solution (25 mM Tris HCl, 250 mM NaCl, 0.01% Triton X-100, 5 mM Glutathione, pH 7.5) was added to each well. Plates were centrifuged at 1000 rpm and incubated for 20 min at rt in dark. The plates were read on a PHERAstar® reader with excitation 340 nm and emission 460 nm. Data were analyzed in Genedata Screener®. $IC_{50}$ values were determined by plotting % inhibition versus log compound concentration and using a one site dose response model. Raw data signals were normalized using 0.5% DMSO as 0% control and Reference Compound B (i.e., (R)—N-(2-(4-cyanothiazolidin-3-yl)-2-oxoethyl)-7-methylquinoline-4-carboxamide) at 50 μM as 100% inhibitor control. Data for the compounds tested are reported in Table 3.

TABLE 3

| Example | PREP $IC_{50}$ (nM)[1] |
|---|---|
| 1 | 27000 |
| 2 | >50000 |
| 3 | >50000 |
| 4 | 22000 |
| 5 | 18000 |
| 6 | 13000 |
| 7 | 18000 |
| 8 | 44000 |
| 9 | >50000 |
| 10 | >50000 |
| 11 | >50000 |
| 12 | >50000 |
| 13 | >50000 |
| 14 | >50000 |
| 15 | >50000 |
| 16 | >50000 |
| 17 | >50000 |
| 18 | >50000 |
| 19 | 43000 |
| 20 | 31000 |
| 21 | >50000 |
| 22 | >50000 |
| 23 | 12000 |
| 24 | >45000 |
| 25 | >50000 |
| 26 | >50000 |
| 27 | >50000 |
| 28 | >50000 |
| 29 | >50000 |
| 30 | >50000 |
| 31 | 38000 |
| 32 | >50000 |
| 34 | >50000 |
| 35 | >50000 |
| 36 | >50000 |
| 37 | >50000 |
| 38 | >50000 |
| 39 | >50000 |
| 40 | >50000 |
| 43 | >50000 |
| 44 | >50000 |
| 45 | >50000 |
| 46 | >50000 |
| B[2] | 5.2 |
| C[3] | 7.1 |

[1] $IC_{50}$ is reported after single measurement (n = 1) or as geometric mean for multiple measurements (n = 2-7).
[2] Reference Compound B: (R)-N-(2-(4-cyanothiazolidin-3-yl)-2-oxoethyl)-7-methylquinoline-4-carboxamide
[3] Reference Compound C: (R)-N-(2-(4-cyanothiazolidin-3-yl)-2-oxoethyl)-quinoline-4-carboxamide Example 49: hDPP Inhibition Assays A. hDPP7 Inhibition Assay Compounds were tested in a biochemical inhibition assay using human dipeptidylpeptidase 7 (hDPP7) enzyme (BPS Bioscience, #80070) and the substrate Ala-Pro-amino-methylcoumarin (BPS Bioscience, #80305) at 10 μM FAC. The enzymatic reactions were conducted in duplicate at rt for 20 min in 50 μL assay buffer (10 mM Tris-HCl, pH 7.4, 10 mM $MgCl_2$, 1 mM $MnCl_2$). Compound solutions (in DMSO) at 10 CR, 3-fold dilution series were prepared in assay buffer ten-fold higher than the final concentration, and 5 μL of the dilution was added to a 50 μL reaction so that the highest compound concentration was 10 μM FAC and the concentration of DMSO was 1% in all wells. The plates were read on a PHERAstarPLUS (BMG) using kinetic mode with excitation 340 nm and emission 460 nm. Data were analyzed in Graph Pad Prism. Raw data signals were normalized using 1% DMSO as 0% control and no enzyme as 100% inhibitor control. Data for the compounds tested are reported in Table 4.

B. hDPP8 Inhibition Assay

Compounds were tested in a biochemical inhibition assay using human dipeptidylpeptidase 8 (hDPP8) enzyme (BPS Bioscience, #80800) and the substrate Gly-Pro-amino-methylcoumarin (Enzo #BML-P189-0005) at 10 μM FAC. The enzymatic reactions were conducted in duplicate at rt for 20 min in 50 μL assay buffer (50 mM Tris, pH 7.5, 0.1% BSA).

Compound solutions (in DMSO), were prepared in assay buffer ten-fold higher than the final concentration, and 5 μL of the dilution was added to a 50 μL reaction so that the compound concentration was 10 μM FAC and the concentration of DMSO was 1% in all wells. The plates were read on a PHERAstarPLUS (BMG) using kinetic mode with excitation 340 nm and emission 460 nm. Data were analyzed in Graph Pad Prism. Raw data signals were normalized using 1% DMSO as 0% control and no enzyme as 100% inhibitor control. Inhibition data for the compounds tested (% effect) are reported in Table 4.

C. hDPP9 Inhibition Assay

Compounds were tested in a biochemical inhibition assay using human dipeptidylpeptidase 9 (hDPP9) enzyme (R&D, #5419-SE-010) and the substrate Gly-Pro-amino-methyl-coumarin (Enzo #BML-P189-0005) at 10 μM FAC. The enzymatic reactions were conducted in duplicate at rt for 30 min in 50 μL assay buffer (50 mM Tris, pH 7.5, 0.1% BSA). Compound solutions (in DMSO) at 10 CR, 3-fold dilution series were prepared in assay buffer ten-fold higher than the final concentration, and 5 μL of the dilution was added to a 50 μL reaction so that the highest compound concentration was 10 μM FAC and the concentration of DMSO was 1% in all wells. The plates were read on a PHERAstarPLUS (BMG) using kinetic mode with excitation 340 nm and emission 460 nm. Data were analyzed in Graph Pad Prism. $IC_{50}$ values were determined by plotting % inhibition versus log compound concentration and using a one site dose response model. Raw data signals were normalized using 1% DMSO as 0% control and no enzyme as 100% inhibitor control. Data for the compounds tested are reported in Table 4.

TABLE 4

| Example | hDPP7 $IC_{50}$ (nM)[1] | hDPP8 Activity at Compound Concentration 10 μM[2] | hDPP9 $IC_{50}$ (nM)[1] |
|---|---|---|---|
| 20 | >10.000 | Not Active | >10.000 |
| 23 | >10.000 | Not Active | >10.000 |

[1]$IC_{50}$ is reported after single measurement (n = 1).
[2]Activity is reported for the compound tested at a single concentration of 10 μM after single measurement (n = 1).

Example 50: Metabolic Stability Assays

A. Aldehyde Oxidase (AO) Metabolism Assay 1

AO-mediated metabolism was measured essentially as described in *Drug Metab. Disp.* 2010, 38, 1322. Human liver cytosol (Corning life sciences, UltraPool Human Cytosol 150, Product 452115) in phosphate buffer, pH 7.4, was pre-incubated for 5 min at 37° C. shaking at 900 rpm. The reactions were initiated by addition of pre-diluted test compounds including positive control, zaleplon, and incubated at 37° C. with final conditions 2.5 mg/mL human liver cytosolic fraction, 1 μM test compound, 0.01% DMSO and 0.09% MeCN. The samples were incubated for 120 min with time points taken at 0, 10, 30, 60, 90 and 120 min. The aliquots (25 L) were precipitated with 100 μL MeCN containing internal standard (4-((2'-(1H-tetrazol-5-yl)-[1,1'-biphenyl]-4-yl)methoxy)-2-ethylquinoline, (*J Med Chem* 1992, 35, 4027), centrifuged at 3500 rpm for 10 min and the supernatant diluted 1 in 7 (v/v) with ultra-pure HPLC water before analysis by LC-MS/MS. All incubations were carried out in duplicate. The in vitro elimination rate constant corresponding to parent compound depletion was determined for each reaction using the 1st order decay calculation in Microsoft Excel Sheet. In some cases the experiment was conducted additionally in presence of an aldehyde oxidase inhibitor: The cytosol mix was pre-incubated with 3 μM raloxifene shaking at 900 rpm for 5 min at 37° C. prior to addition of test compound. Data for the compounds tested are reported in Table 5.

B. Aldehyde Oxidase (AO) Metabolism Assay 2

AO-mediated metabolism was measured essentially as described in *Drug Metab. Disp.* 2010, 38, 1322. Human liver cytosol (BioreclamationIVT, stored at −80° C. prior to use, protein concentration 2.5 mg/mL) and 0.1 M phosphate buffer (with 0.1 mM EDTA) pH 7.4 is preincubated at 37° C. The reaction was initiated by addition of test compound (final substrate concentration 1 μM, final DMSO concentration 0.3% and final incubation volume 500 μL). Phthalazine (known to be metabolized by AO) was used as a control compound. Test compounds were incubated for 0, 5, 15, 30, 60 and 120 min. The reactions were stopped by removing an aliquot of incubate into organic solvent containing internal standard at the appropriate time points. The termination plates were centrifuged at 2500 rpm for 30 min at 4° C. to precipitate the protein. Sample supernatants were combined in cassettes of up to four compounds and analyzed using generic LC MS/MS conditions. From a plot of ln peak area ratio (compound peak area/internal standard peak area) against time, the gradient of the line was determined. Subsequently, half-life and intrinsic clearance were calculated using the equations below:

$$\text{Elimination rate constant}(k)=(-\text{gradient})$$

$$\text{Half-life}(t_{1/2})(\text{min})=0.693/k$$

$$\text{Intrinsic clearance}(CL_{in}t)(\mu L/\text{min/mg protein})=V\times 0.693/t_{1/2}$$

where V=Incubation volume (μL)/protein (mg)

The percentage of the parent compound remaining at each time point, along with the intrinsic clearance value (CLint), half-life and standard error of the CLint were reported. Data for the compounds tested are reported in Table 5.

TABLE 5

| Example | AO-Assay 1 $CL_{int}$ (μL/min/mg)[1] | AO-Assay 2 $CL_{int}$ (μL/min/mg)[1] |
|---|---|---|
| 2 | | <0.50 |
| 9 | 0.34 | |
| 20 | −0.23 | |
| 24 | −0.92 | |
| 40 | −0.92 | |
| 42 | 0.7 | |
| Compound A[2] | 3.8 | |
| Compound C[3] | 5.3 | |

[1]$CL_{int}$ is reported after single measurement (n = 1).
[2]Compound A ((S)-N-(2-(2-cyano-4,4-difluoropyrrolidin-1-yl)-2-oxoethyl)quinoline-4-carboxamide, *J Med Chem* 2014, 57, 3053).
[3]Compound C (R)-N-(2-(4-cyanothiazolidin-3-yl)-2-oxoethyl)quinoline-4-carboxamide C. Human Liver Microsomes (HLM)

Metabolic stability in HLM was measured as described in *J Comput Aided Mol Des* 2015, 29, 795. Data for the compounds tested are reported in Table 6.

D. Rat Hepatocytes (rHep)

Metabolic stability in rat hepatocytes was measured as described in *J Comput Aided Mol Des* 2015, 29, 795. Data for the compounds tested are reported in Table 6.

E. Human Hepatocytes (hHep)

Metabolic stability in human hepatocytes was measured as described in *Xenobiotica* 2010, 40, 637. Data for the compounds tested are reported in Table 6.

TABLE 6

| Example | HLM $CL_{int}$[1] (μL/min/mg) | rHeps $CL_{int}$[2] (μL/min/1E6) | hHep $CL_{int}$[3] (μL/min/1E6) |
|---|---|---|---|
| 1 | 9.7 | 3.8 | 2.8 |
| 2 | 8.1 | 4.1 | <1 |
| 3 | <3 | 4.5 | <1 |
| 4 | <3 | 1.2 | <1 |
| 5 | 11 | 2.8 | |
| 6 | 23 | 5.8 | |
| 7 | 43 | 12 | |
| 8 | <3 | 1.3 | <1 |
| 9 | <4.2 | 2.2 | <1 |
| 10 | 37 | 6.7 | 7 |
| 11 | <3 | 5.3 | |
| 12 | 100 | 20 | |
| 13 | <3 | 2 | <1 |
| 14 | <3 | <1 | |
| 15 | 30 | 9.4 | 3.3 |
| 16 | 72 | 21 | |
| 17 | 110 | 21 | |
| 18 | 120 | 18 | |
| 19 | 12 | <1 | |
| 20 | <3.2 | <2 | <1 |
| 21 | 13 | 70 | |
| 22 | <5.8 | 2.9 | <1 |
| 23 | 9.9 | 7.7 | 1.6 |
| 24 | <3 | 2.7 | |
| 25 | <3 | <1 | |
| 26 | <3 | <1 | |
| 27 | 21 | 7.2 | 3.1 |
| 28 | 36 | 5.2 | |
| 29 | 8.9 | 81 | |
| 30 | 42 | 16 | |
| 31 | 6.2 | 1.6 | <1 |
| 32 | 46 | 72 | |
| 33 | 170 | 9.8 | 25 |
| 34 | 160 | 20 | 15 |
| 35 | 90 | 16 | 12 |
| 36 | 180 | 92 | |
| 37 | 8.4 | 49 | 2.3 |
| 38 | 190 | 55 | |
| 39 | 77 | 13 | |
| 40 | <3 | 2.6 | <1 |
| 41 | <3 | <1 | <1 |
| 42 | 31 | 11 | 5.6 |
| 43 | 260 | 67 | |
| 44 | >300 | 150 | |
| 45 | 120 | 40 | |
| 46 | 20 | 6.6 | <1 |

[1]$CL_{int}$ is reported after single measurement (n = 1) or as an average for multiple measurements (n = 2-3).
[2]$CL_{int}$ is reported after single measurement (n = 1) or as geometric mean for multiple measurements (n = 2-3).
[3]$CL_{int}$ is reported after single measurement (n = 1) or as geometric mean for multiple measurements (n = 2).

Example 51: Caco-2 Cell Permeability

Caco-2 cell permeability was measured as described in Mol/Pharm 2017, 14, 1601. Data for the compounds tested are reported in Table 7.

TABLE 7

| Example | Caco2 AB Intrinsic $P_{app}$[1] (1E−6 · cm/s) | Caco2 Bidirectional (ABBA) A to B $P_{app}$[1] (1E−6 · cm/s) | Caco2 Bidirectional (ABBA) B to A $P_{app}$[1] (1E−6 · cm/s) | Caco2 Bidirectional (ABBA) Efflux Ratio |
|---|---|---|---|---|
| 2 | | 28 | 29 | 1.1 |
| 9 | 32 | 19 | 21 | 1.2 |
| 20 | 60 | 24 | 19 | 0.80 |
| 31 | 56 | | | |
| 37 | 29 | 18 | 33 | 1.8 |
| 40 | 9.3 | 2.8 | 28 | 10 |

[1]$P_{app}$ is reported after single measurement (n = 1) or as an average for multiple measurements (n = 2).

Example 52: Kinetic Solubility

Kinetic solubility was measured as described in *Comput Aided Mol Des* 2015, 29, 795. Data for the compounds tested are reported in Table 8.

TABLE 8

| Example | Solubility (μM)[1] |
|---|---|
| 1 | 290 |
| 2 | 160 |
| 3 | 210 |
| 4 | >1000 |
| 5 | 140 |
| 6 | 61 |
| 7 | 23 |
| 8 | 890 |
| 9 | >940 |
| 10 | 140 |
| 11 | 970 |
| 12 | 300 |
| 13 | >1000 |
| 14 | >1000 |
| 15 | >1000 |
| 16 | >1000 |
| 17 | 340 |
| 18 | 800 |
| 19 | >1000 |
| 20 | >1000 |
| 21 | 56 |
| 22 | >1000 |
| 23 | >1000 |
| 24 | >1000 |
| 25 | 960 |
| 26 | >1000 |
| 27 | >1000 |
| 28 | >1000 |
| 29 | 23 |
| 30 | 200 |
| 31 | >1000 |
| 32 | 37 |
| 33 | 700 |
| 34 | 850 |
| 35 | 590 |
| 36 | 210 |
| 37 | 810 |
| 38 | 430 |
| 39 | 960 |
| 40 | 570 |
| 41 | 120 |
| 42 | >1000 |
| 43 | 820 |
| 44 | 510 |
| 45 | >1000 |
| 46 | 110 |
| 47 | 590 |

[1]Solubility is reported after single measurement (n = 1) or as an average for multiple measurements (n = 2-3).

Example 53: FAP Target Engagement Enzyme Activity in Mouse Plasma

The effect of test compound on FAP enzyme activity in mouse plasma was evaluated in an enzymatic assay using the Fibroblast Activation Protein alpha (FAP) specific fluorogenic substrate dipeptide-Coumarin, Ala-Pro-AMC, (ARI-3144). In this assay, FAP cleaves Ala-Pro-AMC to release free AMC which is measured as a fluorescent signal that correlates with enzyme activity.

Male C57Bl/6 mice (Charles River, Germany), 8 weeks of age, were single housed in a temperature-controlled room with a 12-hour light/dark cycle (06:00-18:00 light). The mice had ad libitum access to water and rodent chow diet (R70, Lactamin, Kimstad, Sweden), and were acclimated for 5 days upon arrival. After acclimation, all mice received a single oral dose of test compound (3 or 10 mg/kg). Blood samples for whole blood compound exposure measurements were taken at 0.25, 0.5, 1, 2, 4, 8 and 24 h post oral dosing. Samples were collected in EDTA capillary tubes (20 μL, K2E, REF 19.447) and were transferred to a 96-deep well plate (NUNC, Thermo Discher Scientific) and stored at −20° C. until further analyses were performed. Blood samples for plasma FAP enzyme activity measurements were taken at 0, 0.25, 0.5, 1, 2, 8 and 24 h post dosing. 25 μL of whole blood was collected in EDTA Microvette® CB 300 (K2E, REF 16.444.100) tubes, and were centrifuged at 4,000×g for 5 min. 10 μL of plasma was then transferred to PCR tubes and stored at −20° C. until further analysis was performed. All blood samples were taken by vena saphena puncture.

Recombinant human FAP (PB-17-1837, construct PL-17-0278, cd33-FAP (27-757)-6His, Mw85926 Da) was used as a standard for this assay. Protein was secreted from Sf21 cells (insect cells) in media, purified with affinity (batch mode, Ni excel resin) and size exclusion chromatography (Superdex200), concentrated and aliquoted to be frozen in liquid $N_2$ for storage at −80° C. Recombinant FAP was diluted in protein buffer (25 mM Tris/HCl, pH 7.6, 150 mM NaCl, 5% glycerol, 1 mM EDTA, 0.25 mM TCEP) and 5 μL aliquots (0.1 mg/mL, 1.15 μM) were stored at −80° C. Standards were prepared using 2-fold dilution steps, 8 concentrations, 4 replicates (FAC: 1.2 nM, 0.6 nM, 0.3 nM). The plates were read on a Beckman Paradigm reader with excitation 360 nm and emission 465 nm. Fluorescence measurements were performed with kinetic read every 5 minutes for 60 min at room temperature. Data were analyzed in Excel (IDBS XLfit Add-In) using a Linear Regression (y=k*x+m) model to prepare a human recombinant FAP standard curve.

On the day of the assay, plasma was diluted (1:2) to 20 μL volume in buffer (PBS, 0.1% BSA) and 7.5 μL was transferred to the assay plate (384-well black, fluotrack PS, Greiner 781076). Ala-Pro-AMC (stock solution in 10 mM DMSO) was diluted in buffer (PBS, 0.1% BSA) to 150 μM concentration (180 μL stock solution to 12 mL buffer) and 7.5 μL added to the assay plate followed by a pipetting mix. The plates were read on a Beckman Paradigm reader with excitation 360 nm and emission 465 nm. Fluorescence measurements were performed with kinetic read every 5 minutes for 60 minutes at room temperature. As noted above, FAP cleaves Ala-Pro-AMC to release free AMC which is measured as a fluorescent signal.

The in vivo potency IC50 of each test compound was then estimated by relating the plasma exposure C of the compound to target engagement E in plasma using the following equation:

$$E = E_0\left(1 - \frac{I_{max}C}{IC_{50} + C}\right)$$

where $E_0$ is the FAP baseline in plasma prior to dosing and $I_{max}$ is the maximum effect of the compound. Data from each target engagement experiment were considered separately and therefore slightly different estimates of FAP baseline for each compound were obtained. Full inhibition was achieved for all tested compounds at the earlier timepoints and therefore the parameter $I_{max}$ was fixed to 1 for all compounds. The parameter estimation was done in Phoenix WinNonlin Certara build 8.1.0.3530 with the algorithm 'Naïve pooled' as parameter estimation method. In vivo $IC_{50}$ estimates for the test compounds are reported in Table 9.

TABLE 9

| Example | In vivo Mouse $IC_{50}$ (nM) |
|---|---|
| 2 | 21 |
| 20 | 3.0 |
| 40 | 36 |

Although specific embodiments and examples have been described above, these embodiments and examples are only illustrative and do not limit the scope of the disclosure. Changes and modifications can be made in accordance with ordinary skill in the art without departing from the disclosure in its broader aspects as defined in the following claims. For example, any embodiment described herein can be combined with any other suitable embodiment described herein to provide additional embodiments.

As will be understood by the skilled artisan, all numbers, including those expressing quantities of ingredients, properties such as molecular weight, reaction conditions, and so forth, are approximations and understood as being modified in all instances by the term "about." These values can vary depending upon the desired properties sought to be obtained by those skilled in the art utilizing the present teachings of the present disclosure. It is also understood that such values inherently contain variability necessarily resulting from the standard deviations found in their respective testing measurements.

One skilled in the art will also readily recognize that where members are grouped together in a common manner, such as in a Markush group, the present disclosure encompasses not only the entire group listed as a whole, but each member of the group individually and all possible subgroups of the main group. Additionally, for all purposes, the present disclosure encompasses not only the main group, but also the main group absent one or more of the group members. The present disclosure also envisages the explicit exclusion or disclaimer of one or more of any of the group members in the claimed disclosure.

As will be understood by one skilled in the art, for any and all purposes, particularly in terms of providing a written description, all ranges disclosed herein also encompass any and all possible subranges and combinations of subranges thereof as well as the individual values making up the range, particularly integer values. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. For example, the range $C_{(1-6)}$, includes the subranges $C_{(2-6)}$, $C_{(3-6)}$, $C_{(3-5)}$, $C_{(4-6)}$, etc., as well as $C_1$ (methyl), $C_2$ (ethyl), $C_3$ (propyl), $C_4$ (butyl), $C_5$ (pentyl) and $C_6$ (hexyl) individually. As will also be understood by one skilled in the art, all language such as "up to," "at least," "greater than," "less than," "more than," "or more" and the like include the number recited and refer to ranges which can be subsequently broken down into subranges as discussed above. In the same manner, all ratios disclosed herein also include all subratios falling within the broader ratio.

Reference to a "step" in this disclosure is used for convenience purposes only and does not categorize, define or limit the disclosure as set forth herein.

What is claimed is:

1. A compound having the structure of Formula (I):

(I)

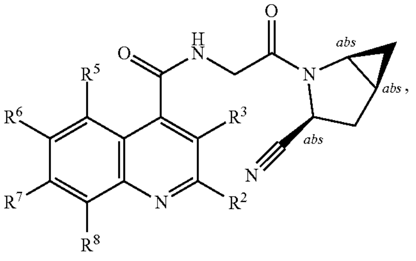

or a pharmaceutically acceptable salt thereof, wherein:

$R^2$ is selected from the group consisting of hydrogen, halogen, and methyl;

$R^3$ is hydrogen or halogen;

$R^5$ is selected from the group consisting of hydrogen, hydroxy, halogen, methyl, and methoxy;

one of $R^6$ and $R^7$ is hydrogen and the other of $R^6$ and $R^7$ is selected from the group consisting of:

(a) halogen;

(b) $C_{1-6}$-alkyl, wherein the $C_{1-6}$-alkyl is optionally substituted with one or more substituents independently selected from the group consisting of halogen, hydroxy, $C_{1-6}$-alkoxy, halo-$C_{1-6}$-alkoxy, $C_{3-6}$-cycloalkyl, and $C_{3-6}$-cycloalkoxy;

(c) cyclopropyl, wherein the cyclopropyl is optionally substituted with one or more substituents independently selected from the group consisting of cyano, fluoro, $C_{1-6}$-alkyl, halo-$C_{1-6}$-alkyl, and $C_{1-6}$-alkoxy;

(d) $C_{1-6}$-alkoxy, wherein the $C_{1-6}$-alkoxy is optionally substituted with one or more substituents independently selected from the group consisting of halogen and cyclopropyl; and (e) $C_{3-6}$-cycloalkoxy, wherein the $C_{3-6}$-cycloalkoxy is optionally substituted with one or more substituents independently selected from the group consisting of halogen and $C_{1-3}$-alkyl; and $R^8$ is selected from the group consisting of hydrogen, halogen, and methyl.

2. The compound of claim 1, or a pharmaceutically acceptable salt thereof, wherein the compound has the structure of Formula (II-A):

(II-A)

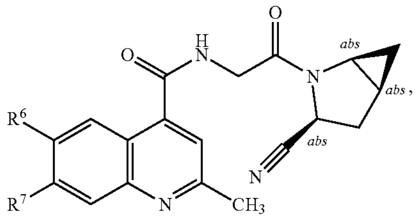

and wherein one of $R^6$ and $R^7$ is hydrogen and the other of $R^6$ and $R^7$ is selected from the group consisting of:

(a) halogen;

(b) $C_{1-6}$-alkyl, wherein the $C_{1-6}$-alkyl is optionally substituted with one or more substituents independently selected from the group consisting of halogen, hydroxy, $C_{1-6}$-alkoxy, halo-$C_{1-6}$-alkoxy, $C_{3-6}$-cycloalkyl, and $C_{3-6}$-cycloalkoxy;

(c) cyclopropyl, wherein the cyclopropyl is optionally substituted with one or more substituents independently selected from the group consisting of cyano, fluoro, $C_{1-6}$-alkyl, halo-$C_{1-6}$-alkyl, and $C_{1-6}$-alkoxy;

(d) $C_{1-6}$-alkoxy, wherein the $C_{1-6}$-alkoxy is optionally substituted with one or more substituents independently selected from the group consisting of halogen and cyclopropyl; and (e) $C_{3-6}$-cycloalkoxy, wherein the $C_{3-6}$-cycloalkoxy is optionally substituted with one or more substituents independently selected from the group consisting of halogen and $C_{1-3}$-alkyl.

3. The compound of claim 1, or a pharmaceutically acceptable salt thereof, wherein the compound has the structure of Formula (III-A):

(III-A)

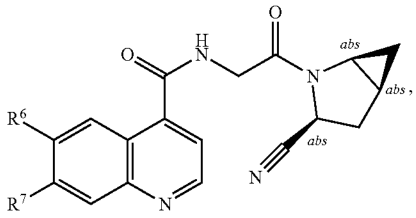

and wherein one of $R^6$ and $R^7$ is hydrogen and the other of $R^6$ and $R^7$ is selected from the group consisting of:

(a) halogen;

(b) $C_{1-6}$-alkyl, wherein the $C_{1-6}$-alkyl is optionally substituted with one or more substituents independently selected from the group consisting of halogen, hydroxy, $C_{1-6}$-alkoxy, halo-$C_{1-6}$-alkoxy, $C_{3-6}$-cycloalkyl, and $C_{3-6}$-cycloalkoxy;

(c) cyclopropyl, wherein the cyclopropyl is optionally substituted with one or more substituents independently selected from the group consisting of cyano, fluoro, $C_{1-6}$-alkyl, halo-$C_{1-6}$-alkyl, and $C_{1-6}$-alkoxy;

(d) $C_{1-6}$-alkoxy, wherein the $C_{1-6}$-alkoxy is optionally substituted with one or more substituents independently selected from the group consisting of halogen and cyclopropyl; and (e) $C_{3-6}$-cycloalkoxy, wherein the $C_{3-6}$-cycloalkoxy is optionally substituted with one or more substituents independently selected from the group consisting of halogen and $C_{1-3}$-alkyl.

4. The compound of claim 1, or a pharmaceutically acceptable salt thereof, wherein one of $R^6$ and $R^7$ is hydrogen and the other is halogen.

5. The compound of claim 1, or a pharmaceutically acceptable salt thereof, wherein one of $R^6$ and $R^7$ is hydrogen and the other is $C_{1-6}$-alkyl, wherein the $C_{1-6}$-alkyl is optionally substituted with one or more substituents independently selected from the group consisting of halogen, hydroxy, $C_{1-6}$-alkoxy, halo-$C_{1-6}$-alkoxy, $C_{3-6}$-cycloalkyl, and $C_{3-6}$-cycloalkoxy.

6. The compound of claim 1, or a pharmaceutically acceptable salt thereof, wherein one of $R^6$ and $R^7$ is hydrogen and the other is selected from the group consisting of methyl, ethyl, fluoromethyl, difluoromethyl, trifluoromethyl, fluoropropyl, hydroxyethyl, hydroxypropyl, methoxyethyl, methoxypropyl, trifluoromethoxymethyl, and trifluoromethoxyethyl.

7. The compound of claim 1, or a pharmaceutically acceptable salt thereof, wherein one of $R^6$ and $R^7$ is hydrogen and the other is methyl.

8. The compound of claim 1, or a pharmaceutically acceptable salt thereof, wherein one of $R^6$ and $R^7$ is hydrogen and the other is cyclopropyl, wherein the cyclopropyl is optionally substituted with one or more substituents independently selected from the group consisting of cyano, fluoro, $C_{1-6}$-alkyl, halo-$C_{1-6}$-alkyl, and $C_{1-6}$-alkoxy.

9. The compound of claim 1, or a pharmaceutically acceptable salt thereof, wherein one of $R^6$ and $R^7$ is hydrogen and the other is cyclopropyl, wherein the cyclopropyl is optionally substituted with one or more substituents independently selected from the group consisting of cyano, methyl, trifluoromethyl, and ethoxy.

10. The compound of claim 1, or a pharmaceutically acceptable salt thereof, wherein one of $R^6$ and $R^7$ is hydrogen and the other is $C_{1-6}$-alkoxy, wherein the $C_{1-6}$-alkoxy is optionally substituted with one or more substituents independently selected from the group consisting of halogen and cyclopropyl.

11. The compound of claim 1, or a pharmaceutically acceptable salt thereof, wherein one of $R^6$ and $R^7$ is hydrogen and the other is selected from the group consisting of methoxy, propoxy, trifluoroethoxy, and cyclopropylmethoxy.

12. The compound of claim 1, or a pharmaceutically acceptable salt thereof, wherein one of $R^6$ and $R^7$ is hydrogen and the other is $C_{3-6}$-cycloalkoxy, wherein the $C_{3-6}$-cycloalkoxy is optionally substituted with one or more halogen.

13. The compound of claim 1, or a pharmaceutically acceptable salt thereof, wherein:

one of Re and $R^7$ is hydrogen and the other of $R^6$ and $R^7$ is selected from the group consisting of:

(a) halogen;

(b) $C_{1-6}$-alkyl, wherein the $C_{1-6}$-alkyl is optionally substituted with one or more substituents independently selected from the group consisting of halogen, hydroxy, $C_{1-6}$-alkoxy, halo-$C_{1-6}$-alkoxy, $C_{3-6}$-cycloalkyl, and $C_{3-6}$-cycloalkoxy; and (c) cyclopropyl, wherein the cyclopropyl is optionally substituted with one or more substituents independently selected from the group consisting of cyano, fluoro, $C_{1-6}$-alkyl, halo-$C_{1-6}$-alkyl, and $C_{1-6}$-alkoxy.

14. The compound of claim 1, or a pharmaceutically acceptable salt thereof, wherein one of $R^6$ and $R^7$ is hydrogen and the other of $R^6$ and $R^7$ is selected from the group consisting of:

(a) the group consisting of chloro, fluoro, bromo, and iodo;

(b) $C_{1-3}$-alkyl, wherein the $C_{1-3}$-alkyl is optionally substituted with one or more substituents independently selected from the group consisting of halogen, hydroxy, $C_{1-3}$-alkoxy, and halo-$C_{1-3}$-alkoxy; and (c) cyclopropyl, wherein the cyclopropyl is optionally substituted with one or more substituents independently selected from the group consisting of cyano, $C_{1-3}$-alkyl, halo-$C_{1-3}$-alkyl, and $C_{1-3}$-alkoxy.

15. The compound of claim 1, or a pharmaceutically acceptable salt thereof, wherein one of $R^6$ and $R^7$ is hydrogen and the other of $R^6$ and $R^7$ is selected from the group consisting of:

(a) the group consisting of chloro and fluoro;

(b) $C_{1-3}$-alkyl, wherein the $C_{1-3}$-alkyl is optionally substituted with one or more substituents independently selected from the group consisting of halogen, hydroxy, methoxy, and halomethoxy; and (c) cyclopropyl, wherein the cyclopropyl is optionally substituted with one or more substituents independently selected from the group consisting of cyano, methyl, trifluoromethyl, and ethoxy.

16. The compound of claim 1, or a pharmaceutically acceptable salt thereof, wherein one of $R^6$ and $R^7$ is hydrogen and the other of $R^6$ and $R^7$ is selected from the group consisting of:

(a) the group consisting of chloro and fluoro;

(b) $C_{1-3}$-alkyl, wherein the $C_{1-3}$-alkyl is optionally substituted with one or more substituents independently selected from the group consisting of methyl, ethyl, propyl, fluoromethyl, difluoromethyl, trifluoromethyl, fluoropropyl, hydroxyethyl, hydroxypropyl, methoxyethyl, methoxypropyl, trifluoromethoxymethyl, and trifluoromethoxyethyl; and (c) cyclopropyl, wherein the cyclopropyl is optionally substituted with one or more substituents independently selected from the group consisting of cyano, methyl, trifluoromethyl, and ethoxy.

17. The compound of claim 1, or a pharmaceutically acceptable salt thereof, wherein $R^6$ is hydrogen.

18. The compound of claim 1, or a pharmaceutically acceptable salt thereof, wherein $R^7$ is hydrogen.

19. The compound of claim 1, or a pharmaceutically acceptable salt thereof, wherein the compound is selected from the group consisting of:

7-Chloro-N-(2-((1S,3S,5S)-3-cyano-2-azabicyclo[3.1.0]hexan-2-yl)-2-oxoethyl)-quinoline-4-carboxamide;

6-Bromo-N-(2-((1S,3S,5S)-3-cyano-2-azabicyclo[3.1.0]hexan-2-yl)-2-oxoethyl)-quinoline-4-carboxamide;

7-Bromo-N-(2-((1S,3S,5S)-3-cyano-2-azabicyclo[3.1.0]hexan-2-yl)-2-oxoethyl)-quinoline-4-carboxamide;

N-(2-((1S,3S,5S)-3-Cyano-2-azabicyclo[3.1.0]hexan-2-yl)-2-oxoethyl)-6-fluoro-2-methylquinoline-4-carboxamide;

6-Chloro-N-(2-((1S,3S,5S)-3-cyano-2-azabicyclo[3.1.0]hexan-2-yl)-2-oxoethyl)-2-methylquinoline-4-carboxamide;

6-Bromo-N-(2-((1S,3S,5S)-3-cyano-2-azabicyclo[3.1.0]hexan-2-yl)-2-oxoethyl)-2-methylquinoline-4-carboxamide;

N-(2-((1S,3S,5S)-3-Cyano-2-azabicyclo[3.1.0]hexan-2-yl)-2-oxoethyl)-6-iodo-2-methylquinoline-4-carboxamide; and N-(2-((1S,3S,5S)-3-Cyano-2-azabicyclo[3.1.0]hexan-2-yl)-2-oxoethyl)-7-fluoro-2-methylquinoline-4-carboxamide.

20. The compound of claim 1, or a pharmaceutically acceptable salt thereof, wherein the compound is selected from the group consisting of:

N-(2-((1S,3S,5S)-3-Cyano-2-azabicyclo[3.1.0]hexan-2-yl)-2-oxoethyl)-7-methyl-quinoline-4-carboxamide;
N-(2-((1S,3S,5S)-3-Cyano-2-azabicyclo[3.1.0]hexan-2-yl)-2-oxoethyl)-6-methyl-quinoline-4-carboxamide;
N-(2-((1S,3S,5S)-3-Cyano-2-azabicyclo[3.1.0]hexan-2-yl)-2-oxoethyl)-6-(trifluoromethyl)quinoline-4-carboxamide;
N-(2-((1S,3S,5S)-3-Cyano-2-azabicyclo[3.1.0]hexan-2-yl)-2-oxoethyl)-6-(fluoromethyl)quinoline-4-carboxamide;
N-(2-((1S,3S,5S)-3-Cyano-2-azabicyclo[3.1.0]hexan-2-yl)-2-oxoethyl)-6-(2-fluoropropan-2-yl)quinoline-4-carboxamide;
N-(2-((1S,3S,5S)-3-Cyano-2-azabicyclo[3.1.0]hexan-2-yl)-2-oxoethyl)-6-(2-hydroxypropan-2-yl)quinoline-4-carboxamide;
N-(2-((1S,3S,5S)-3-Cyano-2-azabicyclo[3.1.0]hexan-2-yl)-2-oxoethyl)-6-(1-hydroxyethyl)quinoline-4-carboxamide;
N-(2-((1S,3S,5S)-3-Cyano-2-azabicyclo[3.1.0]hexan-2-yl)-2-oxoethyl)-6-(1-methoxyethyl)quinoline-4-carboxamide;
N-(2-((1S,3S,5S)-3-Cyano-2-azabicyclo[3.1.0]hexan-2-yl)-2-oxoethyl)-6-(2-methoxypropan-2-yl)quinoline-4-carboxamide;
N-(2-((1S,3S,5S)-3-Cyano-2-azabicyclo[3.1.0]hexan-2-yl)-2-oxoethyl)-6-((trifluoromethoxy) methyl)-quinoline-4-carboxamide;
N-(2-((1S,3S,5S)-3-Cyano-2-azabicyclo[3.1.0]hexan-2-yl)-2-oxoethyl)-6-ethyl-2-methylquinoline-4-carboxamide;
N-(2-((1S,3S,5S)-3-Cyano-2-azabicyclo[3.1.0]hexan-2-yl)-2-oxoethyl)-2,6-dimethylquinoline-4-carboxamide;
N-(2-((1S,3S,5S)-3-Cyano-2-azabicyclo[3.1.0]hexan-2-yl)-2-oxoethyl)-7-(2-fluoropropan-2-yl)quinoline-4-carboxamide;
N-(2-((1S,3S,5S)-3-Cyano-2-azabicyclo[3.1.0]hexan-2-yl)-2-oxoethyl)-7-(difluoromethyl)quinoline-4-carboxamide;
N-(2-((1S,3S,5S)-3-Cyano-2-azabicyclo[3.1.0]hexan-2-yl)-2-oxoethyl)-7-(trifluoromethyl)quinoline-4-carboxamide;
N-(2-((1S,3S,5S)-3-Cyano-2-azabicyclo[3.1.0]hexan-2-yl)-2-oxoethyl)-7-(fluoromethyl)quinoline-4-carboxamide;
N-(2-((1S,3S,5S)-3-Cyano-2-azabicyclo[3.1.0]hexan-2-yl)-2-oxoethyl)-7-(1-hydroxyethyl)quinoline-4-carboxamide;
N-(2-((1S,3S,5S)-3-Cyano-2-azabicyclo[3.1.0]hexan-2-yl)-2-oxoethyl)-7-(2-hydroxypropan-2-yl)quinoline-4-carboxamide;
N-(2-((1S,3S,5S)-3-Cyano-2-azabicyclo[3.1.0]hexan-2-yl)-2-oxoethyl)-7-(1-methoxyethyl)quinoline-4-carboxamide;
N-(2-((1S,3S,5S)-3-Cyano-2-azabicyclo[3.1.0]hexan-2-yl)-2-oxoethyl)-7-(2-methoxypropan-2-yl)quinoline-4-carboxamide;
N-(2-((1S,3S,5S)-3-Cyano-2-azabicyclo[3.1.0]hexan-2-yl)-2-oxoethyl)-7-((trifluoromethoxy) methyl)quinoline-4-carboxamide;
N-(2-((1S,3S,5S)-3-Cyano-2-azabicyclo[3.1.0]hexan-2-yl)-2-oxoethyl)-7-(1-(trifluoromethoxy) ethyl)quinoline-4-carboxamide; and
N-(2-((1S,3S,5S)-3-Cyano-2-azabicyclo[3.1.0]hexan-2-yl)-2-oxoethyl)-2,7-dimethylquinoline-4-carboxamide.

21. The compound of claim 1, or a pharmaceutically acceptable salt thereof, wherein the compound is selected from the group consisting of:

N-(2-((1S,3S,5S)-3-Cyano-2-azabicyclo[3.1.0]hexan-2-yl)-2-oxoethyl)-7-(1-cyanocyclopropyl)quinoline-4-carboxamide;
N-(2-((1S,3S,5S)-3-Cyano-2-azabicyclo[3.1.0]hexan-2-yl)-2-oxoethyl)-6-cyclopropylquinoline-4-carboxamide;
N-(2-((1S,3S,5S)-3-Cyano-2-azabicyclo[3.1.0]hexan-2-yl)-2-oxoethyl)-6-(1-methylcyclopropyl)quinoline-4-carboxamide;
N-(2-((1S,3S,5S)-3-Cyano-2-azabicyclo[3.1.0]hexan-2-yl)-2-oxoethyl)-6-(1-(trifluoromethyl)cyclopropyl)quinoline-4-carboxamide;
N-(2-((1S,3S,5S)-3-Cyano-2-azabicyclo[3.1.0]hexan-2-yl)-2-oxoethyl)-6-(1-ethoxycyclopropyl)quinoline-4-carboxamide;
N-(2-((1S,3S,5S)-3-Cyano-2-azabicyclo[3.1.0]hexan-2-yl)-2-oxoethyl)-6-(1-cyanocyclopropyl)quinoline-4-carboxamide;
N-(2-((1S,3S,5S)-3-Cyano-2-azabicyclo[3.1.0]hexan-2-yl)-2-oxoethyl)-7-cyclopropylquinoline-4-carboxamide;
N-(2-((1S,3S,5S)-3-Cyano-2-azabicyclo[3.1.0]hexan-2-yl)-2-oxoethyl)-7-(1-methylcyclopropyl)quinoline-4-carboxamide;
N-(2-((1S,3S,5S)-3-Cyano-2-azabicyclo[3.1.0]hexan-2-yl)-2-oxoethyl)-7-(1-(trifluoromethyl)cyclopropyl)quinoline-4-carboxamide; and
N-(2-((1S,3S,5S)-3-Cyano-2-azabicyclo[3.1.0]hexan-2-yl)-2-oxoethyl)-7-(1-ethoxycyclopropyl)quinoline-4-carboxamide.

22. The compound of claim 1, or a pharmaceutically acceptable salt thereof, wherein the compound is selected from the group consisting of:

N-(2-((1S,3S,5S)-3-Cyano-2-azabicyclo[3.1.0]hexan-2-yl)-2-oxoethyl)-6-(2,2,2-trifluoroethoxy)quinoline-4-carboxamide;
N-(2-((1S,3S,5S)-3-Cyano-2-azabicyclo[3.1.0]hexan-2-yl)-2-oxoethyl)-6-isopropoxyquinoline-4-carboxamide; and
N-(2-((1S,3S,5S)-3-Cyano-2-azabicyclo[3.1.0]hexan-2-yl)-2-oxoethyl)-6-(cyclopropylmethoxy)quinoline-4-carboxamide.

23. The compound of claim 1, or a pharmaceutically acceptable salt thereof, wherein the compound is N-(2-((1S,3S,5S)-3-Cyano-2-azabicyclo[3.1.0]hexan-2-yl)-2-oxoethyl)-7-methoxy-2-methylquinoline-4-carboxamide having the structure:

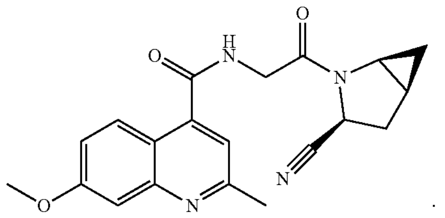 [SMILES: COc1ccc2c(C(=O)NCC(=O)N3[C@H](C#N)C[C@@H]4C[C@@H]43)cc(C)nc2c1]

24. The compound of claim 1, or a pharmaceutically acceptable salt thereof, wherein the compound is N-(2-((1S, 3S,5S)-3-Cyano-2-azabicyclo[3.1.0]hexan-2-yl)-2-oxoethyl)-6-((4,4-difluorocyclohexyl)oxy)quinoline-4-carboxamide having the structure:

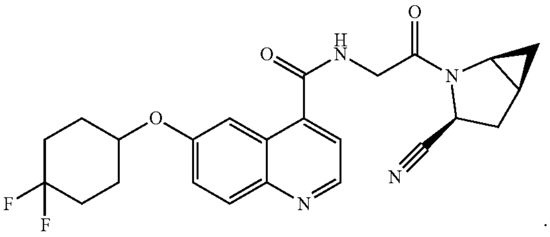 [SMILES: N#C[C@@H]1C[C@@H]2C[C@@H]2N1C(=O)CNC(=O)c1ccnc2ccc(OC3CCC(F)(F)CC3)cc12]

.

25. The compound of claim 1, or a pharmaceutically acceptable salt thereof, wherein the compound is N-(2-((1S,3S,5S)-3-Cyano-2-azabicyclo[3.1.0]hexan-2-yl)-2-oxoethyl)-7-methylquinoline-4-carboxamide having the structure:

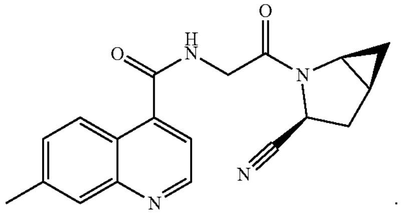 [SMILES: Cc1ccc2c(C(=O)NCC(=O)N3[C@H](C#N)C[C@@H]4C[C@@H]43)ccnc2c1]

.

26. A pharmaceutical composition comprising a compound of claim 1, or a pharmaceutically acceptable salt thereof, and one or more pharmaceutically acceptable excipients.

* * * * *